US010196436B2

(12) United States Patent
Miduturu

(10) Patent No.: US 10,196,436 B2
(45) Date of Patent: Feb. 5, 2019

(54) INHIBITORS OF THE FIBROBLAST GROWTH FACTOR RECEPTOR

(71) Applicant: BLUEPRINT MEDICINES CORPORATION, Cambridge, MA (US)

(72) Inventor: Chandrasekhar V. Miduturu, Cambridge, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 15/867,637

(22) Filed: Jan. 10, 2018

(65) Prior Publication Data
US 2018/0362613 A1 Dec. 20, 2018

Related U.S. Application Data

(60) Continuation of application No. 15/097,995, filed on Apr. 13, 2016, which is a continuation of application No. 14/677,162, filed on Apr. 2, 2015, now Pat. No. 9,340,514, which is a continuation of application No. 14/318,149, filed on Jun. 27, 2014, now Pat. No. 9,126,951, which is a division of application No. 13/939,967, filed on Jul. 11, 2013, now Pat. No. 8,802,697.

(60) Provisional application No. 61/746,666, filed on Dec. 28, 2012, provisional application No. 61/670,379, filed on Jul. 11, 2012.

(51) Int. Cl.
| | | |
|---|---|---|
| *C07D 239/78* | (2006.01) | |
| *C07K 14/71* | (2006.01) | |
| *A61K 31/4375* | (2006.01) | |
| *C07D 401/04* | (2006.01) | |
| *A61K 31/519* | (2006.01) | |
| *A61K 31/517* | (2006.01) | |
| *C07D 475/04* | (2006.01) | |
| *C07D 471/04* | (2006.01) | |
| *C07D 295/155* | (2006.01) | |
| *C07D 239/84* | (2006.01) | |
| *C07D 487/04* | (2006.01) | |
| *C07D 475/00* | (2006.01) | |
| *C07D 239/42* | (2006.01) | |

(52) U.S. Cl.
CPC .......... *C07K 14/71* (2013.01); *A61K 31/4375* (2013.01); *A61K 31/517* (2013.01); *A61K 31/519* (2013.01); *C07D 239/42* (2013.01); *C07D 239/84* (2013.01); *C07D 295/155* (2013.01); *C07D 401/04* (2013.01); *C07D 471/04* (2013.01); *C07D 475/00* (2013.01); *C07D 475/04* (2013.01); *C07D 487/04* (2013.01)

(58) Field of Classification Search
CPC .................................................... C07D 239/78
See application file for complete search history.

(56) References Cited

U.S. PATENT DOCUMENTS

| | | |
|---|---|---|
| 6,605,615 B2 | 8/2003 | Medina et al. |
| 6,936,612 B2 | 8/2005 | Barvian et al. |
| 8,802,697 B2 * | 8/2014 | Bifulco, Jr. .......... C07D 239/42 |
| | | 514/303 |
| 9,034,898 B2 | 5/2015 | Clary-Ceccato et al. |
| 9,126,951 B2 * | 9/2015 | Bifulco, Jr. .......... C07D 239/42 |
| 9,200,002 B2 | 12/2015 | Hodous et al. |
| 9,266,883 B2 | 2/2016 | Buschmann et al. |
| 9,321,786 B2 | 4/2016 | D'Agostino et al. |
| 9,334,263 B2 | 5/2016 | Hodous et al. |
| 9,340,514 B2 * | 5/2016 | Bifulco, Jr. .......... C07D 239/42 |
| 9,434,700 B2 * | 9/2016 | Bifulco, Jr. .......... C07D 239/84 |
| 9,499,522 B2 | 11/2016 | DiPietro et al. |
| 9,533,988 B2 | 1/2017 | Buschmann et al. |
| 9,688,680 B2 | 6/2017 | Hodous |
| 9,695,165 B2 * | 7/2017 | Bifulco, Jr. .......... C07D 471/04 |
| 9,745,311 B2 | 8/2017 | Lu et al. |
| 9,884,861 B2 | 2/2018 | Hodous et al. |
| 9,944,651 B2 | 4/2018 | Hodous et al. |
| 9,994,552 B2 | 6/2018 | DiPietro et al. |
| 9,994,575 B2 | 6/2018 | Hodous et al. |
| 10,000,490 B2 * | 6/2018 | Bifulco, Jr. .......... C07D 471/04 |
| 10,000,496 B2 | 6/2018 | Hodous et al. |
| 10,017,512 B2 | 7/2018 | Wenglowsky et al. |
| 10,030,005 B2 | 7/2018 | Brubaker et al. |
| 10,035,789 B2 | 7/2018 | Brubaker et al. |
| 2005/0124562 A1 | 6/2005 | Guiles et al. |
| 2013/0035366 A1 | 2/2013 | Swayze et al. |
| 2013/0150342 A1 | 6/2013 | Brain et al. |
| 2014/0187559 A1 | 7/2014 | Miduturu |

(Continued)

FOREIGN PATENT DOCUMENTS

| | | |
|---|---|---|
| EP | 1 836 174 B1 | 2/2013 |
| EP | 2 657 233 A1 | 10/2013 |

(Continued)

OTHER PUBLICATIONS

U.S. Appl. No. 15/097,995, filed Apr. 13, 2016.

(Continued)

Primary Examiner — Alexander R Pagano
(74) Attorney, Agent, or Firm — Finnegan, Henderson, Farabow, Garrett & Dunner, LLP

(57) ABSTRACT

Described herein are inhibitors of FGFR, pharmaceutical compositions including such compounds, and methods of using such compounds and compositions to inhibit the activity of tyrosine kinases.

1 Claim, 8 Drawing Sheets

(56) References Cited

U.S. PATENT DOCUMENTS

| | | |
|---|---|---|
| 2016/0002223 A1 | 1/2016 | Chekal et al. |
| 2016/0102097 A1 | 4/2016 | Hodous et al. |
| 2016/0115164 A1 | 4/2016 | Wu et al. |
| 2017/0022206 A1 | 1/2017 | Hodous et al. |
| 2017/0029409 A1 | 2/2017 | Dipietro et al. |
| 2017/0057953 A1 | 3/2017 | Hodous et al. |
| 2017/0066773 A1 | 3/2017 | Wenglowsky et al. |
| 2017/0066812 A1* | 3/2017 | Bifulco, Jr. ........... C07D 239/42 |
| 2017/0121312 A1 | 5/2017 | Brubaker et al. |
| 2017/0145018 A1 | 5/2017 | Wenglowsky et al. |
| 2017/0174652 A1* | 6/2017 | Bifulco, Jr. ........... C07D 239/84 |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |

FOREIGN PATENT DOCUMENTS

| | | | |
|---|---|---|---|
| JP | 2004-519422 A | 7/2004 | |
| JP | 2008-515812 A | 5/2008 | |
| JP | 2011-526299 A | 10/2011 | |
| JP | 2012-501654 A | 1/2012 | |
| JP | 2014-513729 A | 6/2014 | |
| RU | 2015 104 342 A | 8/2016 | |
| WO | WO 96/015128 A2 | 5/1996 | |
| WO | WO 01/29013 A1 | 4/2001 | |
| WO | WO 01/38315 A1 | 5/2001 | |
| WO | WO 01/64646 A2 | 9/2001 | |
| WO | WO 02/12238 A2 | 2/2002 | |
| WO | WO 02/076985 A1 | 10/2002 | |
| WO | WO 2004/063195 A1 | 7/2004 | |
| WO | WO 2005/030131 A2 | 4/2005 | |
| WO | WO 2006/039718 A2 | 4/2006 | |
| WO | WO 2008/079988 A2 | 7/2008 | |
| WO | WO 2009/046448 A1 | 4/2009 | |
| WO | WO 2009/158571 A1 | 12/2009 | |
| WO | WO 2010/026291 A1 | 3/2010 | |
| WO | WO 2010/028236 A1 | 3/2010 | |
| WO | WO 2010/076238 A1 | 7/2010 | |
| WO | WO 2011/016528 A1 | 2/2011 | |
| WO | WO 2011/034907 A2 | 3/2011 | |
| WO | WO 2011/101409 A1 | 8/2011 | |
| WO | WO 2011/135376 A1 | 11/2011 | |
| WO | WO 2012/158843 A2 | 11/2012 | |
| WO | WO 2013/179034 A1 | 12/2013 | |
| WO | WO 2014/011900 A2 | 1/2014 | |
| WO | WO 2014/044846 A1 | 3/2014 | |
| WO | WO 2014/128588 A1 | 8/2014 | |
| WO | WO 2014/144737 A1 | 9/2014 | |
| WO | WO 2015/057938 A1 | 4/2015 | |
| WO | WO 2015/057963 A1 | 4/2015 | |
| WO | WO 2015/059668 A1 | 4/2015 | |
| WO | WO 2015/061572 A1 | 4/2015 | |
| WO | WO-2015061572 A1 * | 4/2015 | ........... C07D 239/84 |
| WO | WO 2015/08992 A1 | 7/2015 | |
| WO | WO 2016/064960 A1 | 4/2016 | |
| WO | WO 2016/134294 A1 | 8/2016 | |
| WO | WO 2016/134314 A1 | 8/2016 | |
| WO | WO 2016/134320 A1 | 8/2016 | |
| WO | WO 2017/070708 A1 | 4/2017 | |
| WO | WO 2018/049233 A9 | 7/2018 | |

OTHER PUBLICATIONS

U.S. Appl. No. 14/677,162, filed Apr. 2, 2015, issued as U.S. Pat. No. 9,340,514.

U.S. Appl. No. 14/318,149, filed Jun. 27, 2014, issued as U.S. Pat. No. 9,126,951.

U.S. Appl. No. 14/939,967, filed Jul. 11, 2013, issued as U.S. Pat. No. 8,802,697.

"Chemotherapy of Neoplastic Diseases" in, *Goodman & Gilman's: The Pharmacological Basis of Therapeutics*. 11th ed., L.L. Brunton et al. (Eds.), The McGraw Hill Cos., 2008; pp. 853-903.

Antczak, C. et al. (2009) "Structure-activity relationships of 6-(2,6-dichlorophenyl)-8-methyl-2-(phenylamino)pyrido[2,3-d]pyrimidin-7-ones: Toward selective Abl inhibitors" *Bioorg Med Chem Lett*, 19:6872-6876.

Bennett; J.C. and F. Plum (Eds.) (1996) *Cecil Textbook of Medicine*. 20th Edition, vol. 1. W.B. Saunders Co.; pp. 1004-1010.

Brown, A.P. et al. (2005) "Cartilage Dysplasia and Tissue Mineralization in the Rat Following Administration of a FGF Receptor Tyrosine Kinase Inhibitor" *Toxicologic Pathology*, 33:449-455.

Bruix, J. et al. (2016) "Efficacy and safety of regorafenib versus placebo in patients with hepatocellular carcinoma (HCC) progressing on sorafenib: results of the international, randomized phase 3 RESORCE trial" *Annals of Oncology*, 27(Suppl 2):ii140-ii141, Abstract LBA-03.

Brunton, L. et al (Eds.) (2008) "Chemotherapy of Neoplastic Diseases" in *Goodman & Gilman's: Manual of Pharmacology and Therapeutics*. New York: McGraw-Hill Medical; pp. 853-908.

Cao, L. et al. (2010) "Genome-Wide Identification of PAX3-FKHR Binding Sites in Rhabdomyosarcoma Reveals Candidate Target Genes Important for Development and Cancer" *Cancer Research*, 70(16):6497-6508.

Carmi, C. et al. (2012) "Irreversible inhibition of epidermal growth factor receptor activity by 3-aminopropanamides" *J Med Chem*, 55(5):2251-2264.

Cheng, A.L. et al. (2009) "Efficacy and safety of sorafenib in patients in the Asia-Pacific region with advanced hepatocellular carcinoma: a phase III randomised, double-blind, placebo-controlled trial" *Lancet Oncol*, 10(1):25-34.

Chiang, D.Y. et al. (2008) "Focal Gains of VEGFA and Molecular Classification of Hepatocellular Carcinoma" *Cancer Res*, 68(16):6779-6788.

Cohen, P. (1999) "The development and therapeutic potential of protein kinase inhibitors" *Current Opinions in Chemical Biology*, 3(4):459-465.

Dermer, G. (Mar. 1994) "Another Anniversary for the War on Cancer" *Bio/Technology*, 12:320.

Dieci, M.V. et al. (2013) "Fibroblast Growth Factor Receptor Inhibitors as a Cancer Treatment: From a Biologic Rationale to Medical Perspectives" *Cancer Disc*, 3:264-279.

Ding, L. et al. (Oct. 23, 2008) "Somatic mutations affect key pathways in lung adenocarcinoma" *Nature*, 455:1069-1075.

Freshney, R. et al. (1983) *Culture of Animal Cells, A Manual of Basic Techniques*. Alan R. Liss, Inc., pp. 1-6.

Gao, H. et al. (2015) "High-throughput screening using patient-derived tumor xenografts to predict clinical trial drug response" *Nature Medicine*, 21(11):1318-1325.

Golub, T.R. et al. (1999) "Molecular Classification of Cancer: Class Discovery and Class Prediction by Gene Expression Monitoring" *Science*, 286:531-537.

Guagnano, V. et al. (2011) "Discovery of 3-(2,6-Dichloro-3,5-dimethoxy-phenyl)-1-(6-[4-(4-ethyl-piperazin-1-yl)phenylamino]-pyrimidin-4-yl}-1-methyl-urea (NVP-BGJ398), A Potent and Selective Inhibitor of the Fibroblast Growth Factor Receptor Family of Receptor Tyrosine Kinase" *J Med Chem*, 54:7066-7083.

Hagel, M. et al. (2015) "First Selective Small Molecule inhibitor of FGFR4 for the Treatment of Hepatocellular Carcinomas with an Activated FGFR4 Signaling Pathway" *Cancer Discovery*, 5(4):425-437.

Ho, H.K. et al. (2009) "Fibroblast growth factor receptor 4 regulates proliferation, anti-apoptosis and alpha-fetoprotein secretion during hepatocellular carcinoma progression and represents a potential target for therapeutic intervention" *Journal of Hepatology*, 50:118-127.

Ho, H.K. et al. (2013) "Developing FGFR4 Inhibitors as Potential Anti-Cancer Agents via In Silico Design, Supported by In Vitro and Cell-Based Testing" *Curr Med Chem*, 20:1203-1217.

International Search Report and Written Opinion for International Application No. PCT/US2013/050106, dated Jan. 10, 2014 (16 pages).

(56) References Cited

OTHER PUBLICATIONS

International Search Report and Written Opinion for International Application No. PCT/US2014/061974, dated Dec. 23, 2014 (8 pages).
International Search Report and Written Opinion for International Application No. PCT/US2015/011424, dated May 29, 2015 (12 pages).
International Search Report and Written Opinion for International Application No. PCT/US2017/050782, dated Nov. 24, 2017 (13 pages).
Jain, V.K. and N.C. Turner (2012) "Challenges and opportunities in the targeting of fibroblast growth factor receptors in breast cancer" *Breast Cancer Research*, 14:208 (9 pages).
Kamb, A. (1998) "Cyclin-dependent kinase inhibitors and human cancer" *Curr Top Microbiol Immunol*, 227:139-148.
Katoh, Y. and M. Katoh (2009) "FGFR2-related pathogenesis and FGFR2-targeted therapeutics" *Int'l J Mol Med*, 23:307-311.
Kelland, L.R. (2004) "'Of mice and men': values and liabilities of the athymic nude mouse model in anticancer drug development" *Eur J Cancer*, 40:827-836.
Lehàr J. et al. (2009) "Synergistic drug combinations improve therapeutic relevant selectivity" *Nat Biotechnol*, 27(7):659-666. HHS Public Access Author Manuscript; available in PMC Jan. 1, 2010 (23 pages).
Leproult, E. et al. (2011) "Cysteine Mapping in Conformationally Distinct Kinase Nucleotide Binding Sites: Application to the Design of Selective Covalent Inhibitors" *J Med Chem*, 54(5):1347-1355.
Liang, G. et al. (2013) "Small molecule inhibition of fibroblast growth factor receptors in cancer" *Cytokine & Growth Factor Reviews*, 24:467-475.
Llovet, J.M. et al. (2008) "Sorafenib in advanced hepatocellular carcinoma" *N Engl J Med*, 359:378-390.
Neidle, S. et al. (eds). (2008) *Cancer Drug Design and Discovery*. Elsevier/Academic Press; pp. 427-431.
Notice of Allowance dated Sep. 26, 2017, in U.S. Appl. No. 15/093,354, filed Apr. 7, 2016, by Blueprint Medicines Corp.
Notice of Allowance dated Oct. 25, 2017, in U.S. Appl. No. 15/340,428, filed Nov. 1, 2016, by Blueprint Medicines Corp.
Notice of Allowance dated Dec. 15, 2017, in U.S. Appl. No. 15/4622,255, filed Mar. 17, 2017, by Blueprint Medicines Corp.
Notice of Allowance dated Nov. 30, 2017, in U.S. Appl. No. 15/479,145, filed Apr. 4, 2017, by Blueprint Medicines Corp.
Rocca, A. et al. (2014) "Palbociclib (PD 0332991): targeting the cell cycle machinery in breast cancer" *Expert Opin Pharmacother*, 15(3):407-420.
Roidl, A. et al. (2010) "The FGFR4 Y367C mutant is a dominant oncogene in MDA-MB453 breast cancer cells" *Oncogene*, 29:1543-1552.
Sawey, E.T. et al. (Mar. 2011) "identification of a Therapeutic Strategy Targeting Amplified FGF19 in Liver Cancer by Oncogenomic Screening" *Cancer Cell*, 19:347-358.
Taylor, J.G. et al. (Nov. 2009) "Identification of FGFR4-activating mutations in human rhabdomyosarcomas that promote metastasis in xenotransplanted models" *J Clin Invest*, 119(11):3395-3407.
Torre, L.A. et al. (2015) "Global Cancer Statistics, 2012" *CA Cancer J Clin*, 65:87-108.
U.S. Appl. No. 15/548,925, filed Aug. 4, 2017, by Blueprint Medicines Corp.
U.S. Appl. No. 15/657,057, filed Jul. 21, 2017, by Blueprint Medicines Corp.
U.S. Appl. No. 15/660,840, filed Jul. 26, 2017, by Blueprint Medicines Corp.
Vergnes, L. et al. (Jun. 2013) "Dietl Functions in the FGF15/19 Enterohepatic Signaling Axis to Modulate Bile Acid and Lipid Levels" *Cell Metabolism*, 17:916-928.
Wu, D. et al. (2008) "A solid-phase Bcr-Abl kinase assay in 96-well hydrogel plates" *Analytical Biochemistry*, 375:18-26.
Wu, X. et al. (2010) "FGF19-Induced Hepatocyte Proliferation Is Mediated through FGFR4 Activation" *J Biol Chem*, 285:5165-5170.
Zad, T.M. et al. (Feb. 2013) "Identification of FGFR4 as a Potential Therapeutic Target for Advanced-Stage, High-Grade Serous Ovarian Cancer" *Clinical Cancer Research*, 19(4):809-820.
Zhou, W. et al. (Mar. 2010) "A Structure-Guided Approach to Creating Covalent FGFR Inhibitors" *Chemistry & Biology*, 17(3):285-295.
Huang, X. et al. (2007) "FGFR4 Prevents Hyperlipidemia and Insulin Resistance but Underlies High-Fat Diet-Induced Fatty Liver" *Diabetes*, 56(10):2501-2510.
Notice of Allowance dated Jun. 27, 2018, in U.S. Appl. No. 15/222,523, filed Jul. 28, 2016, by Blueprint Medicines Corp.
Notice of Allowance dated Jul. 27, 2018, in U.S. Appl. No. 15/488,257, filed Apr. 14, 2017, by Blueprint Medicines Corp.
Notice of Allowance dated Aug. 6, 2018, in U.S. Appl. No. 15/462,255, filed Mar. 17, 2017, by Blueprint Medicines Corp.
U.S. Appl. No. 15/973,340, filed May 7, 2018, by Blueprint Medicines Corp.
U.S. Appl. No. 15/973,378, filed May 7, 2018, by Blueprint Medicines Corp.
U.S. Appl. No. 16/002,587, filed Jun. 7, 2018, by Blueprint Medicines Corp.
U.S. Appl. No. 16/027,166, filed Jul. 3, 2018, by Blueprint Medicines Corp.
Wu, X. et al. (2013) "Dual actions of fibroblast growth factor 19 on lipid metabolism" *J Lipid Res*, 54:325-332.
Yu, C. et al. (May 2000) "Elevated Cholesterol Metabolism and Bile Acid Synthesis in Mice Lacking Membrane Tyrosine Kinase Receptor FGFR4" *J Biol Chem*, 275(20):15482-15489.

* cited by examiner

Caspase3/7 activity in compounds treated Hep3B cells

|  | Compound 25 | BGJ398 |
|---|---|---|
| IC50 [nM] | 3.055e-008 | 3.234e-007 |

INHIBITORS OF THE FIBROBLAST GROWTH FACTOR RECEPTOR

CLAIM OF PRIORITY

This patent application is a continuation of U.S. patent application Ser. No. 15/097,995, filed Apr. 13, 2016, which is a continuation of U.S. patent application Ser. No. 14/677,162, filed Apr. 2, 2015, now U.S. Pat. No. 9,340,514, which is a continuation of U.S. patent application Ser. No. 14/318,149, filed Jun. 27, 2014, now U.S. Pat. No. 9,126,951, which is a divisional of U.S. patent application Ser. No. 13/939,967, filed Jul. 11, 2013, now U.S. Pat. No. 8,802,697, which claims priority from U.S. Provisional Application No. 61/670,379, filed Jul. 11, 2012, and U.S. Provisional Application No. 61/746,666, filed Dec. 28, 2012, each of which is incorporated by reference in its entirety.

FIELD OF THE INVENTION

Described herein are compounds, methods of making such compounds, pharmaceutical compositions, and methods of using such compounds and compositions to inhibit the activity of tyrosine kinases.

BACKGROUND

Fibroblast growth factor receptor 4 (FGFR-4) is a protein that in humans is encoded by the FGFR-4 gene. This protein is a member of the fibroblast growth factor receptor family, where amino acid sequence was highly conserved between members throughout evolution. FGFR family members 1-4 differ from one another in their ligand affinities and tissue distribution. A full-length representative protein consists of an extracellular region composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. The genomic organization of the FGFR-4 gene encompasses 18 exons. Although alternative splicing has been observed, there is no evidence that the C-terminal half of the IgIII domain of this protein varies between three alternate forms, as indicated for FGFR 1-3.

Ectopic mineralization, characterized by inappropriate calcium-phosphorus deposition in soft tissue, has been observed in rats treated with an FGFR-1 inhibitor (Brown, A P et al. (2005), Toxicol. Pathol., p. 449-455). This suggests that selective inhibition of FGFR-4 without inhibition of other isoforms of FGFR, including FGFR-1, may be desirable in order to avoid certain toxicities. FGFR-4 preferentially binds fibroblast growth factor 19 (FGF19) and has recently been associated with the progression of certain sarcomas, renal cell cancer, breast cancer, and liver cancer.

SUMMARY OF THE INVENTION

Described herein are inhibitors of FGFR-4. Further described herein are pharmaceutical formulations that include an inhibitor of FGFR-4.

In one aspect, the invention features a compound of Formula 1, or pharmaceutically acceptable salt thereof:

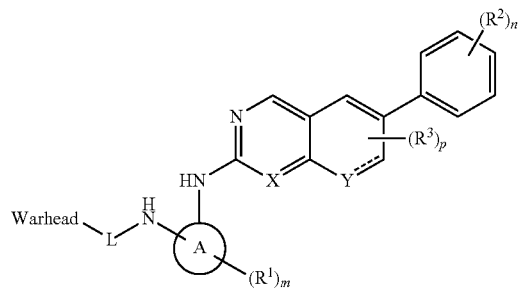

Formula I wherein Warhead is a moiety that is capable of forming a covalent bond with a nucleophile; ring A is a 3-8 membered aryl, heteroaryl, heterocyclic or alicyclic group; X is CH or N; Y is CH or N—$R^4$ where $R^4$ is H or $C_{1-6}$ alkyl; L is —[C($R^5$)($R^6$)]$_q$—, where each of $R^5$ and $R^6$ is, independently, H or $C_{1-6}$ alkyl; and q is 0-4; each of $R^1$-$R^3$ is, independently, halo, cyano, optionally substituted $C_{1-6}$ alkoxy, hydroxy, oxo, amino, amido, alkyl urea, optionally substituted $C_{1-6}$ alkyl, optionally substituted $C_{1-6}$ heterocyclyl; m is 0-3; n is 0-4; and p is 0-2. In some embodiments, ring A is phenyl, e.g., a 1,2-disubstituted phenyl; $R^2$ is halo or methoxy; n is 2 or 4; X is N; $R^1$ is methyl; and/or m is 1.

In another aspect, the invention features a compound of Formula II, or pharmaceutically acceptable salt thereof:

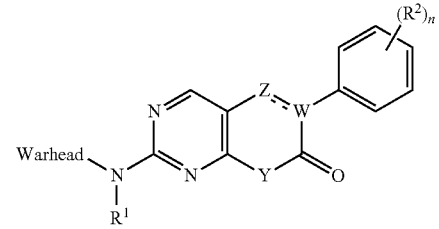

Formula II wherein Warhead is a moiety that is capable of forming a covalent bond with a nucleophile; W is C or N; Z is CH or N; Y is CH or N—$R^4$ where $R^4$ is H or $C_{1-6}$ alkyl; $R^1$ is H or $C_{1-6}$ alkyl; each of $R^2$ and $R^3$ is, independently, halo, cyano, optionally substituted $C_{1-6}$ alkoxy, hydroxy, amino, amido, optionally substituted alkyl urea, optionally substituted $C_{1-6}$ alkyl, optionally substituted $C_{1-6}$ heterocyclyl; n is 0-4; and p is 0-2. In some embodiments, $R^2$ is halo or methoxy; n is 2 or 4; Y is N—$R^4$, where $R^4$ is methyl; and/or $R^1$ is methyl.

In another aspect, the invention features a compound of Formula III, or pharmaceutically acceptable salt thereof:

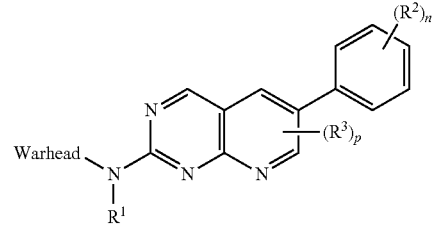

Formula III wherein Warhead is a moiety that is capable of forming a covalent bond with a nucleophile; $R^1$ is H or optionally substituted $C_{1-6}$ alkyl, including dialkylaminoalkyl; each of $R^2$ and $R^3$ is, independently, halo, cyano, optionally substituted $C_{1-6}$ alkoxy, hydroxy, amino, amido, optionally substituted alkyl urea, optionally substituted $C_{1-6}$ alkyl, optionally substituted $C_{1-6}$ heterocyclyl; n is 0-4; and p is 0-2. In some embodiments, $R^2$ is halo or methoxy; n is 2 or 4. In some embodiments; $R^1$ is methyl; in other embodiments, $R^1$ is diethylaminobutyl.

In another aspect, the invention features a compound of Formula IV, or a pharmaceutically acceptable salt thereof:

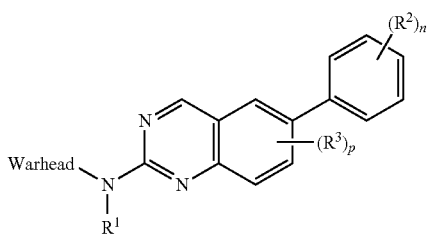

Formula IV wherein Warhead is a moiety that is capable of forming a covalent bond with a nucleophile; $R^1$ is H or optionally substituted $C_{1-6}$ alkyl; each of $R^2$ and $R^3$ is, independently, halo, cyano, optionally substituted $C_{1-6}$ alkoxy, hydroxy, amino, amido, optionally substituted alkyl urea, optionally substituted $C_{1-6}$ alkyl, optionally substituted $C_{1-6}$ heterocyclyl; n is 0-4; and p is 0-2. In some embodiments, $R^2$ is halo or methoxy; n is 2 or 4; and/or $R^1$ is methyl.

In another aspect, the invention features a compound of Formula V, or a pharmaceutically acceptable salt thereof:

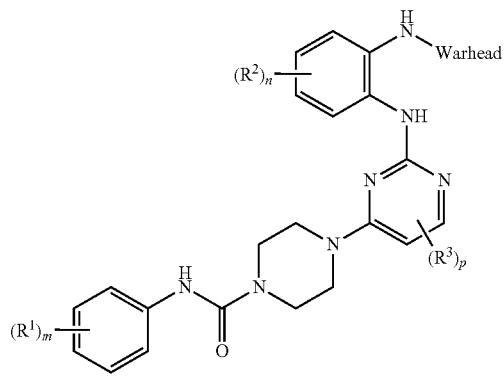

Formula V wherein Warhead is a moiety that is capable of forming a covalent bond with a nucleophile; each of $R^1$-$R^3$ is, independently, halo, cyano, optionally substituted $C_{1-6}$ alkoxy, hydroxy, amino, amido, optionally substituted alkyl urea, optionally substituted $C_{1-6}$ alkyl, optionally substituted $C_{1-6}$ heterocyclyl; optionally substituted $C_{1-6}$ heterocyclylamido; m is 0-3; n is 0-4; and p is 0-2.

In another aspect, the invention features a compound of Formula VI, or a pharmaceutically acceptable salt thereof:

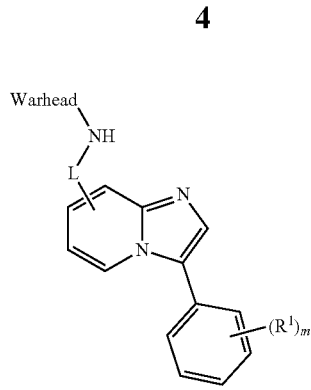

Formula VI wherein Warhead is a moiety that is capable of forming a covalent bond with a nucleophile; L is aryl, heteroaryl, or —[C($R^5$)($R^6$)]$_q$—, where each of $R^5$ and $R^6$ is, independently, H or $C_{1-6}$ alkyl; and q is 0-4; each of $R^1$ is, independently, halo, cyano, optionally substituted $C_{1-6}$ alkoxy, hydroxy, oxo, amino, amido, optionally substituted alkyl urea, optionally substituted $C_{1-6}$ alkyl, optionally substituted $C_{1-6}$ heterocyclyl; and m is 0-3. In some embodiments, L is alkylene; in other embodiments, L is phenyl. In some embodiments, $R^1$ is trifluoroethylurea.

In another aspect, the invention features a compound of Formula VII, or a pharmaceutically acceptable salt thereof:

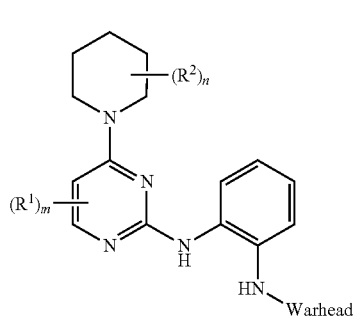

Formula VII where Warhead is a moiety that is capable of forming a covalent bond with a nucleophile; each of $R^1$ and $R^2$ is, independently, halo, cyano, optionally substituted $C_{1-6}$ alkoxy, hydroxy, oxo, amino, amido, optionally substituted alkylsulfonamido, optionally substituted alkyl urea, optionally substituted $C_{1-6}$ alkyl, optionally substituted $C_{1-6}$ heterocyclyl; m is 0-3; and n is 0-4.

In another aspect, the invention features a compound of Formula VIII, or a pharmaceutically acceptable salt thereof:

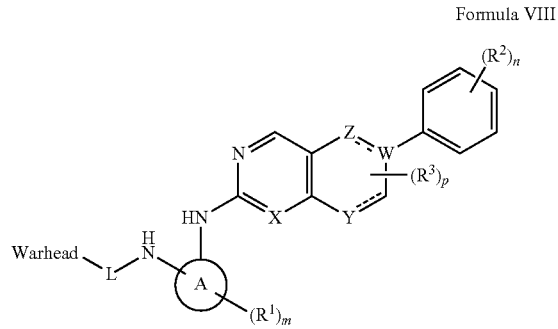

Formula VIII wherein Warhead is a moiety that is capable of forming a covalent bond with a nucleophile; ring A is a 3-8 membered aryl, heteroaryl, heterocyclic or alicyclic group; W is C or N, each of X and Z is, independently, CH or N; Y is CH or N—$R^4$ where $R^4$ is H or $C_{1-6}$ alkyl; L is —$[C(R^5)(R^6)]_q$—, where each of $R^5$ and $R^6$ is, independently, H or $C_{1-6}$ alkyl; and q is 0-4; each of $R^1$-$R^3$ is, independently, halo, cyano, optionally substituted $C_{1-6}$ alkoxy, hydroxy, oxo, amino, amido, alkyl urea, optionally substituted $C_{1-6}$ alkyl, optionally substituted $C_{1-6}$ heterocyclyl; m is 0-3; n is 0-4; and p is 0-2. In some embodiments, ring A is phenyl; $R^2$ is halo or methoxy; n is 2 or 4; X is N; $R^1$ is methyl; and/or m is 1.

In other aspects, the compound is a compound of Formula IX, or pharmaceutically acceptable salt thereof:

Formula IX

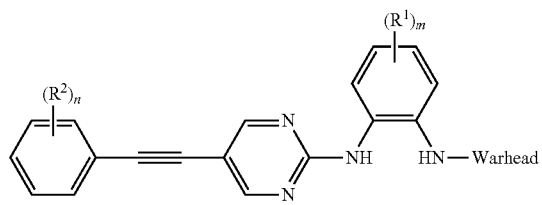

Wherein Warhead is a moiety that is capable of forming a covalent bond with a nucleophile; each of $R^1$ and $R^2$ is, independently, halo, cyano, optionally substituted $C_{1-6}$ alkoxy, hydroxy, oxo, amino, amido, optionally substituted alkyl urea, optionally substituted $C_{1-6}$ alkyl, optionally substituted heterocyclyl; m is 0-3; and n is 0-4.

In other aspects, the invention features a compound of Formula X, or a pharmaceutically acceptable salt thereof:

Formula X

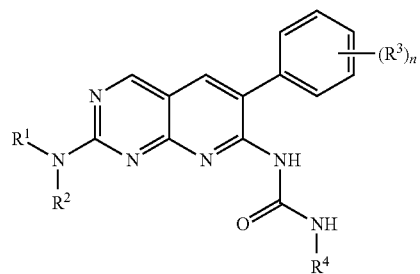

wherein $R^1$ is a warhead moiety; $R^2$ is $C_{1-6}$ alkyl, which is optionally substituted with halo, amino, hydroxy, or cyano; each $R^3$ is, independently, halo, amino, cyano, $C_{1-6}$ alkyl, or $C_{1-6}$ alkoxy, and n is 2-5; and $R^4$ is optionally substituted $C_{1-6}$ alkyl.

In the compounds disclosed herein, a warhead is a moiety that is reactive with a nucleophile, for example, capable of forming a covalent bond with a nucleophile. Examples of warheads include, without limitation, alkyl halides, alkyl sulfonates, heteroaryl halides, epoxides, haloacetamides, maleimides, sulfonate esters, alpha-beta unsaturated ketones, alpha-beta unsaturated esters, vinyl sulfones, propargyl amides, acrylamides. In some of these instances, e.g., acrylamide and propargyl amide, the N of the warhead is the adjacent N in the formulae shown above. Structures of exemplary warheads are shown below:

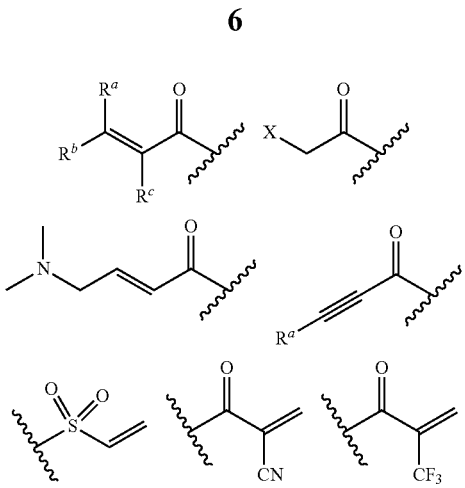

wherein X is a leaving group such as halo, or an activated hydroxyl moiety (e.g., triflate); and each of $R^a$, $R^b$, and $R^c$ is, independently, H, substituted or unsubstituted $C_{1-4}$ alkyl, substituted or unsubstituted $C_{1-4}$ cycloalkyl, or cyano.

In the formulae shown above, the warheads are typically attached to a N atom on the inhibitor. In other embodiments, the warhead can alternatively be attached to an atom other than N. Examples of exemplary warheads include, without limitation,

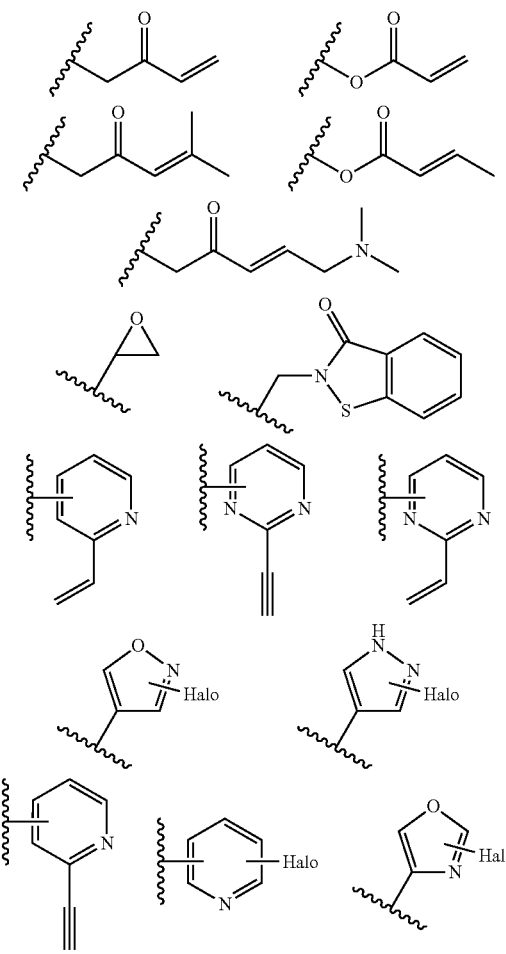

-continued

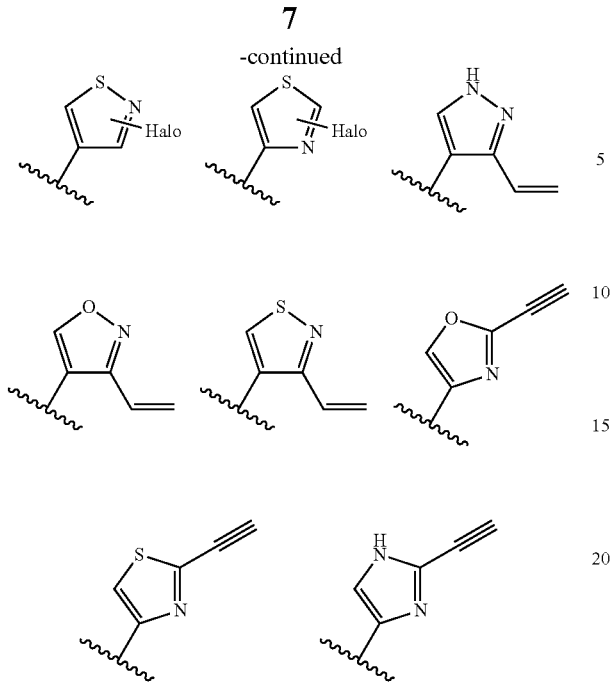

Other examples of warheads can be found, e.g., in WO 2010/028236 and WO 2011/034907.

In certain embodiments, the FGFR-4 inhibitors of the invention inhibit FGFR-4 activity more potently than they inhibit FGFR-1 activity. For example, the FGFR-4 inhibitors of the invention can inhibit FGFR-4 activity at least 10 times, at least 50 times, at least 100 times, at least 200 times, or at least 500 times more potently than they inhibit FGFR-1 activity.

In one aspect, selectivity is measured by comparing the inhibition of FGFR-1 and FGFR-4 caused by the compound of this invention in the same type of assay. In one embodiment, the assays used to measure inhibition of FGFR-1 and FGFR-4 are any of the assays described herein. Typically, inhibition is expressed as $IC_{50}$ (the concentration of inhibitor at which 50% of the activity of the enzyme is inhibited) and thus fold-selectivity is measured by the equation: ($IC_{50}$ FGFR-1)/($IC_{50}$ FGFR-4). The same measurements and calculations can be used to measure selectivity over FGFR-2 and FGFR-3 as well.

Any other assays of FGFR activity may be utilized to determine the relative inhibition of FGFR-1and FGFR-4 by the compounds of this invention as long as such assays utilize what one of skill in the art would deem to be the same parameters in measuring FGFR activity.

In another aspect, the invention features a pharmaceutical composition comprising a pharmaceutically acceptable carrier and a compound disclosed herein.

In another aspect, the invention features a covalent inhibitor of FGFR-4. In some embodiments, the covalent inhibitor of FGFR-4 inhibits FGFR-4 activity more potently, when measured in a biochemical assay, than it inhibits FGFR-1 activity. The inhibitor can contain a warhead.

In another aspect, the invention features a compound that inhibits FGFR-4 activity more potently, when measured in a biochemical assay, than it inhibits FGFR-1 activity, wherein the compound has a molecular weight of less than 1500 daltons. For example, the compound can inhibits FGFR-4 activity at least 10, 50, 100, 200, or 500 times more potently, when measured in a biochemical assay, than it inhibits FGFR-1 activity. In some instances, this compound can form a covalent bond to FGFR-4, e.g. with Cys 522 of FGFR-4.

In another aspect, the invention features an inhibited FGFR-4 protein comprising an inhibitor having a covalent bond to a cysteine residue of FGFR-4. The covalent bond can be formed between a portion of a warhead moiety on the inhibitor and a portion of a cysteine residue of FGFR-4, e.g., cysteine residue 552 of the protein. The warhead can be

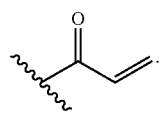

In another aspect the invention features a method for treating a condition mediated by FGFR-4, a condition characterized by overexpression of FGFR-4, a condition characterized by amplification of FGFR4, a condition mediated by FGF19, a condition characterized by amplified FGF-19, or a condition characterized by overexpression of FGF19, any of these methods comprising administering a therapeutically effective amount of a compound disclosed herein to a subject.

In another aspect, the invention features a method of treating any of the following conditions by administering a therapeutically effective amount of a compound disclosed herein to a subject: hepatocellular carcinoma, breast cancer, ovarian cancer, lung cancer, liver cancer, a sarcoma, or hyperlipidemia.

The invention includes all possible combinations of the embodiments described above.

DETAILED DESCRIPTION

Figure 1A:
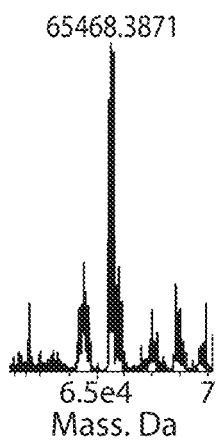
FIG. 1A shows the mass of the unmodified protein.

Pan-FGFR inhibitors, such as BGJ398 and AZD4547, are known.

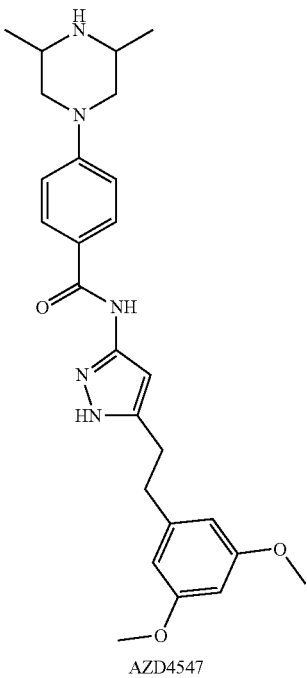

AZD4547

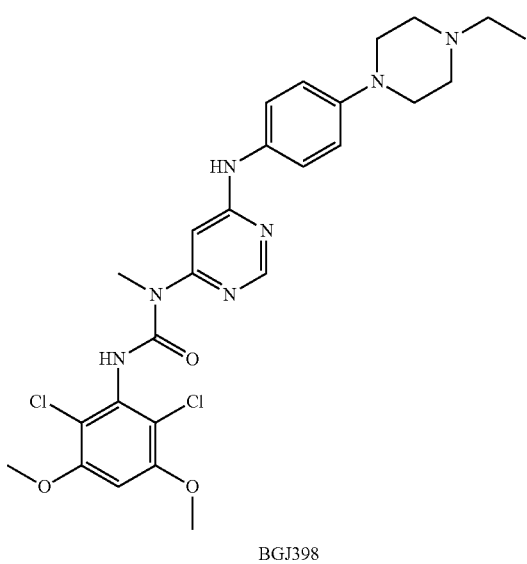 [SMILES: CCN1CCN(c2ccc(Nc3cc(N(C)C(=O)Nc4c(Cl)c(OC)cc(OC)c4Cl)ncn3)cc2)CC1]

BGJ398

These compounds (i.e., the pan-FGFR inhibitors) have not been reported to be more potent against FGFR4 than against the other isoforms of FGFR, i.e., FGFR1, FGFR2, and FGFR3. In fact, AZD 4547 is less potent against FGFR4 than it is against the other three isoforms.

Unlike BGJ398 and AZD4547, the compounds disclosed below can form a covalent bond with FGFR4 protein; for example, the compounds can form a covalent bond with a cysteine residue of FGFR4, for example, the cysteine at residue 552. FGFRs1-3 do not contain this cysteine. The ability to form a covalent bond between the compound and FGFR4 is therefore an important factor in the selectivity of the compounds disclosed herein for FGFR4.

The details of construction and the arrangement of components set forth in the following description or illustrated in the drawings are not meant to be limiting. Other embodiments and different ways to practice the invention are expressly included. Also, the phraseology and terminology used herein are for the purpose of description and should not be regarded as limiting. The use of "including," "includes," "include," "comprising," or "having," "containing", "involving", and variations thereof herein, is meant to encompass the items listed thereafter and equivalents thereof as well as additional items.

Definitions

"Aliphatic group", as used herein, refers to a straight-chain, branched-chain, or cyclic hydrocarbon group and includes saturated and unsaturated groups, such as an alkyl group, an alkenyl group, and an alkynyl group.

"Alkenyl", as used herein, refers to an aliphatic group containing at least one double bond.

"Alkoxyl" or "alkoxy", as used herein, refers to an alkyl group having an oxygen radical attached thereto. Representative alkoxyl groups include methoxy, ethoxy, propyloxy, tert-butoxy and the like.

"Alkyl", as used herein, refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. "Alkylene" refers to a double radical, that is, an aliphatic group substituted on two ends. In some embodiments, a straight chain or branched chain alkyl has 30 or fewer carbon atoms in its backbone (e.g., C1-C30 for straight chains, C3-C30 for branched chains), and in other embodiments can have 20 or fewer, or 10 or fewer. Likewise, certain cycloalkyls may have from 3-10 carbon atoms in their ring structure, and in some embodiments may have 5, 6 or 7 carbons in the ring structure. The term "alkenyl", as used herein, refers to an aliphatic group containing at least one double bond; the term "alkynyl", as used herein, refers to an aliphatic group containing at least one triple bond.

"Alkylthio", as used herein, refers to a hydrocarbyl group having a sulfur radical attached thereto. In some embodiments, the "alkylthio" moiety is represented by one of —S-alkyl, —S— alkenyl, or —S-alkynyl. Representative alkylthio groups include methylthio, ethylthio, and the like.

"Amido", as used herein, refers to —C(=O)—N($R^1$)($R^2$) or —N($R^1$)—C(=O)—$R^2$ where each of $R^1$ and $R^2$ is H or alkyl.

"Amino", as used herein, refers to —$NH_2$, —NH(alkyl), or —N(alkyl)(alkyl).

"Amplified," as used herein, means additional copies of a gene or chromosome segment are produced in cancer cells that may confer a growth or survival advantage.

"Aralkyl", as used herein, refers to an alkyl group substituted with an aryl group (e.g., an aromatic or heteroaromatic group).

"Aryl", as used herein, refers to 5-, 6-, and 7-membered single-ring aromatic groups that may include from zero to four heteroatoms, for example, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members.

The term "carbocycle" or "cycloalkyl," as used herein, refers to an aromatic or non-aromatic ring in which each atom of the ring is carbon.

"Covalent inhibitor," as used herein, means an inhibitor that can form a covalent bond with a protein.

The "enantiomeric excess" or "% enantiomeric excess" of a composition can be calculated using the equation shown below. In the example shown below a composition contains 90% of one enantiomer, e.g., the S-enantiomer, and 10% of the other enantiomer, i.e., the R-enantiomer.

$$ee=(90-10)/100=80\%.$$

Thus, a composition containing 90% of one enantiomer and 10% of the other enantiomer is said to have an enantiomeric excess of 80%. Some of the compositions described herein contain an enantiomeric excess of at least 50%, at least 75%, at least 80%, at least 85%, at least 90%, at least 95%, or at least 99% of Compound 1 (the S-enantiomer). In other words, the compositions contain an enantiomeric excess of the S-enantiomer over the R-enantiomer.

"FGFR-4" or "FGFR-4 protein" refers to any form of the FGFR-4 protein, including wild type and all variant forms (including, without limitation, mutant forms and splice variants). The FGFR-4 protein is a product of the FGFR-4 gene, and the FGFR-4 protein therefore includes any protein encoded by any form of the FGFR-4 gene, including all aberrations, e.g., point mutations, indels, translocation fusions, and focal amplifications.

"Heteroarylalkyl" refers to an alkyl group substituted with a heteroaryl group.

"Heterocyclyl" or "heterocyclic group" refers to a ring structure, such as a 3- to 7-membered ring structure, whose ring(s) include one or more heteroatoms. Heterocycles can also be polycycles, with each group having, e.g., 3-7 ring members. The term "heterocyclyl" or "heterocyclic group" includes "heteroaryl" and "saturated or partially saturated heterocyclyl" structures. "Heteroaryl" refers to an aromatic 5-8 membered monocyclic, 8-12 membered bicyclic, or 11-14 membered tricyclic ring system having one or more heteroatoms, selected from O, N, or S. Any ring atom can be substituted (e.g., by one or more substituents). The term "saturated or partially saturated heterocyclyl" refers to a non-aromatic cylic structure that includes at least one heteroatom. Heterocyclyl groups include, for example, thiophenyl, thianthrenyl, furanyl, pyranyl, isobenzofuranyl, chromenyl, xanthenyl, phenoxathiin, pyrrolyl, imidazolyl, pyrazolyl, isothiazolyl, isoxazolyl, pyridinyl, pyrazinyl, pyrimidinyl, pyridazinyl, indolizinyl, isoindolyl, indolyl, indazolyl, purinyl, quinolizinyl, isoquinolinyl, quinolinyl, phthalazinyl, naphthyridinyl, quinoxalinyl, quinazolinyl, cinnolinyl, pteridinyl, carbazolyl, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

"Heterocyclylalkyl" refers to an alkyl group substituted with a heterocycle group.

"Inhibitor" refers to a compound that inhibits an enzyme such that a reduction in activity of the enzyme can be observed, e.g., in a biochemical assay. In certain embodiments, an inhibitor has an IC$_{50}$ of less than about 1 µM, less than about 500 nM, less than about 250 nM, less than about 100 nM, less than about 50 nM, or less than about 10 nM. An inhibitor of FGFR-4 refers to a compound that inhibits FGFR-4.

"Overexpressed," as used herein, means there is production of a gene product in a sample that is substantially higher than that observed in a population of control samples (e.g. normal tissue).

"Selective" refers to a compound that inhibits the activity of a target protein, e.g., FGFR-4, more potently than it inhibits activity of other proteins. In this instance, the isoforms FGFR-1, FGFR-2, FGFR-3, and FGFR-4 are all considered distinct proteins. In some embodiments, a compound can inhibit the activity of the target protein, e.g., FGFR-4, at least 1.5, at least 2, at least 5, at least 10, at least 20, at least 30, at least 40, at least 50, at least 60, at least 70, at least 80, at least 90, at least 100, at least 200, at least 500, or at least 1000 or more times potently than it inhibits the activity of a non-target protein.

"Substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

"Warhead moiety" or "warhead" refers to a moiety of an inhibitor which participates, either reversibly or irreversibly, with the reaction of a donor, e.g., a protein, with a substrate. Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. In embodiments, the warhead is an electrophile and the "donor" is a nucleophile such as the side chain of a cysteine residue. Examples of suitable warheads include, without limitation, the groups shown below:

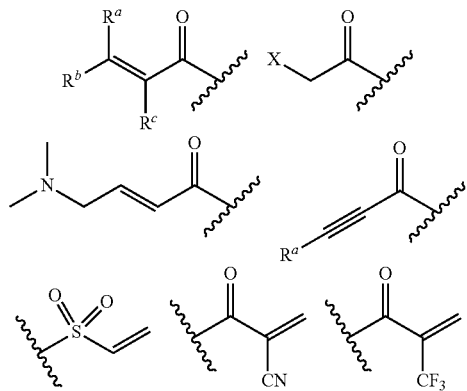

wherein X is a leaving group such as halo, or an activated hydroxyl moiety (e.g., triflate); and each of R$^a$, R$^b$, and R$^c$ is, independently, H, substituted or unsubstituted C$_{1-4}$ alkyl, substituted or unsubstituted C$_{1-4}$ cycloalkyl, or cyano.

The compounds described herein may contain unnatural proportions of atomic isotopes at one or more of the atoms that constitute such compounds. For example, the compounds may be radiolabeled with radioactive isotopes, such as for example tritium ($^3$H) or carbon-14 ($^{14}$C). All isotopic variations of the compounds disclosed herein, whether radioactive or not, are intended to be encompassed within the scope of the present invention. For example, deuterated compounds or compounds containing $^{13}$C are intended to be encompassed within the scope of the invention.

Certain compounds can exist in different tautomeric forms, and all possible tautomeric forms of all of the compounds described herein are intended to be encompassed within the scope of the invention.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The compounds described herein can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Exemplary compounds include the following:

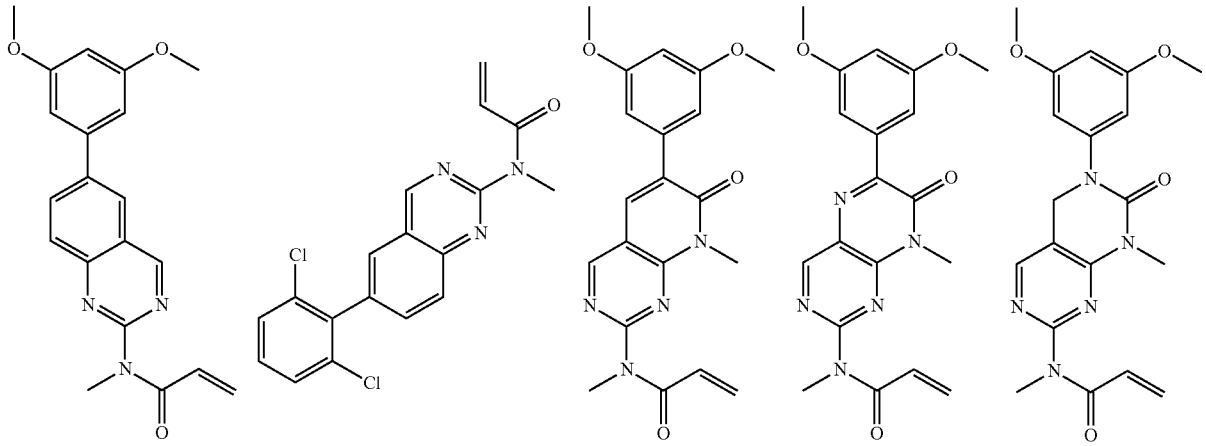

-continued
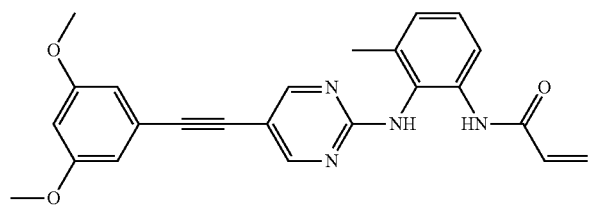 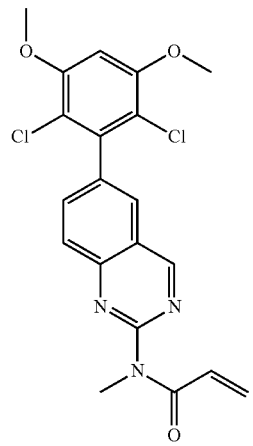 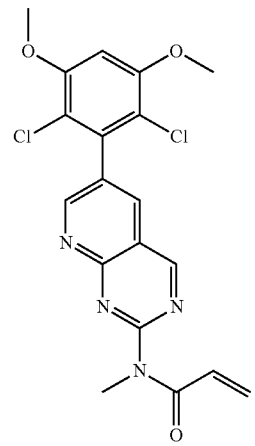
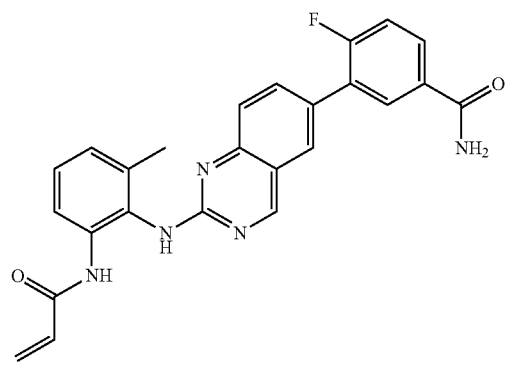 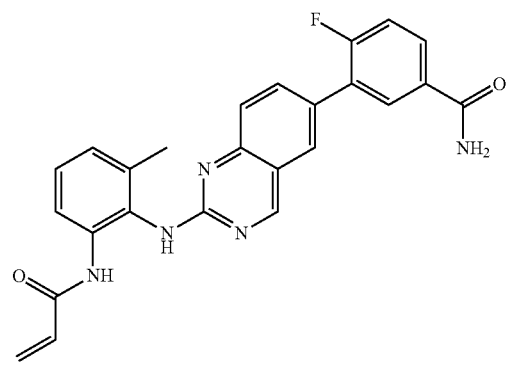
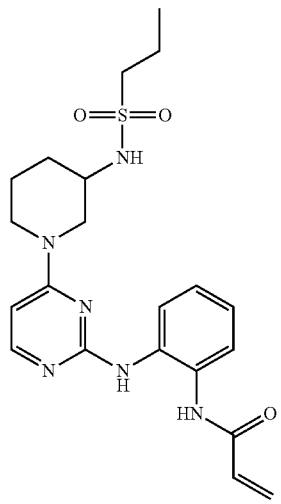 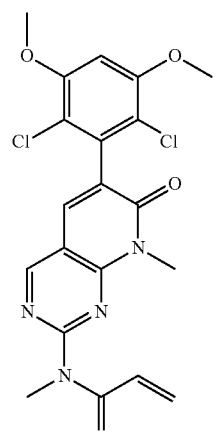 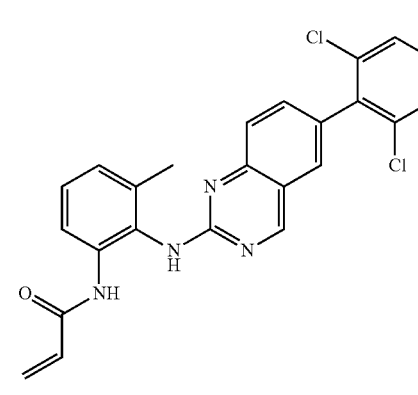 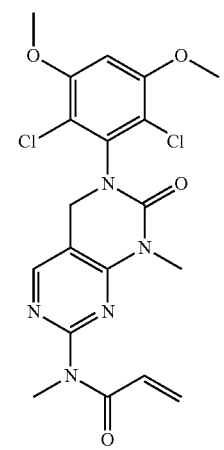

-continued
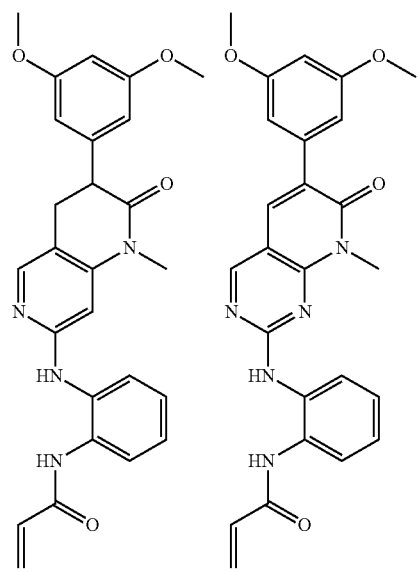
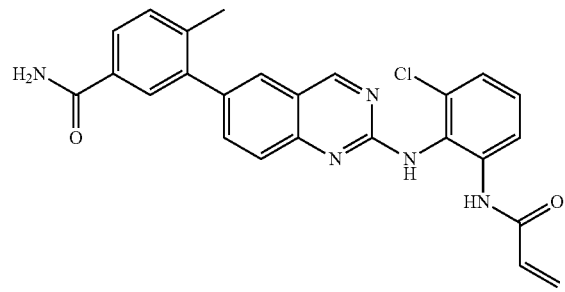
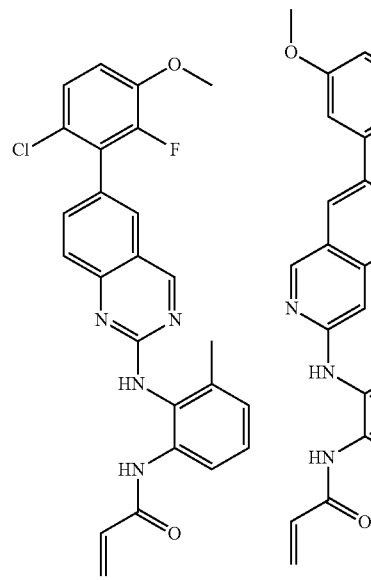
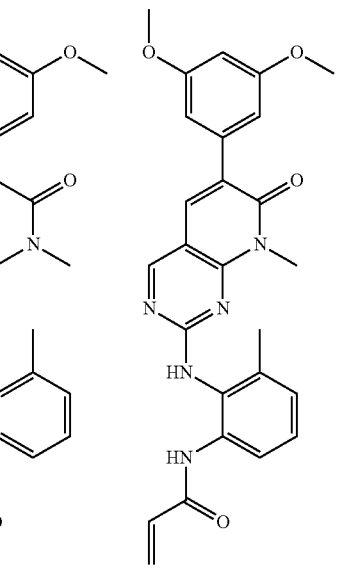
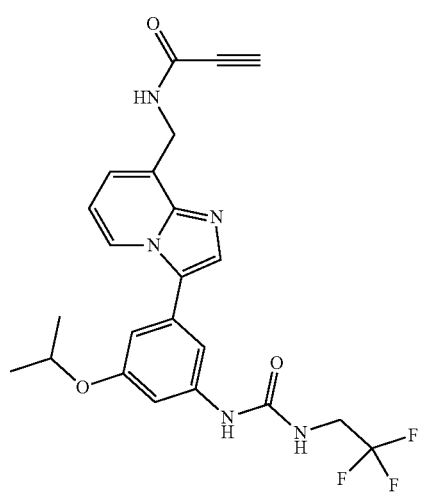
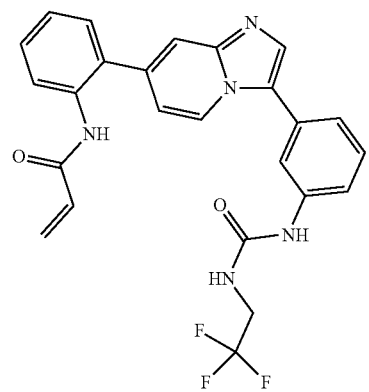
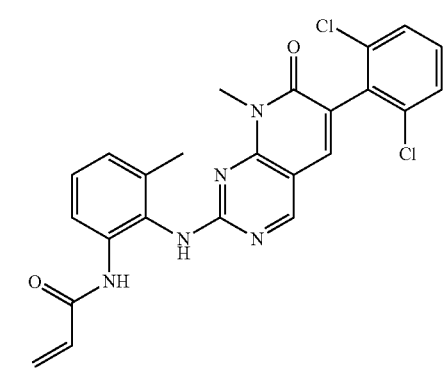

19
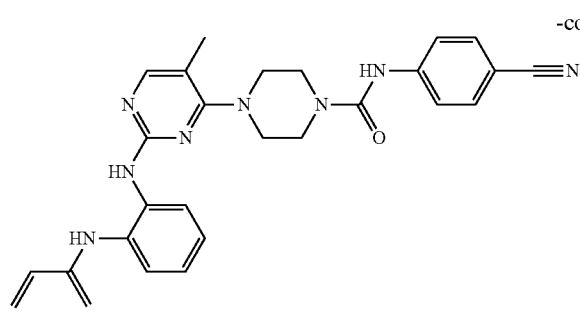
20
-continued
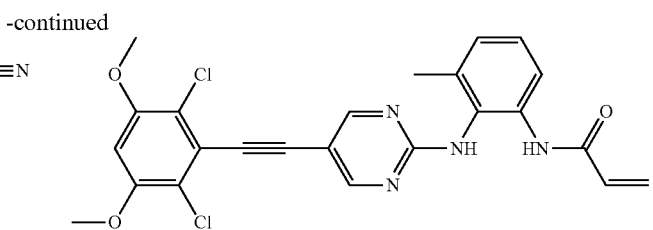
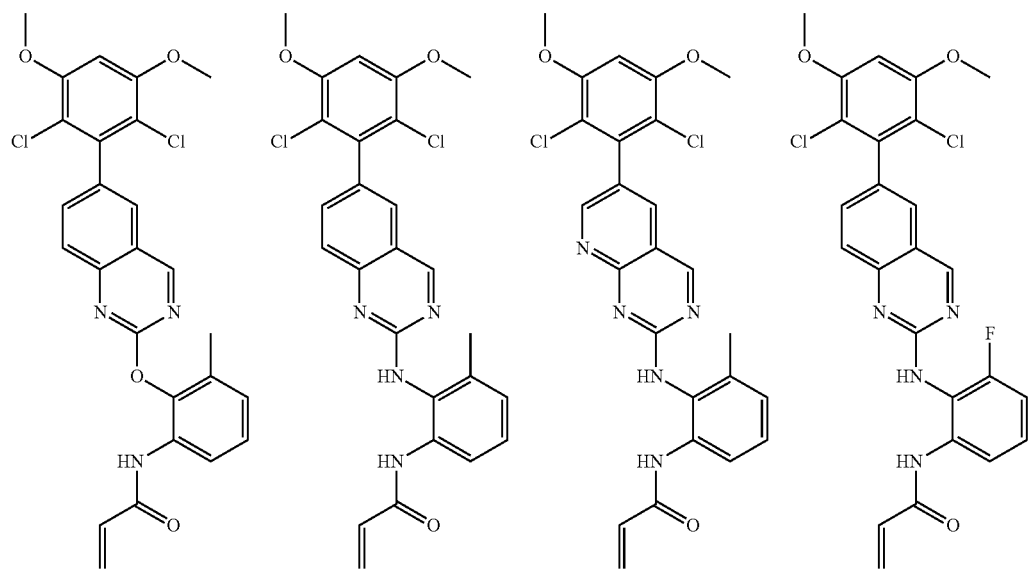
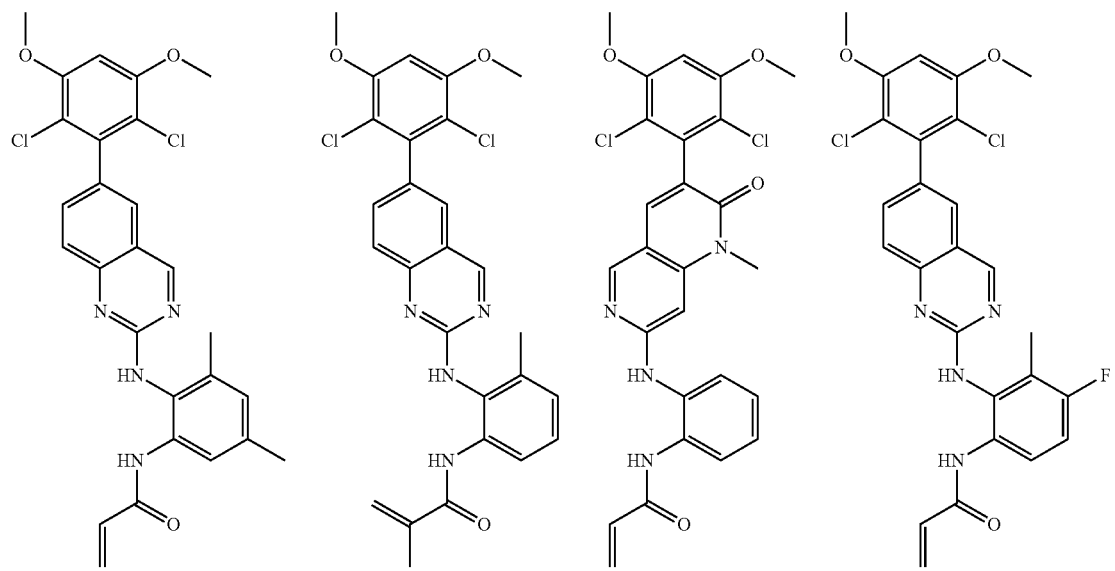

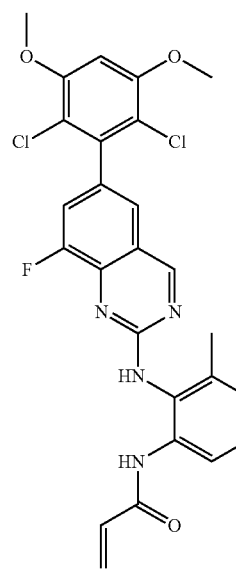
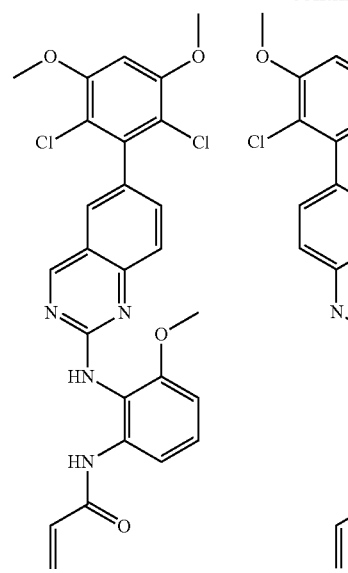
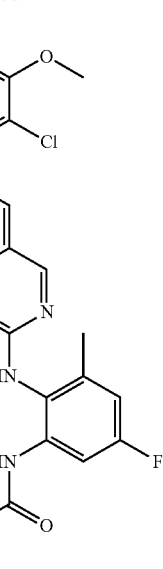
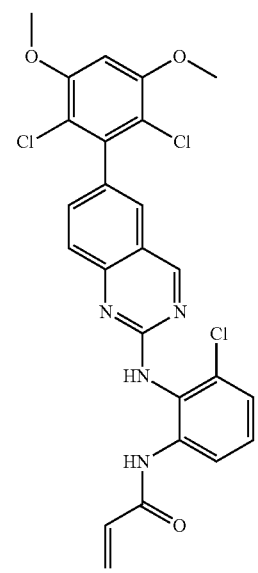
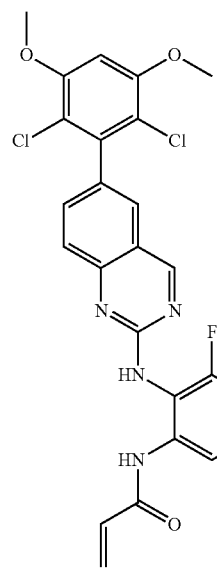
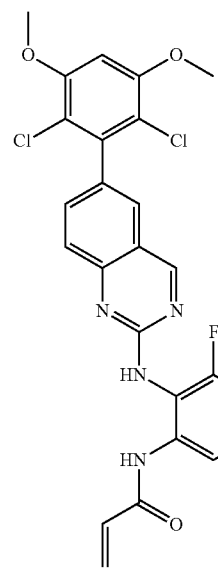
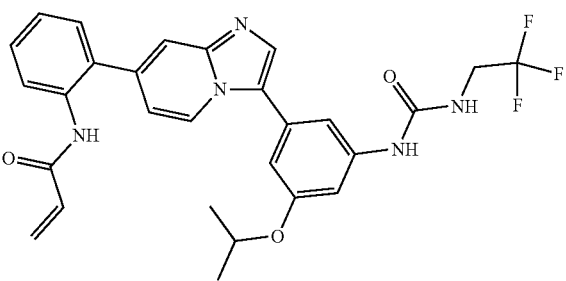
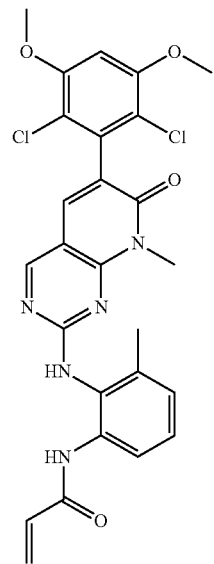
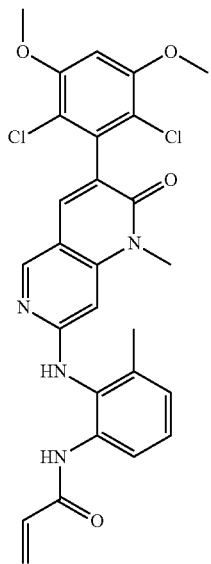
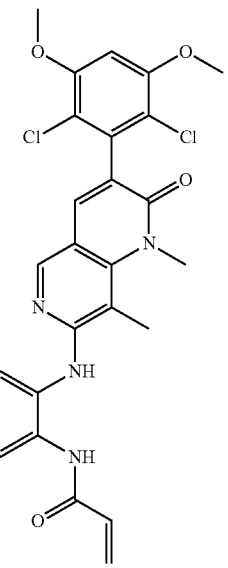
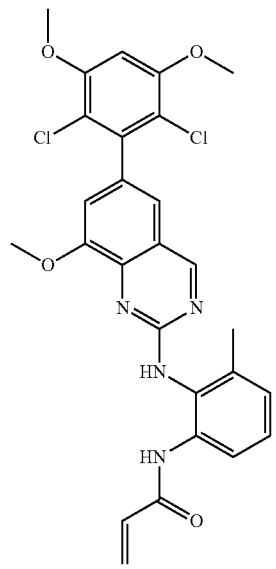

-continued
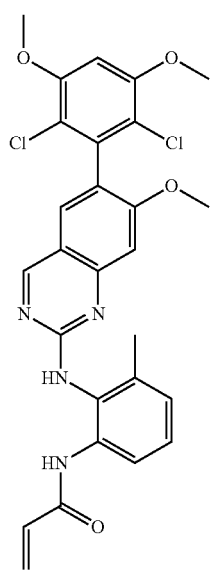
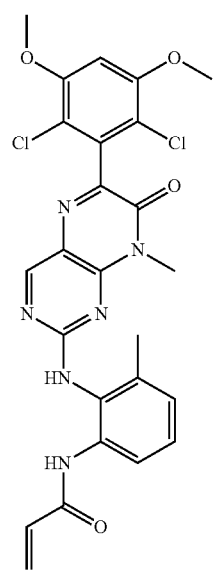
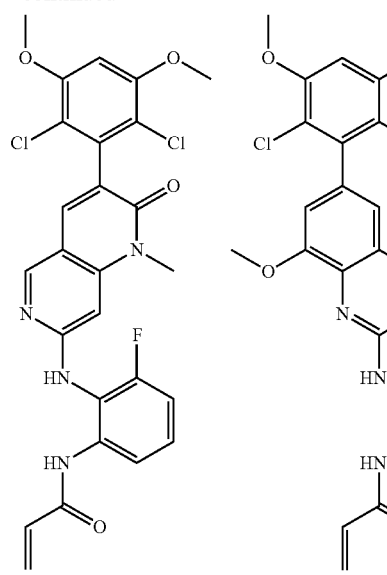
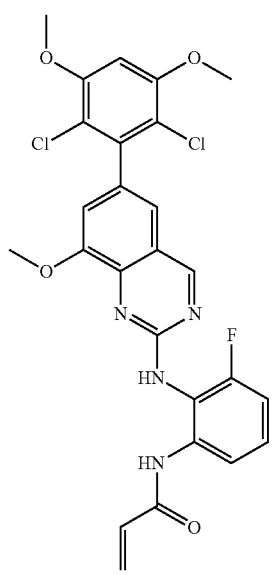
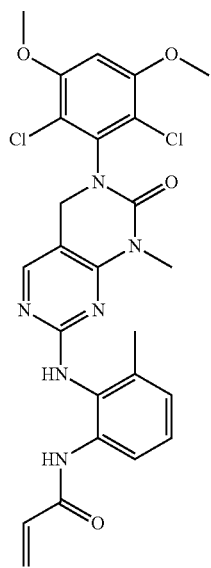
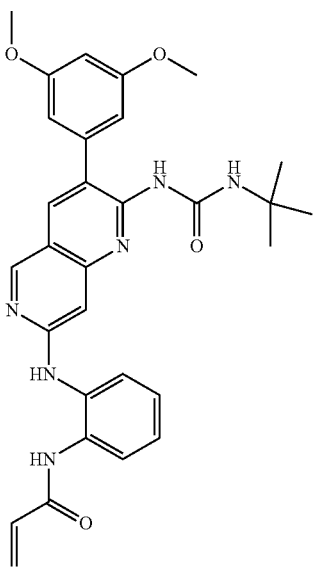
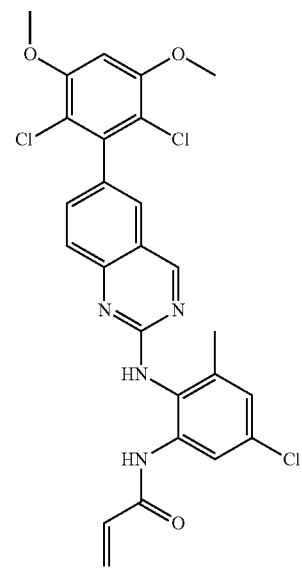
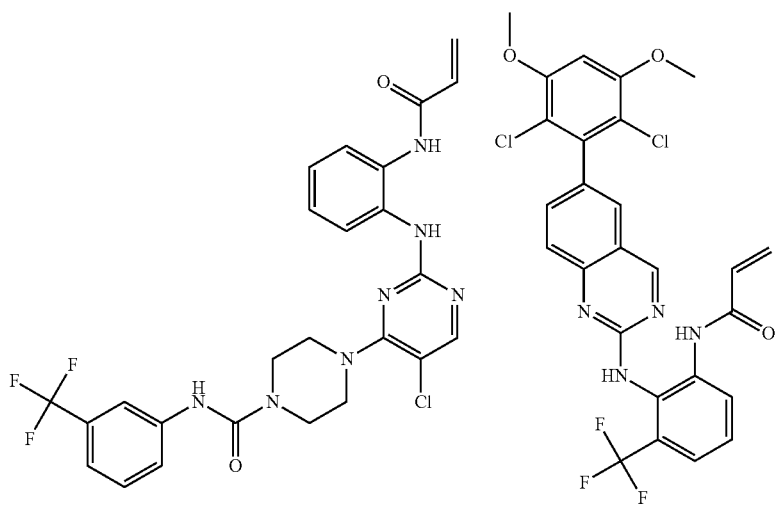

-continued

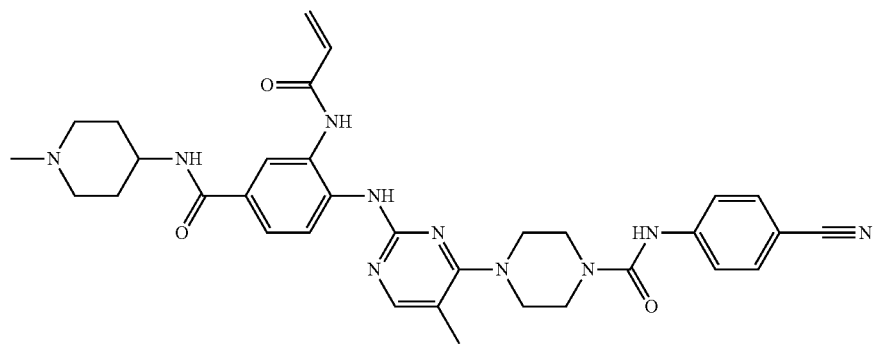
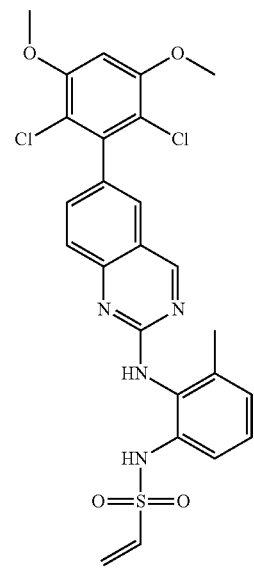
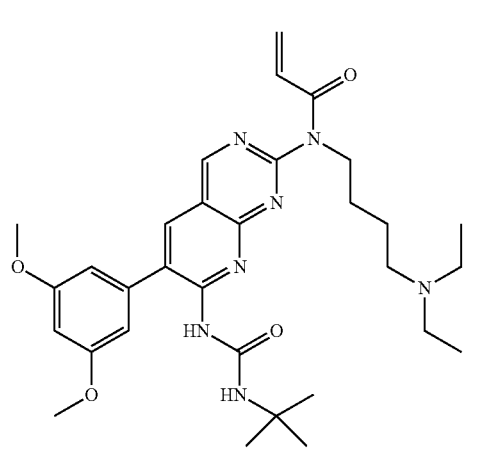
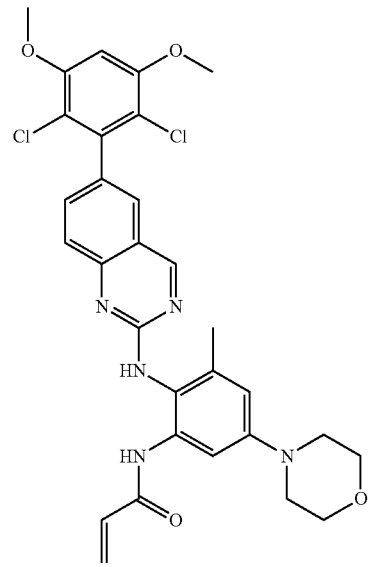
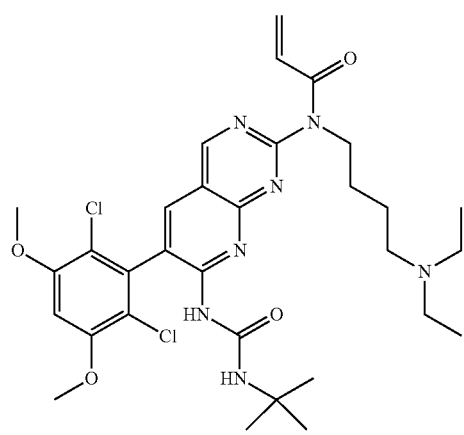 [SMILES: C=CC(=O)N(CCCCN(CC)CC)c1ncc2cc(-c3c(Cl)c(OC)cc(OC)c3Cl)c(NC(=O)NC(C)(C)C)nc2n1]

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting. In certain embodiments, the compounds provided herein include their hydrates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable salts of a compound described herein include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds described herein. Water or oil-soluble or dispersible products may be obtained by such quaternization.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; targeting ligands attached to nanoparticles, such as Accurins™; and (22) other non-toxic compatible substances, such as polymer-based compositions, employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Indications

FGFR-4 regulates proliferation, survival, and alpha-fetoprotein secretion during hepatocellular carcinoma (HCC) progression; inhibitors of FGFR-4 are therefore promising potential therapeutic agents for this unmet medical need (Ho et al., Journal of Hepatology, 2009, 50:118-27). HCC afflicts more than 550,000 people worldwide every year and has one of the worst 1-year survival rates of any cancer type.

Further evidence of the link between FGFR-4 and HCC is shown through the involvement of FGF19, a member of the fibroblast growth factor (FGF) family, which consists of hormones that regulate glucose, lipid, and energy homeostasis. Increased hepatocyte proliferation and liver tumor formation have been observed in FGF19 transgenic mice. FGF19 activates FGFR-4, its predominant receptor in the liver, and it is believed that activation of FGFR-4 is the mechanism whereby FGF19 can increase hepatocyte proliferation and induce hepatocellular carcinoma formation (Wu et al., J Biol Chem (2010) 285(8):5165-5170). FGF19 has been identified as a driver gene in HCC by others as well (Sawey et al., Cancer Cell (2011) 19: 347-358). It is therefore believed that the compounds disclosed herein, which are potent and selective inhibitors of FGFR-4, can be used to treat HCC and other liver cancers.

Oncogenome screening has identified an activating fibroblast growth factor receptor 4 (FGFR-4) Y367C mutation in the human breast cancer cell line MDA-MB-453. This mutation was shown to elicit constitutive phosphorylation, leading to an activation of the mitogen-activated protein kinase cascade. Accordingly, it has been suggested that FGFR-4 may be a driver of tumor growth in breast cancer (Roidl et al., Oncogene (2010) 29(10):1543-1552). It is therefore believed that the compounds disclosed herein, which are potent and selective inhibitors of FGFR-4, can be used to treat FGFR-4 modulated breast cancer.

Molecular changes (e.g., translocations) in genes upstream of FGFR-4 can lead to activation/overexpression of FGFR-4. For example, a PAX3-FKHR translocation/gene fusion can lead to FGFR-4 overexpression. Overexpression of FGFR-4 due to this mechanism has been associated with rhabdomyosarcoma (RMS) (Cao et al., Cancer Res (2010) 70(16): 6497-6508). Mutations in FGFR-4 itself (e.g., kinase domain mutations) can lead to over-activation of the protein; this mechanism has been associated with a sub-population of RMS (Taylor et al., J Clin Invest (2009) 119: 3395-3407). It is therefore believed that the compounds disclosed herein, which are potent and selective inhibitors of FGFR-4, can be used to treat FGFR-4 modulated RMS and other sarcomas.

Other diseases have been associated with changes in genes upstream of FGFR-4 or with mutations in FGFR-4 itself. For example, mutations in the kinase domain of FGFR-4 lead to over-activation, which has been associated with lung adenocarcinoma (Ding et al., Nature (2008) 455 (7216): 1069-1075). Amplification of FGFR-4 has been associated with conditions such as renal cell carcinoma (TCGA provisional data). In addition, silencing FGFR4 and inhibiting ligand-receptor binding significantly decrease ovarian tumor growth, suggesting that inhibitors of FGFR4 could be useful in treating ovarian cancer. (Zaid et al., Clin. Cancer Res. (2013) 809).

Pathogenic elevations of bile acid levels have been linked to variations in FGF19 levels (Vergnes et al., Cell Metabolism (2013) 17, 916-28). Reduction in the level of FGF19 may therefore be of benefit in promoting the synthesis of bile acid and thus in the treatment of hyperlipidemia.

Dose Levels

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, doses of the compounds of this invention for a patient will range from about 0.0001 to about 100 mg per kilogram of body weight per day. For example, the dose could be between 0.1 and 10 g per day; between 0.5 and 5 g per day; or 1-2 g per day. If desired, the effective daily dose of the active compound may be administered as one, two, three, four, five, six or more sub-doses administered separately at appropriate intervals throughout the day, optionally, in unit dosage forms.

Combination and Targeted Therapy

Administration of the FGFR-4 inhibitors disclosed herein can be combined with other cancer treatments. For example, the inhibitors can be administered in combination with surgical treatments, radiation, or other therapeutic agents such as antibodies, other selective kinase inhibitors, or chemotherapeutics. The inhibitors may also be administered in combination with RNAi therapy or antisense therapy. The FGFR-4 inhibitors described herein may be combined with one, two, or more other therapeutic agents. In the examples outlined below, it is understood that "second therapeutic agent" also includes more than one therapeutic agent other than the FGFR-4 inhibitor. A FGFR-4 inhibitor described herein may be administered with one, two, or more other therapeutic agents.

The FGFR-4 inhibitors described herein and the second therapeutic agent do not have to be administered in the same pharmaceutical composition, and may, because of different physical and chemical characteristics, be administered by different routes. For example, the FGFR-4 inhibitor can be administered orally, while the second therapeutic agent is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The FGFR-4 inhibitor and the second therapeutic agent may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent to be administered.

In addition, the FGFR-4 inhibitors disclosed herein can be administered as part of an antibody-drug conjugate, where the FGFR-4 inhibitor is the "payload" portion of the conjugate.

Analytical Instruments and Methods for Compound Characterization:

LCMS: Unless otherwise indicated, all liquid chromatography-mass spectrometry (LCMS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Proton NMR: Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d$^6$ solvent as parts-per million (ppm) with respect to residual DMSO (2.50 ppm).

Preparative instruments for purification of compounds: Silica gel chromatography was performed on either a Teledyne Isco CombiFlash® Rf unit or a Biotage® Isolera Four unit.

Prep LCMS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Example 1: Synthesis of N-(2-((6-(2,6-dichloro-3,5-dimethoxyphenyl)-8-methyl-7-oxo-7,8-dihydropyrido[2,3-d]pyrimidin-2-yl)amino)-3-methylphenyl)acrylamide Compound 43

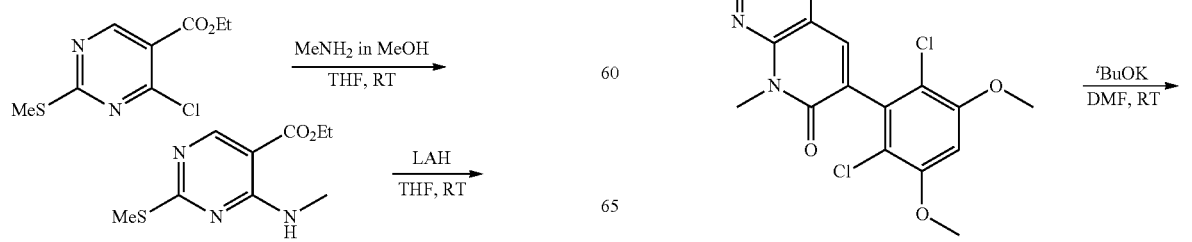

-continued

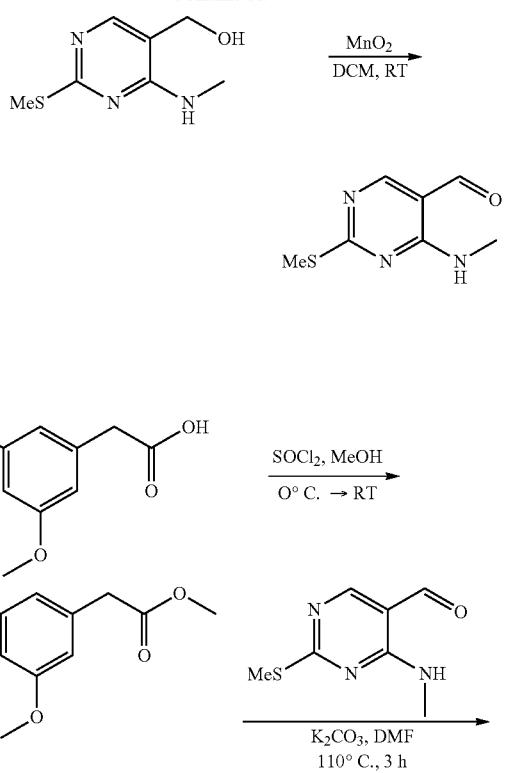

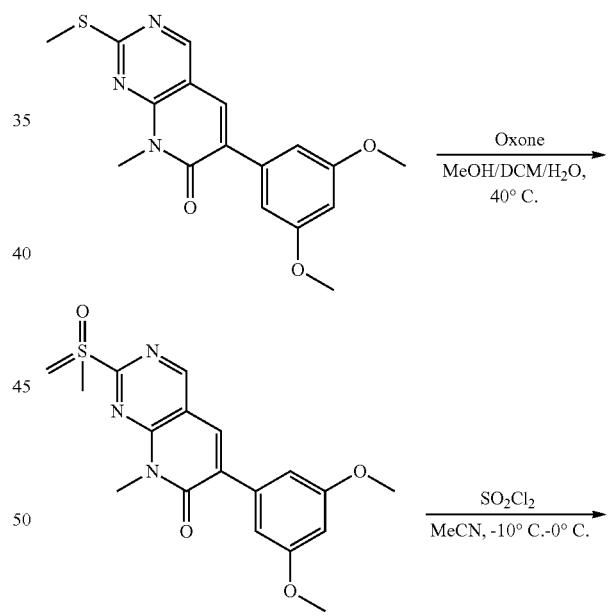

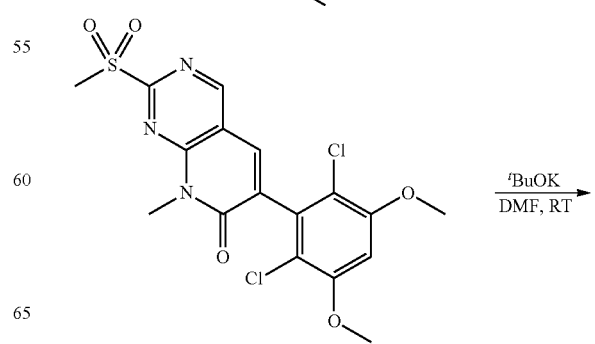

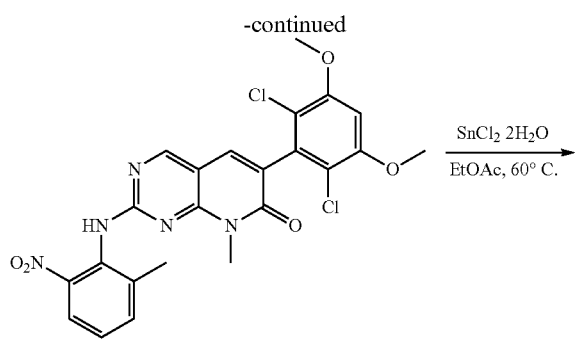

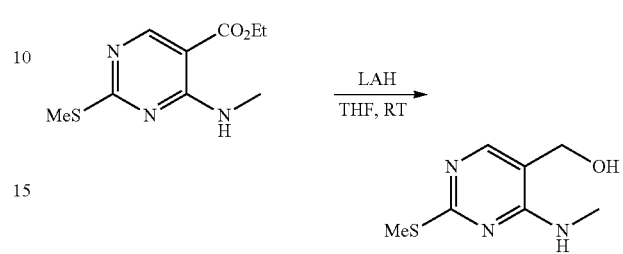

amino)-2-(methylthio)pyrimidine-5-carboxylate (4.68 g, 96%) as a yellowish solid. MS (ES+) $C_9H_{13}N_3O_2S$ requires: 227, found: 228 $[M+H]^+$.

Step 2: Synthesis of (4-(methylamino)-2-(methylthio)pyrimidin-5-yl)methanol

To a suspension of lithium aluminum hydride (LiAlH$_4$) (1.140 g, 30 mmol) in THF (100 mL) was added ethyl 4-(methylamino)-2-(methylthio)pyrimidine-5-carboxylate (4.536 g, 20 mmol), and the reaction mixture was stirred at room temperature for 2 hours. The solution was carefully quenched with H$_2$O (2 mL), sodium hydroxide (NaOH) (aq., 15%, 2 mL) and additional H$_2$O (7 mL), and then stirred for 1 hour. The mixture was extracted with EtOAc (2×100 mL), and the combined organic layers were washed with water and brine, dried over sodium sulfate, and concentrated to give (4-(methylamino)-2-(methylthio)pyrimidin-5-yl)methanol (3.2 g, 85%) as a yellowish solid. MS (ES+) $C_7H_{11}N_3OS$ requires: 185, found: 186 $[M+H]^+$.

Step 3: Synthesis of 4-(methylamino)-2-(methylthio)pyrimidine-5-carbaldehyde

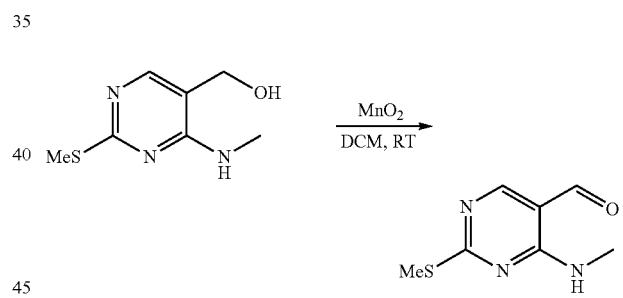

A suspension of (4-(methylamino)-2-(methylthio)pyrimidin-5-yl)methanol (3.1 g, 16.73 mmol) and manganese dioxide (7.27 g, 83.67 mmol) in DCM (40 mL) was stirred at room temperature for 12 hours. The resulting precipitate was filtered off, and the filtrate was concentrated to give 4-(methylamino)-2-(methylthio)pyrimidine-5-carbaldehyde (2.8 g, 91%) as a yellowish solid. MS (ES+) $C_7H_9N_3OS$ requires: 183, found: 184 $[M+H]^+$.

Step 4: Synthesis of methyl 2-(3,5-dimethoxyphenyl)acetate

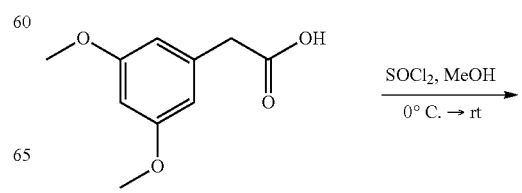

Step 1: Synthesis of ethyl 4-(methylamino)-2-(methylthio)pyrimidine-5-caboxylate

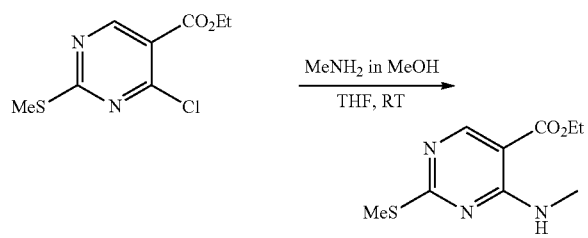

A mixture of ethyl 4-chloro-2-(methylthio)pyrimidine-5-carboxylate (5.0 g, 21.5 mmol) and 29% methylamine (5.75 g, 53.72 mmol, methanol (MeOH) solution) in tetrahydrofuran (THF) (100 mL) was stirred at room temperature for 2 hours. The reaction mixture was then concentrated, followed by the addition of sodium bicarbonate (NaHCO$_3$) (aq., 20 mL), and the resulting solution was extracted with ethyl acetate (EtOAc) (3×50 mL). The combined organic layers were washed with water and brine, dried over sodium sulfate, filtered, and concentrated to afford ethyl 4-(methyl-

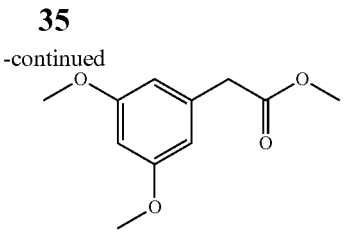

To a solution of 2-(3,5-dimethoxyphenyl)acetic acid (5) (600 mg, 3.06 mmol) in MeOH (30 mL) was added dropwise thionyl chloride (3 mL) at 0° C., and the reaction mixture was stirred at room temperature overnight. The reaction was monitored by liquid chromatography-mass spectrometry (LCMS). The mixture was diluted with saturated sodium bicarbonate (aq., 20 mL) and extracted by EtOAc (3×20 mL). The combined organic layers were washed with water and brine, dried over sodium sulfate, filtered and concentrated to give methyl 2-(3,5-dimethoxyphenyl)acetate (crude, 700 mg) as a yellow oil. MS (ES+) $C_{11}H_{14}O_4$ requires: 210, found: 211 $[M+H]^+$.

Step 5: Synthesis of 6-(3,5-dimethoxyphenyl)-8-methyl-2-(methylthio)pyrido[2,3-d]pyrimidin-7(8H)-one

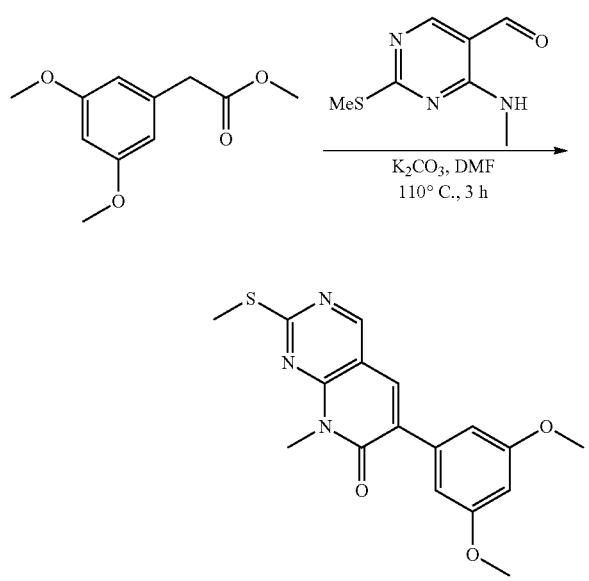

A solution of 2-(3,5-dimethoxyphenyl)acetate (6) (440 mg, 2.40 mmol), 4-amino-2-(methylthio)pyrimidine-5-carbaldehyde (4) (605 mg, 2.88 mmol) and potassium carbonate (662 mg, 4.8 mmol) in DMF (30 mL) was stirred at 110° C. for 3 hours. The reaction was monitored by LCMS. The reaction mixture was diluted with $H_2O$ (30 mL), and extracted by EtOAc (3×40 mL). The combined organic layers were washed with water and brine, dried over sodium sulfate, filtered and concentrated. The residue was purified by column chromatography (silica gel, petroleum ether/EtOAc=2:1) to afford 6-(3,5-dimethoxyphenyl)-8-methyl-2-(methylthio)pyrido[2,3-d]pyrimidin-7(8H)-one (7) (683 mg, 83%) as a white solid. MS (ES+) $C_{17}H_{17}N_3O_5S$ requires: 343, found: 344 $[M+H]^+$.

Step 6: Synthesis of 6-(3,5-dimethoxyphenyl)-8-methyl-2-(methylsulfonyl)pyrido[2,3-d]pyrimidin-7(8H)-one

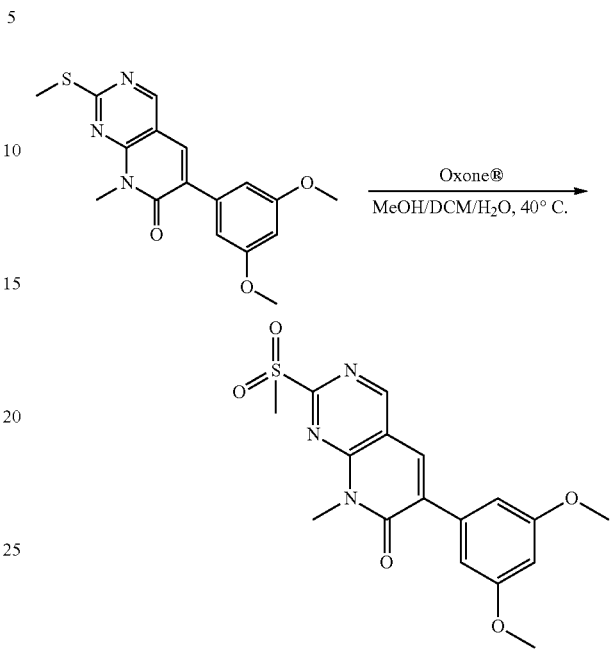

To a solution of 6-(3,5-dimethoxyphenyl)-8-methyl-2-(methylthio)pyrido[2,3-d]pyrimidin-7(8H)-one (1.05 g, 3.1 mmol) in methanol/dichloromethane (MeOH/DCM) (20 mL/20 mL) was added a solution of Oxone® (potassium peroxymonosulfate) (11.3 g, 18.4 mmol) in $H_2O$ (20 mL) at room temperature, and the reaction mixture was stirred at 40° C. for 18 hours. The reaction was monitored by LCMS. The reaction mixture was diluted with $H_2O$/DCM (150 mL/100 mL), and the aqueous phase was extracted with DCM (100 mL). The combined organic layers were washed with water (200 mL) and brine (200 mL), dried over sodium sulfate, filtered, and concentrated. The crude product was recrystallizated with EtOAc to afford 6-(3,5-dimethoxyphenyl)-8-methyl-2-(methylsulfonyl)pyrido[2,3-d]pyrimidin-7(8H)-one (8) (910 mg, yield 78%) as yellow solid. MS (ES+) $C_{17}H_{17}N_3O_5S$, requires: 375, found: 376 $[M+H]^+$.

Step 7: Synthesis of 6-(2,6-dichloro-3,5-dimethoxyphenyl)-8-methyl-2-(methylsulfonyl)pyrido[2,3-d]pyrimidin-7 (8H)-one

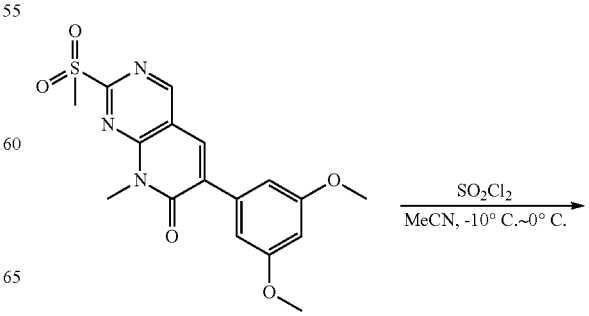

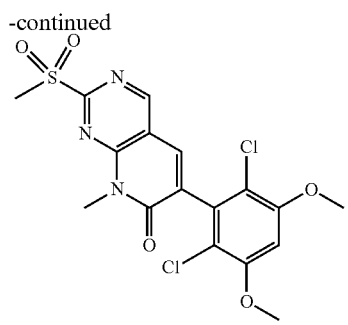

To a solution of 6-(3,5-dimethoxyphenyl)-8-methyl-2-(methylsulfonyl)pyrido[2,3-d]pyrimidin-7(8H)-one (8) (938 mg, 2.5 mmol) in acetonitrile (50 mL) was slowly added a solution of sulfuryl chloride (1.34 g, 10.0 mmol) in acetonitrile (25 mL) over a period of 0.5 hour at a temperature ranging from −10° C. to 0° C. The reaction was monitored by thin layer chromatography (TLC). The reaction mixture was quenched by adding H$_2$O (10 mL). The resultant reaction solution was concentrated under reduced pressure, and the residue was recrystallized with EtOAc/petroleum ether=1:2 to give 6-(2,6-dichloro-3,5-dimethoxyphenyl)-8-methyl-2-(methylsulfonyl)pyrido[2,3-d]pyrimidin-7(8H)-one (9) (760 mg, 69% yield) as yellow solid. MS (ES+) C$_{17}$H$_{15}$C$_{12}$N$_3$O$_5$S requires: 443, 445, found: 444, 446 [M+H]$^+$.

Step 8: Synthesis of 6-(2,6-dichloro-3,5-dimethoxyphenyl)-8-methyl-2-(2-methyl-6-nitrophenylamino)pyrido[2,3-d]pyrimidin-7 (8H)-one

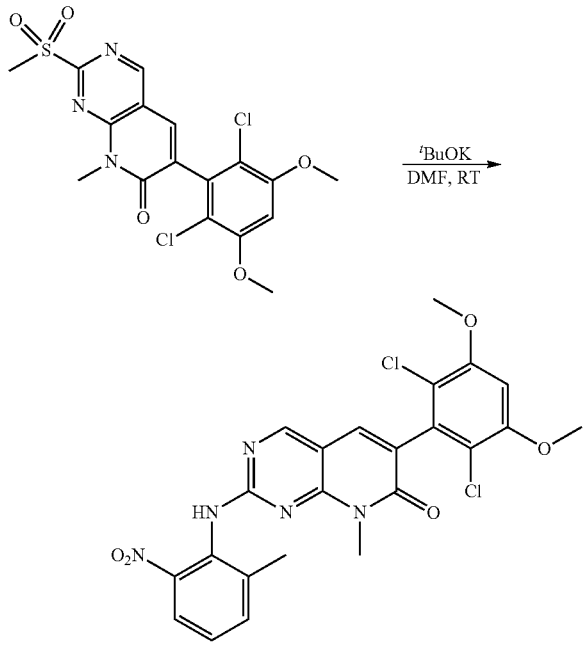

To a mixture of 6-(2,6-dichloro-3,5-dimethoxyphenyl)-8-methyl-2-(methylsulfonyl)pyrido[2,3-d]pyrimidin-7(8H)-one (9) (1.0 g, 2.26 mmol) and 2-methyl-6-nitrobenzenamine (684 mg, 4.5 mmol) in DMF (20 mL), potassium tert-butoxide (756 mg, 6.75 mmol) was added at ∼10 OC, and the reaction mixture was stirred at room temperature for 5 minutes. The reaction mixture was diluted with EtOAc (150 mL), and the organic phase was separated, washed with water (2×150 mL) and then brine (150 mL), dried over sodium sulfate, filtered, and concentrated. The residue was recrystallizated with EtOAc to give 2-(2-amino-6-methylphenylamino)-6-(2,6-dichloro-3,5-dimethoxyphenyl)-8-methylpyrido[2,3-d]pyrimidin-7(8H)-one (10) (810 mg, yield 70%) as a yellow solid. MS (ES+) C$_{23}$H$_{19}$C$_{12}$N$_5$O$_5$ requires: 515, 517, found: 516, 518 [M+H]$^+$.

Step 9: Synthesis of 2-(2-amino-6-methylphenylamino)-6-(2,6-dichloro-3,5-dimethoxyphenyl)-8-methylpyrido[2,3-d]pyrimidin-7(8H)-one

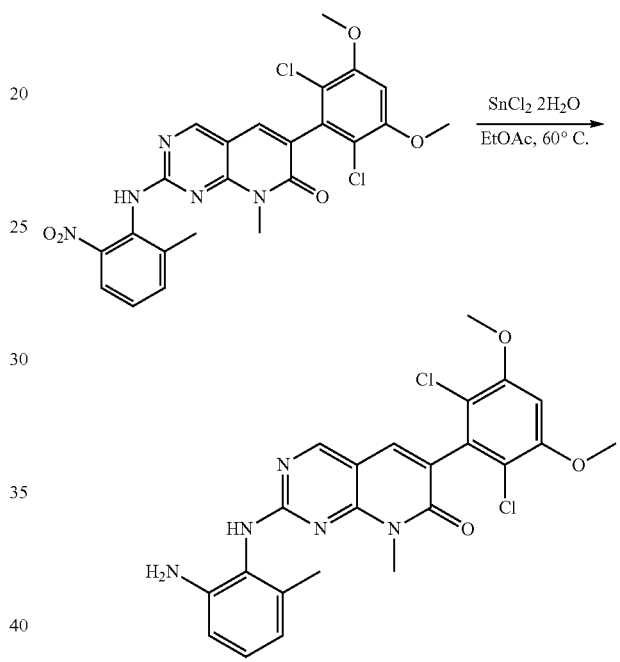

A mixture of 2-(2-nitro-6-methylphenylamino)-6-(2,6-dichloro-3,5-dimethoxyphenyl)-8-methylpyrido[2,3-d]pyrimidin-7(8H)-one (10) (810 mg, 1.57 mmol) and tin(II) chloride hydrate (1.77 g, 7.86 mmol) in EtOAc (50 mL) was stirred at 60° C. for 2 hours. The reaction was monitored by LCMS. The reaction mixture was basified with saturated aqueous sodium bicarbonate to pH=8-9, diluted with H$_2$O (100 mL), and then extracted with EtOAc (3×100 mL). The combined organic layers were washed with brine (150 mL), dried over sodium sulfate, filtered, and concentrated. The residue was recrystallized with dichloromethane/ethyl acetate/petroleum ether (DCM/EtOAc/PE)=1/1/2 to give 2-(2-amino-6-methylphenylamino)-6-(2,6-dichloro-3,5-dimethoxyphenyl)-8-methylpyrido[2,3-d]pyrimidin-7(8H)-one (11) (640 mg, 83% yield) as a grey solid. (MS (ES+) C$_{23}$H$_{21}$C$_{12}$N$_5$O$_3$ requires: 485, 487, found: 486, 488 [M+H]$^+$; $^1$H-NMR (500 MHz, CDCl$_3$) δ ppm 8.54 (s, 1H), 7.45 (s, 1H), 7.08 (t, J=7.5 Hz, 1H), 6.71 (dd, J=3.5, 7.5 Hz, 2H), 6.65 (br s, 1H), 6.62 (s, 1H), 3.94 (s, 6H), 3.88 (br s, 2H), 3.62 (br s, 3H), 2.24 (s, 3H).

Step 10: Synthesis of N-(2-((6-(2,6-dichloro-3,5-dimethoxyphenyl)-8-methyl-7-oxo-7,8-dihydropyrido[2,3-d]pyrimidin-2-yl)amino)-3-methylphenyl)acrylamide Compound 43

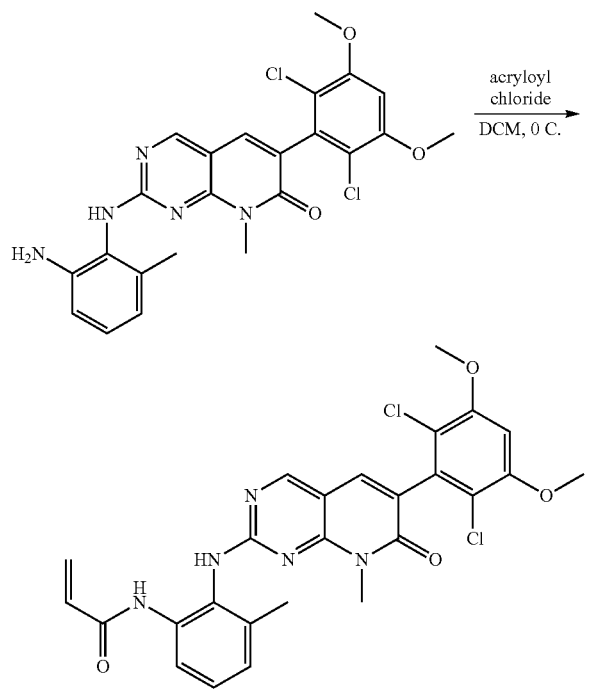

2-(2-amino-6-methylphenylamino)-6-(2,6-dichloro-3,5-dimethoxyphenyl)-8-methylpyrido[2,3-d]pyrimidin-7(8H)-one (11) was taken up in DCM (2 ml) and cooled to 0° C., followed by addition of acryloyl chloride (0.010 mL, 0.13 mmol). The reaction was allowed to warm to room temperature and stirred overnight. The mixture was loaded directly onto silica gel and purified by flash chromatography using 0-100% EtOAc/Hexanes gradient to provide the product, N-(2-((6-(2,6-dichloro-3,5-dimethoxyphenyl)-8-methyl-7-oxo-7,8-dihydropyrido[2,3-d]pyrimidin-2-yl)amino)-3-methylphenyl)acrylamide (Compound E). The product was obtained as an off-white solid (10 mg; 19% yield). MS (ES+) $C_{26}H_{23}Cl_2N_5O_4$, 540 [M+H]$^+$.

Example 2: Synthesis of N-(2-((6-(2,6-dichloro-3,5-dimethoxyphenyl)quinazolin-2-yl)amino)-3-methoxyphenyl)acrylamide Compound 30

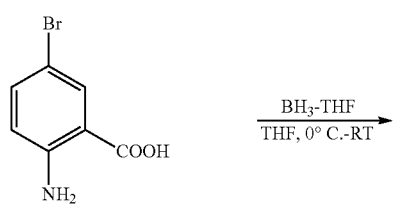

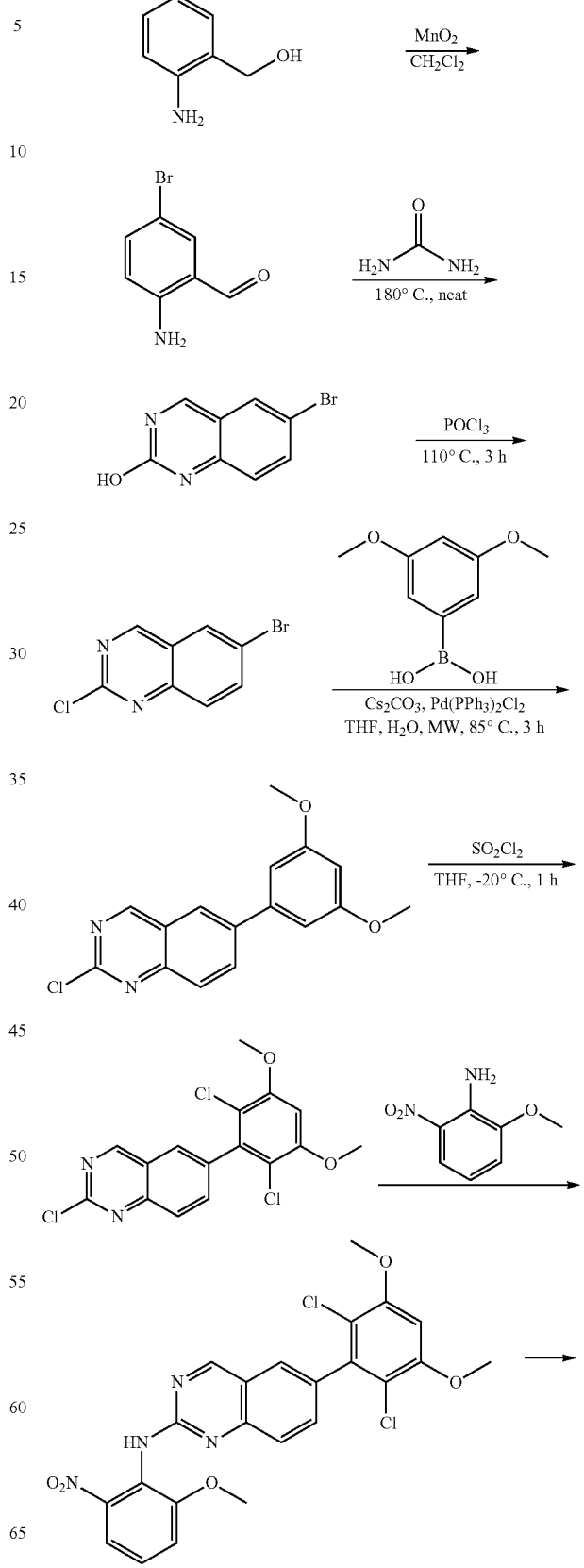

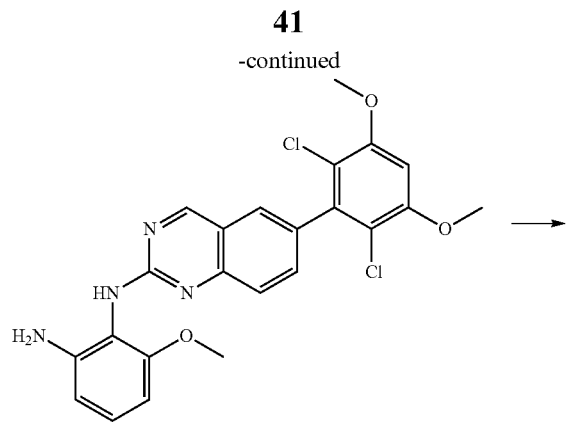

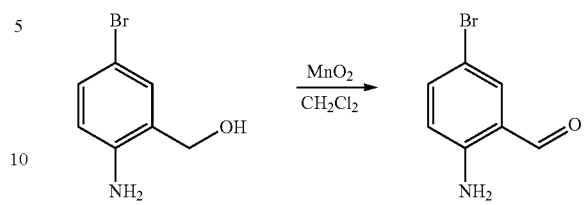

Step 2: Synthesis of 2-amino-5-bromobenzaldehyde

A mixture of (2-amino-5-bromophenyl)methanol (10 g, 49.5 mmol) and MnO$_2$ (25.8 g, 296.6 mmol) in CH$_2$Cl$_2$ (400 mL) was stirred at RT overnight. LCMS showed the reaction was completed. The solid was filtered off, and the filtrate was concentrated to give the title compound as a light yellow solid (8 g, 81%), which was directly used in next step without further purification. MS (ES+) C$_7$H$_6$BrNO requires: 199, found: 200, 202 [M+H]$^+$.

Step 3: Synthesis of 6-bromoquinazolin-2-ol

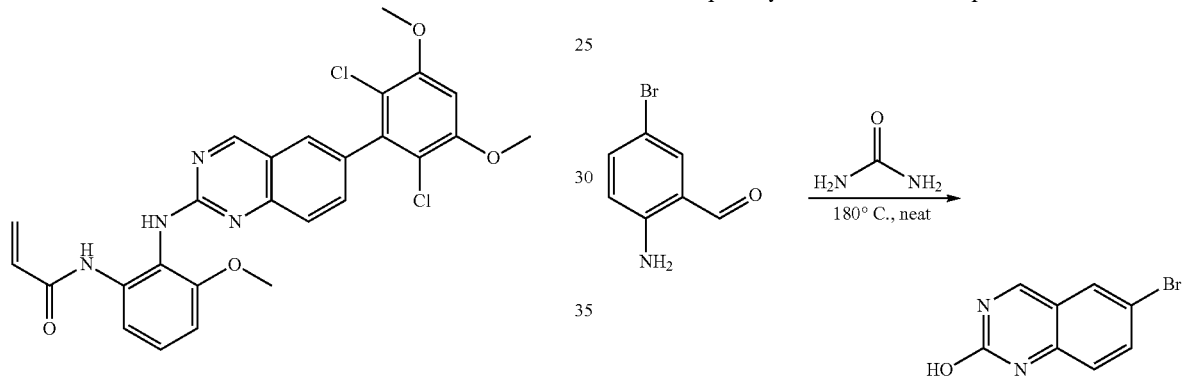

A mixture of 2-amino-5-bromobenzaldehyde (29) (6 g, 30.0 mmol) and urea (30) (27 g, 450.0 mmol) was heated to 180° C. and stirred for 5 hours. LCMS showed the reaction was completed. The reaction mixture was cooled to room temperature, and the resulting precipitate was washed with H$_2$O (3×500 mL) and co-evaporated with toluene three times to completely remove the moisture trapped. 6-bromoquinazolin-2-ol (31)(6 g, 89%) was obtained as a yellow solid. MS (ES+) C$_8$H$_5$BrN$_2$O requires: 224, found: 225, 227 [M+H]$^+$.

Step 4: Synthesis of 6-bromo-2-chloroquinazoline

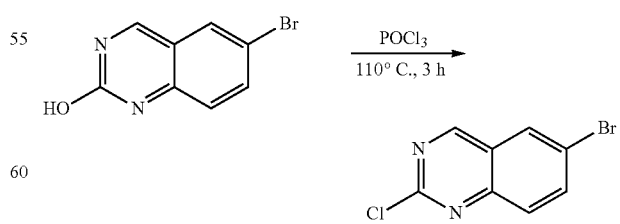

A solution of 6-bromoquinazolin-2-ol (31) (6.0 g, 26.7 mmol) in POCl$_3$ (80 mL) was refluxed at 110° C. for 5 hours. An aliquot of the reaction mixture was analyzed by LCMS and indicated that the reaction had proceeded to completion.

Step 1: Synthesis of (2-amino-5-bromophenyl)methanol

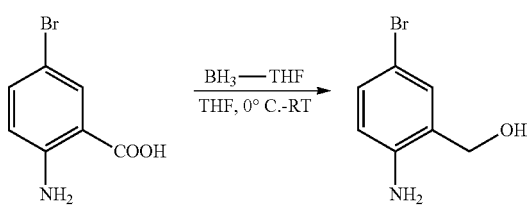

To a solution of 2-amino-5-bromobenzoic acid (10.0 g, 46.3 mmol) in THF (150 mL) was added BH$_3$-THF (1 M, 231 mL) at room temperature, and the reaction mixture was stirred overnight. An aliquot of the reaction mixture was analyzed by LCMS and indicated that the reaction had proceeded to completion. The reaction was quenched with water (150 mL) and extracted with EtOAc (3×500 mL). The organic layers were separated, combined, washed with water (200 mL) and brine (200 mL), dried over sodium sulfate, filtered, and concentrated to afford the title compound (10 g, crude), which was directly used in the next step without further purification. MS (ES+) C$_7$H$_8$BrNO requires: 201, found: 202, 204 [M+H]$^+$.

Most of POCl₃ was removed under reduced pressure, and the residue was added dropwise to ice water (500 mL). The resulting precipitate was collected via filtration as a yellow solid (3.5 g, 54%). MS (ES+) C₈H₄BrClN₂ requires: 242, found: 243, 245 [M+H]⁺.

Step 5: Synthesis of 2-chloro-6-(3,5-dimethoxyphenyl)quinazoline

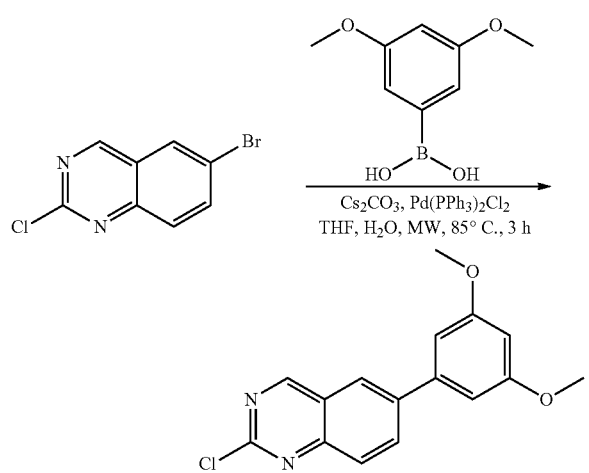

A mixture of 6-bromo-2-chloroquinazoline (32) (5.0 g, 20.5 mmol), 3,5-dimethoxyphenylboronic acid (33) (3.7 g, 20.5 mmol), Cs₂CO₃ (20.0 g, 61.5 mmol) and Pd(PPh₃)₂Cl₂ (1.4 g, 2.1 mmol) in THF (50 mL), dioxane (50 mL) and water (10 mL) was degassed with N₂ three times, and stirred at 80° C. for 3 hours. An aliquot of the reaction mixture was analyzed by both TLC and LCMS, which indicated that the reaction had proceeded to completion. The mixture was cooled to room temperature, and extracted with EtOAc (3×200 mL). The combined organic layers were washed with water and brine, dried over sodium sulfate, filtered and concentrated. The residue was purified by silica gel chromatography (petroleum ether/EtOAc=8:1) to obtain 2-chloro-6-(3,5-dimethoxyphenyl)quinazoline (34) as a light yellow solid (2.4 g, 38%). MS (ES+) C₁₆H₁₃ClN₂O₂ requires: 300, found: 301, 303 [M+H]⁺.

Step 6: Synthesis of 2-chloro-6-(2,6-dichloro-3,5-dimethoxyphenyl)quinazoline

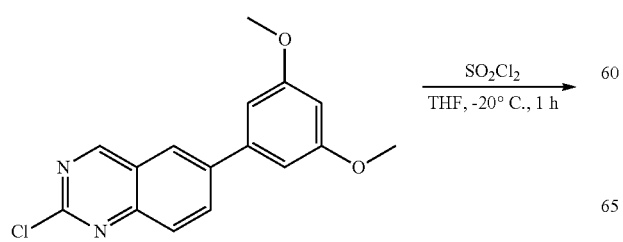

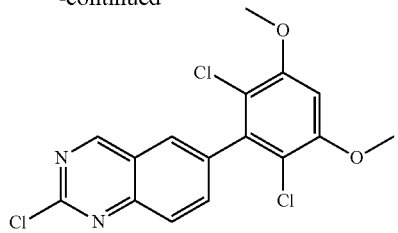

To a solution of 2-chloro-6-(3,5-dimethoxyphenyl)quinazoline (34) (2.7 g, 8.9 mmol) in dry THF (80 mL) was added dropwise SO₂Cl₂ (3.0 g, 22.3 mmol) at −20 OC, and the reaction mixture was stirred for an additional hour. An aliquot of the reaction mixture was analyzed by both TLC and LCMS, which indicated that the reaction had proceeded to completion. The reaction mixture was quenched with water (1 mL), and the solvents were removed under reduced pressure. The precipitate was washed with CH₃CN and dried to obtain 2-chloro-6-(2,6-dichloro-3,5-dimethoxyphenyl)quinazoline (35) (2.6 g, 79%) as a white solid. (MS (ES+) C₁₆H₁₁Cl₃N₂O₂ requires: 368, found: 369, 371 [M+H]⁺; ¹H-NMR (500 MHz, DMSO) δ ppm 9.67 (s, 1H), 8.168 (d, J=1.5 Hz, 1H), 8.10 (d, J=8.5 Hz, 1H), 7.56 (dd, J=2.0, 8.5 Hz, 1H), 7.07 (s, 1H), 4.00 (s, 6H).

Step 7: Synthesis of 6-(2,6-dichloro-3,5-dimethoxyphenyl)-N-(2-methoxy-6-nitrophenyl)quinazolin-2-amine

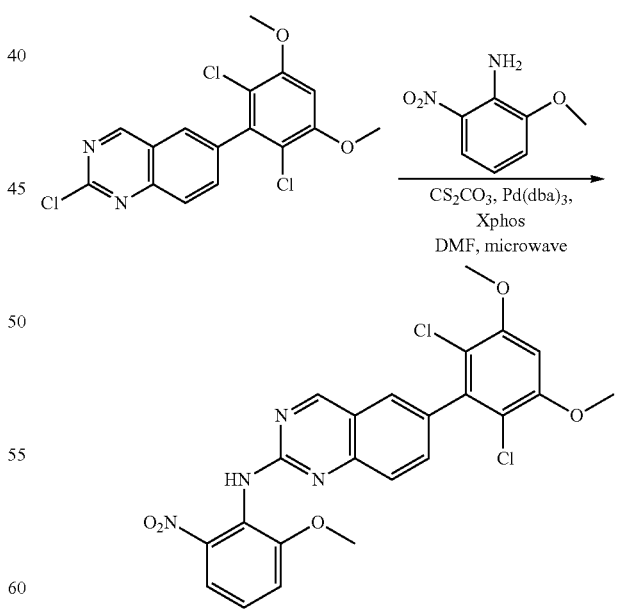

2-Chloro-6-(2,6-dichloro-3,5-dimethoxyphenyl)quinazoline (35) (100 mg, 0.27 mmol), 2-methoxy-6-nitroaniline (36) (57 mg, 0.40 mmol), Cs₂CO₃ (176 mg, 0.54 mmol), Pd₂(dba)₃ (25 mg, 0.027 mmol), and 2-Dicyclohexylphosphino- 2',4',6'-triisopropylbiphenyl (Xphos) (26 mg, 0.054 mmol) were taken up in DMF (3 mil) in a microwave vial and purged with $N_2$ for 5 minutes. The vial was capped and heated to 115° C. in microwave for 30 minutes. After cooling to room temperature the reaction mixture was diluted with DCM and washed with brine three times. The organic mixture was dried over sodium sulfate and loaded directly onto silica gel and purified using 0-100% EtOAc/Hexanes gradient. 6-(2,6-dichloro-3,5-dimethoxyphenyl)-N-(2-methoxy-6-nitrophenyl)quinazolin-2-amine (37) was recovered as a yellow solid (100 mg, 73% yield). MS (ES+) $C_{23}H_{18}Cl_2N_4O_5$, 501 $[M+H]^+$.

Step 8: Synthesis of $N^1$-(6-(2,6-dichloro-3,5-dimethoxyphenyl)quinazolin-2-yl)-6-methoxybenzene-1,2-diamine

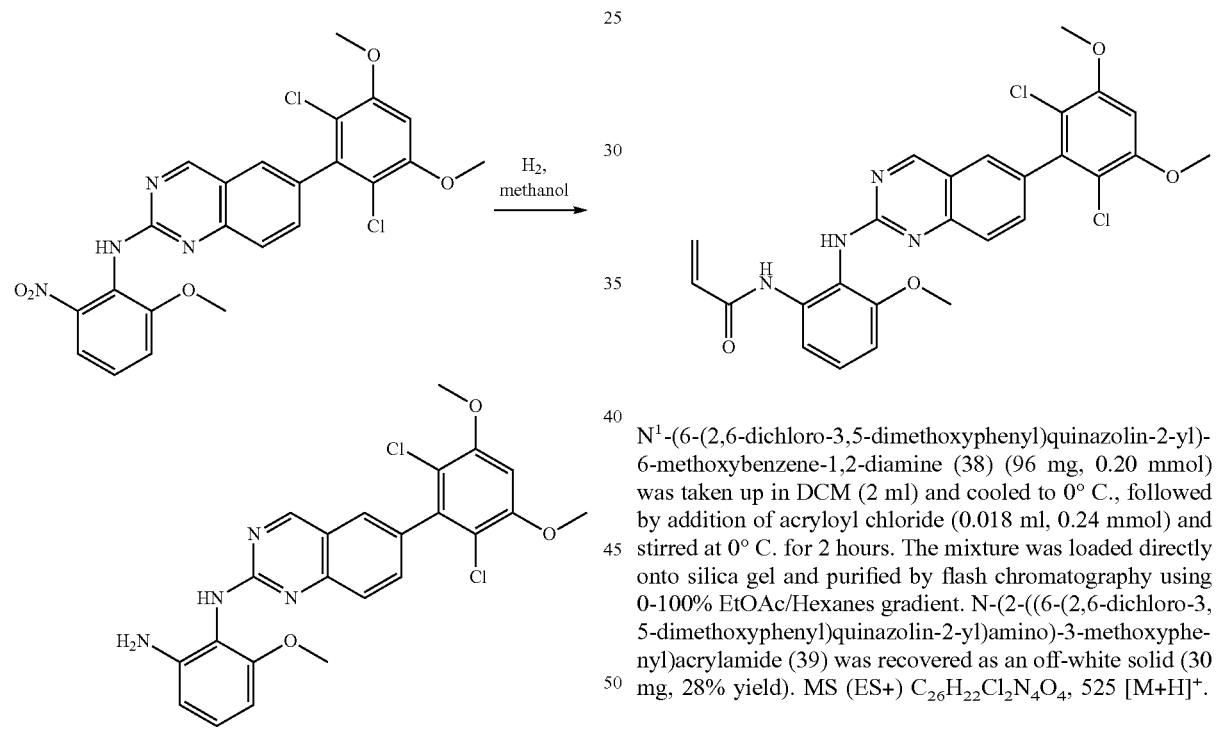

6-(2,6-Dichloro-3,5-dimethoxyphenyl)-N-(2-methoxy-6-nitrophenyl)quinazolin-2-amine (38) (100 mg, 0.14 mmol) was taken up in methanol (10 ml), 10% Pd/C (15 mg) was added. The mixture was stirred under $H_2$ balloon for 4 hours. The reaction mixture was filtered through celite and the solvent was removed to give N-(6-(2,6-dichloro-3,5-dimethoxyphenyl)quinazolin-2-yl)-6-methoxybenzene-1,2-diamine (38) in quantitative yield. Compound 38 was carried on to the next step without further purification. MS (ES+) $C_{23}H_{20}Cl_2N_4O_3$, 471 $[M+H]^+$ Step 9: Synthesis of N-(2-((6-(2,6-dichloro-3,5-dimethoxyphenyl)quinazolin-2-yl)amino)-3-methoxyphenyl)acrylamide $N^1$-(6-(2,6-dichloro-3,5-dimethoxyphenyl)quinazolin-2-yl)-6-methoxybenzene-1,2-diamine (38) (96 mg, 0.20 mmol) was taken up in DCM (2 ml) and cooled to 0° C., followed by addition of acryloyl chloride (0.018 ml, 0.24 mmol) and stirred at 0° C. for 2 hours. The mixture was loaded directly onto silica gel and purified by flash chromatography using 0-100% EtOAc/Hexanes gradient. N-(2-((6-(2,6-dichloro-3,5-dimethoxyphenyl)quinazolin-2-yl)amino)-3-methoxyphenyl)acrylamide (39) was recovered as an off-white solid (30 mg, 28% yield). MS (ES+) $C_{26}H_{22}Cl_2N_4O_4$, 525 $[M+H]^+$.

Example 3: Synthesis of Compound 25

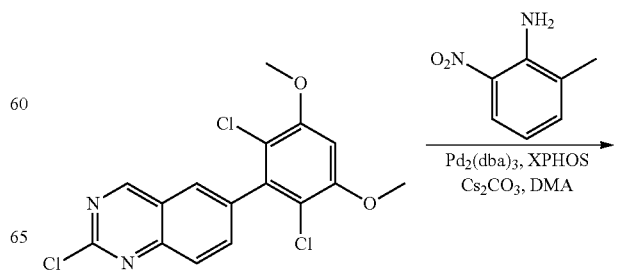

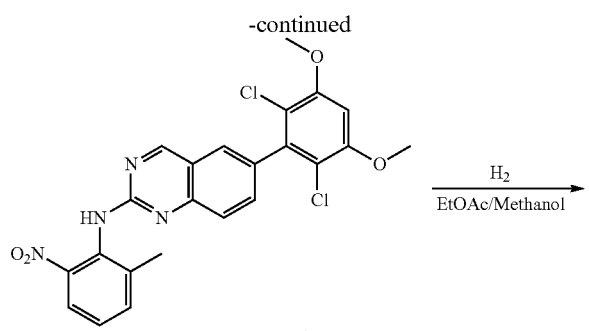

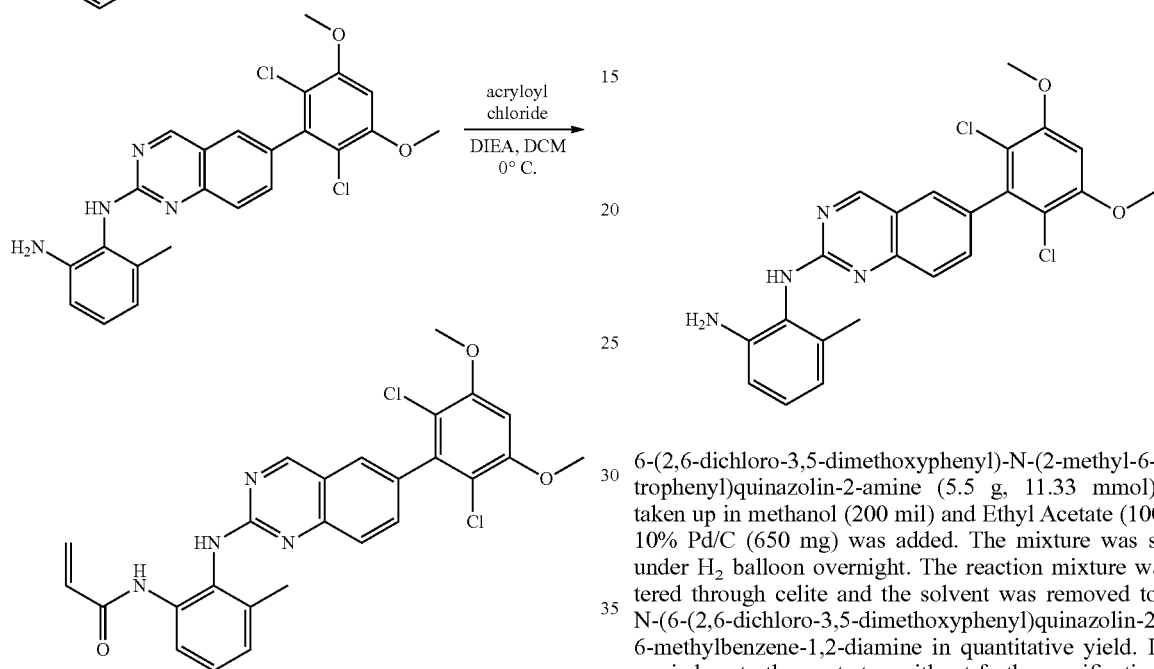

Synthesis of 6-(2,6-dichloro-3,5-dimethoxyphenyl)-N-(2-methyl-6-nitrophenyl)quinazolin-2-amine 2-Chloro-6-(2,6-dichloro-3,5-dimethoxyphenyl)quinazoline (35) (5 g, 13.5 mmol), 2-methyl-6-nitroaniline (3.09 g, 20.3 mmol), $Cs_2CO_3$ (13.2 g, 40.6 mmol), $Pd_2(dba)_3$ (1.24 g, 1.35 mmol), and 2-Dicyclohexylphosphino-2',4',6'-triisopropylbiphenyl (Xphos) (1.29 g, 2.71 mmol) were taken up in DMA (100 ml) and purged with $N_2$ for 5 minutes. The reaction mixture was heated to 110° C. in for 3 hours. After cooling to room temperature the reaction mixture was diluted with DCM (500 ml) and washed with 10% HCl three times (3×300 ml) and brine three times. The organic mixture was dried over sodium sulfate and loaded directly onto silica gel and purified using 0-100% EtOAc/Hexanes gradient. 6-(2,6-dichloro-3,5-dimethoxyphenyl)-N-(2-methyl-6-nitrophenyl)quinazolin-2-amine was recovered as a yellow solid (5.5 g, 81% yield). MS (ES+) $C_{23}H_{18}Cl_2N_4O_4$, 485 $[M+H]^+$.

Synthesis of $N^1$-(6-(2,6-dichloro-3,5-dimethoxyphenyl)quinazolin-2-yl)-6-methylbenzene-1,2-diamine

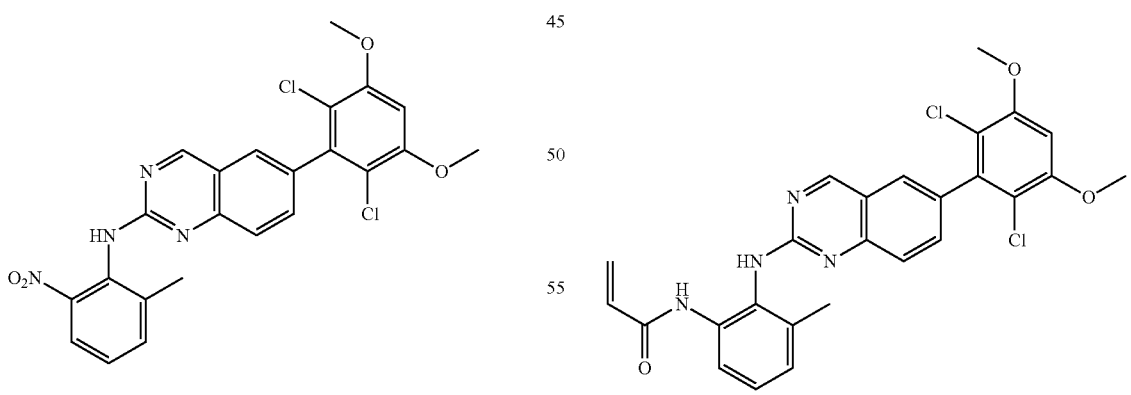

6-(2,6-dichloro-3,5-dimethoxyphenyl)-N-(2-methyl-6-nitrophenyl)quinazolin-2-amine (5.5 g, 11.33 mmol) was taken up in methanol (200 ml) and Ethyl Acetate (100 ml), 10% Pd/C (650 mg) was added. The mixture was stirred under $H_2$ balloon overnight. The reaction mixture was filtered through celite and the solvent was removed to give N-(6-(2,6-dichloro-3,5-dimethoxyphenyl)quinazolin-2-yl)-6-methylbenzene-1,2-diamine in quantitative yield. It was carried on to the next step without further purification. MS (ES+) $C_{23}H_{20}Cl_2N_4O_2$, 455 $[M+H]^+$ Synthesis of N-(2-((6-(2,6-dichloro-3,5-dimethoxyphenyl)quinazolin-2-yl)amino)-3-methylphenyl)acrylamide $N^1$-(6-(2,6-dichloro-3,5-dimethoxyphenyl)quinazolin-2-yl)-6-methylbenzene-1,2-diamine (5.16 g, 11.33 mmol) was taken up in DCM (100 ml) and cooled to 0° C., followed by addition of DIEA (1.781 ml, 10.20 mmol) and acryloyl chloride (1.013 ml, 12.47 mmol) and stirred at 0° C. for 2 hours. The mixture was loaded directly onto silica gel and purified by flash chromatography using 0-100% EtOAc/

Hexanes gradient. N-(2-((6-(2,6-dichloro-3,5-dimethoxyphenyl)quinazolin-2-yl)amino)-3-methylphenyl)acrylamide was recovered as an off-white solid (3.5 g, 61% yield). MS (ES+) $C_{26}H_{22}Cl_2N_4O_3$, 509 [M+H]$^+$. $^1$H NMR (400 MHz, DMSO-d$_6$) δ 9.53 (s, 1H), 9.23 (s, 1H), 8.68 (s, 1H), 7.82-7.65 (m, 2H), 7.51 (s, 2H), 7.21 (m, 1H), 7.12 (d, J=6.8 Hz, 1H), 7.01 (s, 1H), 6.49 (dd, J=17.0, 10.2 Hz, 1H), 6.28-6.15 (m, 1H), 5.68 (dd, J=10.2, 2.0 Hz, 1H), 3.97 (s, 6H), 2.19 (s, 3H).
Example 4: Syntheses of Compound 26 and Compound 10
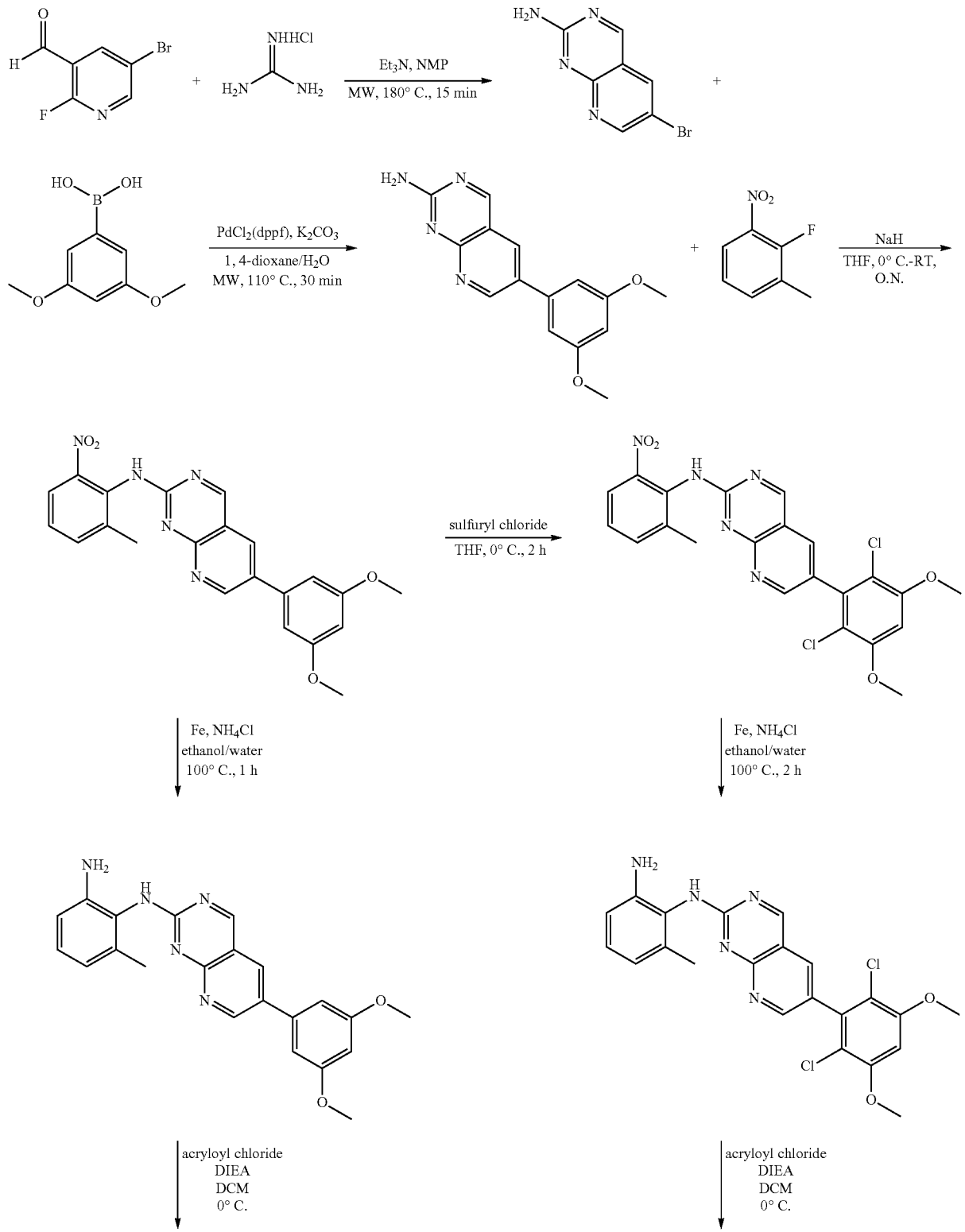

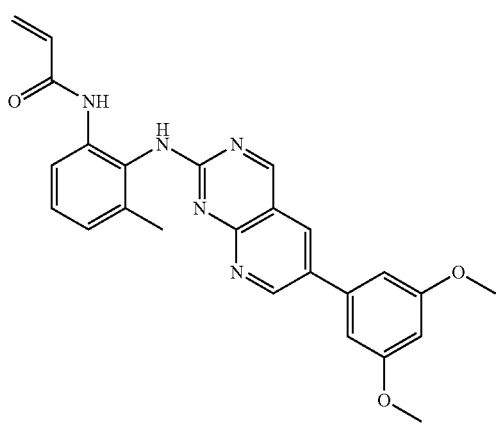
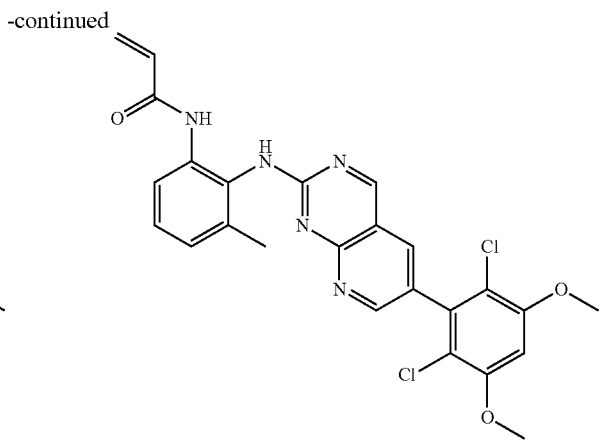

Synthesis of 6-bromopyrido[2,3-d]pyrimidin-2-amine

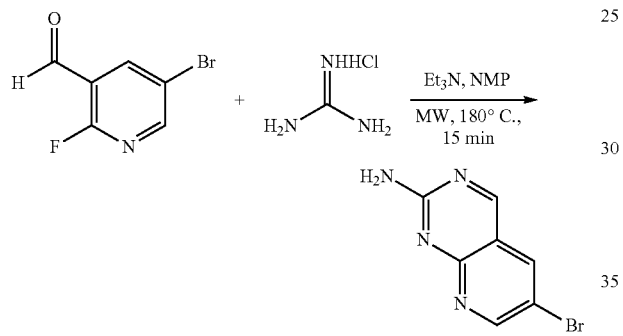

5-bromo-2-fluoronicotinaldehyde (3.0 g, 14.78 mmol), guanidine hydrochloride (1.69 g, 17.74 mmol) and triethylamine (4.48 g, 44.35 mmol) were dissolved in 1-methyl-2-pyrrolidinone (15 mL), and the reaction mixture was stirred at 180° C. for 15 min under microwave. The mixture was cooled to RT, quenched with water (200 mL) and extracted with ethyl acetate (2×300 mL). The organic layers were combined, washed with water (3×50 mL) and brine (3×50 mL), dried over sodium sulfate, filtered, and concentrated to afford a crude product, which was purified by silica gel column chromatography (ethyl acetate:petroleum ether=3:1) to afford 6-bromopyrido[2,3-d]pyrimidin-2-amine (2.0 g, 60%) as a yellow solid. MS (ES+) $C_7H_5BrN_4$ requires: 224, 226, found: 225, 227 [M+H]$^+$.

Synthesis of 6-(3,5-dimethoxyphenyl)pyrido[2,3-d]pyrimidin-2-amine

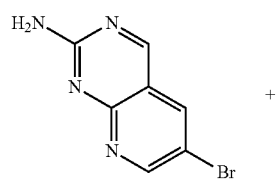
+

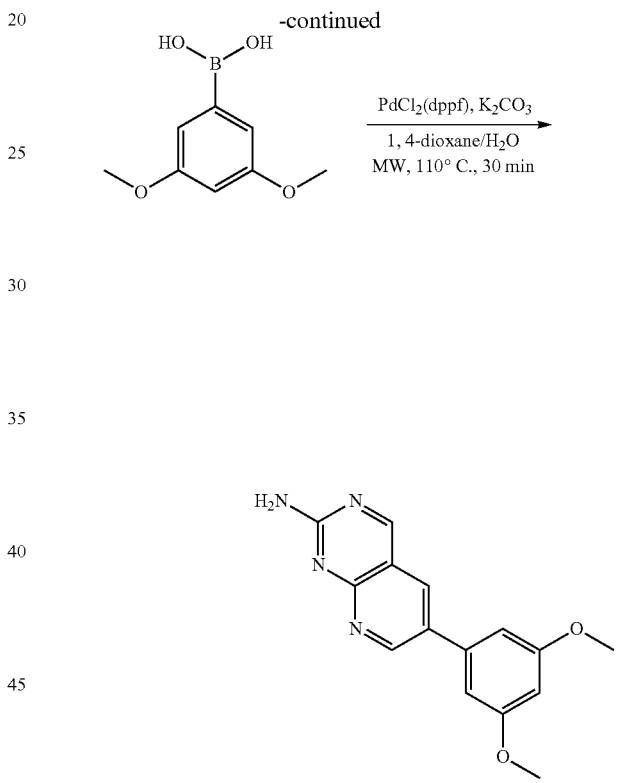

A mixture of 6-bromopyrido[2,3-d]pyrimidin-2-amine (1.0 g, 4.46 mmol), 3,5-dimethoxyphenylboronic acid (1.2 g, 6.70 mmol), PdCl$_2$(dppf) (364 mg, 0.446 mmol) and potassium carbonate (1.8 g, 13.39 mmol) in 1,4-dioxane/water (4 mL/1 mL) was degassed with nitrogen for 5 min and stirred at 110° C. for 30 min under microwave. The reaction mixture was cooled to RT, and concentrated to afford a crude product, which was purified by silica gel column chromatography (ethyl acetate:petroleum ether=4:1) to afford 6-(3,5-dimethoxyphenyl)pyrido[2,3-d]pyrimidin-2-amine as a yellow solid (400 mg, 31%). MS (ES+) $C_{15}H_{14}N_4O_2$ requires: 282, found: 283 [M+H]$^+$.

Synthesis of 6-(3,5-dimethoxyphenyl)-N-(2-methyl-6-nitrophenyl)pyrido[2,3-d]pyrimidin-2-amine

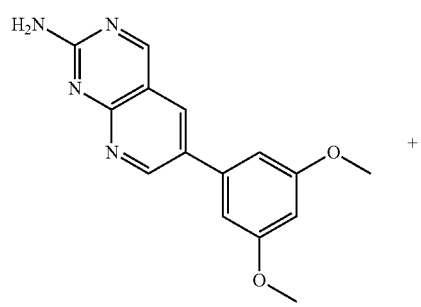

+

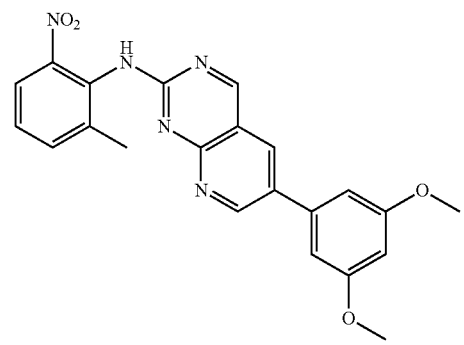

To a solution of 6-(3,5-dimethoxyphenyl)pyrido[2,3-d]pyrimidin-2-amine (400 mg, 1.42 mmol) in THF (20 mL) at 0° C. was added sodium hydride (102 mg, 4.25 mmol). The solution was stirred for 20 mins, followed by the addition of 2-fluoro-1-methyl-3-nitrobenzene (440 mg, 2.84 mmol). The reaction mixture was stirred at RT overnight, quenched by water (20 mL) and extracted with ethyl acetate (3×30 mL). The organic layers were combined, washed with brine (50 mL), dried over sodium sulfate, filtered, and concentrated to afford a crude product, which was purified by silica gel column chromatography (ethyl acetate:petroleum ether=4:1) to afford 6-(3,5-dimethoxyphenyl)-N-(2-methyl-6-nitrophenyl)pyrido[2,3-d]pyrimidin-2-amine (310 mg, 51%) as a brown solid. MS (ES+) $C_{22}H_{19}N_5O_4$ requires: 417, found: 418 [M+H]$^+$.

Synthesis of $N^1$-(6-(3,5-dimethoxyphenyl)pyrido[2,3-d]pyrimidin-2-yl)-6-methylbenzene-1,2-diamine

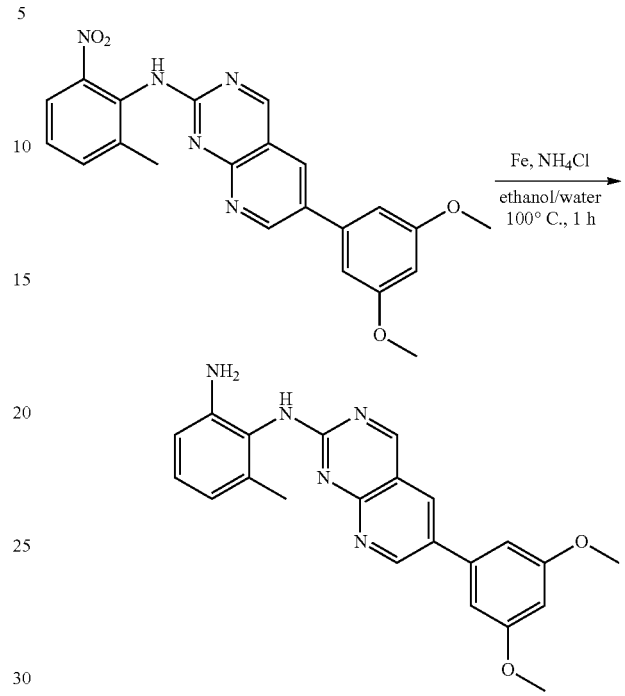

To a solution of 6-(3,5-dimethoxyphenyl)-N-(2-methyl-6-nitrophenyl)pyrido[2,3-d]pyrimidin-2-amine (100 mg, 0.24 mmol) in ethanol (5 mL) and water (5 mL) was added iron powder (110 mg, 1.92 mmol) and ammonium chloride (100 mg, 1.920 mmol). The mixture was stirred at 100° C. for 1 hour, cooled to RT, filtered and concentrated. The residue was purified by Preparative HPLC to afford $N^1$-(6-(3,5-dimethoxyphenyl)pyrido[2,3-d]pyrimidin-2-yl)-6-methylbenzene-1,2-diamine (29.5 mg, 32%) as a yellow solid. MS (ES+) $C_{22}H_{21}N_5O_2$ requires: 387, found: 388 [M+H]; $^1$H-NMR (500 MHz, DMSO-d$_6$) δ ppm 9.30, 9.21 (br, br, 2H), 8.95 (s, 1H), 8.60 (d, 1H, J=3.0 Hz), 6.96-6.92 (m, 3H), 6.63 (d, 1H, J=5.5 Hz), 6.55 (t, 1H, J=2.0 Hz), 6.50-6.48 (m, 1H), 4.79 (s, 2H), 3.84 (s, 6H), 2.08 (s, 3H).

Synthesis of 6-(2,6-dichloro-3,5-dimethoxyphenyl)-N-(2-methyl-6-nitrophenyl)pyrido[2,3-d]pyrimidin-2-amine

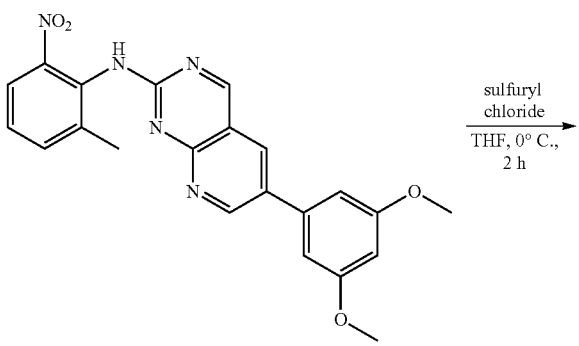

-continued

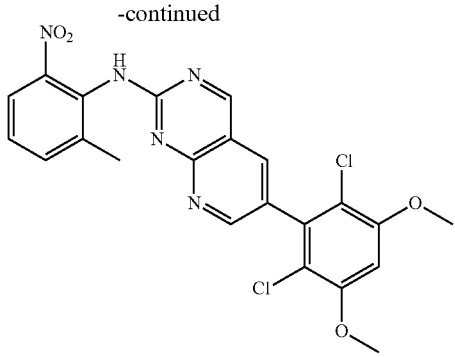

To a stirred solution of 6-(3,5-dimethoxyphenyl)-N-(2-methyl-6-nitrophenyl)pyrido[2,3-d]pyrimidin-2-amine (100 mg, 0.24 mmol) in THF (10 mL) at 0° C. was dropwise added a solution of sulfuryl chloride (0.06 mL, 0.72 mmol) in THF (2 mL). After stirred at 0° C. for 2 hrs, the reaction was quenched with water (10 mL) and extracted with ethyl acetate (3×20 mL). The organic layers were combined, washed with brine (20 mL), dried over sodium sulfate, filtered, and concentrated. The residue was purified by silica gel column chromatography (ethyl acatete:petroleum ether=3:1) to afford 6-(2,6-dichloro-3,5-dimethoxyphenyl)-N-(2-methyl-6-nitrophenyl)pyrido[2,3-d]pyrimidin-2-amine (110 mg, 95%) as a yellow solid. MS (ES+) $C_{22}H_{17}Cl_2N_5O_4$ requires: 485, 487 found: 486, 488 [M+H]$^+$.

Synthesis of $N^1$-(6-(2,6-dichloro-3,5-dimethoxyphenyl)pyrido[2,3-d]pyrimidin-2-yl)-6-methylbenzene-1,2-diamine

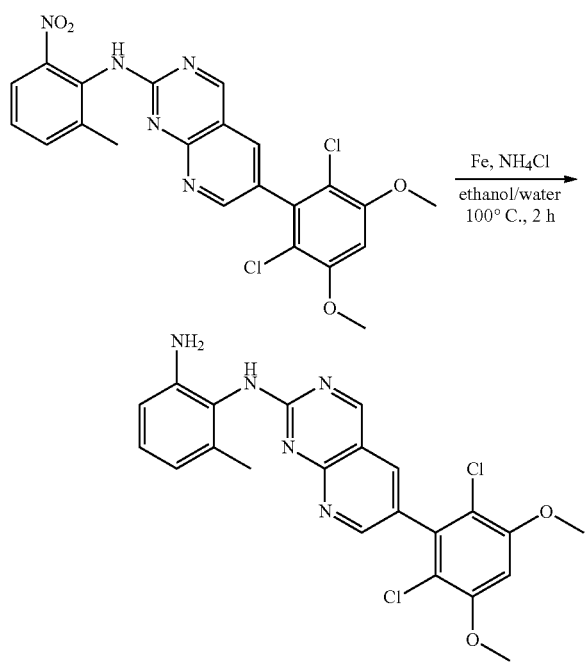

To a solution of 6-(2,6-dichloro-3,5-dimethoxyphenyl)-N-(2-methyl-6-nitrophenyl)pyrido[2,3-d]pyrimidin-2-amine (80 mg, 0.168 mmol) in ethanol (4 mL) and water (4 mL) was added iron powder (75 mg, 1.344 mmol) and ammonium chloride (74 mg, 1.344 mmol). The mixture was stirred at 100° C. for 2 hrs, cooled to RT, filtered and concentrated. The residue was purified by silica gel column chromatography (ethyl acetate:petroleum ether=4:1) to afford $N^1$-(6-(2,6-dichloro-3,5-dimethoxyphenyl)pyrido[2,3-d]pyrimidin-2-yl)-6-methylbenzene-1,2-diamine (40 mg, 53%) as a yellow solid. MS (ES+) $C_{22}H_{19}Cl_2N_5O_2$ requires: 455, 457, found: 456, 458 [M+H]$^+$. $^1$H-NMR (400 MHz, DMSO-d$_6$) δ ppm 9.33 (br. s., 1H), 9.01 (s, 1H), 9.65 (br. s., 1H), 8.23 (s, 1H), 7.05 (s, 1H), 6.93 (br. s., 1H), 6.64-6.63 (m, 1H), 6.50-6.49 (m, 1H), 4.80 (s, 2H), 3.99 (s, 6H), 2.09 (s, 3H).

Synthesis of N-(2-((6-(3,5-dimethoxyphenyl)pyrido[2,3-d]pyrimidin-2-yl)amino)-3-methylphenyl)acrylamide

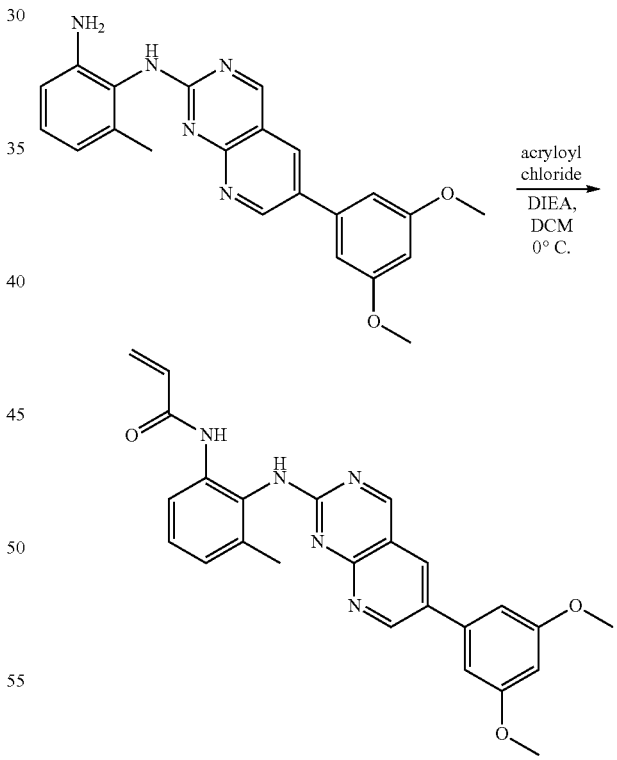

N-(2-((6-(3,5-dimethoxyphenyl)pyrido[2,3-d]pyrimidin-2-yl)amino)-3-methylphenyl)acrylamide was prepared using the procedure similar to COMPOUND 30. The product was purified by flash chromatography using 0-50% EtOAc/DCM gradient to give the title compound. MS (ES+) $C_{25}H_{23}N_5O_3$ requires: 441, found: 442 Synthesis of N-(2-((6-(2,6-dichloro-3,5-dimethoxyphenyl)pyrido[2,3-d]pyrimidin-2-yl)amino)-3-methylphenyl)acrylamide

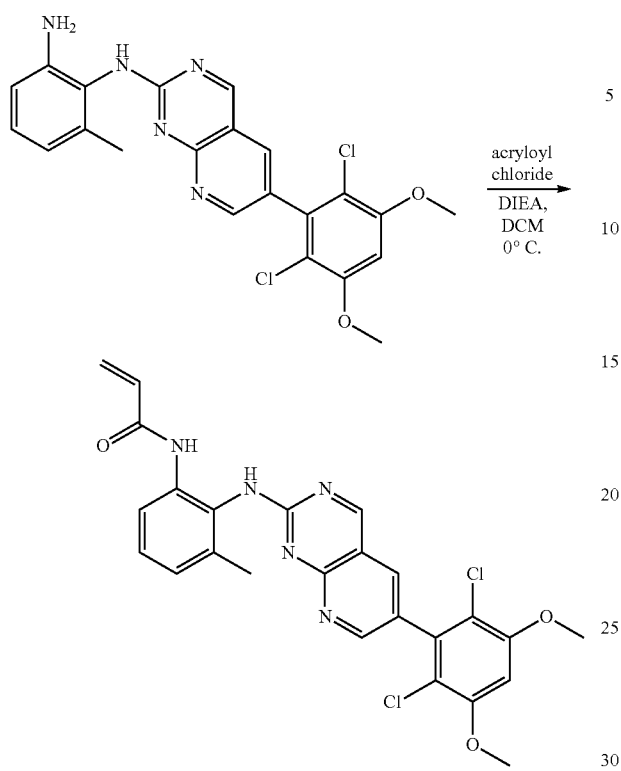
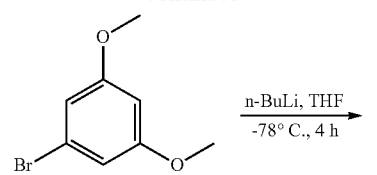
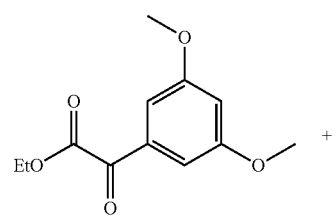
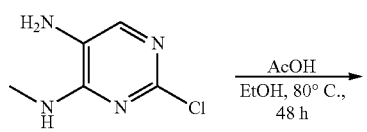
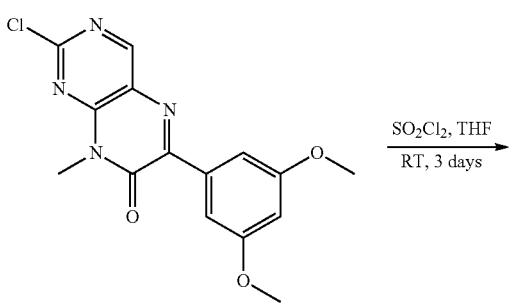
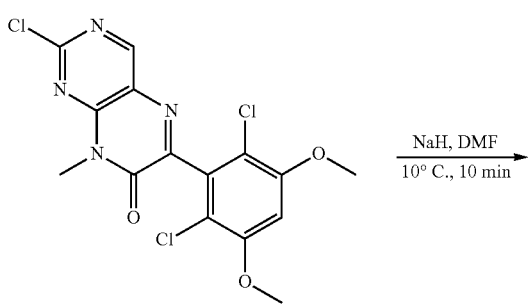
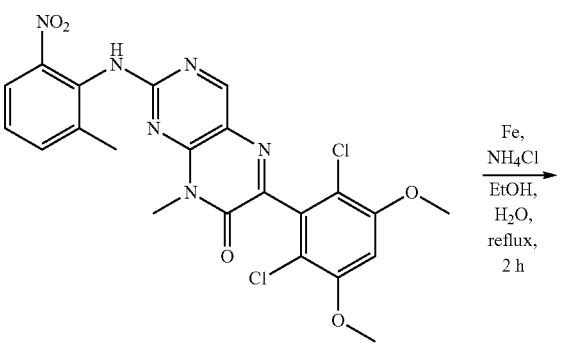

N-(2-(((6-(2,6-dichloro-3,5-dimethoxyphenyl)pyrido[2,3-d]pyrimidin-2-yl)amino)-3-methylphenyl)acrylamide was prepared using the procedure similar to COMPOUND 30. The product was purified by flash chromatography using 0-10% MeOH/DCM gradient to give the title compound. MS (ES+) $C_{25}H_{21}Cl_2N_5O_3$ requires: 510, found: 511 [M+H]+. $^1$H-NMR (400 MHz, DMSO-$d_6$) 9.53 (s, 1H), 9.35 (s, 1H), 9.06 (s, 1H), 8.70 (s, 1H), 8.27 (d, J=2.6 Hz, 1H), 7.78 (s, 1H), 7.23 (d, J=7.9 Hz, 1H), 7.15 (s, 1H), 7.06 (s, 1H), 6.52 (dd, J=17.0, 10.1 Hz, 1H), 6.22 (dd, J=17.0, 2.0 Hz, 1H), 5.69 (d, J=10.6 Hz, 1H), 3.98 (s, 6H), 2.20 (s, 3H).

Example 4: Synthesis of Compound 45

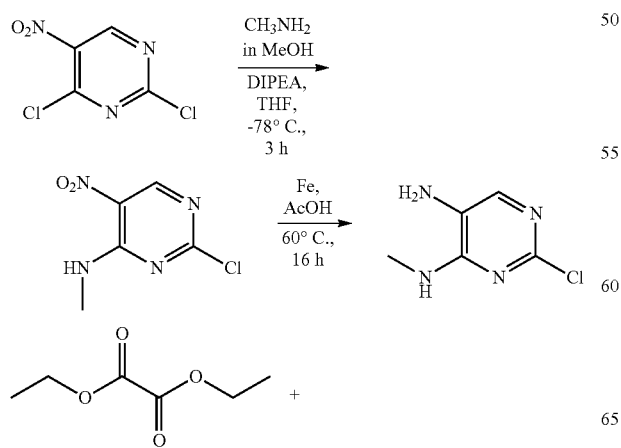

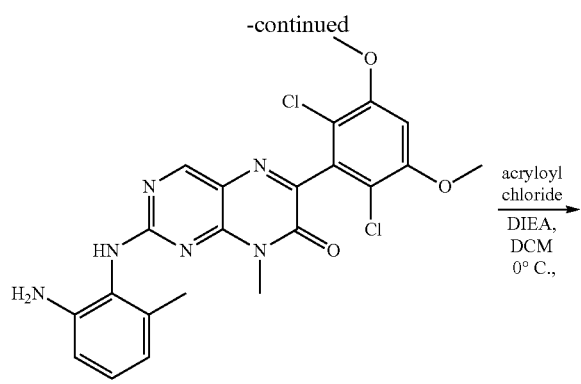

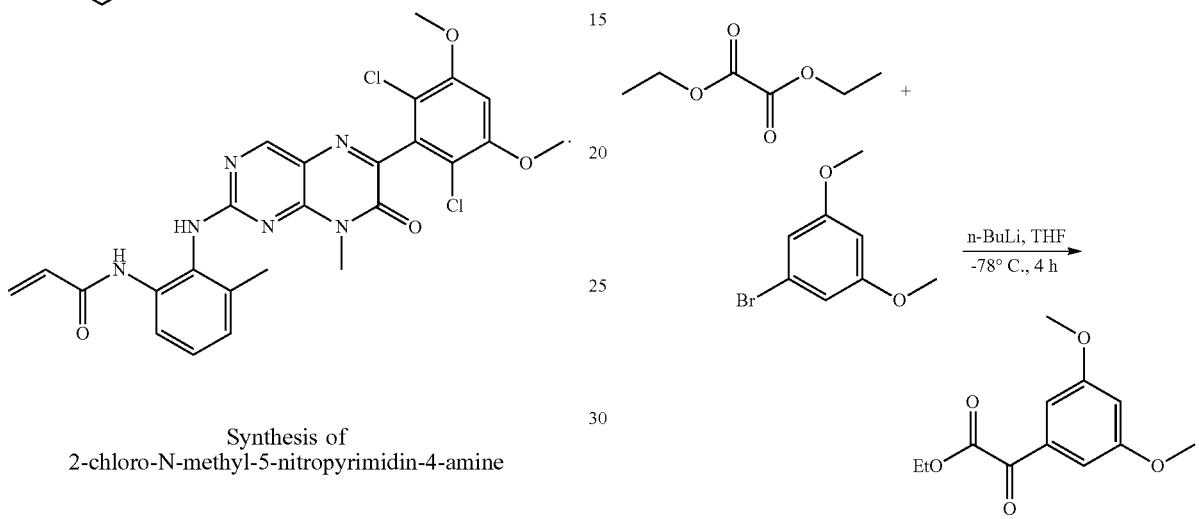

Synthesis of 2-chloro-N-methyl-5-nitropyrimidin-4-amine

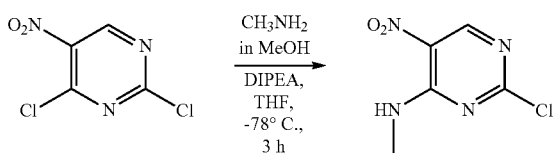

To a solution of 2,4-dichloro-5-nitropyrimidine (5 g, 26 mmol) in THF (50 mL) was added diisopropylethylamine (3.36 g, 26 mmol) at −78° C., followed by the dropwise addition of methylamine (13 mL, 2 mol/L in methanol, 26 mmol). After the addition, the mixture was warmed to RT and stirred for 3 h. The reaction mixture was then diluted with ethyl acetate and washed with brine (50 mL*3). The organic layer was dried over sodium sulfate, filtered and concentrated to give the title compound (4.4 g, 100%) as a yellow solid. MS (ES+) $C_5H_5ClN_4O_2$ requires: 188, 190, found: 189, 191 $[M+H]^+$.

Synthesis of 2-chloro-$N^4$-methylpyrimidine-4,5-diamine

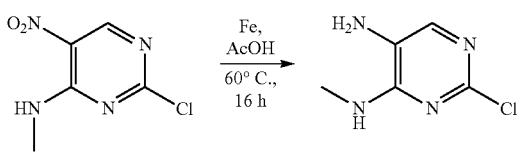

To a stirred solution of 2-chloro-N-methyl-5-nitropyrimidin-4-amine (1.9 g, 10 mmol) in acetic acid (30 mL) was added iron powder (4 g, 71 mmol), and the suspension mixture was heated to 60° C. for 16 hours. The solvent was removed under reduced pressure, and the residue was diluted by brine and ethyl acetate. The solid was filtered off, and the filtrate was extracted with ethyl acetate (50 mL*12). The organic layers were separated, combined, dried over sodium sulfate, filtered and concentrated to give the title compound (1.1 g, 69%). MS (ES+) $C_5H_7ClN_4$ requires: 159, 161, found: 160, 162 $[M+H]^+$.

Synthesis of ethyl 2-(3,5-dimethoxyphenyl)-2-oxoacetate

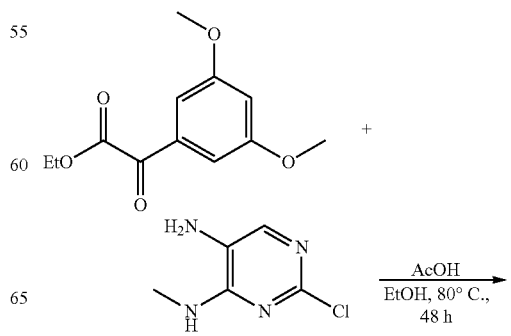

To a solution of 1-bromo-3,5-dimethoxybenzene (2.17 g, 10 mmol) in THF (15 mL) was dropwise added n-butyl lithium (8 mL, 2.5 mol/L in hexane, 20 mmol) at −78° C. After stirring for 50 mins at −78° C., a solution of diethyl oxalate (4 g, 27 mmol) in THF (10 mL) was added.
The mixture was stirred at −78° C. for another 4 h, then quenched with saturated ammonium chloride and extracted with ethyl acetate (50 mL*3). The organic layers were combined, washed by brine, dried over sodium sulfate, filtered and concentrated. The residue was purified by chromatography on silica gel to give the title compound (1.7 g, 71%). MS (ES+) $C_{12}H_{14}O_5$ requires: 238, found: 239 $[M+H]^+$.

Synthesis of 2-chloro-6-(3,5-dimethoxyphenyl)-8-methylpteridin-7(8H)-one

-continued

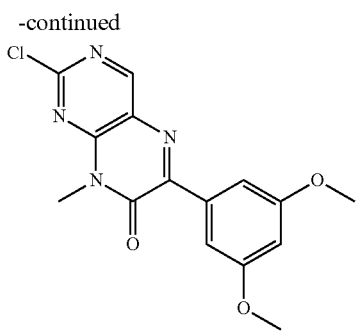

A mixture of ethyl 2-(3,5-dimethoxyphenyl)-2-oxoacetate (1 g, 4.2 mmol) and 2-chloro-N$^4$-methylpyrimidine-4,5-diamine (600 mg, 3.8 mmol) in ethanol (100 mL) and acetic acid (2.5 mL) was stirred at 80° C. for 48 h and cooled to RT (5° C.). The mixture was diluted with dichloromethane and washed with brine. The organic layer was directly concentrated and purified by chromatography on silica gel to give the title compound (700 mg, 50%). MS (ES+) $C_{15}H_{13}ClN_4O_3$ requires: 332, 334, found: 333, 335 [M+H]$^+$.

Synthesis of 2-chloro-6-(2,6-dichloro-3,5-dimethoxyphenyl)-8-methylpteridin-7(8H)-one

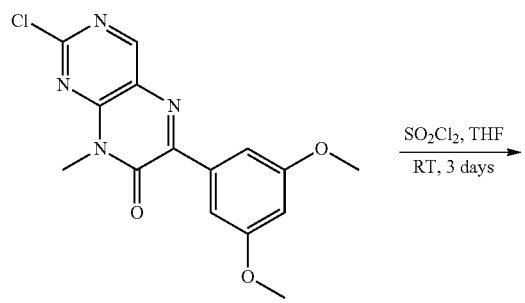

To a solution of 2-chloro-6-(3,5-dimethoxyphenyl)-8-methylpteridin-7(8H)-one (300 mg, 0.9 mmol) in THF (5 mL) was dropwise added sulfuryl chloride (300 mg), and the mixture was stirred at RT for 4 h. The additional sulfuryl chloride (300 mg) was added and stirred at RT for 3 days. The reaction was quenched by 5 drops of water and then stirred for 5 mins. The precipitate was collected via filtration and dried to give the title compound (240 mg, 67%) as a yellow solid. MS (ES+) $C_{15}H_{11}Cl_3N_4O_3$ requires: 400, 402, found: 400, 403 [M+H]$^+$.

Synthesis of 6-(2,6-dichloro-3,5-dimethoxyphenyl)-8-methyl-2-(2-methyl-6-nitrophenylamino)pteridin-7(8H)-one

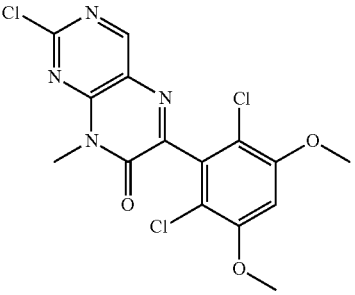

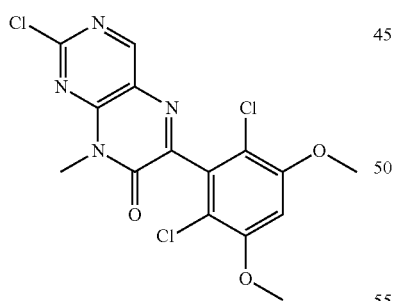

To a solution of 2-methyl-6-nitrobenzenamine (100 mg, 1 mmol) in N,N-dimethylformamide (5 mL) was added sodium hydride (53 mg, 1.3 mmol), and the mixture was stirred at RT (10° C.) for 10 mins, followed by the addition of 2-chloro-6-(2,6-dichloro-3,5-dimethoxyphenyl)-8-methylpteridin-7(8H)-one (322 mg, 1 mmol). The mixture was stirred at RT (10° C.) for another 30 min and then quenched by water. The precipitate was collected via filtration, washed with cold water and dried to give the title compound (180 mg, 75%) as a yellow powder. MS (ES+) $C_{22}H_{18}Cl_2N_6O_5$ requires: 516, 518, found: 517, 519 [M+H]$^+$.

Synthesis of 2-(2-amino-6-methylphenylamino)-6-(3,5-dimethoxyphenyl)-8-methylpteridin-7(8H)-one

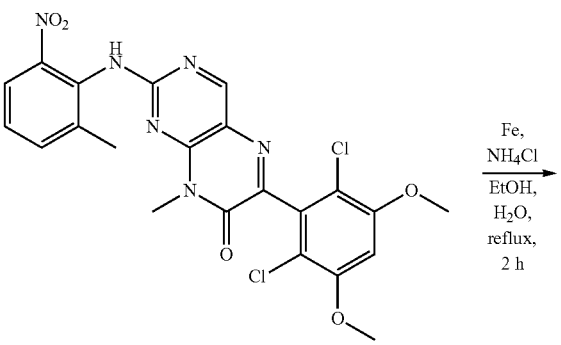

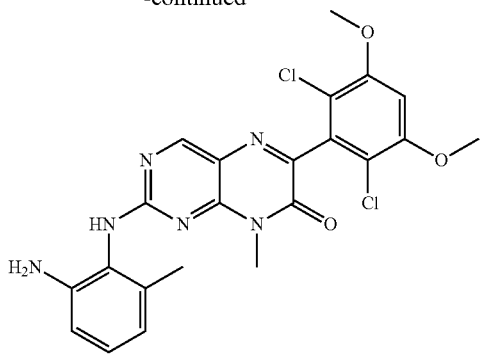

To a solution of 6-(2,6-dichloro-3,5-dimethoxyphenyl)-8-methyl-2-(2-methyl-6-nitrophenylamino)pteridin-7(8H)-one (200 mg, 0.38 mmol) in ethanol (50 mL) and water (2 mL) was added iron powder (210 mg, 3.8 mmol) and ammonium chloride (450 mg, 8 mmol). The mixture was refluxed for 2 h. The solvents were evaporated, and the residue was diluted with brine and dichloromethane. The solid was filtered off, and the filtrate was extracted with dichloromethane (50 mL*6). The organic layers were combined, dried over sodium sulfate, filtered and concentrated to give the title compound (70 mg, 38%). MS (ES+) $C_{22}H_{20}Cl_2N_6O_3$ requires: 486, 488, found: 487, 489 [M+H]+. $^1$H-NMR (500 MHz, CDCl$_3$) δ ppm 8.83 (s, 1H), 7.09 (t, 1H, J=8.0 Hz), 6.74-6.71 (m, 2H), 6.65 (s, 1H), 3.94 (s, 6H), 3.85 (br. s., 2H), 3.63-3.59 (br, 3H), 2.25 (s, 3H).

Synthesis of N-(2-((6-(2,6-dichloro-3,5-dimethoxyphenyl)-8-methyl-7-oxo-7,8-dihydropteridin-2-yl)amino)-3-methylphenyl)acrylamide

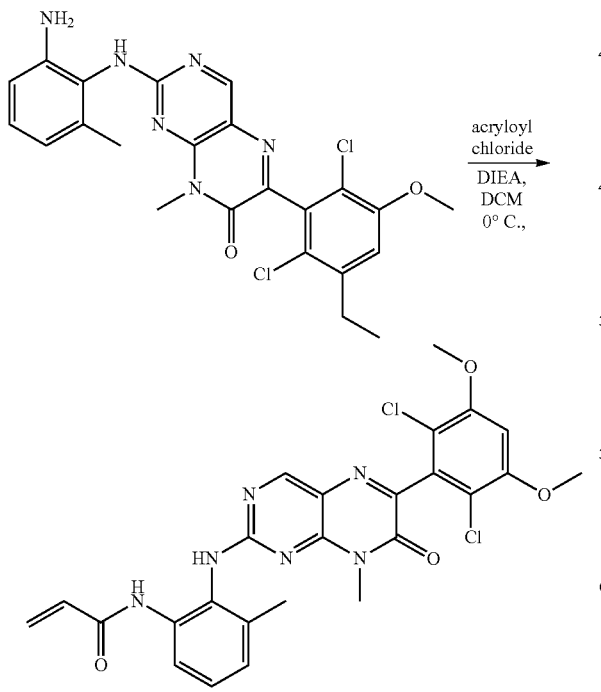

N-(2-((6-(2,6-dichloro-3,5-dimethoxyphenyl)-8-methyl-7-oxo-7,8-dihydropteridin-2-yl)amino)-3-methylphenyl)

acrylamide was prepared using the procedure similar to COMPOUND 30. The product was purified by flash chromatography using 0-10% MeOH/DCM gradient to give the title compound. MS (ES+) $C_{25}H_{22}Cl_2N_6O_4$ requires: 540, found: 541 [M+H]+.

Example 5: Synthesis of Compound 39

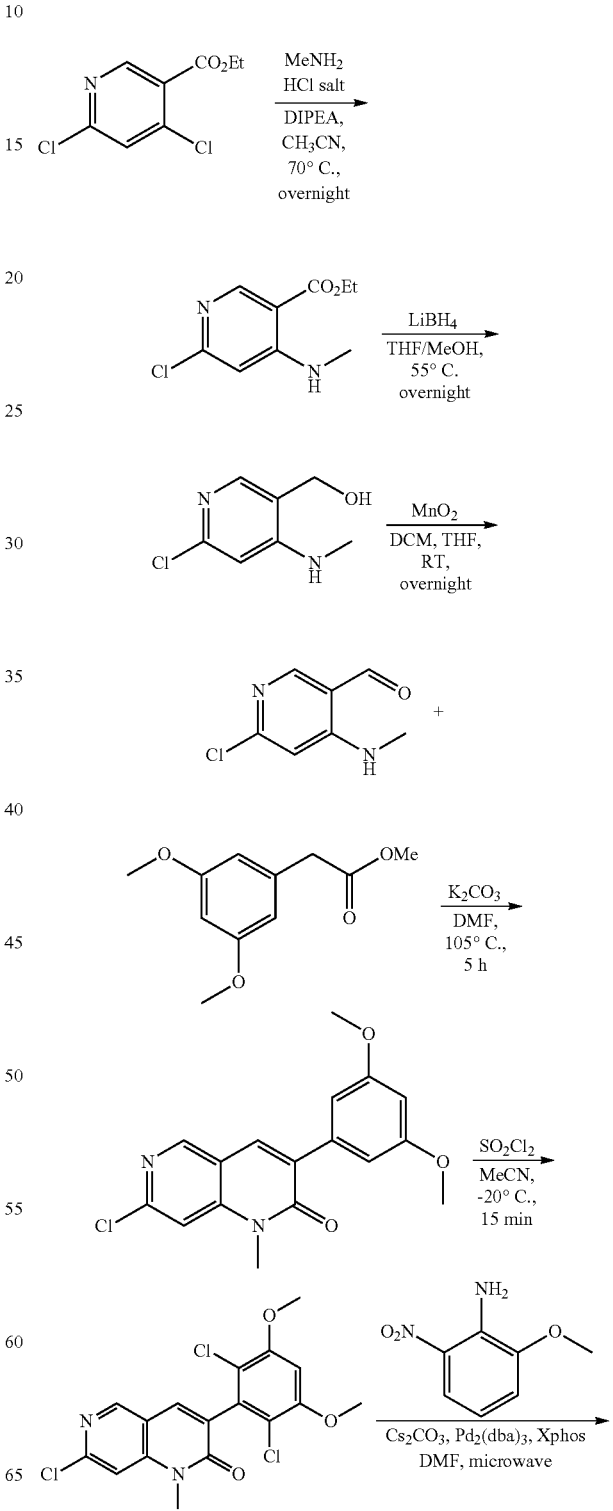

-continued

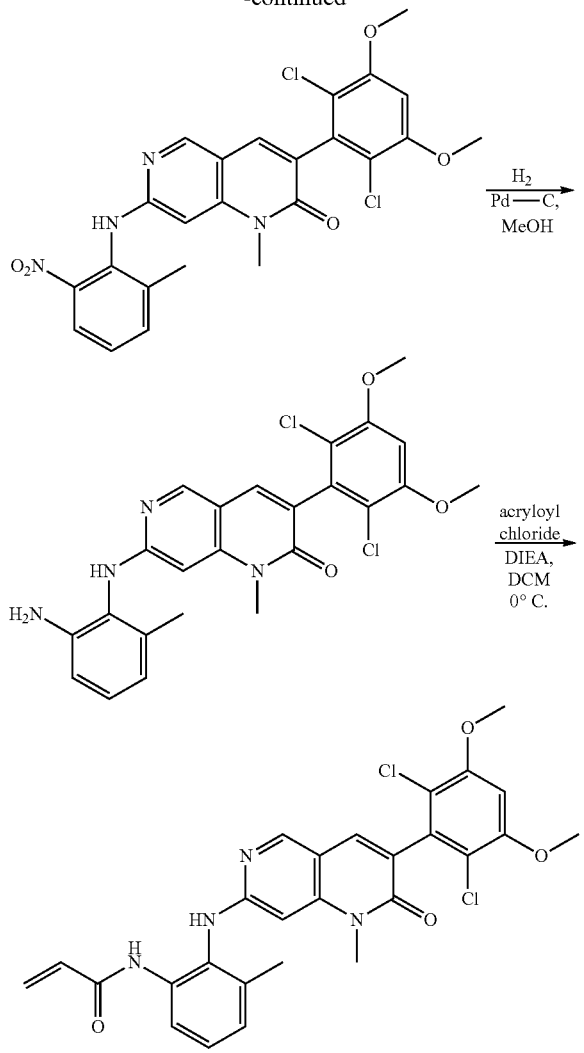

Synthesis of ethyl 6-chloro-4-(methylamino)nicotinate

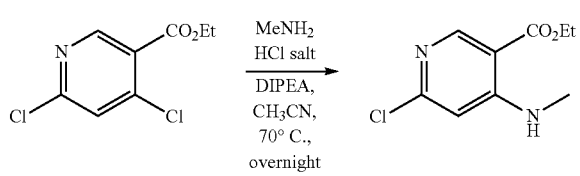

To a solution of ethyl 4,6-dichloronicotinate (5.0 g, 22.7 mmol) in acetonitrile (50 mL) was added methylamine hydrochloride salt (1.84 g, 27.2 mmol) and diisopropylethylamine (14.6 g, 113.6 mmol), and the reaction mixture was heated at 70° C. overnight. LCMS showed the reaction was completed. The reaction was cooled to RT, quenched with water (50 mL) and extracted with ethyl acetate (3×100 mL). The organic layers were separated, combined, washed with water (50 mL) and brine (100 mL), dried over sodium sulfate, filtered, and concentrated to afford the title compound (4.7 g, crude), which was directly used in the next step without further purification. MS (ES+) $C_9H_{11}ClN_2O_2$ requires: 214, 216, found: 215, 217 $[M+H]^+$.

Synthesis of (6-chloro-4-(methylamino)pyridin-3-yl)methanol

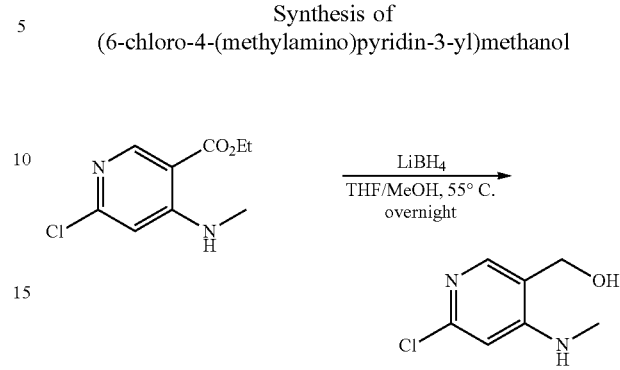

To a solution of ethyl 6-chloro-4-(methylamino)nicotinate (4.7 g, 21.9 mmol) in THF (30 mL) and methanol (30 mL) was added lithium borohydride (2.4 g, 109.8 mmol), and the reaction mixture was heated at 55° C. overnight. LCMS showed the reaction was completed. The reaction was cooled to RT, quenched with water (1 mL) and filtered. The filtrate was concentrated to afford the title compound (4.2 g, crude) as a white solid, which was directly used in the next step without further purification. MS (ES+) $C_7H_9ClN_2O$ requires: 172, 174, found: 173, 175 $[M+H]^+$.

Synthesis of 6-chloro-4-(methylamino)nicotinaldehyde

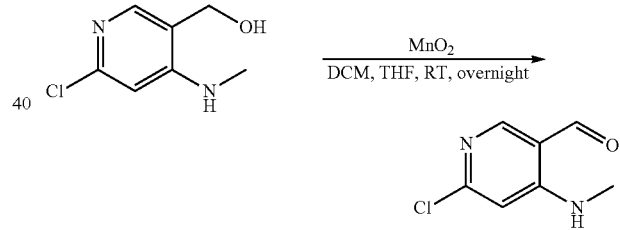

A mixture of (6-chloro-4-(methylamino)pyridin-3-yl)methanol (4.2 g, 24.7 mmol) and manganese(IV) oxide (active, 25.8 g, 296.6 mmol) in dichloromethane (50 mL) and THF (50 mL) was stirred at RT overnight. LCMS showed the reaction was completed. The solid was filtered off, and the filtrate was concentrated to afford the title compound (3.7 g, crude) as a light yellow solid, which was directly used in the next step without further purification. MS (ES+) $C_7H_7ClN_2O$ requires: 170, 172, found: 171, 173 $[M+H]^+$.

Synthesis of 7-chloro-3-(3,5-dimethoxyphenyl)-1-methyl-1,6-naphthyridin-2(1H)-one

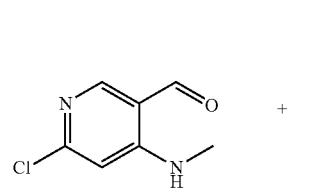

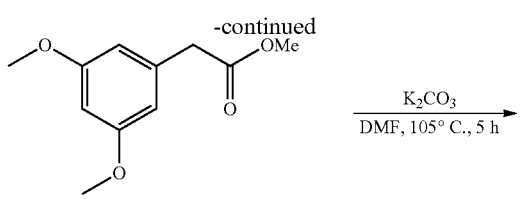

A mixture of 6-chloro-4-(methylamino)nicotinaldehyde (3.7 g, 21.7 mmol), methyl 2-(3,5-dimethoxyphenyl)acetate (4.5 g, 21.7 mmol) and potassium carbonate (9.0 g, 65.1 mmol) in N,N-dimethylformamide (30 mL) was heated at 105° C. for 5 h. LCMS showed the reaction was completed. The reaction was cooled to RT, quenched with water (200 mL), and filtered. The filtration cake was washed by petroleum ether (50 mL) and ethyl acetate (50 mL) to afford the title compound (5.8 g, 77%) as a yellow solid. MS (ES+) $C_{18}H_{19}ClN_2O_3$ requires: 346, 348, found: 347, 349 [M+H]$^+$.

Synthesis of 7-chloro-3-(2,6-dichloro-3,5-dimethoxyphenyl)-1-methyl-1,6-naphthyridin-2(1H)-one

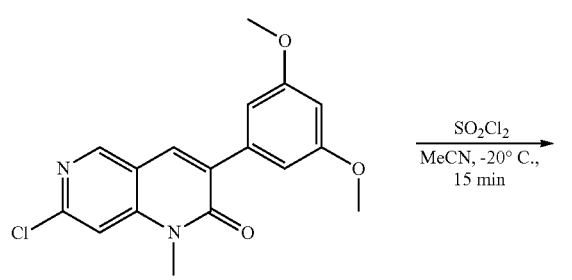

To a solution of 7-chloro-3-(3,5-dimethoxyphenyl)-1-methyl-1,6-naphthyridin-2(1H)-one (5.6 g, 16.9 mmol) in actonitrile (30 mL) was dropwise added sulfuryl chloride (3.36 mL, 42.2 mmol) at -20 OC, and the mixture was stirred for another 15 mins. LCMS showed the reaction was completed. The reaction was quenched with water (1 mL), and the solvents were removed under reduced pressure. The precipitate was washed with acetonitrile and dried to afford the title compound (5.01 g, 75%) as a white solid. MS (ES+) $C_{17}H_{13}Cl_3N_2O_3$ requires: 399, 401, found: 400, 402 [M+H]$^+$; $^1$H-NMR (500 MHz, DMSO-d$_6$) δ ppm 8.82 (s, 1H), 8.01 (s, 1H), 7.71 (s, 1H), 7.04 (s, 1H), 3.98 (s, 6H), 3.66 (s, 3H).

Synthesis of 3-(2,6-dichloro-3,5-dimethoxyphenyl)-1-methyl-7-((2-methyl-6-nitrophenyl)amino)-1,6-naphthyridin-2(1H)-one

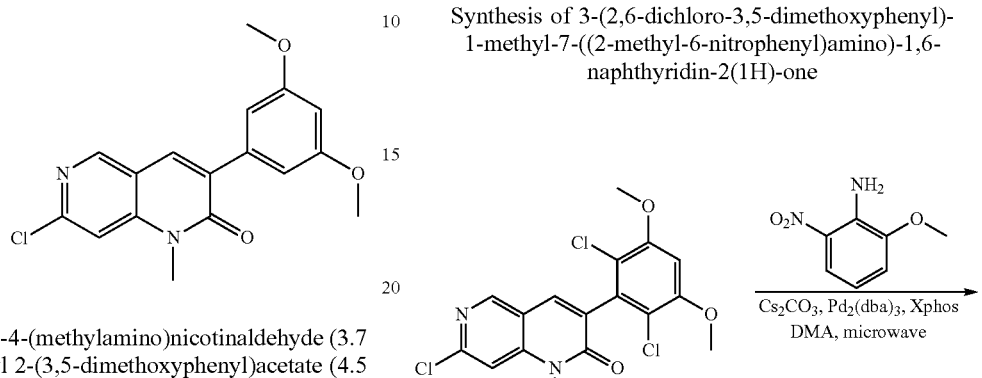

3-(2,6-dichloro-3,5-dimethoxyphenyl)-1-methyl-7-((2-methyl-6-nitrophenyl)amino)-1,6-naphthyridin-2(1H)-one was prepared using the procedure similar to COMPOUND 30.

Synthesis of 7-((2-amino-6-methylphenyl)amino)-3-(2,6-dichloro-3,5-dimethoxyphenyl)-1-methyl-1,6-naphthyridin-2(1H)-one

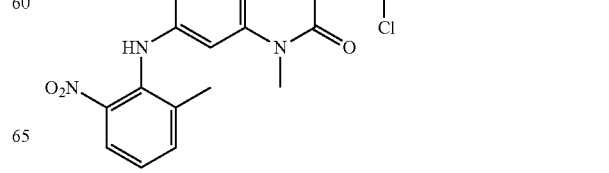

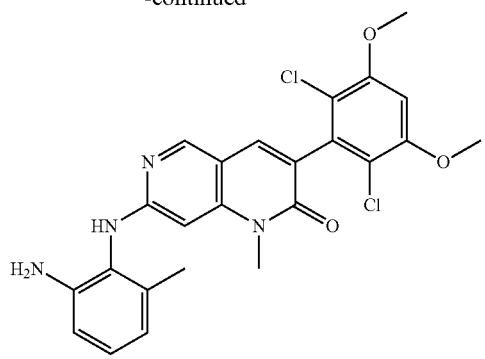

7-((2-amino-6-methylphenyl)amino)-3-(2,6-dichloro-3,5-dimethoxyphenyl)-1-methyl-1,6-naphthyridin-2(1H)-one was prepared using the procedure similar to COMPOUND 30.

Synthesis of 7-((2-amino-6-methylphenyl)amino)-3-(2,6-dichloro-3,5-dimethoxyphenyl)-1-methyl-1,6-naphthyridin-2(1H)-one

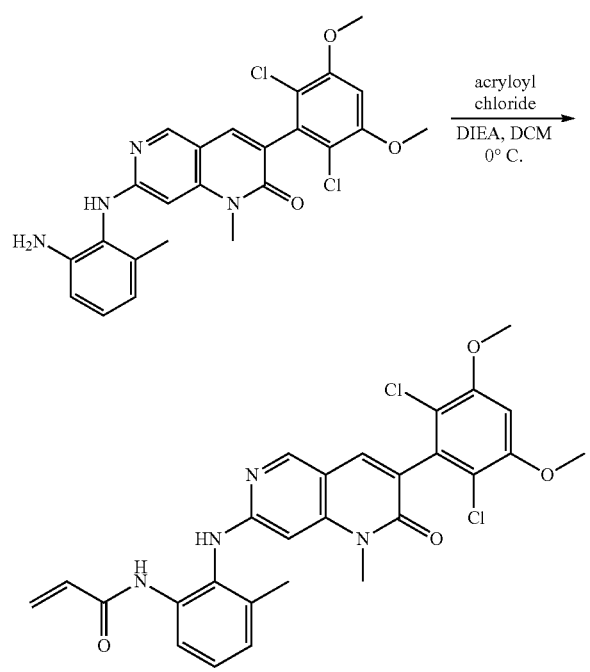

7-((2-amino-6-methylphenyl)amino)-3-(2,6-dichloro-3,5-dimethoxyphenyl)-1-methyl-1,6-naphthyridin-2(1H)-one was prepared using the procedure similar to COMPOUND 30. The product was purified by flash chromatography using 0-100% EtOAc/DCM gradient to give the title compound. MS (ES+) $C_{27}H_{24}Cl_2N_4O_4$ requires: 538, found: 539 [M+H]$^+$. $^1$H NMR (400 MHz, DMSO-d6) δ 9.47 (s, 1H), 8.43 (d, J=10.0 Hz, 2H), 7.70 (d, J=12.6 Hz, 2H), 7.22 (t, J=7.8 Hz, 1H), 7.14 (d, J=7.6 Hz, 1H), 6.97 (s, 1H), 6.46 (dd, J=17.0, 10.2 Hz, 1H), 6.18 (dd, J=17.0, 2.1 Hz, 1H), 6.09 (s, 1H), 5.65 (dd, J=10.2, 2.1 Hz, 1H), 3.95 (s, 6H), 3.39 (s, 3H), 2.20 (s, 3H).

Example 6: Synthesis of Compound 48

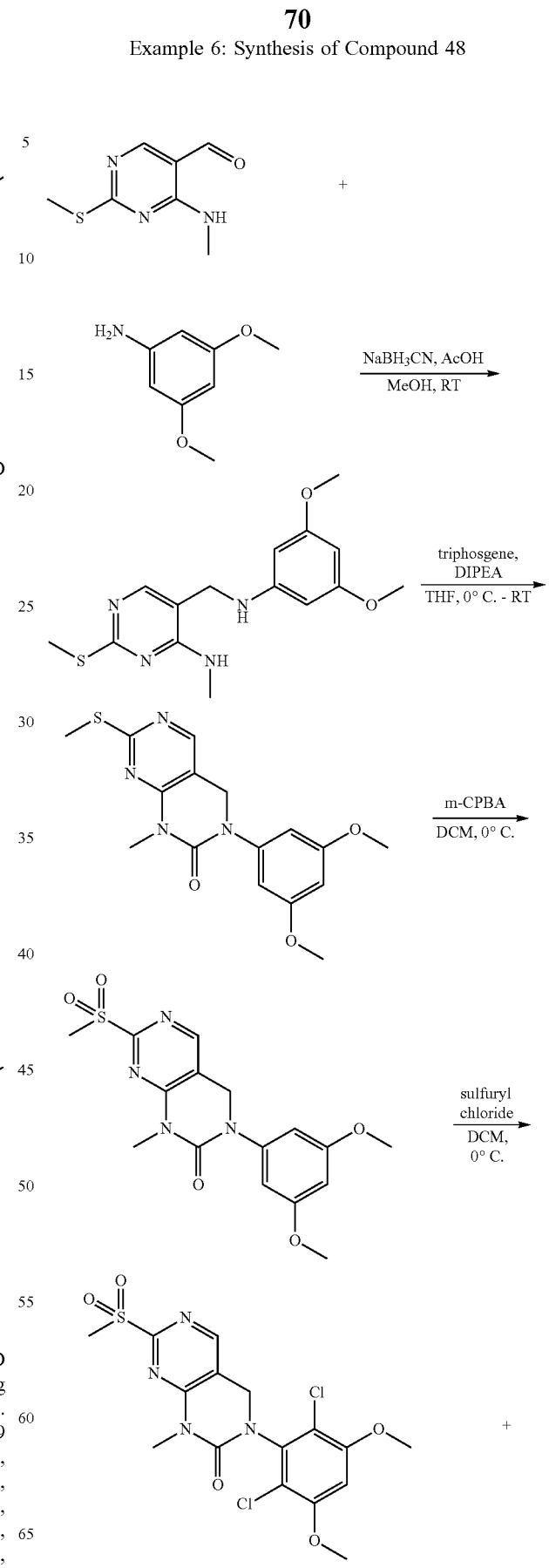

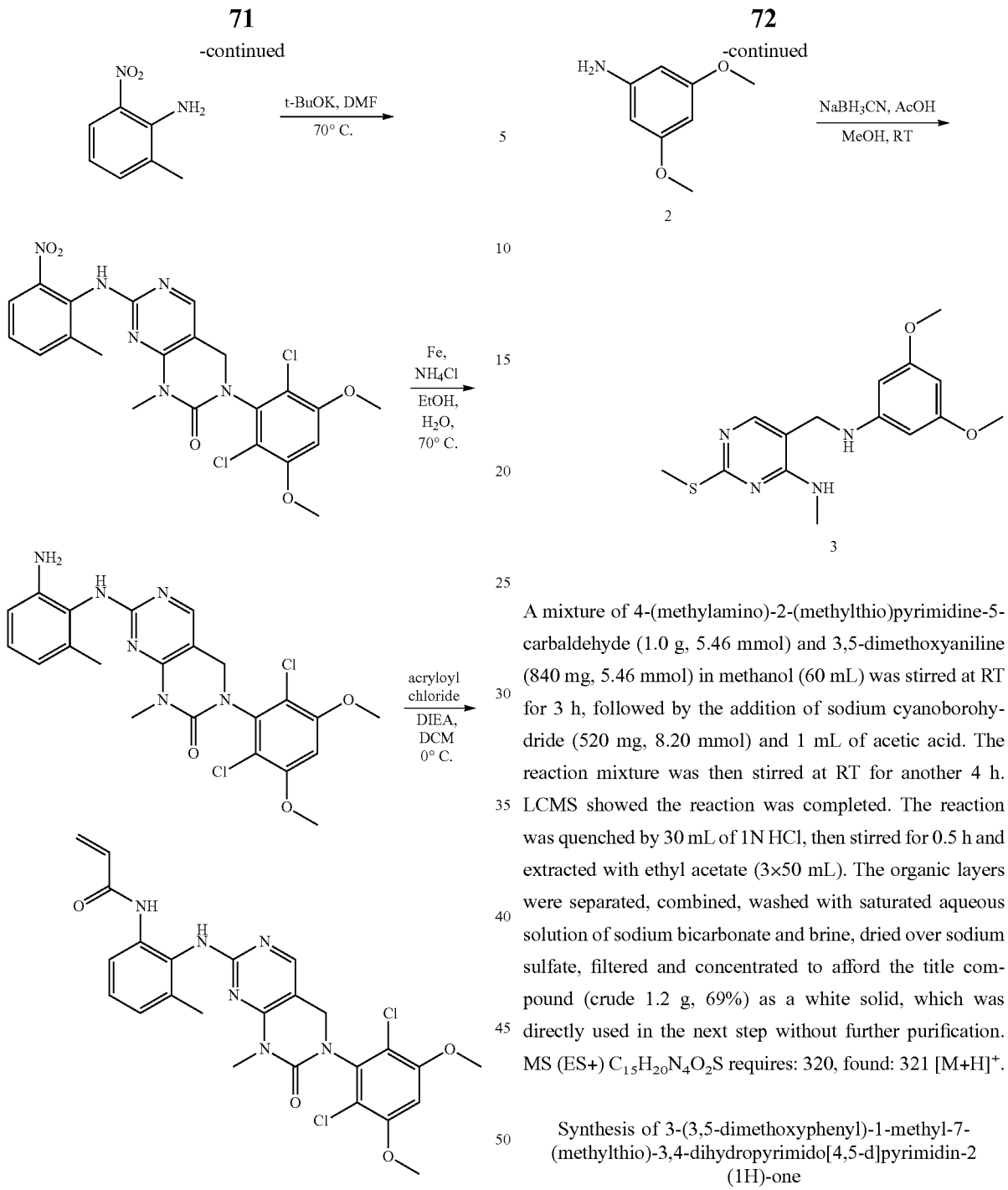

A mixture of 4-(methylamino)-2-(methylthio)pyrimidine-5-carbaldehyde (1.0 g, 5.46 mmol) and 3,5-dimethoxyaniline (840 mg, 5.46 mmol) in methanol (60 mL) was stirred at RT for 3 h, followed by the addition of sodium cyanoborohydride (520 mg, 8.20 mmol) and 1 mL of acetic acid. The reaction mixture was then stirred at RT for another 4 h. LCMS showed the reaction was completed. The reaction was quenched by 30 mL of 1N HCl, then stirred for 0.5 h and extracted with ethyl acetate (3×50 mL). The organic layers were separated, combined, washed with saturated aqueous solution of sodium bicarbonate and brine, dried over sodium sulfate, filtered and concentrated to afford the title compound (crude 1.2 g, 69%) as a white solid, which was directly used in the next step without further purification. MS (ES+) $C_{15}H_{20}N_4O_2S$ requires: 320, found: 321 $[M+H]^+$.

Synthesis of 3-(3,5-dimethoxyphenyl)-1-methyl-7-(methylthio)-3,4-dihydropyrimido[4,5-d]pyrimidin-2(1H)-one

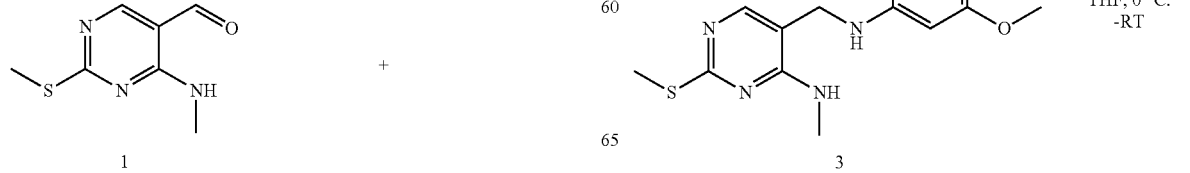

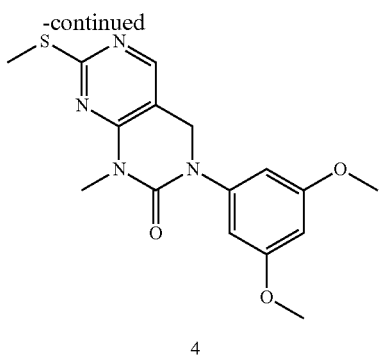

4

To a mixture of 5-((3,5-dimethoxyphenylamino)methyl)-N-methyl-2-(methylthio)pyrimidin-4-amine (1.1 g, 3.43 mmol) and N-ethyl-N-isopropylpropan-2-amine (1.33 g, 10.30 mmol) in 10 mL of THF was added a solution of triphosgene (357 mg, 1.20 mmol) in 5 mL of THF at 0° C., and stirred for 1 h. The reaction mixture was then warmed to RT and stirred for another 5 h.

LCMS showed the reaction was completed. The reaction mixture was quenched by water and extracted with ethyl acetate (3×15 mL). The organic layers were separated, combined, washed with saturated aqueous solution of sodium bicarbonate and brine, dried over sodium sulfate, filtered and concentrated to afford the title compound (crude 1.1 g, 92%) as a white solid, which was directly used in the next step without further purification. MS (ES+) $C_{16}H_{18}N_4O_3S$ requires: 346, found: 347 [M+H]$^+$.

Synthesis of 3-(3,5-dimethoxyphenyl)-1-methyl-7-(methylsulfonyl)-3,4-dihydropyrimido[4,5-d]pyrimidin-2(1H)-one To a solution of 3-(3,5-dimethoxyphenyl)-1-methyl-7-(methylthio)-3,4-dihydropyrimido[4,5-d]pyrimidin-2(1H)-one (1.0 g, 2.89 mmol) in 20 mL of dichloromethane was added 3-chlorobenzoperoxoic acid (1.50 g, 8.66 mmol) at 0° C., and the solution was stirred for 0.5 h at 0° C. The mixture was warmed to RT and stirred overnight. LCMS showed the reaction was completed. The reaction mixture was diluted with 30 mL of dichloromethane, washed with saturated aqueous solution of sodium bicarbonate and brine, dried over sodium sulfate, filtered and concentrated to afford the title compound (800 mg, 73%) as a yellow solid, which was directly used in the next step without further purification. MS (ES+) $C_{16}H_{18}N_4O_5S$ requires: 378, found: 379 [M+H]$^+$.

Synthesis of 3-(2,6-dichloro-3,5-dimethoxyphenyl)-1-methyl-7-(methylsulfonyl)-3,4-dihydropyrimido[4,5-d]pyrimidin-2(1H)-one

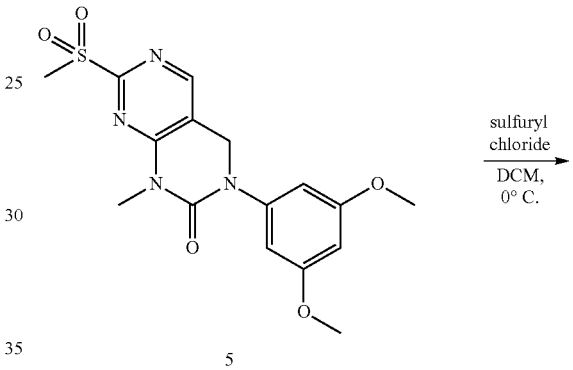

5

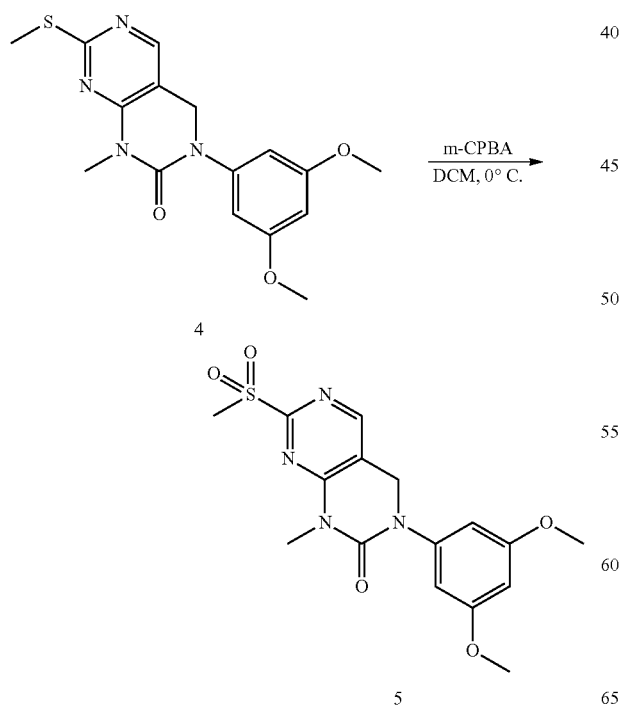

To a solution of 3-(3,5-dimethoxyphenyl)-1-methyl-7-(methylsulfonyl)-3,4-dihydropyrimido[4,5-d]pyrimidin-2(1H)-one (400 mg, 1.06 mmol) in 15 mL of dichloromethane was added sulfuryl chloride (285 mg, 2.12 mmol) at 0° C., and then stirred at 0° C. for 3 h. LCMS showed the reaction was completed. The reaction mixture was diluted with 20 mL of dichloromethane, washed with water and brine, dried over sodium sulfate, filtered and concentrated to afford the title compound (450 mg, 96%) as a yellow solid, which was directly used in the next step without further purification. MS (ES+) $C_{16}H_{16}Cl_2N_4O_5S$ requires: 446, 448, found: 447, 449 [M+H]$^+$.

Synthesis of 3-(2,6-dichloro-3,5-dimethoxyphenyl)-1-methyl-7-(2-methyl-6-nitrophenylamino)-3,4-dihydropyrimido[4,5-d]pyrimidin-2(1H)-one Synthesis of (7-(2-amino-6-methylphenylamino)-3-(2,6-dichloro-3,5-dimethoxyphenyl)-1-methyl-3,4-dihydropyrimido[4,5-d]pyrimidin-2(1H)-one

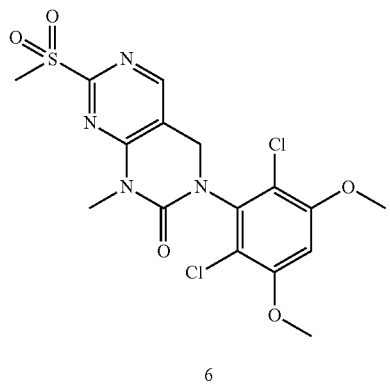

6

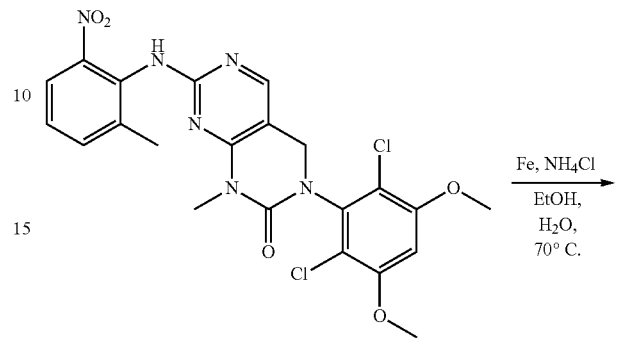

8

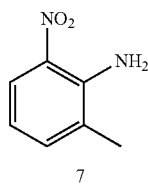

7

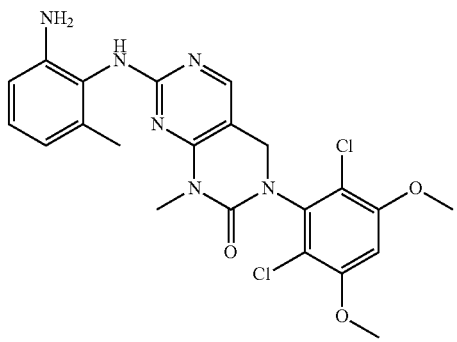

9

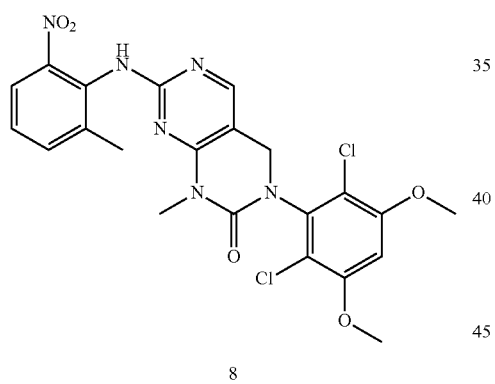

8

To a mixture of 3-(2,6-dichloro-3,5-dimethoxyphenyl)-1-methyl-7-(methylsulfonyl)-3,4-dihydropyrimido[4,5-d]pyrimidin-2(1H)-one (450 mg, 1.01 mmol) and 2-methyl-6-nitroaniline (230 mg, 1.51 mmol) in 5 mL of N,N-dimethylformamide was added potassium tert-butanolate (339 mg, 3.02 mmol) at RT and stirred for 0.5 h. LCMS showed the reaction was completed. The mixture was quenched by 80 mL of water, and the precipitate was collected via the filtration and dried to give the title compound (290 mg, 56%) as a yellow solid, which was directly used in the next step without further purification. MS (ES+) $C_{22}H_{20}Cl_2N_6O_5$ requires: 518, 520, found: 519, 521 $[M+H]^+$.

A mixture of 3-(2,6-dichloro-3,5-dimethoxyphenyl)-1-methyl-7-(2-methyl-6-nitrophenylamino)-3,4-dihydropyrimido[4,5-d]pyrimidin-2(1H)-one (290 mg, 0.56 mmol) in ethanol (10 mL) and water (2 mL) was stirred at 70° C. for 20 mins before iron powder (320 mg, 5.60 mmol) and ammonium chloride (250 mg, 2.79 mmol) were added. The reaction mixture was stirred at 70° C. for another 6 h. LCMS showed the reaction was completed. The solid was filtered off, and the filtrate was concentrated. The residue was dissolved by ethyl acetate (30 mL), washed with water and brine, dried over sodium sulfate, filtered and concentrated. The residue was purified by Prep-HPLC to give the title compound (27 mg, 10%) as a white solid. MS (ES+) $C_{22}H_{22}C_2N_6O_3$ requires: 488, 490, found: 489, 491 $[M+H]^+$. $^1$H-NMR (500 MHz, CDCl$_3$) δ ppm 7.89 (s, 1H), 7.04 (t, 1H, J=8.0 Hz), 6.69 (d, 2H, J=7.5 Hz), 6.60 (s, 1H), 4.53 (s, 2H), 3.94 (s, 6H), 3.34 (s, 3H), 2.24 (s, 3H).

77

Synthesis of N-(2-((6-(2,6-dichloro-3,5-dimethoxyphenyl)-8-methyl-7-oxo-5,6,7,8-tetrahydropyrimido[4,5-d]pyrimidin-2-yl)amino)-3-methylphenyl)acrylamide

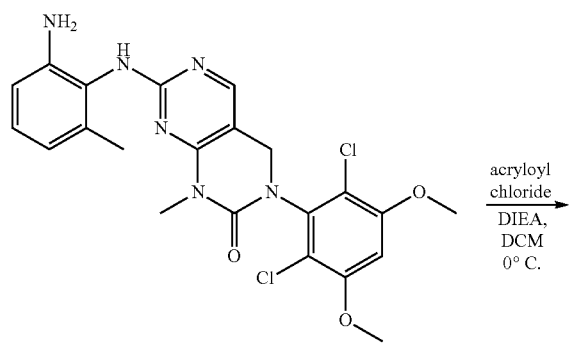

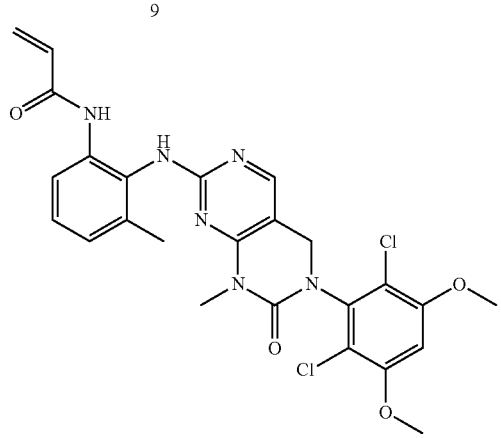

9

N-(2-((6-(2,6-dichloro-3,5-dimethoxyphenyl)-8-methyl-7-oxo-5,6,7,8-tetrahydropyrimido[4,5-d]pyrimidin-2-yl)amino)-3-methylphenyl)acrylamide was prepared using the procedure similar to COMPOUND 30. The product was purified by flash chromatography using 0-10% MeOH/DCM gradient to give the title compound. MS (ES+) $C_{25}H_{24}Cl_2N_6O_4$ requires: 542, found: 543 [M+H]$^+$. H-NMR (400 MHz, DMSO-$d_6$) δ 9.48 (s, 1H), 8.35 (s, 1H), 7.99 (s, 1H), 7.66 (s, 1H), 7.16 (t, J=7.8 Hz, 1H), 7.10-7.06 (m, 1H), 6.99 (s, 1H), 6.53 (dd, J=17.0, 10.2 Hz, 1H), 6.22 (dd, J=16.9, 2.1 Hz, 1H), 5.71 (dd, J=10.2, 2.0 Hz, 1H), 4.48 (s, 2H), 3.96 (s, 6H), 3.44 (s, 3H), 2.17 (s, 3H).

Example 7: Syntheses of Compound 24 and Compound 6

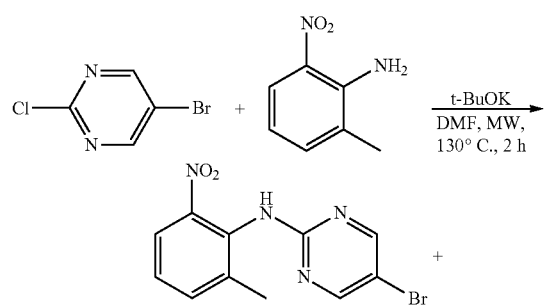

78

-continued

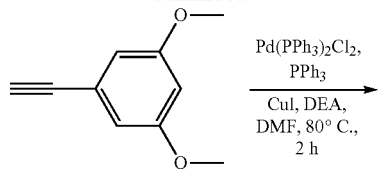

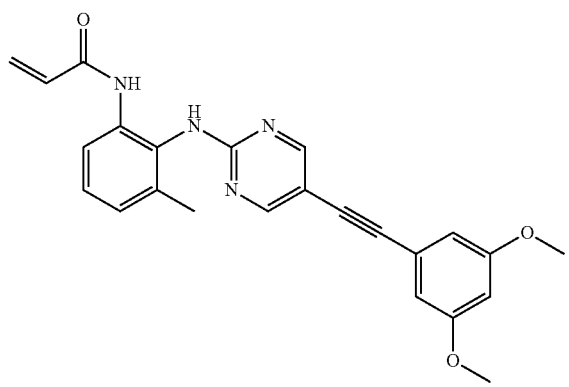

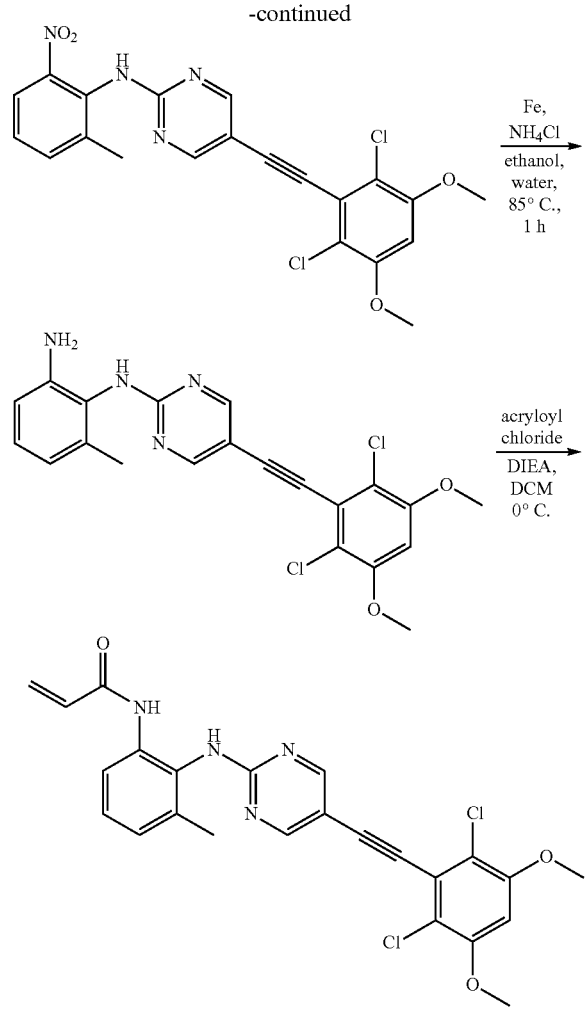

Synthesis of 5-bromo-N-(2-methyl-6-nitrophenyl)pyrimidin-2-amine

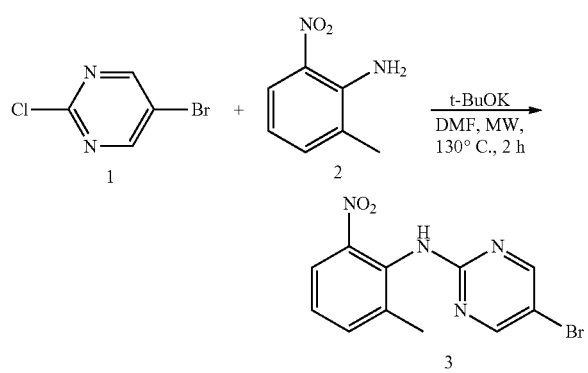

To a solution of 5-bromo-2-chloropyrimidine (1.5 g, 7.89 mmol) and 2-methyl-6-nitroaniline (800 mg, 5.26 mmol) in N,N-dimethylformamide (10 mL) in a sealed tube was added potassium tert-butoxide (1.76 g, 15.78 mmol), and the mixture was heated under microwave at 130° C. for 2 hrs. LCMS showed the reaction was completed. The reaction was cooled to RT, quenched with water (20 mL) and extracted with ethyl acetate (3×100 mL). The organic layers were separated, combined, washed with water (50 mL) and brine (100 mL), dried over sodium sulfate, filtered, and concentrated. The residue was purified by silica gel chromatography (petroleum ether:ethyl acetate=10:1) to afford the title compound as a yellow solid (500 mg, 31%). MS (ES+) $C_{11}H_9BrN_4O_2$ requires: 309, 311, found: 310, 312 [M+H]$^+$.

Synthesis of 5-((3,5-dimethoxyphenyl)ethynyl)-N-(2-methyl-6-nitrophenyl)pyrimidin-2-amine

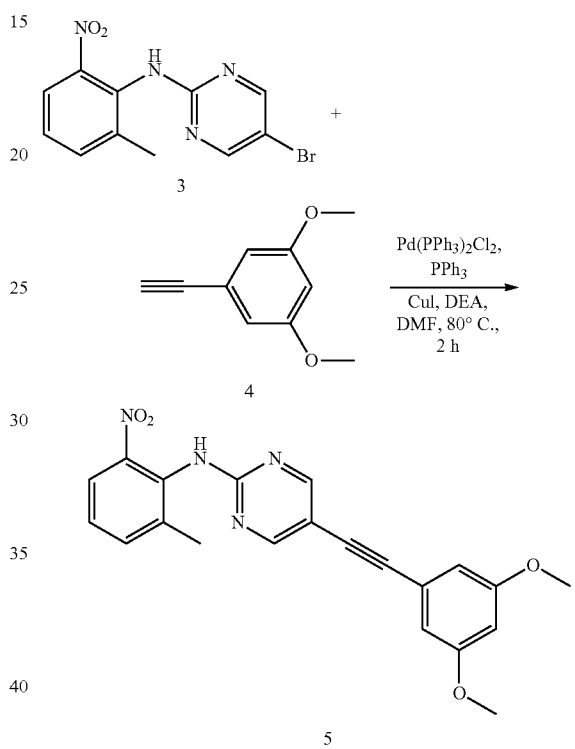

A mixture of 5-bromo-N-(2-methyl-6-nitrophenyl)pyrimidin-2-amine (573 mg, 3.0 mmol), 1-ethynyl-3,5-dimethoxybenzene (483 mg, 3.0 mmol), triphenylphosphine (157 mg, 0.60 mmol), bis(triphenylphosphine)palladium(II) chloride (210 mg, 0.30 mmol), copper(I) iodide (57 mg, 0.30 mmol) and diethylamine (1.50 ml, 15.0 mmol) in N,N-dimethylformamide (10 mL) was degassed with nitrogen three times, and then stirred at 80° C. for 2 hrs. LCMS showed the reaction was completed. The mixture was cooled to RT, quenched with water (20 mL) and extracted with ethyl acetate (3×80 mL). The combined organic layers were separated, washed with water and brine, dried over sodium sulfate, filtered and concentrated. The residue was purified by silica gel chromatography (petroleum ether:ethyl acetate=4:1) to afford the title compound as a yellow solid (460 mg, 39%). MS (ES+) $C_{21}H_{18}N_4O_4$ requires: 390, found: 391 [M+H]$^+$.

Synthesis of N¹-(5-((3,5-dimethoxyphenyl)ethynyl)
pyrimidin-2-yl)-6-methylbenzene-1,2-diamine

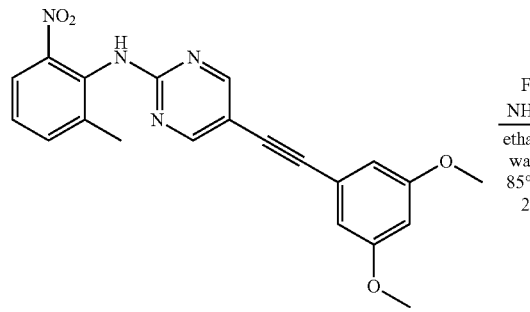

5

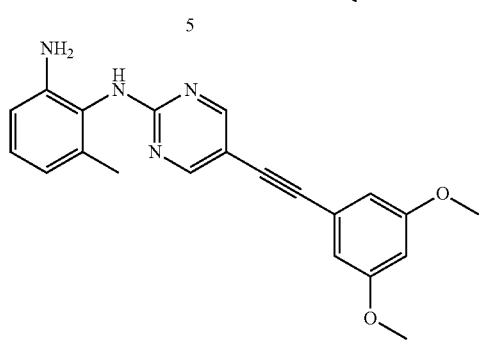

6

A mixture of 5-((3,5-dimethoxyphenyl)ethynyl)-N-(2-methyl-6-nitrophenyl)pyrimidin-2-amine (150 mg, 0.38 mmol), Iron (171 mg, 3.04 mmol) and ammonium chloride (246 mg, 4.56 mmol) in ethanol (20 mL) and water (2 mL) was stirred at 85° C. for 1 h. LCMS showed the reaction was completed. The reaction was cooled to RT, and the solid was filtered off. The filtrate was concentrated, and the residue was purified by Prep-HPLC to afford the title compound as a white solid (55 mg, 44%). MS (ES+) $C_{21}H_{20}N_4O_2$ requires: 360, found: 361 [M+H]⁺. ¹H-NMR (500 MHz, DMSO-$d_6$) c ppm 8.76 (s, 1H), 8.50-8.46 (br, 2H), 6.88 (t, 1H, J=7.0 Hz), 6.66 (s, 2H), 6.57 (d, 1H, J=7.5 Hz), 6.54 (s, 1H), 6.44 (d, 1H, J=6.5 Hz), 4.74 (s, 2H), 3.76 (s, 6H), 2.01 (s, 3H).

Synthesis of N-(2-((5-((3,5-dimethoxyphenyl)ethynyl)pyrimidin-2-yl)amino)-3-methylphenyl) acrylamide

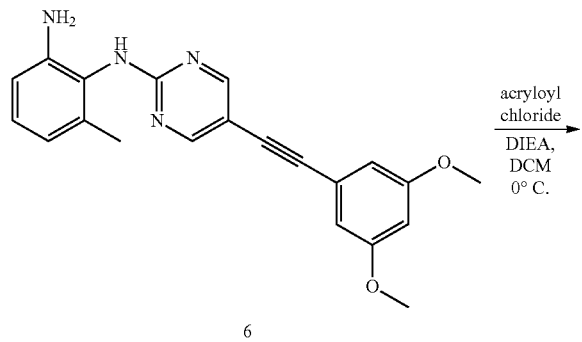

6

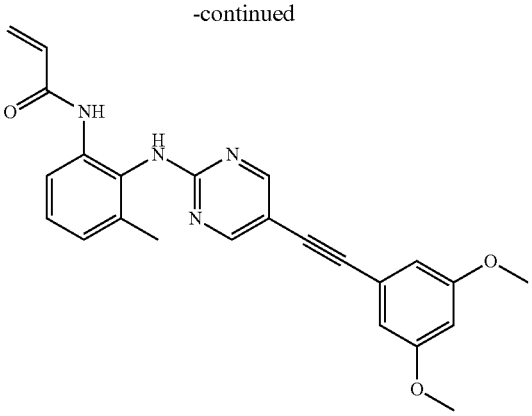

N¹-(5-((3,5-dimethoxyphenyl)ethynyl)pyrimidin-2-yl)-6-methylbenzene-1,2-diamine was prepared using the procedure similar to COMPOUND 30. The product was purified by flash chromatography using 0-100% EtOAc/Hexanes gradient to give the title compound. MS (ES+) $C_{24}H_{22}N_4O_3$ requires: 414, found: 415 [M+H]⁺. ¹H-NMR (400 MHz, DMSO-$d_6$) δ ppm 9.60-9.38 (m, 1H), 8.79 (s, 1H), 8.51 (s, 2H), 7.69 (d, J=8.1 Hz, 1H), 7.19 (t, J=7.8 Hz, 1H), 7.15-7.06 (m, 1H), 6.67 (d, J=2.3 Hz, 2H), 6.60-6.45 (m, 2H), 6.22 (dd, J=17.0, 2.1 Hz, 1H), 5.71 (dd, J=10.2, 2.1 Hz, 1H), 3.76 (s, 6H), 2.12 (s, 3H).

Synthesis of 5-((2,6-dichloro-3,5-dimethoxyphenyl)ethynyl)-N-(2-methyl-6-nitrophenyl)pyrimidin-2-amine

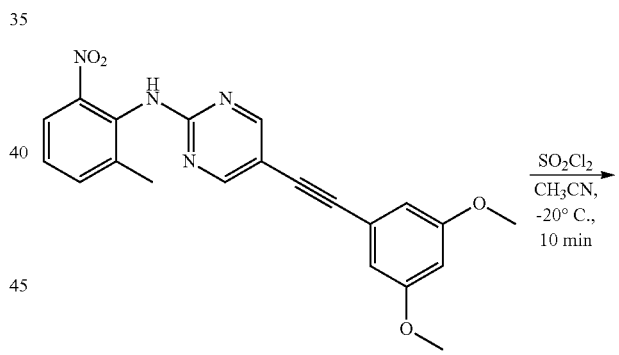

5

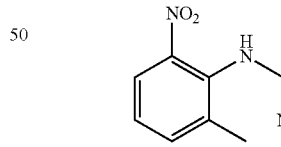

7

To a solution of 5-((3,5-dimethoxyphenyl)ethynyl)-N-(2-methyl-6-nitrophenyl)pyrimidin-2-amine (50 mg, 0.13 mmol) in acetonitrile (5 mL) was dropwise added sulfuryl chloride (44 mg, 0.33 mmol) at −20° C., and the mixture was stirred for another 10 mins. LCMS showed the reaction was completed, and the reaction was quenched with water (0.5 mL). The solvents were evaporated, and the residue was purified by Prep-HPLC to afford the title compound as a yellow solid (30 mg, 50%). (MS (ES+) $C_{21}H_{16}Cl_2N_4O_4$ requires: 459, 461, found: 460, 462 [M+H]$^+$.

Synthesis of $N^1$-(5-((2,6-dichloro-3,5-dimethoxyphenyl)ethynyl)pyrimidin-2-yl)-6-methylbenzene-1,2-diamine

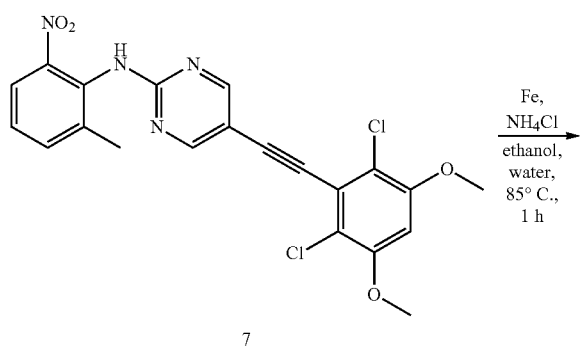

A mixture of 5-((2,6-dichloro-3,5-dimethoxyphenyl)ethynyl)-N-(2-methyl-6-nitrophenyl)pyrimidin-2-amine (150 mg, 0.33 mmol), Iron (147 mg, 2.64 mmol) and ammonium chloride (214 mg, 3.96 mmol) in ethanol (20 mL) and water (2 mL) was stirred at 85° C. for 1 h. LCMS showed the reaction was completed. The reaction was cooled to RT, and the solid was filtered off. The filtrate was concentrated, and the residue was purified by Prep-HPLC to afford the title compound as a white solid (58 mg, 35%). MS (ES+) $C_{21}H_{18}Cl_2N_4O_2$ requires: 429, 431, found: 430, 432 [M+H]$^+$. $^1$H-NMR (400 MHz, DMSO-d$_6$) δ ppm 8.90 (s, 1H), 8.55-8.44 (br, 2H), 6.97 (s, 1H), 6.89-6.86 (m, 1H), 6.57 (d, 1H, J=7.6 Hz), 6.44 (d, 1H, J=7.6 Hz), 4.75 (s, 2H), 3.94 (s, 6H), 2.01 (s, 3H).

Synthesis of N-(2-((5-((2,6-dichloro-3,5-dimethoxyphenyl)ethynyl)pyrimidin-2-yl)amino)-3-methylphenyl)acrylamide

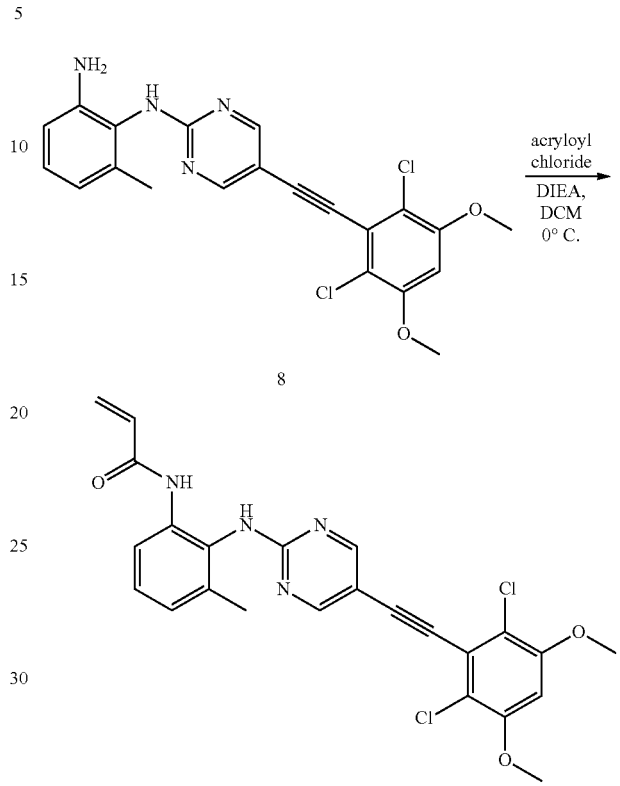

N-(2-((5-((2,6-dichloro-3,5-dimethoxyphenyl)ethynyl)pyrimidin-2-yl)amino)-3-methylphenyl)acrylamide was prepared using the procedure similar to COMPOUND 30. The product was purified by flash chromatography using 0-100% EtOAc/Hexanes gradient to give the title compound. MS (ES+) $C_{24}H_{20}Cl_2N_4O_3$ requires: 482, found: 483 [M+H]$^+$. $^1$H-NMR (400 MHz, DMSO-d$_6$) δ ppm 9.47 (s, 1H), 8.93 (s, 1H), 8.54 (s, 2H), 7.71 (d, J=8.1 Hz, 1H), 7.19 (t, J=7.8 Hz, 1H), 7.09 (d, J=7.4 Hz, 1H), 6.98 (s, 1H), 6.53 (dd, J=17.0, 10.2 Hz, 1H), 6.22 (dd, J=17.0, 2.1 Hz, 1H), 5.70 (dd, J=10.2, 2.1 Hz, 1H), 3.94 (s, 6H), 2.13 (s, 3H).

Example 8: Synthesis of Compound 40

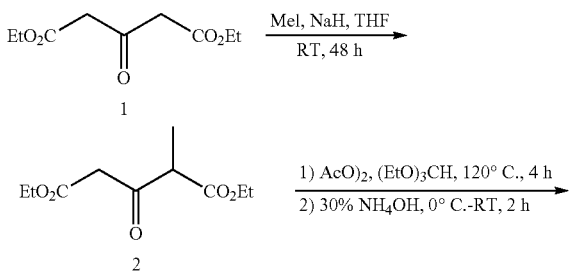

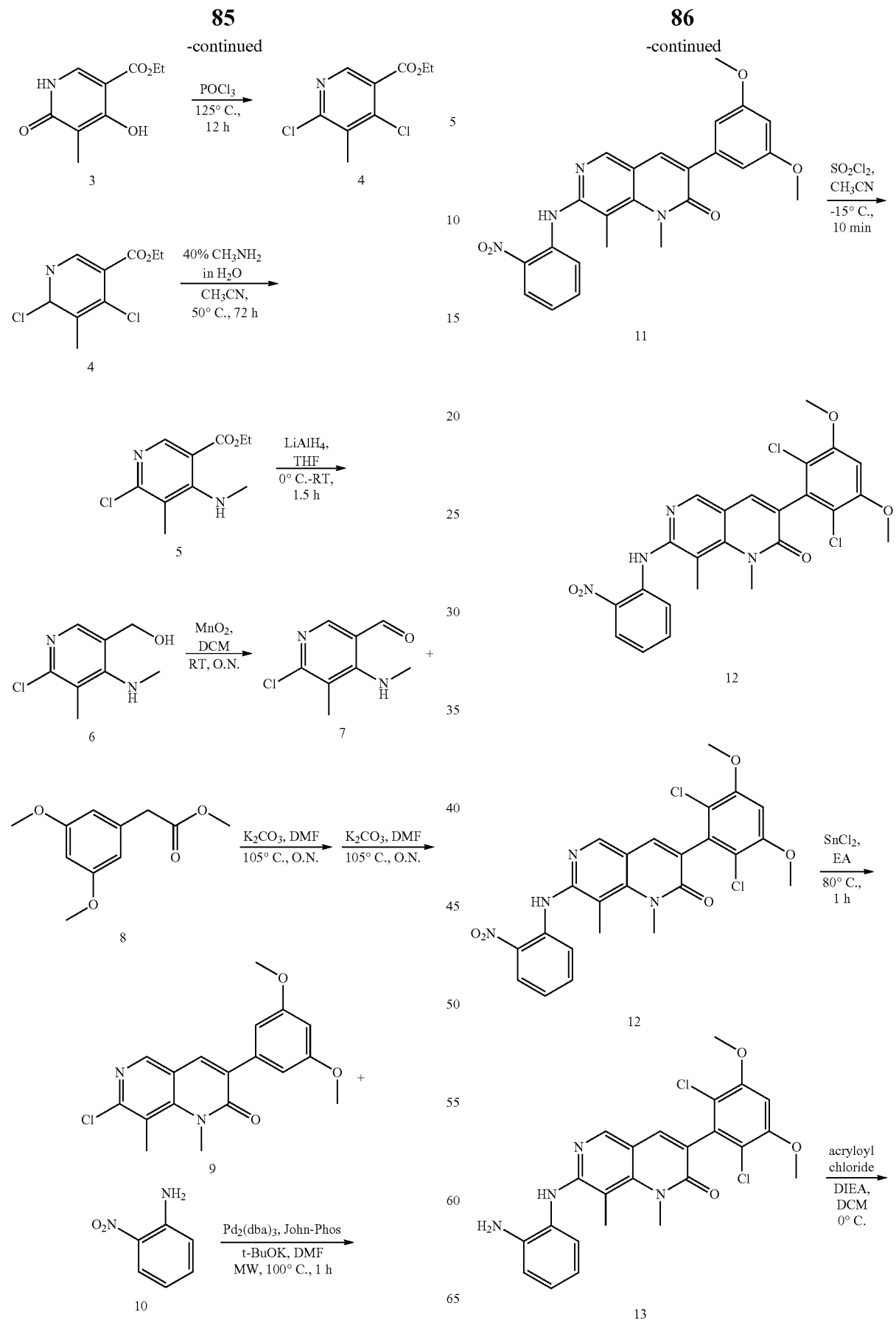

-continued

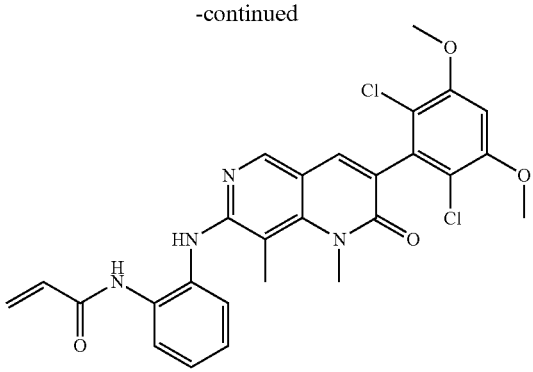

Synthesis of diethyl 2-methyl-3-oxopentanedioate

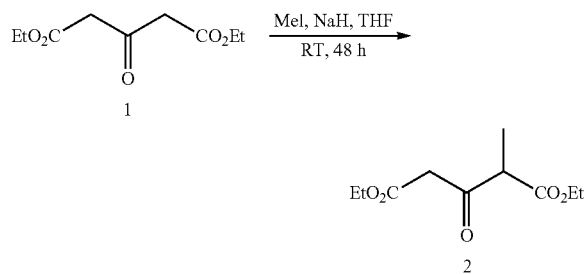

To a solution of diethyl 3-oxopentanedioate (23.2 g, 114.8 mmol) in tetrahydrofuran (100 mL) was added sodium hydride (60%, 4.8 g, 120.5 mmol) at 0° C., and the reaction mixture was stirred at RT for 30 mins, followed by the addition of iodomethane (7.15 ml, 114.8 mmol). The reaction mixture was stirred at RT for 48 h, quenched with water (500 mL) and extracted with ethyl acetate (500 mL×3). The organic layers were separated, combined, washed with water (200 mL) and brine (200 mL), dried over sodium sulfate, filtered and concentrated. The residue was purified by silica gel column (petroleum ether: ethyl acetate=20:1) to get the title compound as a colorless oil (9 g, 36%). MS (ES+) $C_{10}H_{16}O_5$ requires: 216, found: 217 $[M+H]^+$.

Synthesis of ethyl 4-hydroxy-5-methyl-6-oxo-1,6-dihydropyridine-3-carboxylate

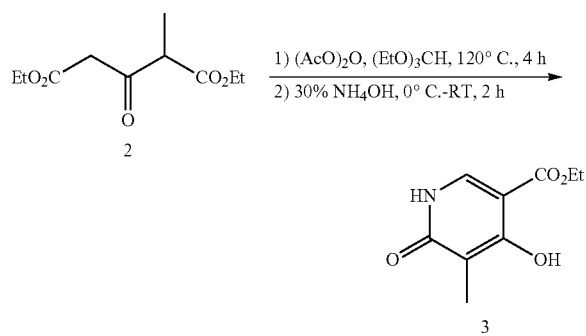

To a solution of diethyl 2-methyl-3-oxopentanedioate (10 g, 46.25 mmol) in 1,1'-trioxidanediyldipropan-1-one (400 mL) was added triethoxymethane (38 mL, 231.25 mmol), and the mixture was heated at 120° C. for 4 h, followed by the addition of 30% ammonia (600 mL) at 0° C. The reaction mixture was stirred at RT for another 2 h. LCMS monitored the reaction was completed. The precipitate was collected via filtration and dissolved in dichloromethane (400 mL). The solid was filtered off, and the filtrate was concentrated to get the title compound (5.5 g, crude) as a yellow solid. MS (ES+) $C_9H_{11}NO_4$ requires: 197, found: 198 $[M+H]^+$.

Synthesis of ethyl 4,6-dichloro-5-methylnicotinate

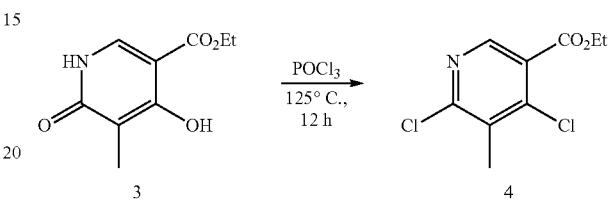

A solution of ethyl 4-hydroxy-5-methyl-6-oxo-1,6-dihydropyridine-3-carboxylate (5.0 g, 21.4 mmol) in phosphoryl trichloride (100 mL) was refluxed at 125° C. for 12 h. LCMS monitored the reaction was completed. Most of phosphoryl trichloride was evaporated, and the residue was dropwise added to ice-water (100 mL). The resulting mixture was neutralized with aq. sodium carbonate (50 mL) and extracted with ethyl acetate (200 mL). The organic layer was separated, combined, washed with water and brine, dried over sodium sulfate, filtered and concentrated. The residue was purified by silica gel column (petroleum ether: ethyl acetate=15:1) to get the title compound (1.6 g, 32%) as a yellow oil. MS (ES+) $C_9H_9Cl_2NO_2$ requires: 232, 234, found: 233, 235 $[M+H]^+$.

Synthesis of ethyl 6-chloro-5-methyl-4-(methylamino)nicotinate

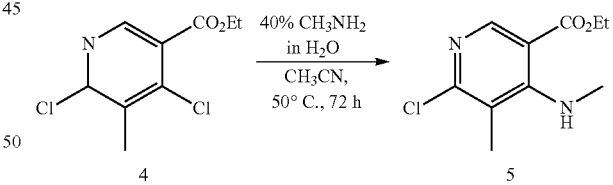

To a solution of ethyl 4,6-dichloro-5-methylnicotinate (2.6 g, 11.1 mmol) in acetonitrile (60 mL) was added dropwise 40% methylamine in water (689 mg, 22.2 mmol, 60 mL), and the mixture was stirred at 50° C. for 72 h. LCMS monitored the reaction was completed. The reaction mixture was concentrated and extracted with ethyl acetate (100 mL). The organic layer was separated, combined, washed with water and brine, dried over sodium sulfate, filtered and concentrated.

The residue was purified by silica gel column (petroleum ether: ethyl acetate=2:1) to get the title compound (2.05 g, 81%) as a colorless oil. MS (ES+) $C_{10}H_{13}ClN_2O_2$ requires: 228, 230, found: 229, 231 $[M+H]^+$.

Synthesis of (6-chloro-5-methyl-4-(methylamino)pyridin-3-yl)methanol

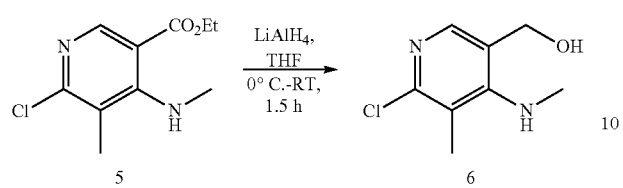

To a solution of ethyl 6-chloro-5-methyl-4-(methylamino)nicotinate (2.0 g, 8.8 mmol) in tetrahydrofuran (60 mL) was added lithium aluminium hydride at 0° C., and the mixture was stirred at RT for 1.5 h. LCMS monitored the reaction was completed. The reaction was quenched by sodium sulfate decahydrate (1.5 g) and filtrated. The filtrate was concentrated to get the title compound (1.4 g, crude) as a white solid. MS (ES+) $C_8H_{11}ClN_2O$ requires: 186, 188, found: 187, 189 $[M+H]^+$.

Synthesis of 6-chloro-5-methyl-4-(methylamino)nicotinaldehyde

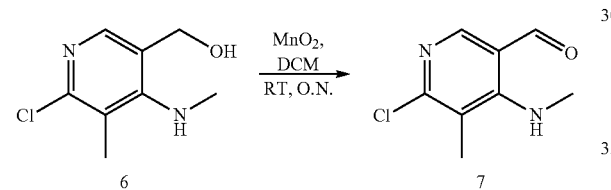

A mixture of (6-chloro-5-methyl-4-(methylamino)pyridin-3-yl)methanol (1.4 g, 8.0 mmol) and manganese oxide (2.8 g, 32 mmol) in dichloromethane (100 mL) was stirred at RT for 4 h. LCMS monitored the reaction was completed. The solid was filtered off, and the filtrate was concentrated to get the title compound (1.2 g, crude) as a yellow oil. MS (ES+) $C_8H_9ClN_2O$ requires: 184, 186, found: 185, 187 $[M+H]^+$.

Synthesis of 7-chloro-3-(3,5-dimethoxyphenyl)-1,8-dimethyl-1,6-naphthyridin-2(1H)-one

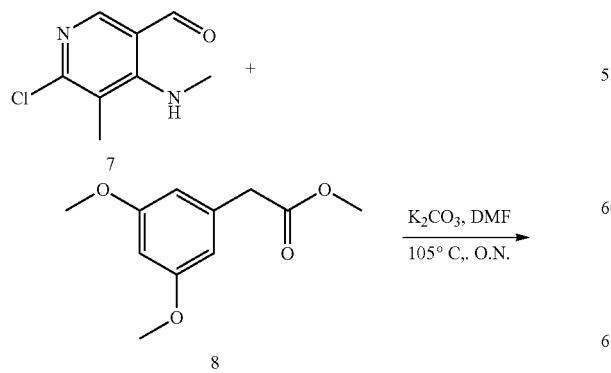

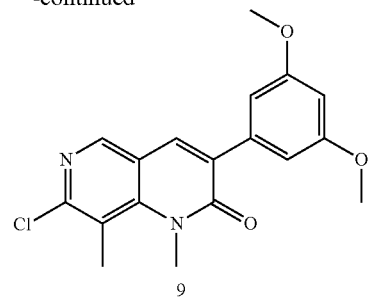

A mixture of 6-chloro-5-methyl-4-(methylamino)nicotinaldehyde (3.11 g, 16.8 mmol), methyl 2-(3,5-dimethoxyphenyl)acetate (4.25 g, 20.2 mmol) and potassium carbonate (2.8 g, 20.3 mmol) in N,N-dimethylformamide (100 mL) was stirred at 105° C. overnight. LCMS monitored the reaction was completed. The reaction mixture was cooled to RT and quenched by water. The precipitate was filtered and dried to get the title compound (5.5 g, crude) as a yellow solid. MS (ES+) $C_{18}H_{17}ClN_2O_3$ requires: 344, 346, found: 345, 347 $[M+H]^+$.

Synthesis of 3-(3,5-dimethoxyphenyl)-1,8-dimethyl-7-(2-nitrophenylamino)-1,6-naphthyridin-2(1H)-one

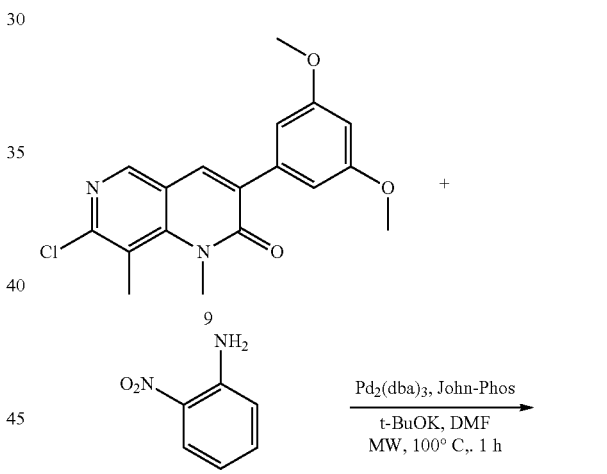

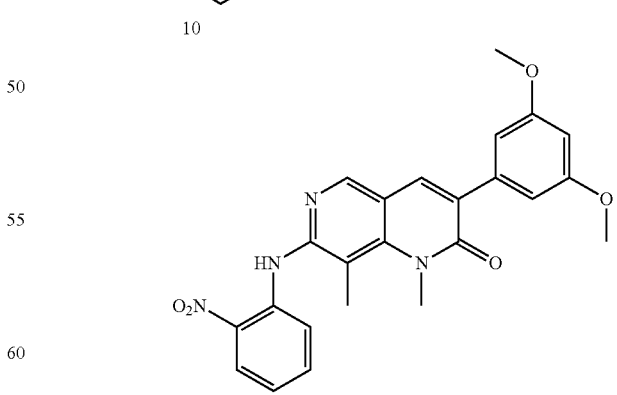

A mixture of 7-chloro-3-(3,5-dimethoxyphenyl)-1,8-dimethyl-1,6-naphthyridin-2(1H)-one (800 mg, 2.32 mmol), 2-nitrobenzenamine (320 mg, 2.32 mmol), $Pd_2(dba)_3$ (100 mg), John-Phos (100 mg) and potassium tert-butanolate (480 mg, 4.64 mmol) in N,N-dimethylformamide (10 mL) was heated in sealed tube at 100° C. under microwave for 1 h. LCMS monitored the reaction was completed. The mixture was concentrated and purified by Prep-HPLC to get the title compound (150 mg, 15%) as a brown solid. MS (ES+) $C_{24}H_{22}N_4O_5$ requires: 446, found: 447 $[M+H]^+$.

Synthesis of 3-(2,6-dichloro-3,5-dimethoxyphenyl)-1,8-dimethyl-7-(2-nitrophenylamino)-1,6-naphthyridin-2(1H)-one Synthesis of 7-(2-aminophenylamino)-3-(2,6-dichloro-3,5-dimethoxyphenyl)-1,8-dimethyl-1,6-naphthyridin-2(1H)-one

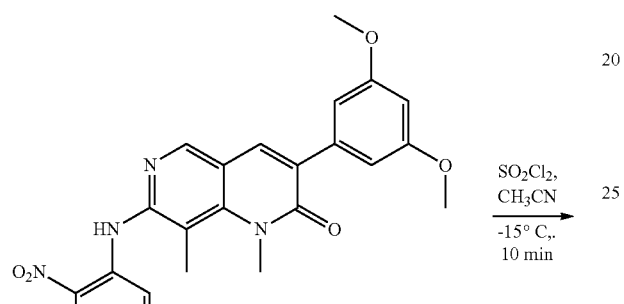

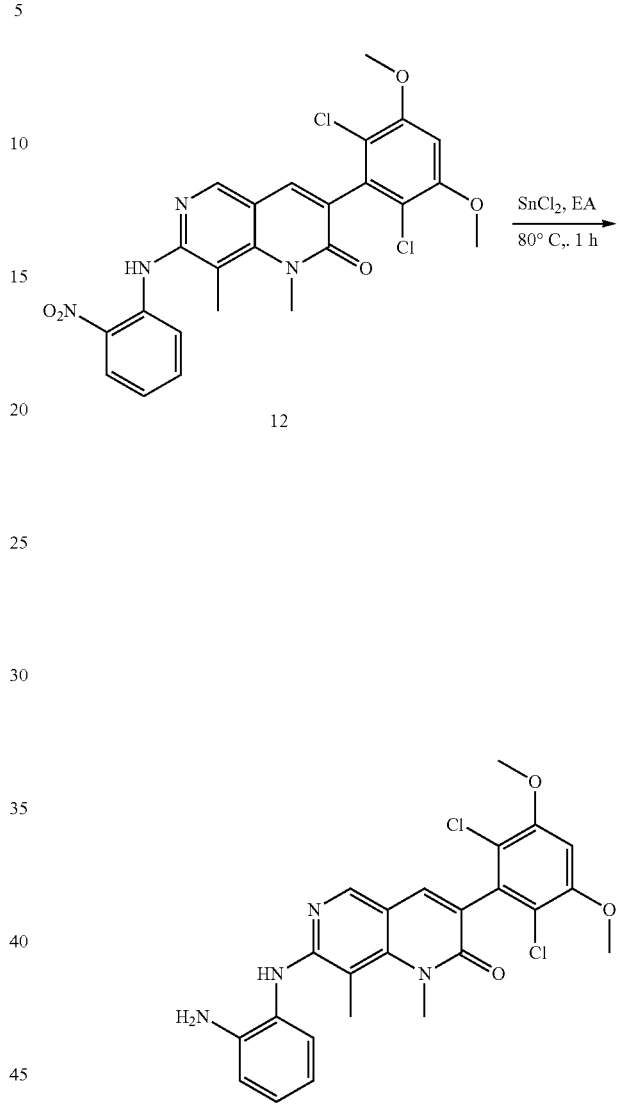

To a solution of 3-(3,5-dimethoxyphenyl)-1,8-dimethyl-7-(2-nitrophenylamino)-1,6-naphthyridin-2(1H)-one (120 mg, 0.27 mmol) in acetonitrile (120 mL) was added sulfuryl chloride (185 mg, 1.35 mmol) at −15 OC, and the mixture was stirred at −15 OC for 10 mins. LCMS monitored the reaction was completed. The reaction mixture was quenched with water (1 mL) and concentrated. The precipitate was collected via filtration, washed by acetone/petroleum ether (1:5) and dried to give the title compound (100 mg, 72%) as a white solid. MS (ES+) $C_{24}H_{20}Cl_2N_4O_5$ requires: 514, 516, found: 515, 517 $[M+H]^+$.

To a solution of 3-(2,6-dichloro-3,5-dimethoxyphenyl)-1,8-dimethyl-7-(2-nitrophenylamino)-1,6-naphthyridin-2(1H)-one (100 mg, 0.2 mmol) in ethyl acetate (20 mL) was added stannous chloride (150 mg, 0.8 mmol), and the mixture was stirred at 80° C. for 1 h. LCMS monitored the reaction was completed. The solid was filtered off, and the filtrate was concentrated. The residue was purified by Prep-HPLC to get the title compound (38.6 mg, 41%) as a yellow solid. MS (ES+) $C_{24}H_{22}Cl_2N_4O_3$ requires: 484, 486, found: 485, 487 $[M+H]^+$; $^1$H-NMR (500 MHz, DMSO-$d_6$) δ ppm 8.24 (s, 1H), 7.76 (s, 1H), 7.67 (s, 1H), 7.03 (d, 1H, J=7.5 Hz), 6.97 (s, 1H), 6.92-6.89 (m, 1H), 6.75-6.73 (m, 1H), 6.57-6.54 (m, 1H), 4.77 (s, 2H), 3.95 (s, 6H), 3.66 (s, 3H), 2.43 (s, 3H).

Synthesis of N-(2-((3-(2,6-dichloro-3,5-dimethoxy-phenyl)-1,8-dimethyl-2-oxo-1,2-dihydro-1,6-naphthyridin-7-yl)amino)phenyl)acrylamide

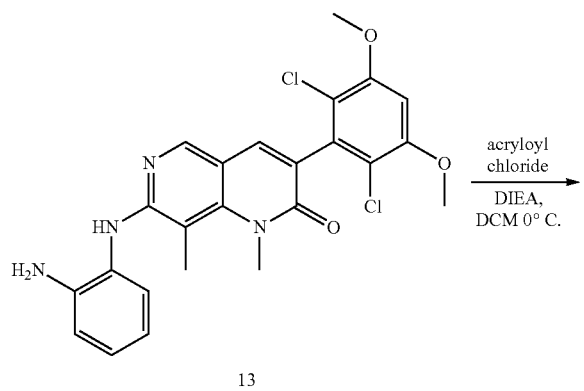

13

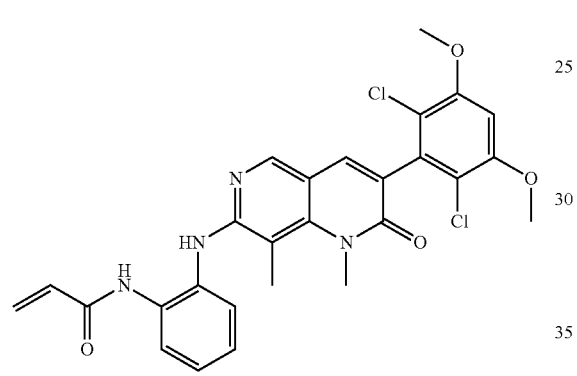

N-(2-((3-(2,6-dichloro-3,5-dimethoxyphenyl)-1,8-dimethyl-2-oxo-1,2-dihydro-1,6-naphthyridin-7-yl)amino)phenyl)acrylamide was prepared using the procedure similar to COMPOUND 30.

The product was purified by preparative thin layer chromatography using 0-5% MeOH/DCM gradient to give the title compound. MS (ES+) $C_{27}H_{24}Cl_2N_4O_4$ requires: 538, found: 539 [M+H]$^+$.

Example 9: Synthesis of Compound 42

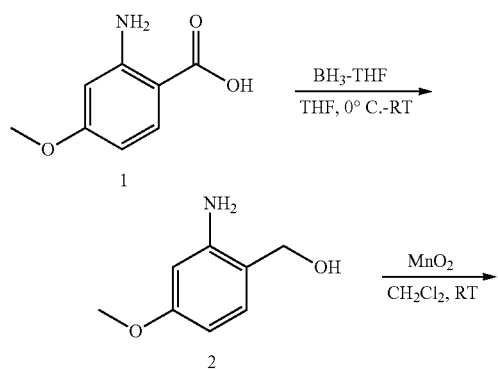

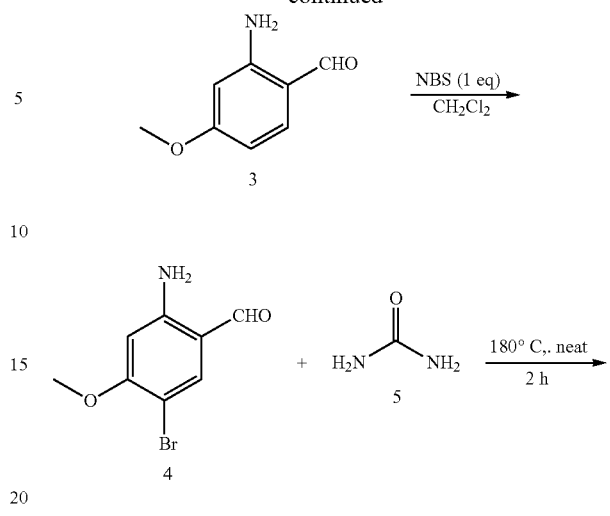

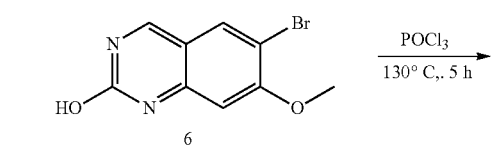

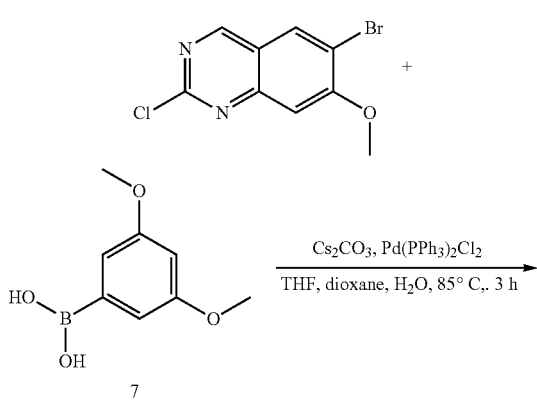

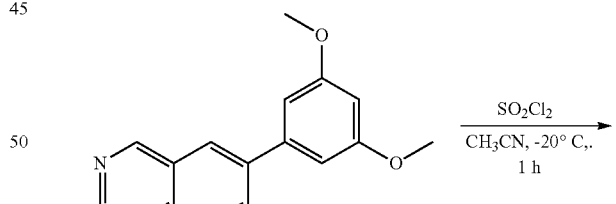

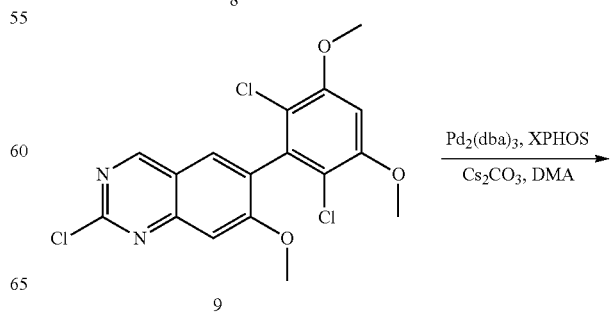

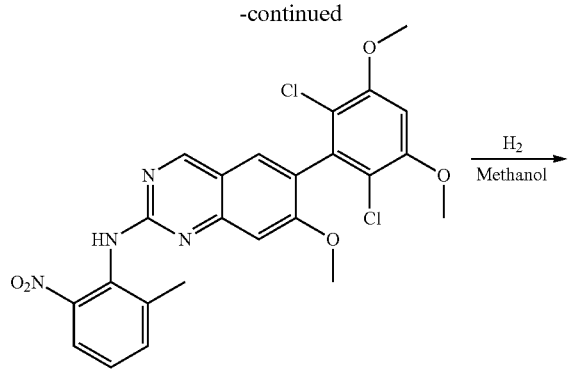

10

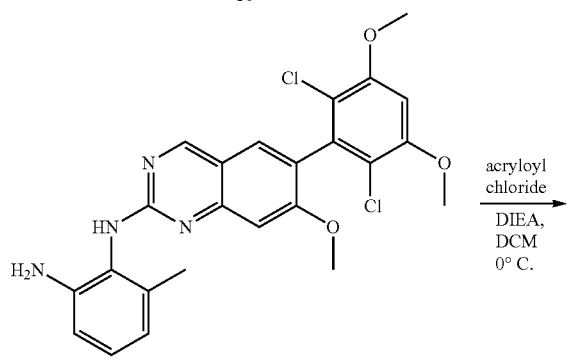

11

Synthesis of (2-amino-4-methoxyphenyl)methanol

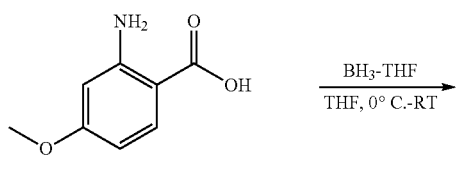

To a solution of 2-amino-4-methoxybenzoic acid (15.0 g, 89.8 mmol) in THF (300 mL) was added borohydride in THF (450 mL, 450 mmol) at 0° C., and the reaction mixture was stirred at RT overnight. LCMS showed the reaction was completed. The reaction was quenched with water (150 mL) and extracted with ethyl acetate (500 mL×3). The organic layers were separated, combined, washed with water (200 mL) and brine (200 mL), dried over sodium sulfate, filtered and concentrated to afford the title compound. MS (ES+) $C_8H_{11}NO_2$ requires: 153, found: 154 $[M+H]^+$.

Synthesis of 2-amino-4-methoxybenzaldehyde

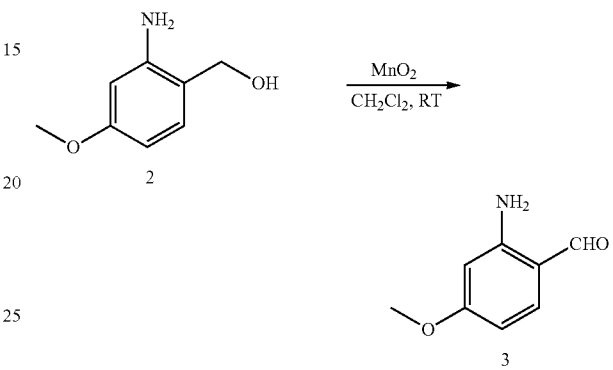

A mixture of (2-amino-4-methoxyphenyl)methanol (20 g, 131.0 mmol) and manganese oxide (68 g, 786.0 mmol) in dichloromethane (300 mL) was stirred at RT overnight. LCMS showed the reaction was completed. The solid was filtered off, and the filtrate was concentrated. The residue was purified by silica gel chromatography (petroleum ether: ethyl acetate=6:1) to give the title compound (7 g, 35%) as a yellow solid. MS (ES+) $C_8H_9NO_2$ requires: 151, found: 152 $[M+H]^+$.

Synthesis of 2-amino-5-bromo-4-methoxybenzaldehyde

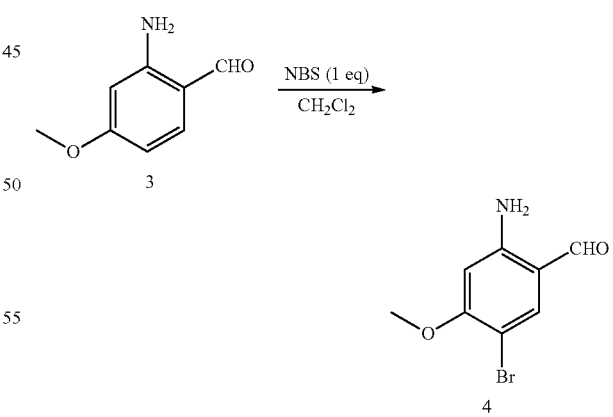

To a stirred solution of 2-amino-4-methoxybenzaldehyde (6 g, 39.7 mmol) in dichloromethane (100 mL) was added N-bromosuccinimide (7 g, 39.7 mmol). LCMS monitored the reaction until the starting material consumed completely. The reaction mixture was diluted with dichloromethane and water. The separated organic layer was dried sodium sulfate, filtered and concentrated to give the title compound (5 g, 56%) as a yellow solid. MS (ES+) $C_8H_8BrNO_2$ requires: 229, 231, found: 230, 232 $[M+H]^+$.

Synthesis of 6-bromo-7-methoxyquinazolin-2-ol

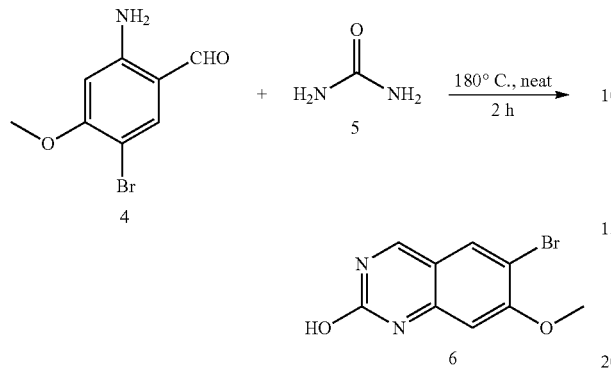

A mixture of 2-amino-5-bromo-4-methoxybenzaldehyde (3 g, 13.1 mmol) and urea (12 g, 196.5 mmol) was stirred at 180° C. for 2 h. LCMS showed the reaction was completed. The reaction mixture was cooled to RT and washed with water (3×100 mL). The precipitate was collected and dried to give the title compound (3 g, crude) as a yellow solid. MS (ES+) $C_8H_7BrN_2O_2$ requires: 254, 256, found: 255, 257 $[M+H]^+$.

Synthesis of 6-bromo-2-chloro-7-methoxyquinazoline

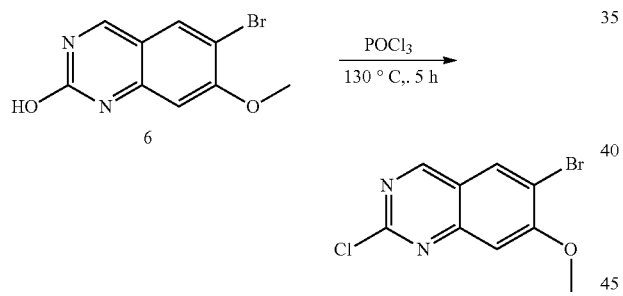

To a solution of 6-bromo-7-methoxyquinazolin-2-ol (3.0 g, 11.8 mmol) in phosphoryl trichloride (30 mL) was refluxed at 130° C. for 5 h. LCMS showed the reaction was completed. The reaction was cooled to RT, and most of phosphoryl trichloride was evaporated. The residue was dropwise added to ice water (100 mL), and the resulting precipitate was collected via filtration to give the title compound as a yellow solid (2.4 g, 75%). MS (ES+) $C_9H_6BrClN_2O$ requires: 272, 274, found: 273, 275 $[M+H]^+$.

Synthesis of 2-chloro-6-(3,5-dimethoxyphenyl)-7-methoxyquinazoline

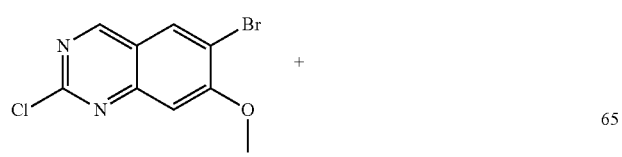

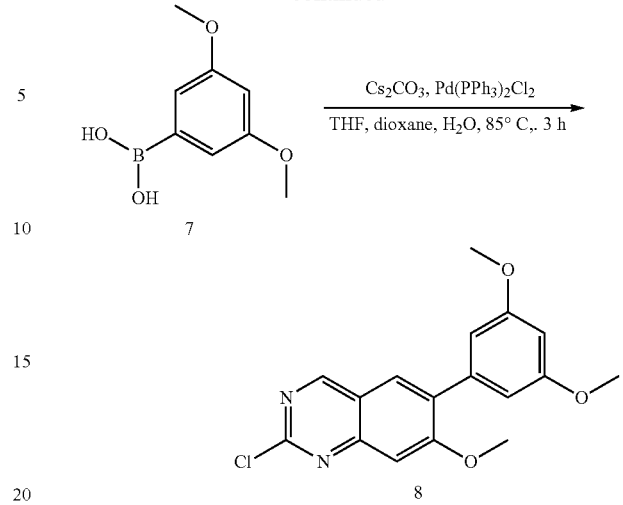

A mixture of 6-bromo-2-chloro-7-methoxyquinazoline (2.4 g, 8.82 mmol), 3,5-dimethoxyphenylboronic acid (1.6 g, 8.82 mmol), cerium carbonate (8.6 g, 26.46 mmol) and $Pd(PPh_3)_2Cl_2$ (1.4 g, 2.1 mmol) in THF (10 mL), dioxane (10 mL) and water (2 mL) was degassed with nitrogen three times and stirred at 85° C. for 3 h. LCMS monitored the reaction was completed. The mixture was cooled to RT and extracted with dichloromethane (3×50 mL).

The organic layers were separated, combined, washed with water and brine, dried over sodium sulfate, filtered and concentrated. The residue was purified by silica gel chromatography (petroleum ether: ethyl acetate=1:4) to give the title compound (1.1 g, 38%) as a white solid.

MS (ES+) $C_{17}H_{15}ClN_2O_3$ requires: 330, 332, found: 331, 333 $[M+H]^+$.

Synthesis of 2-chloro-6-(2,6-dichloro-3,5-dimethoxyphenyl)-7-methoxyquinazoline

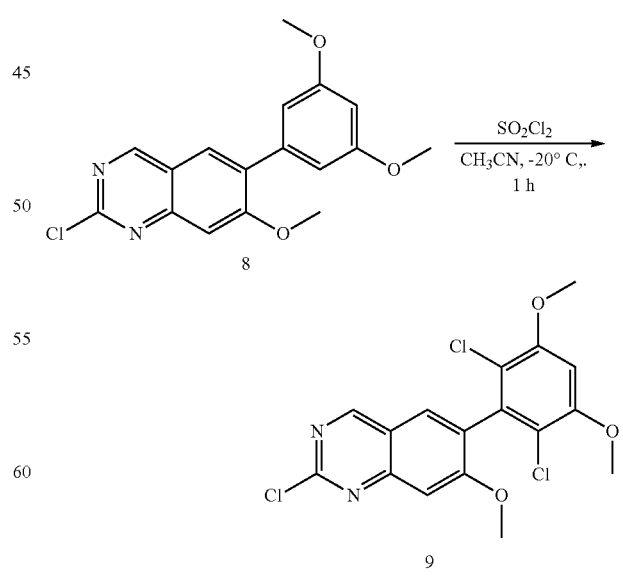

To a solution of 2-chloro-6-(3,5-dimethoxyphenyl)-7-methoxyquinazoline (200 mg, 0.61 mmol) in acetonitrile (5 mL) was added sulfuryl chloride (205 mg, 1.52 mmol), and the mixture was stirred at −20 OC for 1 h. The reaction was quenched with water (1 mL) and concentrated under reduced pressure. The precipitate was washed by acetonitrile and dried to give the title compound as a white solid (120 mg, 50%). MS (ES+) $C_{17}H_{13}Cl_3N_2O_3$ requires: 398, found: 399, 401 [M+H]$^+$; $^1$H-NMR (400 MHz, DMSO-d$_6$) δ ppm 9.43 (s, 1H), 8.02 (s, 1H), 7.55 (s, 1H), 7.03 (s, 1H), 3.98 (s, 6H), 3.93 (s, 3H).

Synthesis of 6-(2,6-dichloro-3,5-dimethoxyphenyl)-7-methoxy-N-(2-methyl-6-nitrophenyl)quinazolin-2-amine

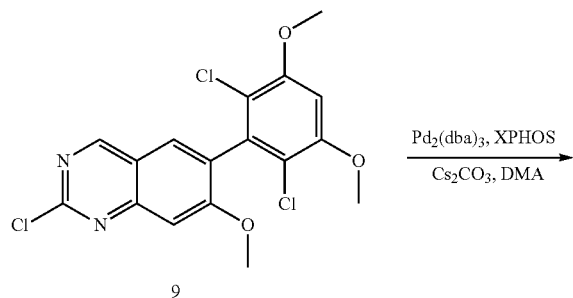

9

6-(2,6-dichloro-3,5-dimethoxyphenyl)-7-methoxy-N-(2-methyl-6-nitrophenyl)quinazolin-2-amine was prepared using the procedure similar to COMPOUND 30. The product was purified by flash chromatography using 0-100% EtOAc/Hexanes gradient to give the title compound. MS (ES+) $C_{24}H_{20}Cl_2N_4O_5$ requires: 514, found: 515 [M+H]$^+$.

Synthesis of N1-(6-(2,6-dichloro-3,5-dimethoxyphenyl)-7-methoxyquinazolin-2-yl)-6-methylbenzene-1,2-diamine

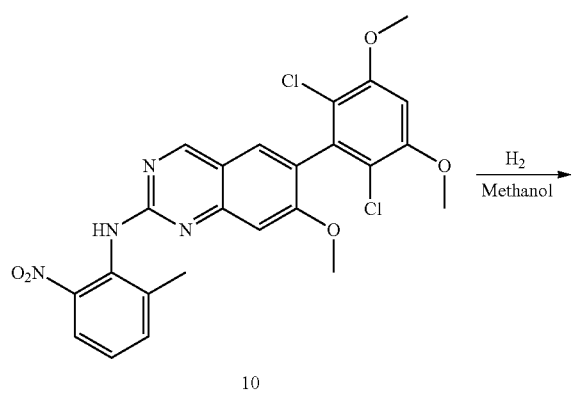

10

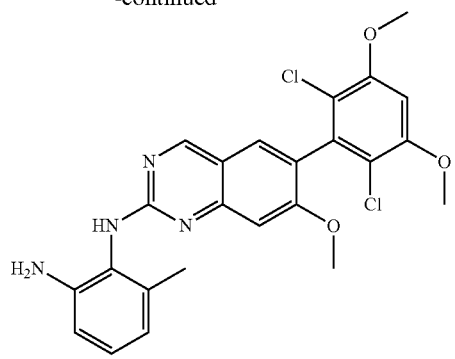

11

N1-(6-(2,6-dichloro-3,5-dimethoxyphenyl)-7-methoxyquinazolin-2-yl)-6-methylbenzene-1,2-diamine was prepared using the procedure similar to COMPOUND 30. The reaction was filtered through celite to give crude product. MS (ES+) $C_{24}H_{22}Cl_2N_4O_3$ requires: 484, found: 485 [M+H]$^+$.

Synthesis of N-(2-((6-(2,6-dichloro-3,5-dimethoxyphenyl)-7-methoxyquinazolin-2-yl)amino)-3-methylphenyl)acrylamide

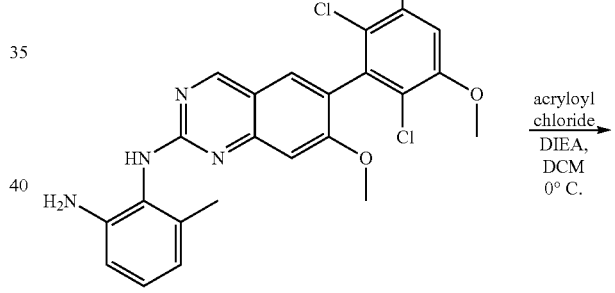

11

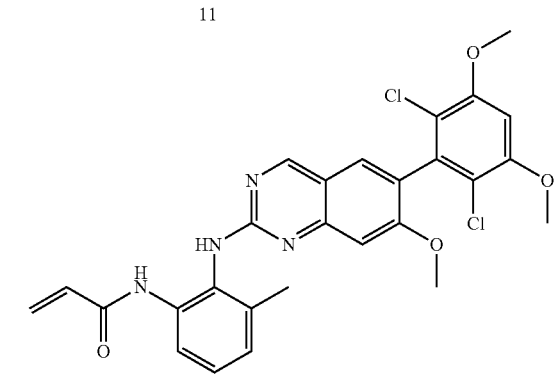

N-(2-((6-(2,6-dichloro-3,5-dimethoxyphenyl)-7-methoxyquinazolin-2-yl)amino)-3-methylphenyl)acrylamide was prepared using the procedure similar to COMPOUND 30. The product was purified by flash chromatography using 0-10% MeOH/DCM gradient to give the title compound. MS (ES+) $C_{27}H_{24}Cl_2N_4O_4$ requires: 538, found: 539 [M+H]$^+$.

Example 10: Synthesis of Compound 34
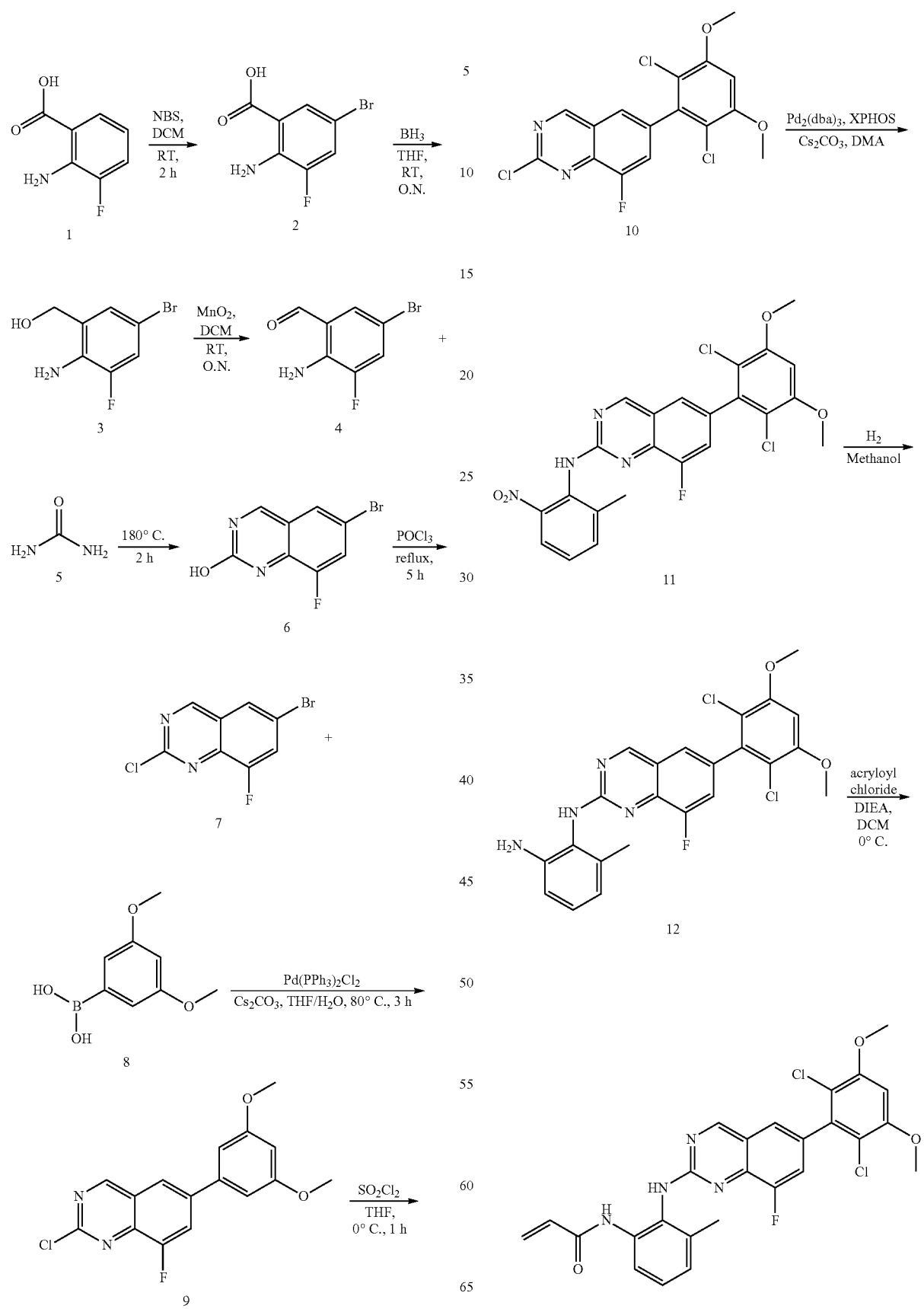

Synthesis of 2-amino-5-bromo-3-fluorobenzoic Acid

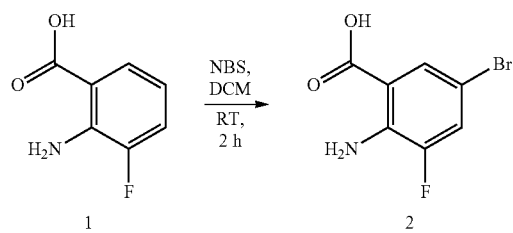 [SMILES: Nc1c(F)cccc1C(=O)O ; Nc1c(F)cc(Br)cc1C(=O)O]

A solution of 2-amino-3-fluorobenzoic acid (10.85 g, 70 mmol) in dichloromethane (175 mL) was added N-bromosuccinimide (12.46 g, 70 mmol), and the mixture was stirred at RT for 2 h. LCMS showed the reaction was completed. The precipitate was filtered and washed with dichloromethane (100 mL*3) to give the title compound (12.7 g, 78%) as a grey solid, which was directly used in the next step without further purification. MS (ES+) $C_7H_5BrFNO_2$ requires: 233, 235, found: 232, 234 [M−H]⁻.

Synthesis of (2-amino-5-bromo-3-fluorophenyl)methanol

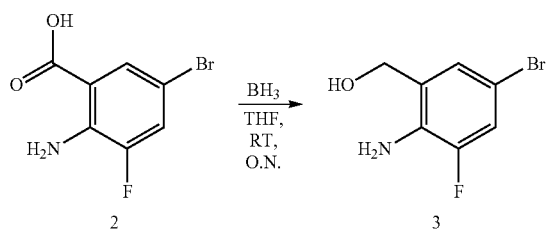

To a solution of 2-amino-5-bromo-3-fluorobenzoic acid (14.5 g, 62.2 mmol) in THF (150 mL) at 0° C. was added borohydride in THF (1 M, 310 mL), and the reaction mixture was stirred at RT overnight. LCMS showed the reaction was completed. The reaction was quenched with methanol (150 mL), concentrated in vacuum, diluted with aqueous sodium bicarbonate (400 mL) and extracted with ethyl acetate (200 mL*3). The organic layers were separated, combined, washed with water (200 mL) and brine (200 mL), dried over sodium sulfate, filtered and concentrated to afford the title compound (13.0 g, crude), which was directly used in the next step without the further purification. MS (ES+) $C_7H_7BrFNO$ requires: 219, 221, found: 220, 222 [M+H]⁺.

Synthesis of 2-amino-5-bromo-3-fluorobenzaldehyde

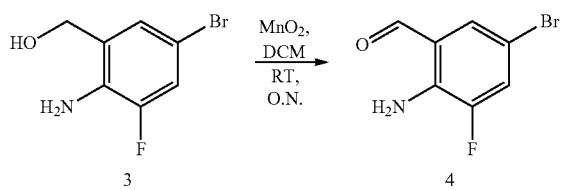

A mixture of (2-amino-5-bromo-3-fluorophenyl)methanol (13 g, 59.4 mmol) and manganese oxide (31 g, 356.4 mmol) in dichloromethane (400 mL) was stirred at RT overnight. TLC showed the starting material consumed completely. The solid was filtered off, and the filtrate was concentrated to give the title compound (11 g, 85%) as a light yellow solid, which was directly used in the next step without further purification.

Synthesis of 6-bromo-8-fluoroquinazolin-2-ol

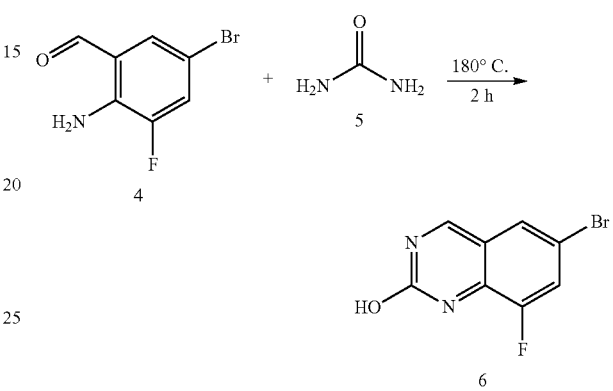

A stirred mixture of 2-amino-5-bromo-3-fluorobenzaldehyde (2.17 g, 10 mmol) and urea (9 g, 150 mmol) was heated at 180° C. for 2 h. LCMS showed the reaction was completed. The reaction mixture was cooled to RT, and the resulting precipitate was filtered and washed with water (500 mL*3). The moisture trapped was completely removed by the co-evaporation with toluene three times. The title compound (2 g, 83%) was obtained as a yellow solid. MS (ES+) $C_8H_4BrFN_2O$ requires: 242, 244, found: 243, 245 [M+H]⁺.

Synthesis of 6-bromo-2-chloroquinazoline

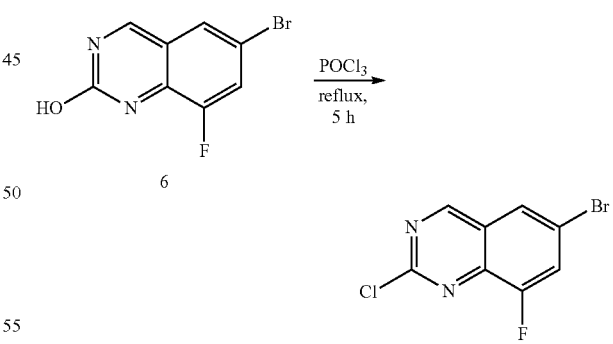

A solution of 6-bromoquinazolin-2-ol (9.72 g, 40 mmol) in phosphorus oxychloride (100 mL) was refluxed for 5 h. LCMS showed the reaction was completed. The reaction was cooled to RT, and most of phosphorus oxychloride was removed under reduced pressure. The residue was dropwise added to ice water (500 mL), and the resulting precipitate was collected by the filtration to give the title compound (9 g, 87%) as a yellow solid. MS (ES+) $C_8H_3BrClFN_2$ requires: 260, 262, found: 261, 263 [M+H]⁺.

Synthesis of 2-chloro-6-(3,5-dimethoxyphenyl)-8-fluoroquinazoline

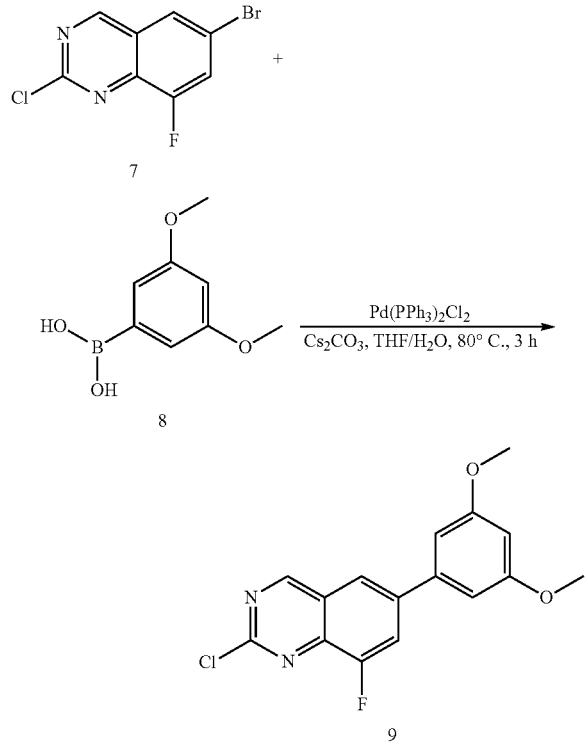

A mixture of 6-bromo-2-chloro-8-fluoroquinazoline (4.0 g, 15.4 mmol), 3,5-dimethoxyphenylboronic acid (4.47 g, 16.9 mmol), cesium carbonate (10.0 g, 30.8 mmol) and Pd(PPh$_3$)$_2$Cl$_2$ (236 mg, 0.77 mmol) in THF (200 mL) and water (10 mL) was degassed with nitrogen three times, and stirred at 80° C. for 3 h. Both TLC and LCMS showed the reaction was completed. The reaction mixture was cooled to RT and directly concentrated. The residue was purified by silica gel chromatography (petroleum ether:dichloromethane=2:1 to 1:1) to afford the title compound (2.5 g, 51%) as a yellow solid. MS (ES+) C$_{16}$H$_{12}$ClFN$_2$O$_2$ requires: 318/320, found: 319/321 [M+H]$^+$.

Synthesis of 2-chloro-6-(2,6-dichloro-3,5-dimethoxyphenyl)-8-fluoroquinazoline

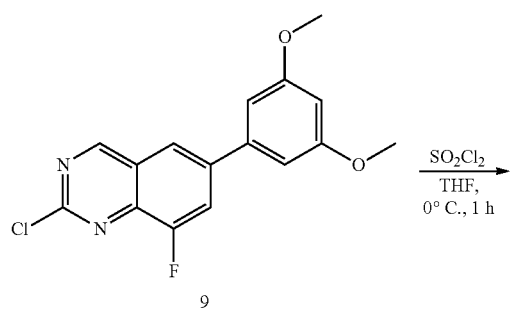

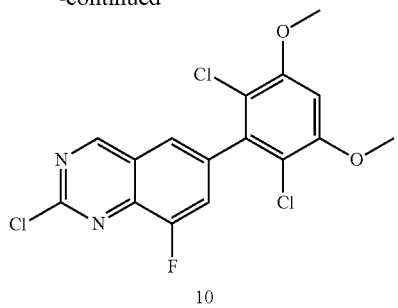

To a solution of 2-chloro-6-(3,5-dimethoxyphenyl)-8-fluoroquinazoline (1.5 g, 4.7 mmol) in dry THF (40 mL) was dropwise added sulfuryl chloride (1.59 g, 1.75 mmol) at 0° C., and the mixture was stirred for 1 h. Both TLC and LCMS showed the reaction was completed. The reaction was quenched with water (1 mL), and the solvents were removed under reduced pressure. The residue was washed with acetonitrile and dried to give the title compound (700 mg, 38%) as a white solid. (MS (ES+) C$_{16}$H$_{10}$Cl$_3$FN$_2$O$_2$ requires: 386, 388, found: 387, 389 [M+H]$^+$; $^1$H-NMR (400 MHz, DMSO-d$_6$) δ ppm 9.74 (d, 1H J=1.0 Hz), 8.03-7.99 (m, 2H), 7.08 (s, 1H), 4.00 (s, 6H).

Synthesis of 6-(2,6-dichloro-3,5-dimethoxyphenyl)-8-fluoro-N-(2-methyl-6-nitrophenyl)quinazolin-2-amine

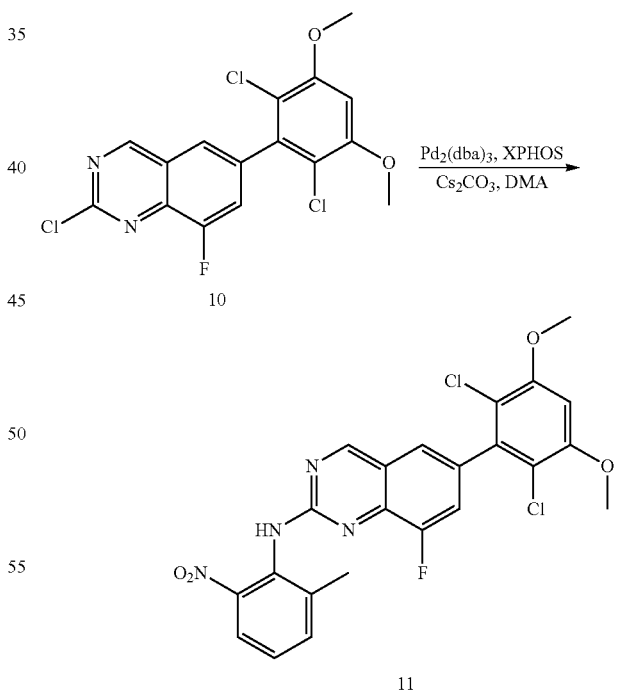

6-(2,6-dichloro-3,5-dimethoxyphenyl)-8-fluoro-N-(2-methyl-6-nitrophenyl)quinazolin-2-amine was prepared using the procedure similar to COMPOUND 30. The product was purified by flash chromatography using 0-100% EtOAc/Hexanes gradient to give the title compound. MS (ES+) C$_{23}$H$_{17}$Cl$_2$FN$_4$O$_4$ requires: 502, found: 503 [M+H]$^+$.

Synthesis of N1-(6-(2,6-dichloro-3,5-dimethoxyphenyl)-8-fluoroquinazolin-2-yl)-6-methylbenzene-1,2-diamine

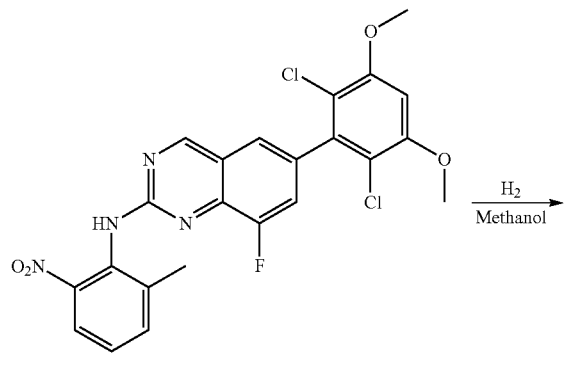

11

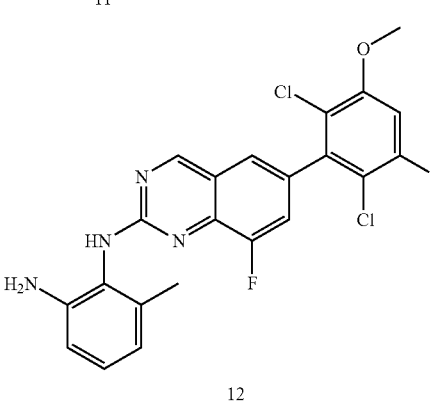

12

N1-(6-(2,6-dichloro-3,5-dimethoxyphenyl)-8-fluoroquinazolin-2-yl)-6-methylbenzene-1,2-diamine was prepared using the procedure similar to COMPOUND 30. The reaction was filtered through celite to give crude product. MS (ES+) $C_{23}H_{19}Cl_2FN_4O_2$ requires: 472, found: 473 [M+H]+.

Synthesis of N-(2-(((6-(2,6-dichloro-3,5-dimethoxyphenyl)-8-fluoroquinazolin-2-yl)amino)-3-methylphenyl) acrylamide

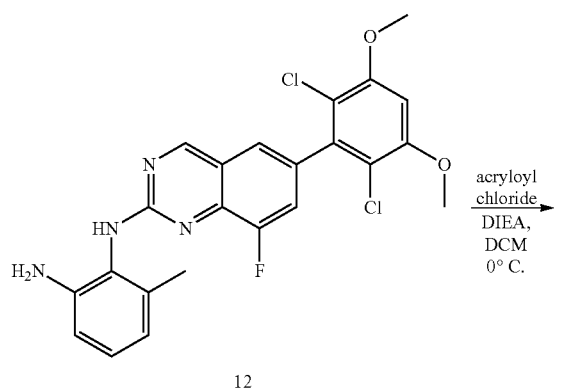

12

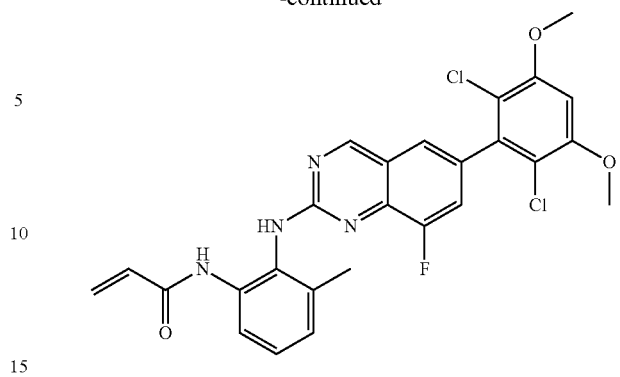

N-(2-(((6-(2,6-dichloro-3,5-dimethoxyphenyl)-8-fluoroquinazolin-2-yl)amino)-3-methylphenyl)acrylamide was prepared using the procedure similar to COMPOUND 30. The product was purified by flash chromatography using 0-10% MeOH/DCM gradient to give the title compound. MS (ES+) $C_{26}H_{21}Cl_2FN_4O_3$ requires: 526, found: 527 [M+H]+. $^1$H-NMR (400 MHz, DMSO-$d_6$) δ 9.53 (d, J=27.9 Hz, 1H), 9.28 (s, 1H), 8.96 (s, 1H), 7.75 (d, J=29.9 Hz, 1H), 7.59 (d, J=1.7 Hz, 1H), 7.49 (d, J=10.8 Hz, 1H), 7.02 (s, 1H), 6.50 (s, 1H), 6.21 (dd, J=16.9, 2.1 Hz, 1H), 5.75 (s, 1H), 5.68 (dd, J=10.2, 2.0 Hz, 1H), 3.98 (d, J=4.6 Hz, 6H), 2.19 (s, 3H).

Example 10: Synthesis of Compound 50

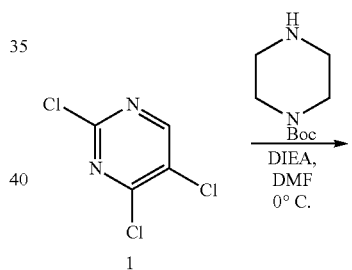

1

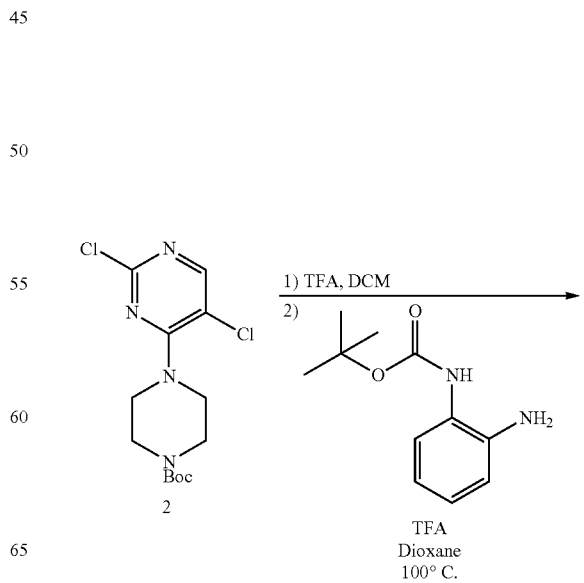

2

Synthesis of tert-butyl 4-(2,5-dichloropyrimidin-4-yl)piperazine-1-carboxylate

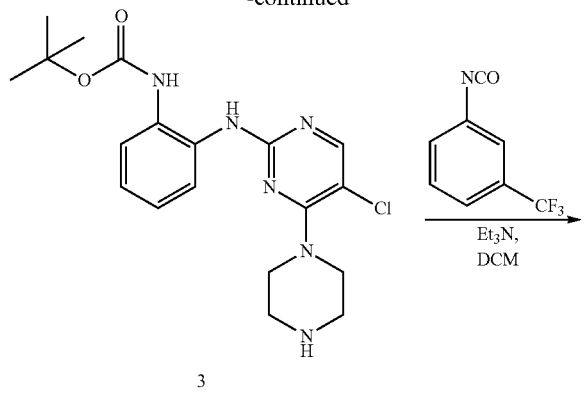

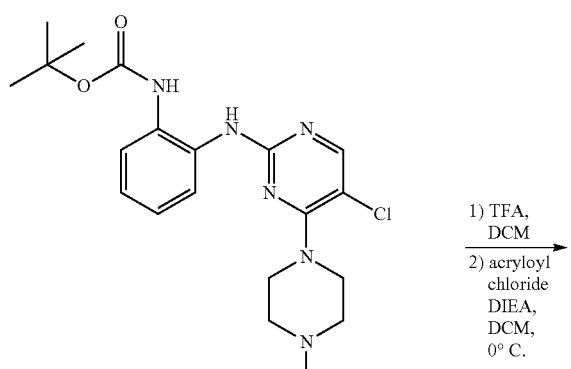

To a solution of 2,4,5-trichloropyrimidine (0.475 g, 2.6 mmol) in dry DMF (8.5 mL) was added tert-butyl piperazine-1-carboxylate (0.51 g, 2.7 mmol) followed by DIEA (0.51 mL, 3.1 mmol) at 0° C., and the mixture was stirred for 1 h. LCMS showed the reaction was completed. The reaction was diluted with water (100 mL), and the white solid was filtered. The residue was washed with water and dried to give the title compound (445 mg, 51%) as a white solid. MS (ES+) $C_{13}H_{18}Cl_2N_4O_2$ requires: 332, found: 333 [M+H]$^+$

Synthesis of tert-butyl (2-((5-chloro-4-(piperazin-1-yl)pyrimidin-2-yl)amino)phenyl)carbamate

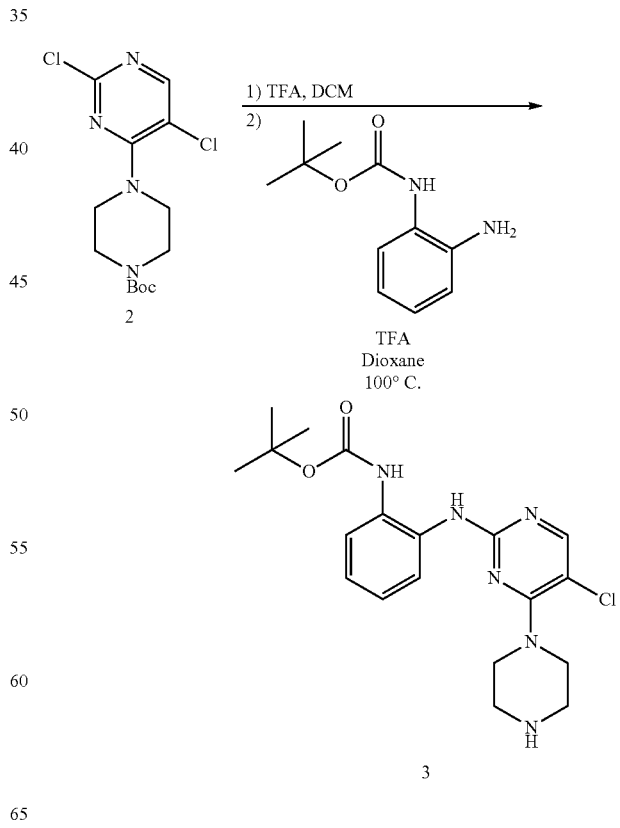

To a solution of tert-butyl 4-(2,5-dichloropyrimidin-4-yl)piperazine-1-carboxylate (0.1 g, 0.3 mmol) in DCM (1.0 mL) was added TFA (1.0 mL) and the mixture was stirred for 1 h. An aliquot of the reaction mixture was analyzed by LCMS, which indicated that the reaction had proceeded to completion. The solvents were removed and the residue was dried on high vacuum. The crude product was used for the next step without further purification.

To a solution of 2,5-dichloro-4-(piperazin-1-yl)pyrimidine (0.3 mmol) in Dioxane (4.0 mL) was added TFA (0.060 mL, 0.75 mmol) and tert-butyl (2-aminophenyl)carbamate (0.094 g, 0.45 mmol) and the mixture was stirred at 100° C. for 24 h. reaction. After cooling to room temperature the reaction mixture was diluted with EtOAc and washed with aqueous saturated sodium bicarbonate solution. The organic mixture was dried over sodium sulfate and loaded onto silica gel and purified using 0-10% MeOH/DCM gradient containing 10% NH$_4$OH to give the title compound (28 mg, 23%) as a white solid. MS (ES+) C$_{19}$H$_{25}$ClN$_6$O$_2$ requires: 404, found: 405 [M+H]$^+$

Synthesis of tert-butyl (2-((5-chloro-4-(4-((3-(trifluoromethyl)phenyl)carbamoyl)piperazin-1-yl)pyrimidin-2-yl)amino)phenyl)carbamate

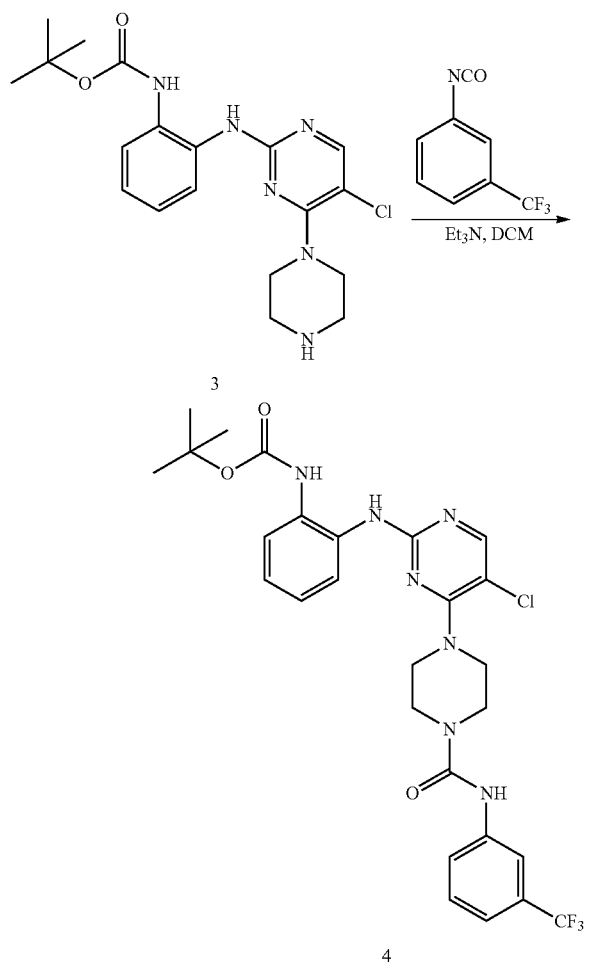

To a solution of tert-butyl (2-((5-chloro-4-(piperazin-1-yl) pyrimidin-2-yl)amino)phenyl)carbamate (28 mg, 0.068 mmol) in DCM (0.7 mL) was added 1-isocyanato-3-(trifluoromethyl)benzene (0.011 mL, 0.082 mmol) and triethylamine (0.015 mL, 0.1 mmol) and the mixture was stirred at 23° C. for 16 h. reaction. The crude reaction mixture was loaded onto silica gel and purified using 0-50% EtOAc/Hexanes gradient to give the title compound (25 mg, 62%). MS (ES+) C$_{27}$H$_{29}$ClF$_3$N$_7$O$_3$ requires: 591, found: 592 [M+H]$^+$

Synthesis of 4-(2-((2-acrylamidophenyl)amino)-5-chloropyrimidin-4-yl)-N-(3-(trifluoromethyl)phenyl)piperazine-1-carboxamide

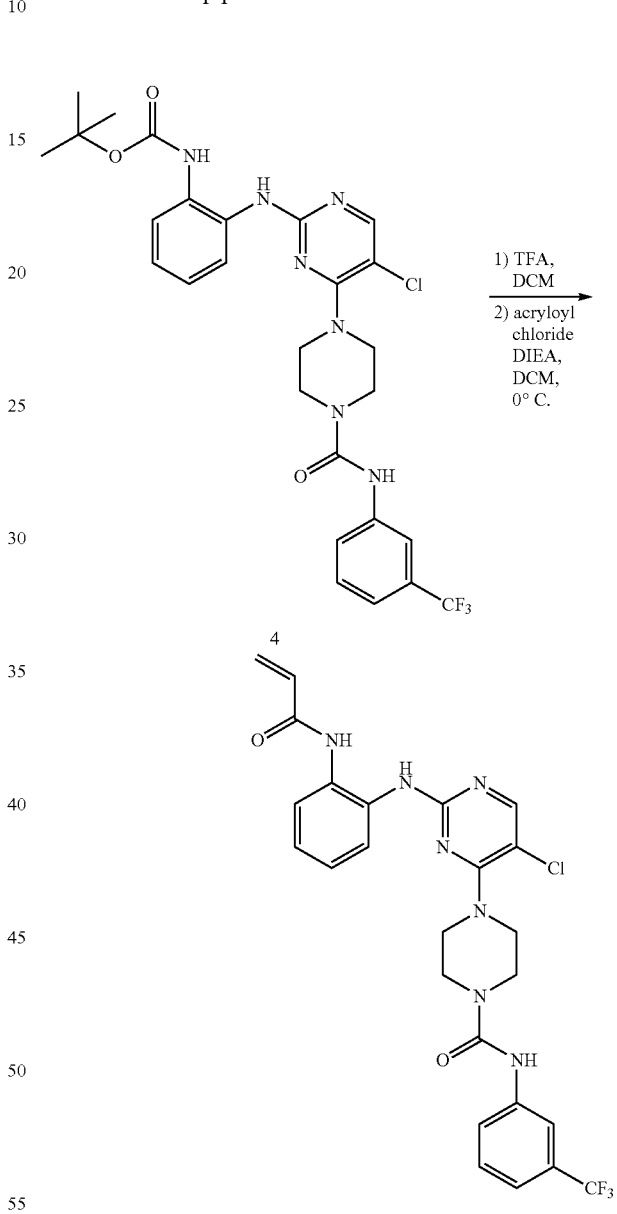

To a solution of tert-butyl (2-((5-chloro-4-(4-((3-(trifluoromethyl)phenyl)carbamoyl)piperazin-1-yl)pyrimidin-2-yl) amino)phenyl)carbamate (0.025 g, 0.043 mmol) in DCM (1.0 mL) was added TFA (1.0 mL) and the mixture was stirred for 1 h. An aliquot of the reaction mixture was analyzed by LCMS, which indicated that the reaction had proceeded to completion. The solvents were removed and the residue was dried on high vacuum. The crude product was used for the next step without further purification.

To a solution of 4-(2-((2-aminophenyl)amino)-5-chloropyrimidin-4-yl)-N-(3-(trifluoromethyl)phenyl)piperazine-1- carboxamide (0.043 mmol) in DCM (0.5 mL) was added acryloyl chloride (0.004 mL, 0.052 mmol) and DIEA (0.018 mL, 0.11 mmol) and the mixture was stirred at 0° C. for 1 h. The crude reaction mixture was loaded onto silica gel and purified using 0-7% MeOH/DCM gradient to give the title compound (10 mg, 43%). MS (ES+) $C_{25}H_{23}ClF_3N_7O_2$ requires: 545, found: 546 $[M+H]^+$
Example 11: Synthesis of Compound 54
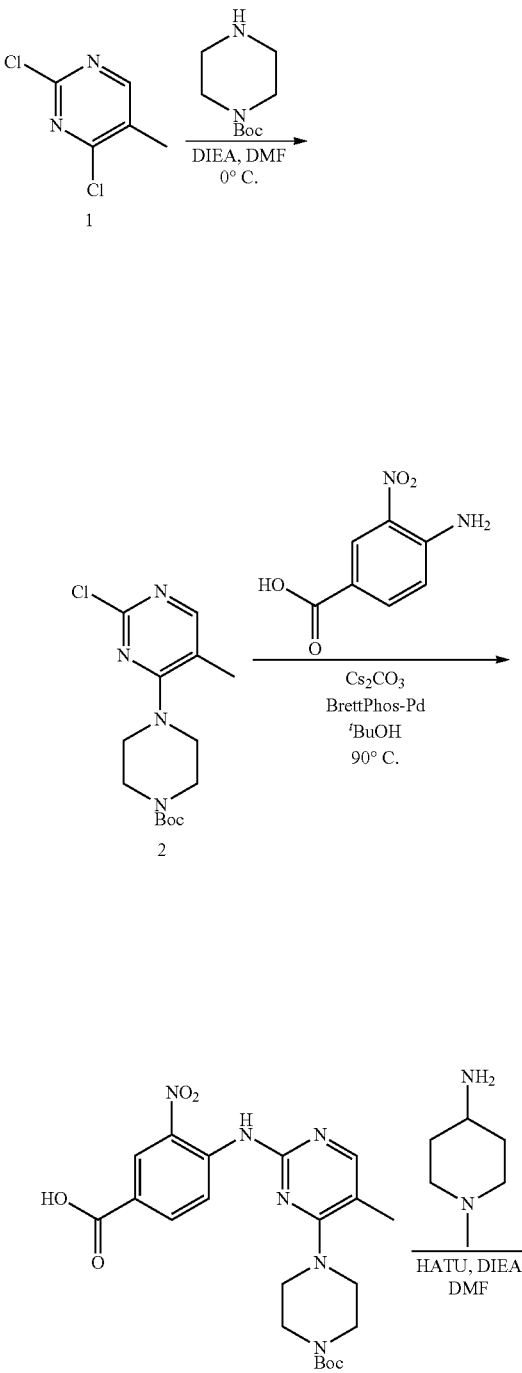
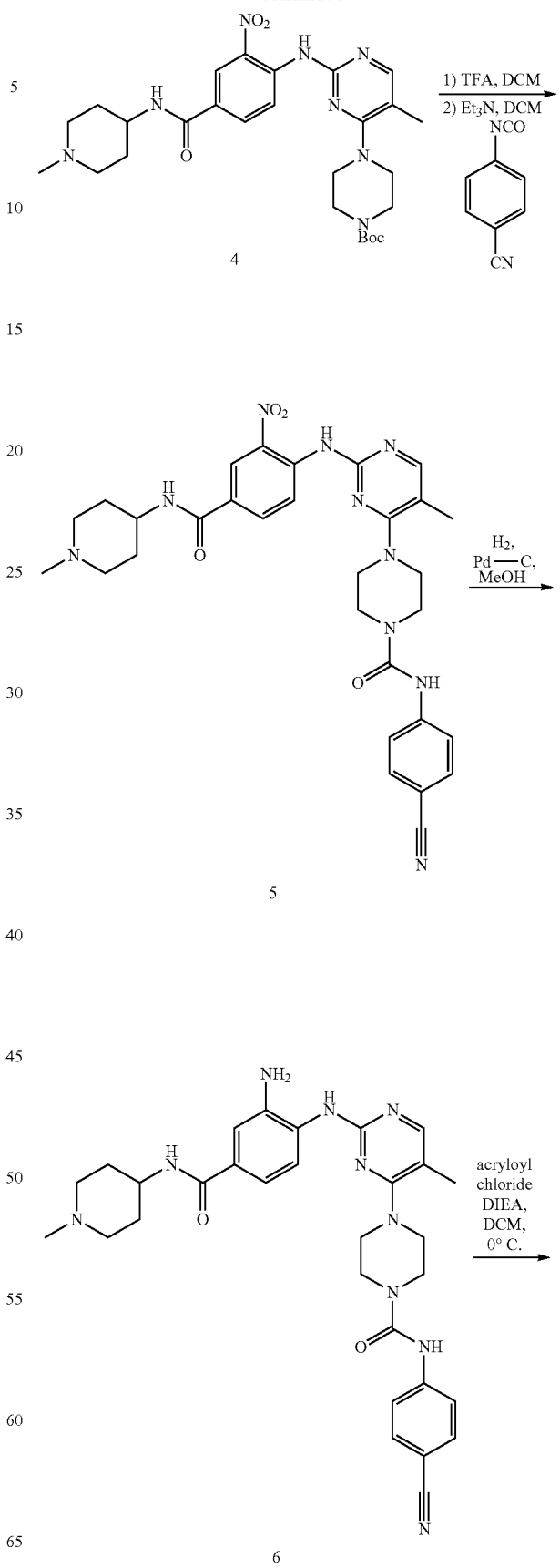

115

-continued

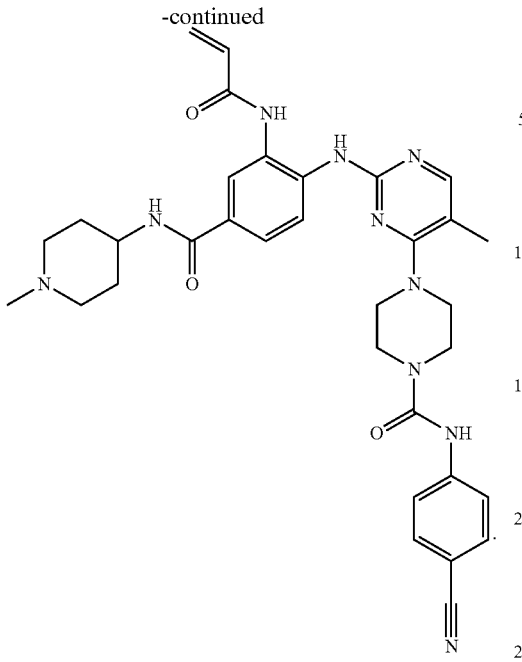

Synthesis of tert-butyl 4-(2-chloro-5-methylpyrimi-
din-4-yl)piperazine-1-carboxylate

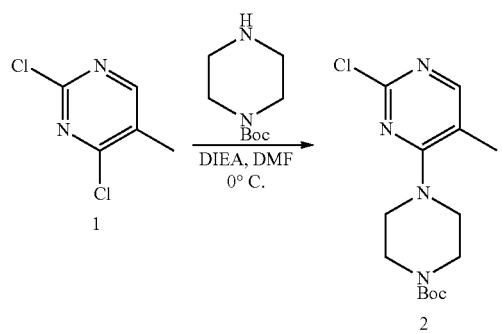

To a solution of 2,4-dichloro-5-methylpyrimidine (0.75 g, 4.6 mmol) in dry DMF (15.5 mL) was added tert-butyl piperazine-1-carboxylate (0.9 g, 4.85 mmol) followed by DIEA (0.91 mL, 5.5 mmol) at 0° C., and the mixture was stirred to room temperature overnight. LCMS showed the reaction was completed. The reaction was diluted with water (120 mL), and the solid was filtered. The residue was washed with water and dried to give the title compound (1.386 g, 96%) as a white solid. MS (ES+) $C_{14}H_{21}ClN_4O_2$ requires: 312, found: 313 [M+H]$^+$

116

Synthesis of 4-((4-(4-(tert-butoxycarbonyl)piper-
azin-1-yl)-5-methylpyrimidin-2-yl)amino)-3-ni-
trobenzoic Acid

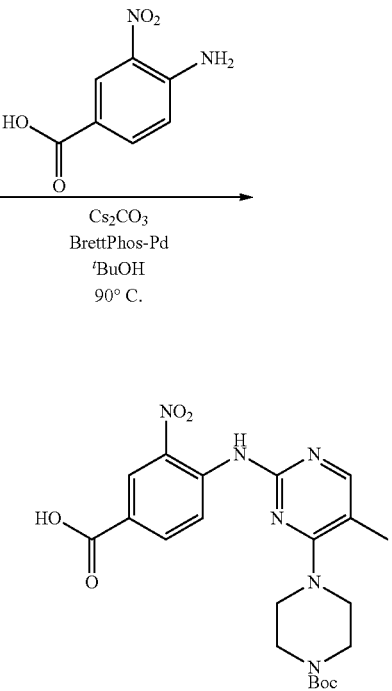

A mixture of tert-butyl 4-(2-chloro-5-methylpyrimidin-4-yl)piperazine-1-carboxylate (0.15 g, 0.48 mmol), 4-amino-3-nitrobenzoic acid (97 mg, 0.53 mmol), BrettPhos-Pd Admixture (20 mg, 0.015 mmol), and cesium carbonate (470 mg, 1.44 mmol) in ${}^tBuOH$ (2.4 mL) was heated in a sealed tube at 100° C. overnight. The mixture was diluted with EtOAc, filtered through a celite plug, loaded onto silica gel and purified using 0-10% MeOH/DCM gradient to give the title compound (75 mg, 34%). MS (ES+) $C_{21}H_{26}N_6O_6$ requires: 458, found: 459 [M+H]$^+$ Synthesis of tert-butyl 4-(5-methyl-2-((4-((1-meth-
ylpiperidin-4-yl)carbamoyl)-2-nitrophenyl)amino)
pyrimidin-4-yl)piperazine-1-carboxylate

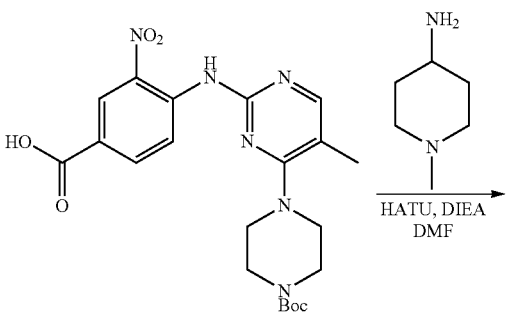

-continued

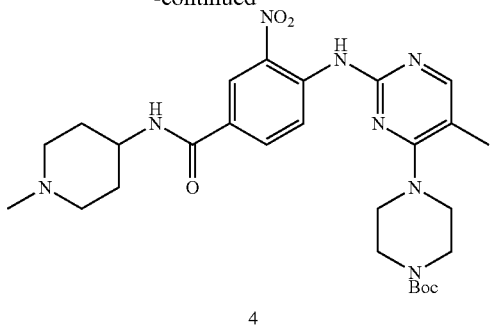

4

A mixture of 4-((4-(4-(tert-butoxycarbonyl)piperazin-1-yl)-5-methylpyrimidin-2-yl)amino)-3-nitrobenzoic acid (0.075 g, 0.164 mmol), 1-methylpiperidin-4-amine (37 mg, 0.33 mmol), HATU (140 mg, 0.37 mmol), and DIEA (0.1 mL, 0.6 mmol) in DMF (3.0 mL) was stirred at room temperature overnight. The reaction mixture was diluted with EtOAc, washed with aqueous saturated sodium bicarbonate solution and saturated brine solution. The crude mixture was loaded onto silica gel and purified using 0-10% MeOH/DCM gradient containing 10% NH$_4$OH to give the title compound (73 mg, 80%). MS (ES+) C$_{27}$H$_{38}$N$_8$O$_5$ requires: 554, found: 555 [M+H]$^+$ Synthesis of N-(4-cyanophenyl)-4-(5-methyl-2-((4-((1-methylpiperidin-4-yl)carbamoyl)-2-nitrophenyl)amino)pyrimidin-4-yl)piperazine-1-carboxamide

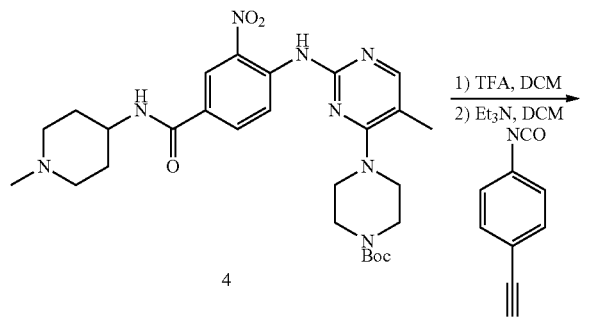

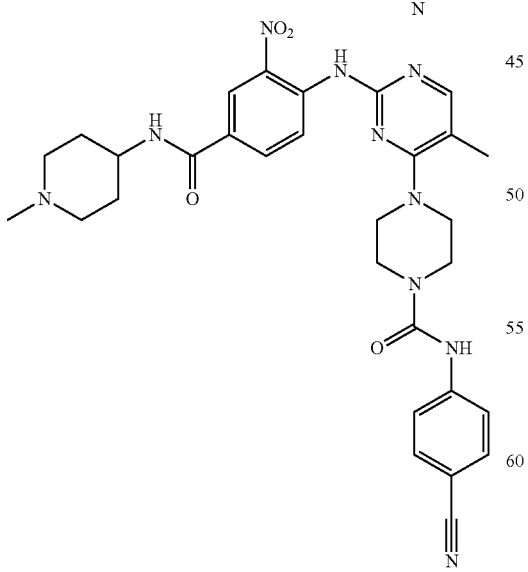

5

To a solution of tert-butyl 4-(5-methyl-2-((4-((1-methylpiperidin-4-yl)carbamoyl)-2-nitrophenyl)amino)pyrimidin-4-yl)piperazine-1-carboxylate (0.073 g, 0.13 mmol) in DCM (1.0 mL) was added TFA (1.0 mL) and the mixture was stirred for 1 h. An aliquot of the reaction mixture was analyzed by LCMS, which indicated that the reaction had proceeded to completion. The solvents were removed and the residue was dried on high vacuum. The crude product was used for the next step without further purification.

To a solution of 4-((5-methyl-4-(piperazin-1-yl)pyrimidin-2-yl)amino)-N-(1-methylpiperidin-4-yl)-3-nitrobenzamide (0.073 mmol) in DCM (1.5 mL) was added 4-isocyanatobenzonitrile (23 mg, 0.16 mmol) and triethylamine (0.055 mL, 0.39 mmol) and the mixture was stirred at 23° C. for 16 h. reaction. The crude reaction mixture was filtered and washed with minimal volume of DCM and then hexanes to give the title compound (97 mg, 100%). MS (ES+) C$_{30}$H$_{34}$N$_{10}$O$_4$ requires: 598, found: 599 [M+H]$^+$ Synthesis of 4-(2-((2-amino-4-((1-methylpiperidin-4-yl)carbamoyl)phenyl)amino)-5-methylpyrimidin-4-yl)-N-(4-cyanophenyl)piperazine-1-carboxamide

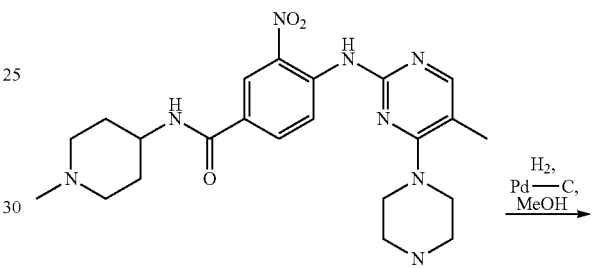

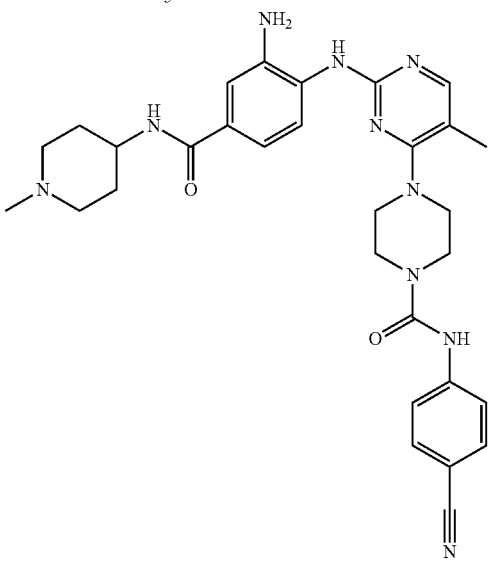

6

4-(2-((2-amino-4-((1-methylpiperidin-4-yl)carbamoyl)phenyl)amino)-5-methylpyrimidin-4-yl)-N-(4-cyanophenyl)piperazine-1-carboxamide was prepared using the procedure similar to COMPOUND 30. The reaction was filtered through celite to give crude product. MS (ES+) $C_{30}H_{36}N_{10}O_2$ requires: 568, found: 569 $[M+H]^+$.

Synthesis of 4-(2-((2-acrylamido-4-((1-methylpiperidin-4-yl)carbamoyl)phenyl)amino)-5-methylpyrimidin-4-yl)-N-(4-cyanophenyl)piperazine-1-carboxamide

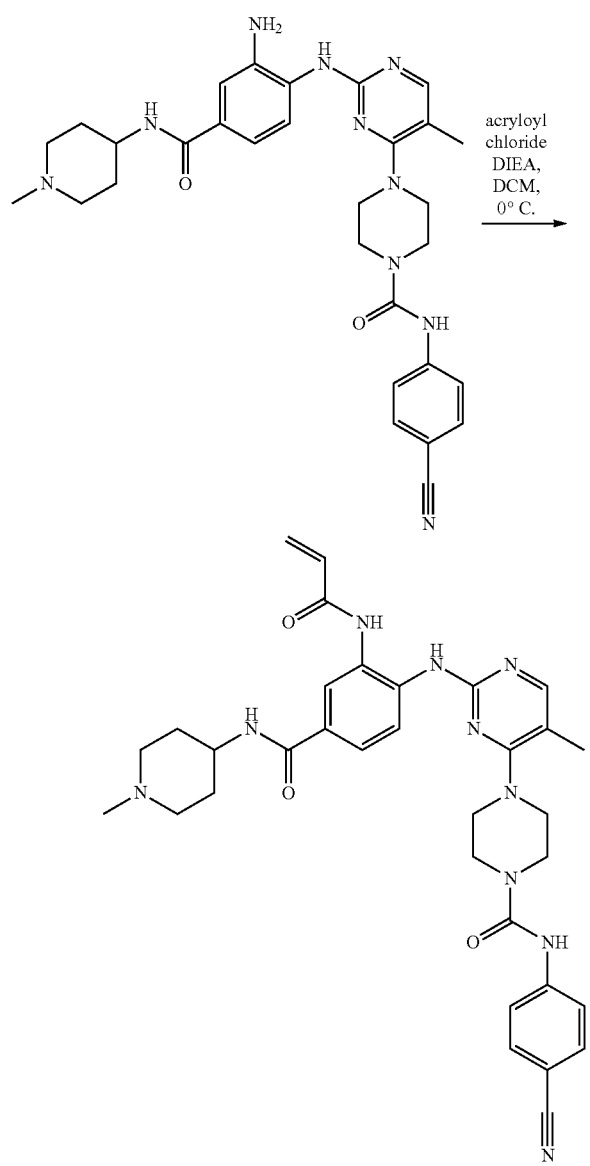

4-(2-((2-acrylamido-4-((1-methylpiperidin-4-yl)carbamoyl)phenyl)amino)-5-methylpyrimidin-4-yl)-N-(4-cyanophenyl)piperazine-1-carboxamide was prepared using the procedure similar to COMPOUND 30. The reaction mixture was purified through a preparative thin layer chromatography to give the title product. MS (ES+) $C_{33}H_{38}N_{10}O_3$ requires: 622, found: 623 $[M+H]^+$. $^1$H NMR (400 MHz, DMSO-d6) δ 9.98 (s, 1H), 9.08 (s, 1H), 8.30 (s, 1H), 8.21-8.07 (m, 3H), 7.93 (d, J=10.7 Hz, 2H), 7.67 (m, 4H), 6.50 (dd, J=16.9, 10.2 Hz, 1H), 6.33-6.25 (m, 1H), 5.83-5.76 (m, 1H), 3.78 (m, 2H), 3.59 (m, 4H), 3.43 (m, 4H), 2.92 (d, J=11.4 Hz, 2H), 2.30 (s, 3H), 2.23 (s, 2H), 2.14 (s, 3H), 1.79 (m, 2H), 1.69-1.54 (m, 2H).

Example 12: Synthesis of Compound 20

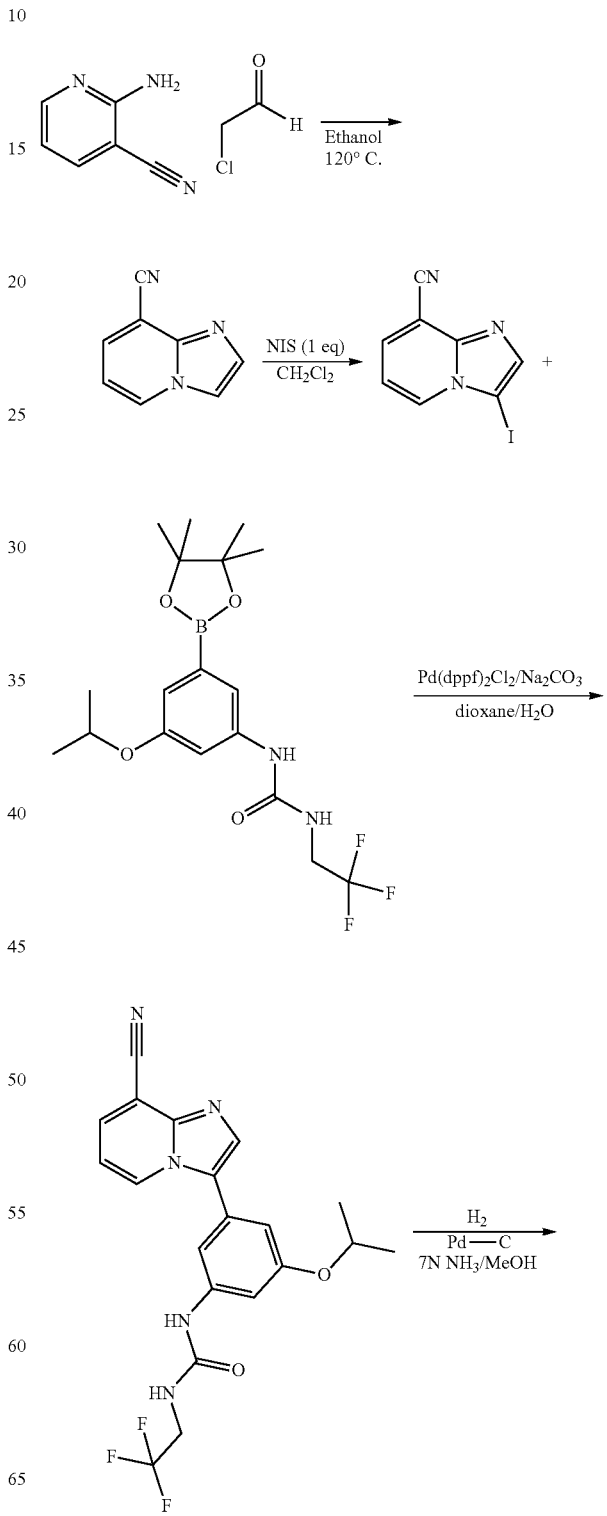

-continued

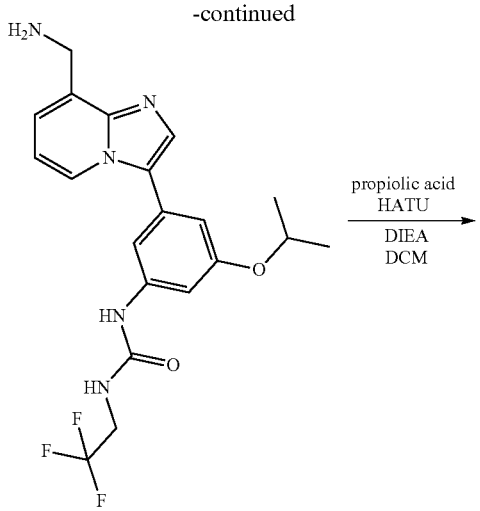

propiolic acid
HATU
DIEA
DCM
→

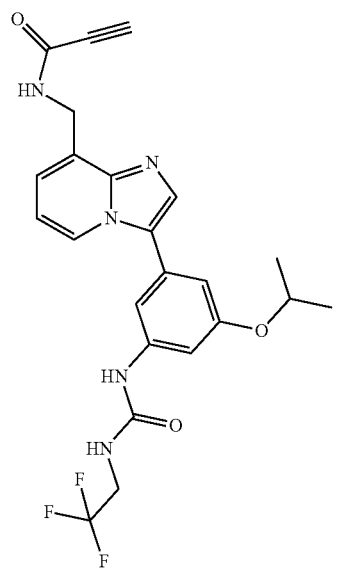 [SMILES: C#CC(=O)NCc1cccn2c(-c3cc(NC(=O)NCC(F)(F)F)cc(OC(C)C)c3)cnc12]

Synthesis of imidazo[1,2-a]pyridine-8-carbonitrile

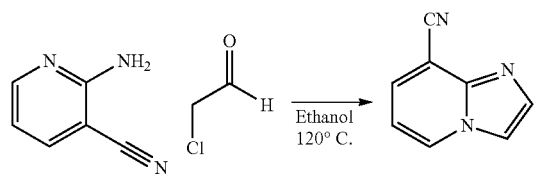

To a solution of 2-aminonicotinonitrile (1.0 g, 8.39 mmol) in EtOH (10 ml) in a 20 ml sealed vial was added 2-chloroacetaldehyde (1.611 ml, 9.23 mmol) vial was then sealed and heated to 120° C. overnight. Reaction was cooled to RT and quenched with 2N Na2CO3, removed EtOH in vaccuo and extracted with DCM×3. Combined organics and washed with water then brine×2. Dried over sodium sulfate and removed solvent to give title compound as a yellow brown solid (1.2 g, 8.38 mmol, 100% yield) was verified by MS (ES+) $C_8H_5N_3$ requires: 143 found: 144 [M+H]$^+$ Synthesis of 3-iodoimidazo[1,2-a]pyridine-8-carbonitrile

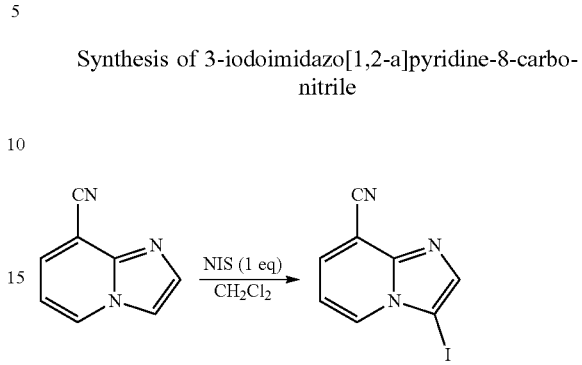

To a stirred solution of imidazo[1,2-a]pyridine-8-carbonitrile (1.2 g, 8.38 mmol) in dichloromethane (10 mL) was added N-iodosuccinimide (1.89 g, 8.38 mmol). LCMS monitored the reaction until the starting material consumed completely. The reaction mixture was diluted with dichloromethane and water. The separated organic layer was dried sodium sulfate, filtered and concentrated to give 3-iodoimidazo[1,2-a]pyridine-8-carbonitrile (1.8 g, 6.69 mmol, 80% yield) as a brown solid. MS (ES+) $C_8H_8IN_3$ requires: 269, found: 270 [M+H]$^+$.

Synthesis of 1-(3-(8-cyanoimidazo[1,2-a]pyridin-3-yl)-5-isopropoxyphenyl)-3-(2,2,2-trifluoroethyl)urea

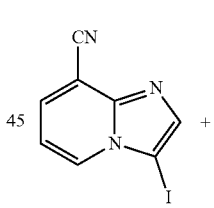
+
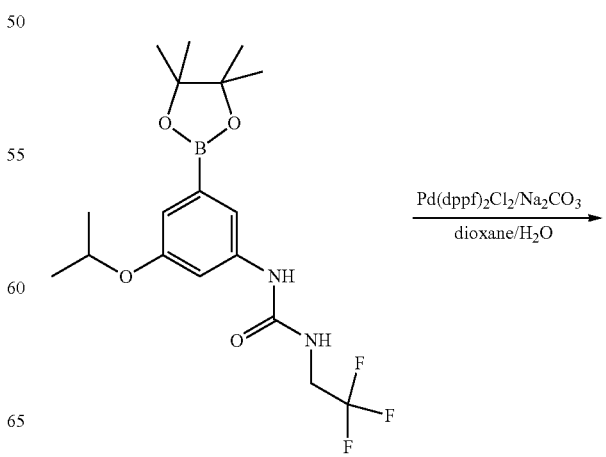

Pd(dppf)$_2$Cl$_2$/Na$_2$CO$_3$
dioxane/H$_2$O
→

123

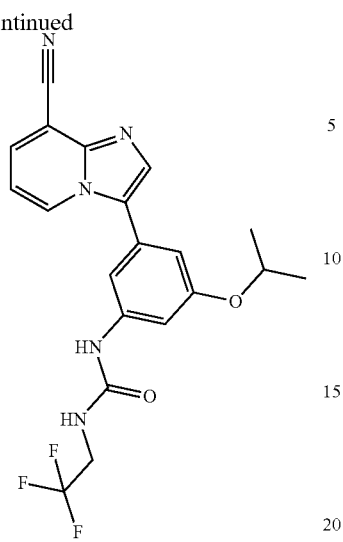

To a mixture of 3-iodoimidazo[1,2-a]pyridine-8-carbonitrile (100 mg, 373 μmol), 1-(3-isopropoxy-5-(4,4,5,5-tetramethyl-1,3,2-dioxaborolan-2-yl)phenyl)-3-(2,2,2-trifluoroethyl)urea (90 mg, 224 μmol), PdCl2 (dppf)-CH2Cl2Adduct (30.5 mg, 37.3 μmol) in Dioxane (3 ml), was added 2M Na2CO3 (0.559 ml, 1119 μmol). The vial was degassed for 5 minutes then capped and heated to 110° C. for 30 minutes in microwave. After cooling to ambient temperature reaction was partioned between EtOAc and brine, separated and organics washed with brine×2. Combined organics were dried directly on to silica and purified via flash chromatography (0-100% Hex/EtOAc; 12 g column). Recovered the title compound (30 mg, 71.9 μmol, 32.1% yield) as a brown solid. MS (ES+) $C_{20}H_{18}F_3N_5O_2$ requires: 417, found: 418 [M+H]+.

Synthesis of 1-(3-(8-(aminomethyl)imidazo[1,2-a]pyridin-3-yl)-5-isopropoxyphenyl)-3-(2,2,2-trifluoroethyl)urea

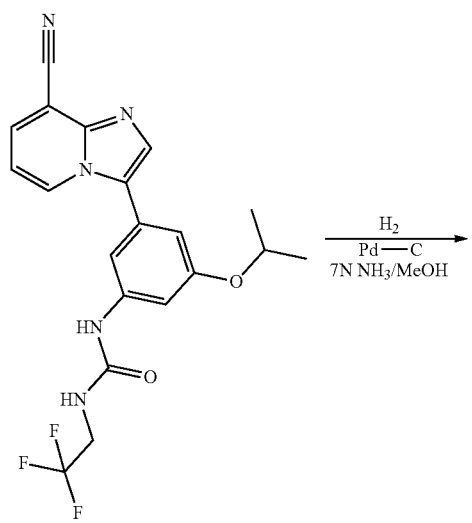

124

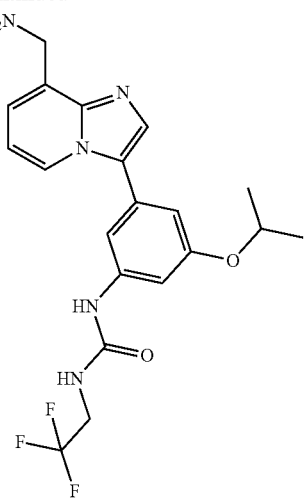

1-(3-(8-cyanoimidazo[1,2-a]pyridin-3-yl)-5-isopropoxyphenyl)-3-(2,2,2-trifluoroethyl)urea (0.030 g, 0.072 mmol) was taken up in 7N AMMONIA in methanol (20 mL, 140 mmol) and Pd—C (10 mg, 0.094 mmol) added. Reaction was stirred under $H_2$ balloon for 1 hour. Mixture was then filtered through celite and solvent removed. Residue was dried under high vacuum overnight to to give title compound as a yellow solid (0.026 g, 0.062 mmol, 86% yield). MS (ES+) $C_{20}H_{22}F_3N_5O_2$ requires: 421, found: 422 [M+H]+.

Synthesis of N-((3-(3-isopropoxy-5-(3-(2,2,2-trifluoroethyl)ureido)phenyl)imidazo[1,2-a]pyridin-8-yl)methyl)propiolamide

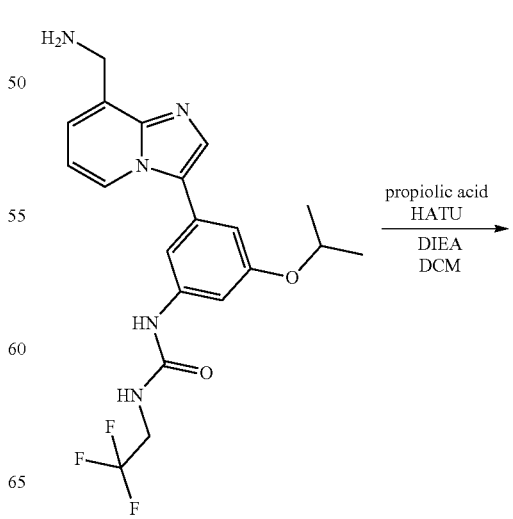

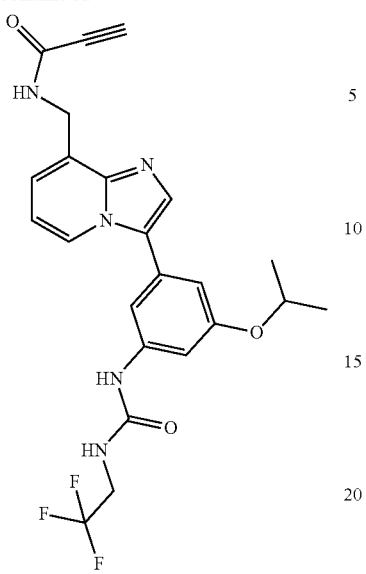

To a solution of 1-(3-(8-(aminomethyl)imidazo[1,2-a]pyridin-3-yl)-5-isopropoxyphenyl)-3-(2,2,2-trifluoroethyl)urea (26 mg, 0.062 mmol) in DCM (3 ml) was added DIEA (0.075 ml, 0.432 mmol) and HATU (35.2 mg, 0.093 mmol) and finally propiolic acid (4.95 μl, 0.080 mmol). Reaction was stirred for 30 minutes at room temperature. Reaction was loaded directly onto silica column and purified by flash chromatography (0-10% CH2Cl2/MeOH) to give the title compound (19 mg, 0.040 mmol, 65.0% yield) as an off white solid. MS (ES+) $C_{23}H_{22}F_3N_5O_3$ requires: 473, found: 474 [M+H]+. $^1$H NMR (400 MHz, DMSO-$d_6$) δ 9.34 (s, 1H), 8.92 (s, 1H), 8.47 (d, J=6.8 Hz, 1H), 7.74 (s, 1H), 7.17 (d, J=1.9 Hz, 2H), 7.10 (s, 1H), 6.98 (s, 1H), 6.82 (s, 1H), 6.74 (s, 1H), 4.69-4.58 (m, 2H), 3.93 (dd, J=9.7, 6.4 Hz, 2H), 2.72-2.64 (m, 1H), 1.30-1.19 (m, 6H).

Example 13: Synthesis of Compound 21

Example 13: Synthesis of COMPOUND 21

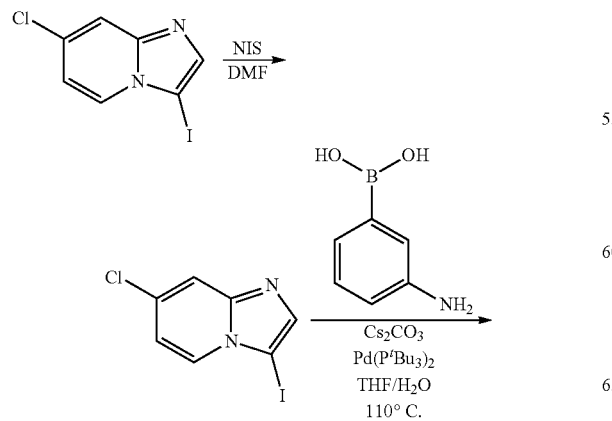

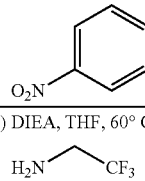

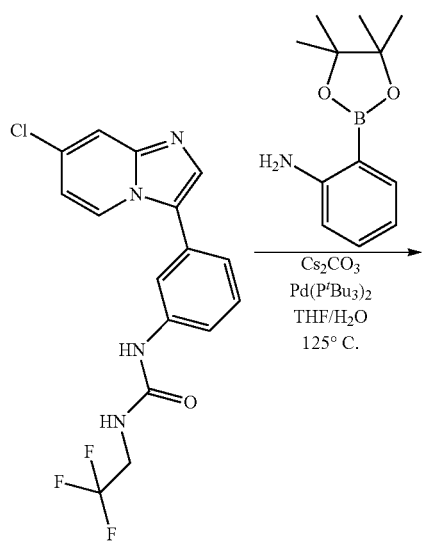

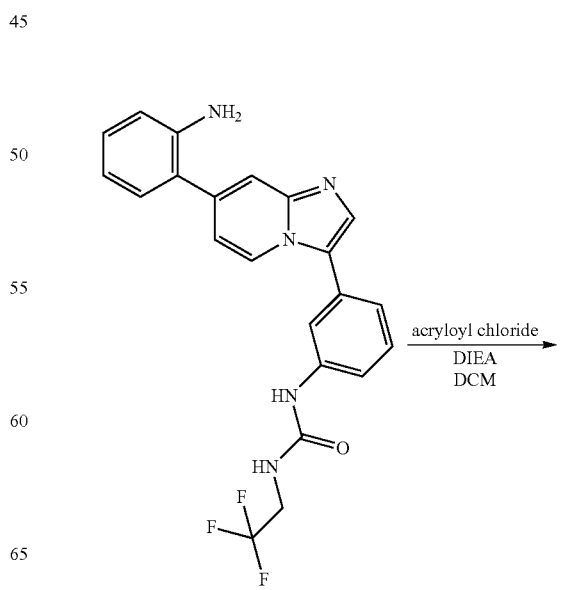

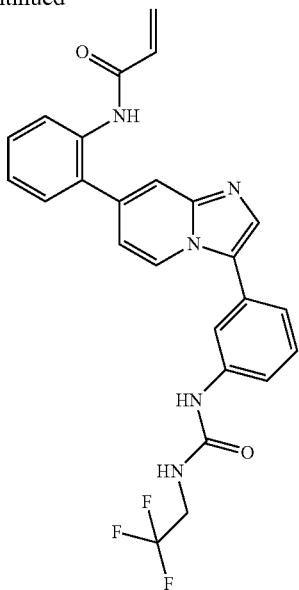

Synthesis of 7-chloro-3-iodoimidazo[1,2-a]pyridine

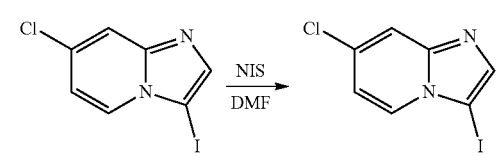

7-chloro-3-iodoimidazo[1,2-a]pyridine was prepared using the procedure described in WO2008078091. MS (ES+) $C_7H_4ClIN_2$ requires: 278, found: 279 [M+H]+.

Synthesis of 3-(7-chloroimidazo[1,2-a]pyridin-3-yl)aniline

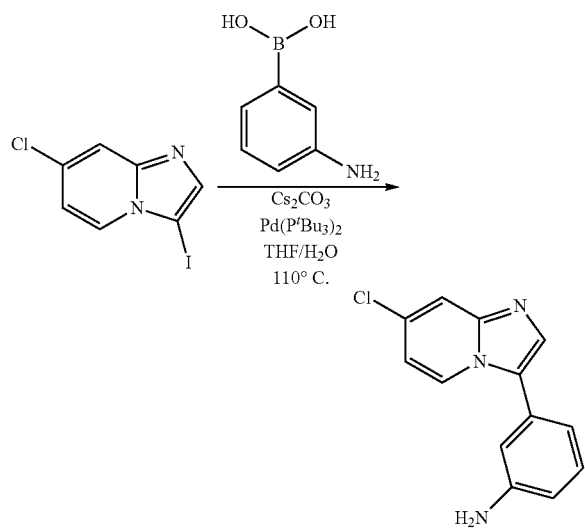

3-(7-chloroimidazo[1,2-a]pyridin-3-yl)aniline was prepared using the procedure described in WO2008078091. MS (ES+) $C_{13}H_{10}ClN_3$ requires: 243, found: 244 [M+H]+.

Synthesis of 1-(3-(7-chloroimidazo[1,2-a]pyridin-3-yl)phenyl)-3-(2,2,2-trifluoroethyl)urea

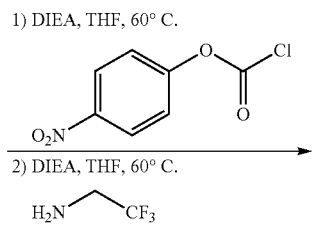

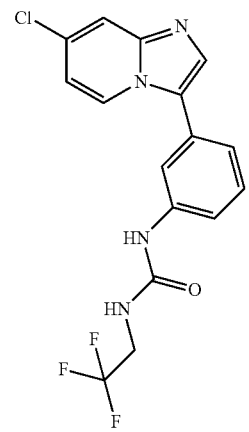

To a solution of 3-(7-chloroimidazo[1,2-a]pyridin-3-yl)aniline (0.15 mmol) in THF (1.5 mL) was added 4-nitrophenyl carbonochloridate (30 mg, 0.15 mmol) and DIEA (0.036 mL, 0.225 mmol). The mixture was heated at 60° C. for 6 h. To the crude carbamate was added DIEA (0.036 mL, 0.225 mmol) and 2,2,2-trifluoroethan-1-amine (0.014 mL, 0.18 mmol) and the solution was heated at 60° C. overnight. The reaction mixture was diluted with EtOAc and water. The separated organic layer was dried with sodium sulfate, filtered and concentrated. The crude mixture was purified by flash chromatography (0-6% MeOH/DCM) to give the title compound (38 mg, 69% yield). MS (ES+) $C_{16}H_{12}ClF_3N_4O$ requires: 368, found: 369 [M+H]+.

129

Synthesis of 1-(3-(7-(2-aminophenyl)imidazo[1,2-a]pyridin-3-yl)phenyl)-3-(2,2,2-trifluoroethyl)urea

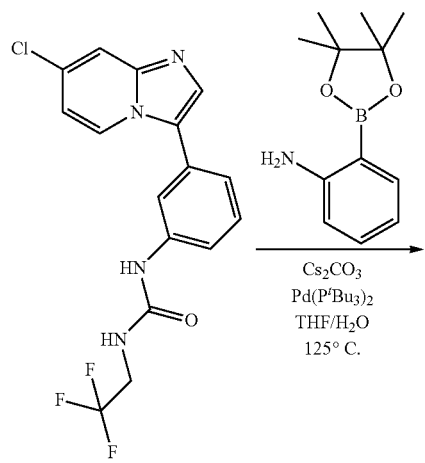

To a mixture of 1-(3-(7-chloroimidazo[1,2-a]pyridin-3-yl)phenyl)-3-(2,2,2-trifluoroethyl)urea (20 mg, 0.052 mmol), 2-(4,4,5,5-tetramethyl-1,3,2-dioxaborolan-2-yl)aniline (15 mg, 0.066 mmol) and cesium carbonate (51 mg, 0.156 mmol) in THF/H$_2$O mixture (2/1, 0.75 ml) was added Pd(P$^t$Bu$_3$)$_2$ (3 mg, 0.005 mmol). The vial was degassed for 5 minutes then capped and heated to 125° C. for 20 minutes in a microwave. After cooling to ambient temperature, the reaction mixture was filtered through a celite pad and purified via flash cromatography (0-10% MeOH/DCM gradient containing 10% NH$_4$OH) to yield the title compound (20 mg, 90% yield). MS (ES+) C$_{22}$H$_{18}$F$_3$N$_5$O requires: 425, found: 426 [M+H]$^+$.

130

Synthesis of N-(2-(3-(3-(2,2,2-trifluoroethyl)ureido)phenyl)imidazo[1,2-a]pyridin-7-yl)phenyl)acrylamide

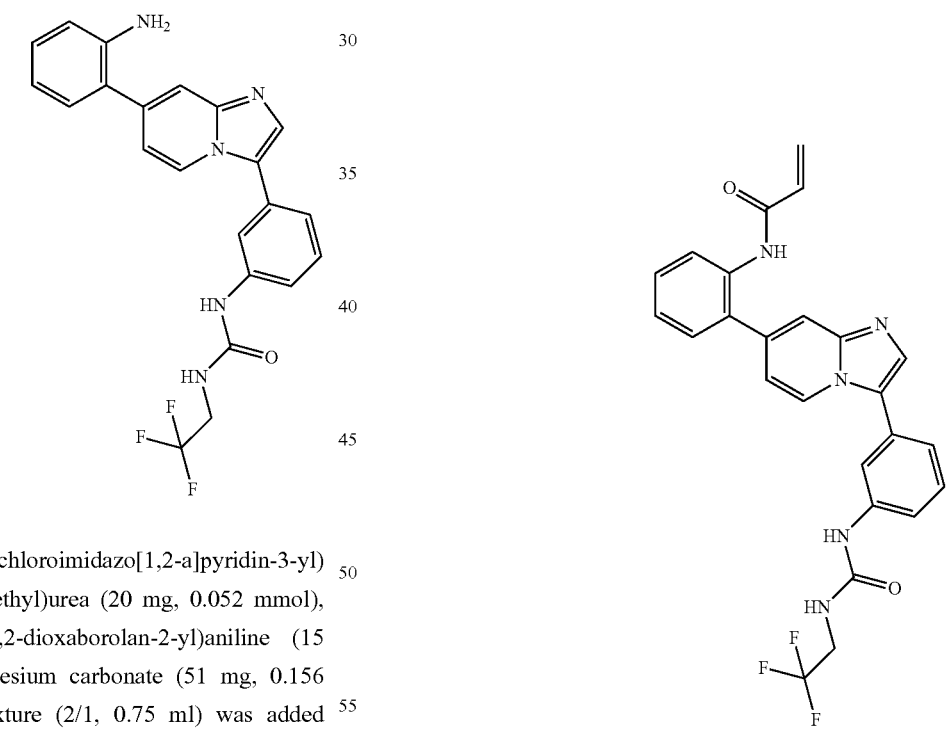

N-(2-(3-(3-(3-(2,2,2-trifluoroethyl)ureido)phenyl)imidazo[1,2-a]pyridin-7-yl)phenyl)acrylamide was prepared using the procedure similar to COMPOUND 30. The product was purified by preparative thin layer chromatographyusing 0-10% MeOH/DCM gradient to give the title compound. MS (ES+) C$_{25}$H$_{20}$F$_3$N$_5$O$_2$ requires: 479, found: 480 [M+H]$^+$.

Example 14: Synthesis of Compound 38

Synthesis of N-(2-(3-(3-isopropoxy-5-(3-(2,2,2-trifluoroethyl)ureido)phenyl)imidazo[1,2-a]pyridin-7-yl)phenyl)acrylamide

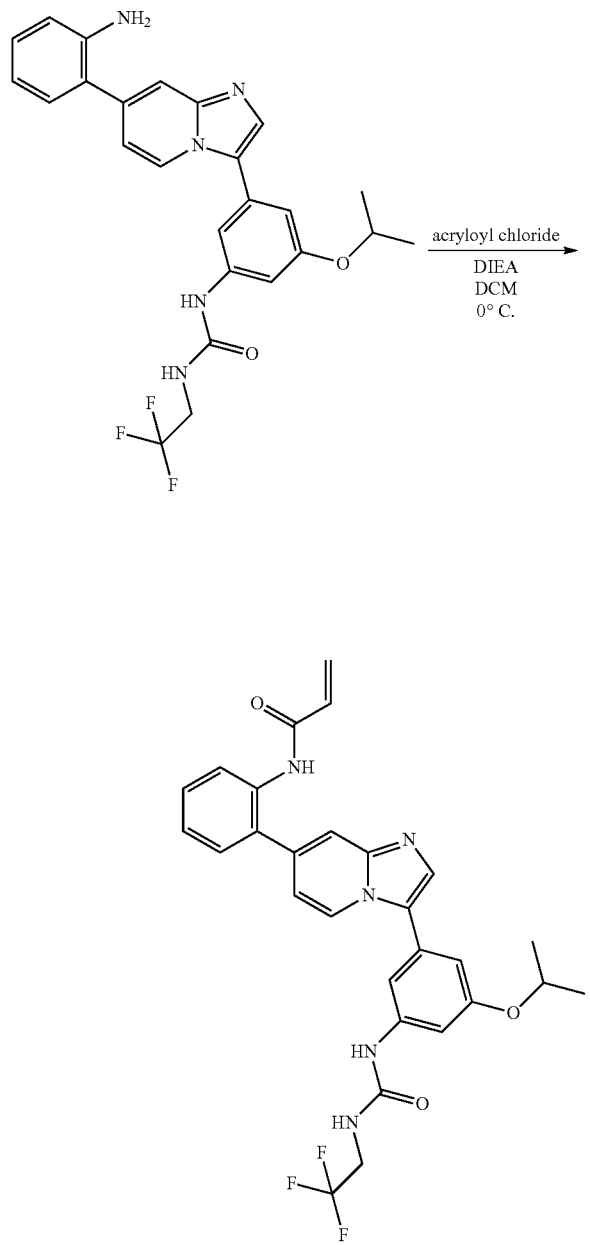

N-(2-(3-(3-isopropoxy-5-(3-(2,2,2-trifluoroethyl)ureido) phenyl)imidazo[1,2-a]pyridin-7-yl)phenyl)acrylamide was prepared using the procedure similar to COMPOUND 30. The product was purified by HPLC using 5-70% Acetonitrile/water+0.1% formic acid gradient to give the title compound as a formate salt. MS (ES+) $C_{28}H_{26}F_3N_5O_3$ requires: 537, found: 538 [M+H]$^+$.

Example 15: Synthesis of Compound 11

Example 15: Synthesis of COMPOUND 11

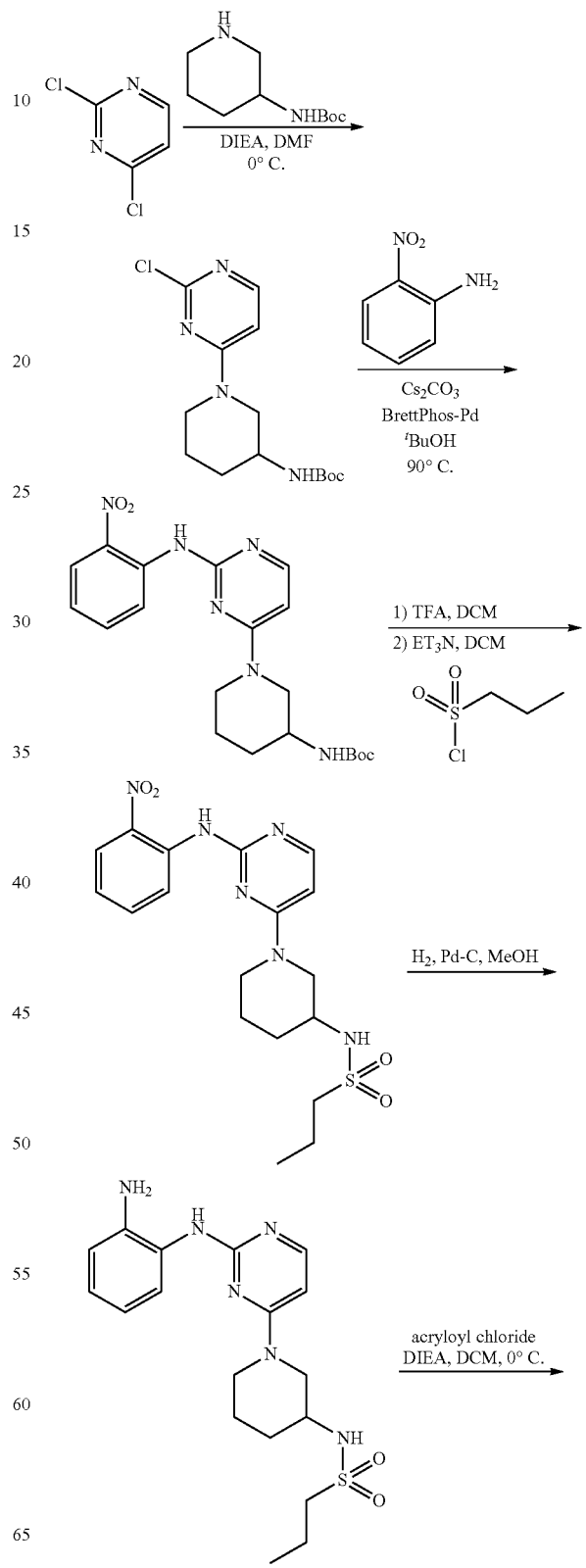

133

-continued

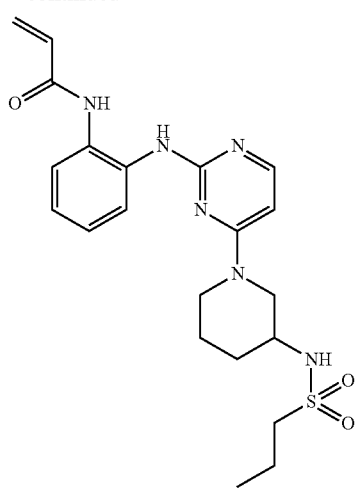 [SMILES: C=CC(=O)Nc1ccccc1Nc1nccc(N2CCCC(NS(=O)(=O)CCC)C2)n1]

Synthesis of tert-butyl (1-(2-chloropyrimidin-4-yl)piperidin-3-yl)carbamate

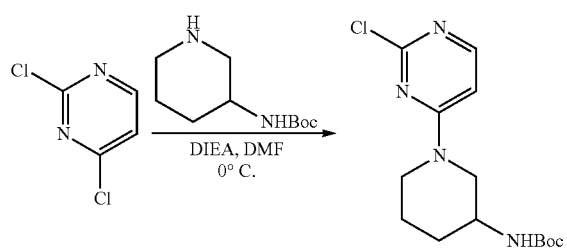

tert-butyl (1-(2-chloropyrimidin-4-yl)piperidin-3-yl)carbamate was prepared using the procedure similar to COMPOUND 54 using 2,4-dichloropyrimidine and tert-butyl piperidin-3-ylcarbamate. MS (ES+) $C_{14}H_{21}ClN_4O_2$ requires: 312, found: 313 [M+H]$^+$

Synthesis of tert-butyl (1-(2-((2-nitrophenyl)amino)pyrimidin-4-yl)piperidin-3-yl)carbamate

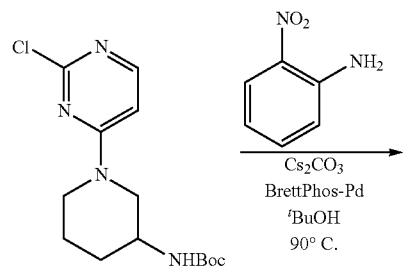

134

-continued

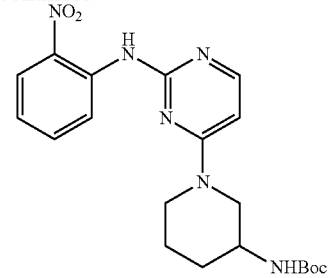

tert-butyl (1-(2-((2-nitrophenyl)amino)pyrimidin-4-yl)piperidin-3-yl)carbamate was prepared using the procedure similar to COMPOUND 54 using 2-nitroaniline. MS (ES+) $C_{20}H_{26}N_6O_4$ requires: 414, found: 415 [M+H]$^+$

Synthesis of N-(1-(2-((2-nitrophenyl)amino)pyrimidin-4-yl)piperidin-3-yl)propane-1-sulfonamide

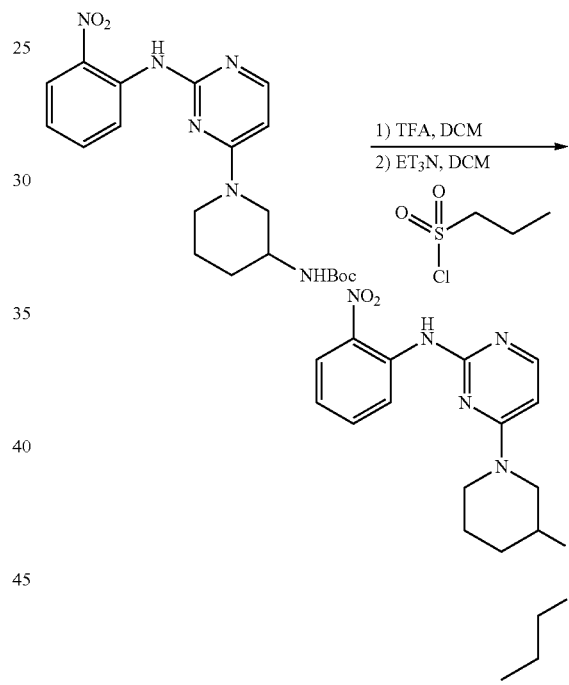

To a solution tert-butyl (1-(2-((2-nitrophenyl)amino)pyrimidin-4-yl)piperidin-3-yl)carbamate (0.14 g, 0.34 mmol) in DCM (2.0 mL) was added TFA (1.0 mL) and the mixture was stirred for 1 h. An aliquot of the reaction mixture was analyzed by LCMS, which indicated that the reaction had proceeded to completion. The solvents were removed and the residue was dried on high vacuum. The crude product was used for the next step without further purification.

To a solution of 4-(3-aminopiperidin-1-yl)-N-(2-nitrophenyl)pyrimidin-2-amine (0.34 mmol) in DCM (3.5 mL) at 0° C. was added propane-1-sulfonyl chloride (0.045 mL, 0.4 mmol) and triethylamine (0.12 mL, 0.85 mmol) and the mixture was warmed to room temperature overnight. The crude reaction mixture was concentrated and purified by flash chromatography (0-7.5% MeOH/DCM) to give the title compound (36 mg, 24% yield). MS (ES+) $C_{18}H_{24}N_6O_4S$ requires: 420, found: 421 [M+H]$^+$.

Synthesis of N-(1-(2-((2-aminophenyl)amino)pyrimidin-4-yl)piperidin-3-yl)propane-1-sulfonamide

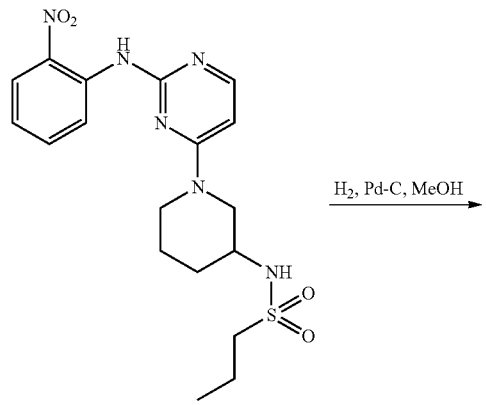

H₂, Pd-C, MeOH

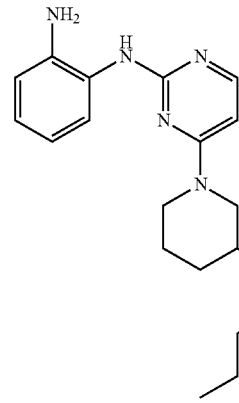

N-(1-(2-((2-aminophenyl)amino)pyrimidin-4-yl)piperidin-3-yl)propane-1-sulfonamide was prepared using the procedure similar to COMPOUND 30. The reaction was filtered through celite to give crude product. MS (ES+) $C_{18}H_{26}N_6O_2S$ requires: 390, found: 391 [M+H]⁺.

Synthesis of N-(2-((4-(3-(propylsulfonamido)piperidin-1-yl)pyrimidin-2-yl)amino)phenyl)acrylamide

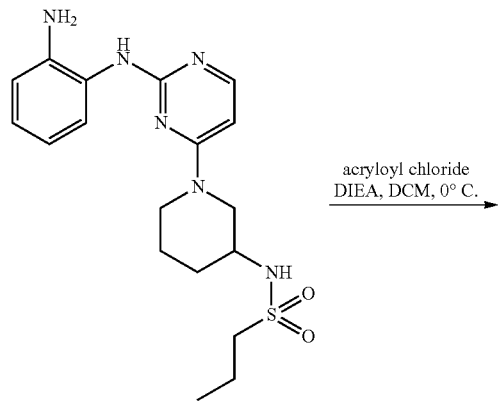

acryloyl chloride
DIEA, DCM, 0° C.

-continued

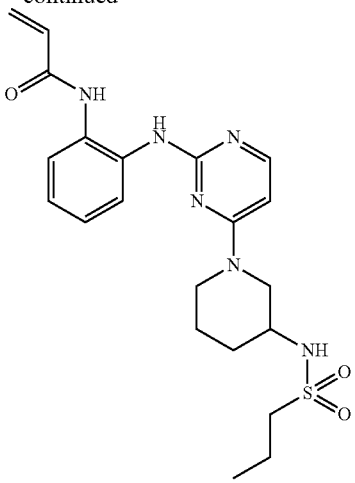

N-(2-((4-(3-(propylsulfonamido)piperidin-1-yl)pyrimidin-2-yl)amino)phenyl)acrylamide was prepared using the procedure similar to COMPOUND 30. The product was purified by preparative thin layer chromatographyusing 0-6% MeOH/DCM gradient to give the title compound. MS (ES+) $C_{21}H_{28}N_6O_3S$ requires: 444, found: 445 [M+H]⁺.

Example 16: Synthesis of Compound 52

Example 16: Synthesis of COMPOUND 52

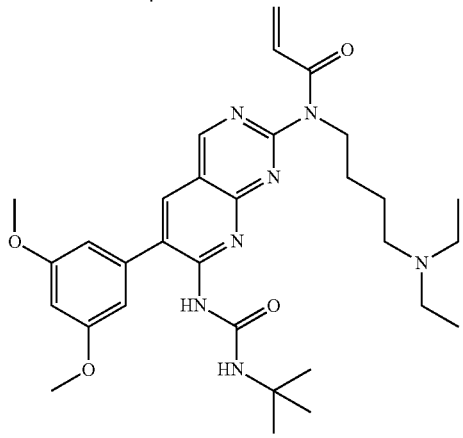

The starting material 1-(tert-butyl)-3-(2-((4-(diethylamino)butyl)amino)-6-(3,5-dimethoxyphenyl)pyrido[2,3-d]pyrimidin-7-yl)urea (PD173074) can be purchased from, e.g., SelleckChem.com. In a dried vessel, acryloyl chloride (2 equiv.) and diisopropylethylamine (4.3 equiv.) are added to a solution of 1-(tert-butyl)-3-(2-((4-(diethylamino)butyl)amino)-6-(3,5-dimethoxyphenyl)pyrido[2,3-d]pyrimidin-7-yl)urea (1 equiv.) in anhydrous dichloromethane at 0° C. After stirring at room temperature for 2 hours, the reaction mixture is concentrated, diluted with DMSO and purified by reverse phase HPLC (5-95% water/acetonitrile). After concentrating the fractions, the product N-(7-(3-(tert-butyl)ureido)-6-(3,5-dimethoxyphenyl)pyrido[2,3-d]pyrimidin-2-yl)-N-(4-(diethylamino)butyl)acrylamide is obtained as a pale yellow foam. LCMS (M+1)=578.2.

Example 17: Synthesis of Compound 55

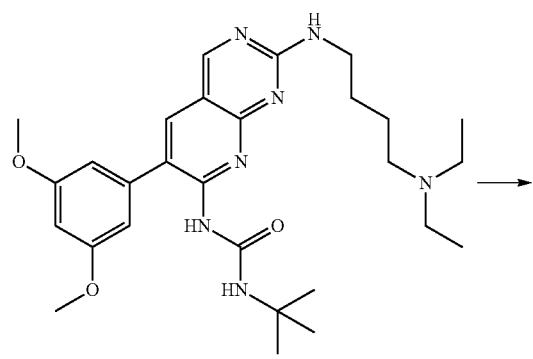

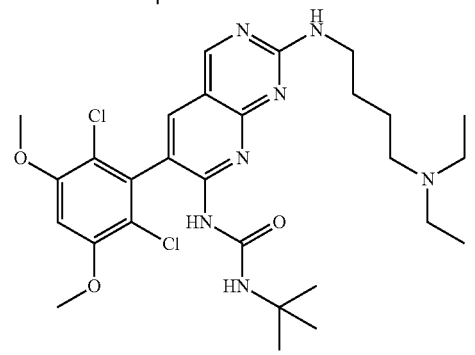

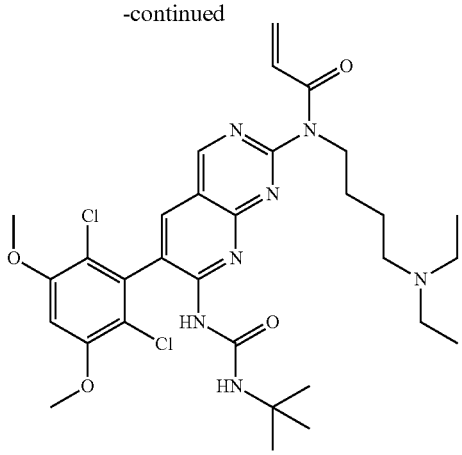

In a dried vessel, sulfuryl chloride (2 equiv.) is added to a solution of 1-(tert-butyl)-3-(2-((4-(diethylamino)butyl)amino)-6-(3,5-dimethoxyphenyl)pyrido[2,3-d]pyrimidin-7-yl)urea (1 equiv.) in anhydrous acetonitrile at 0° C. After stirring for 2 hours, the reaction mixture is diluted with dichloromethane and washed with aqueous saturated sodium bicarbonate solution. The crude product, 1-(tert-butyl)-3-(6-(2,6-dichloro-3,5-dimethoxyphenyl)-2-((4-(diethylamino)butyl)amino)pyrido[2,3-d]pyrimidin-7-yl)urea, is used in the next step without further purification.

In a dried vessel, acryloyl chloride (2 equiv.) and diisopropylethylamine (4.3 equiv.) are added to a solution of the product obtained above (1 equiv.) in anhydrous dichloromethane at 0° C. After stirring at room temperature for 2 hours, the reaction mixture is concentrated, diluted with DMSO and purified by reverse phase HPLC (5-95% water/acetonitrile). After drying on high vacuum, the product N-(7-(3-(tert-butyl)ureido)-6-(2,6-dichloro-3,5-dimethoxyphenyl)pyrido[2,3-d]pyrimidin-2-yl)-N-(4-(diethylamino)butyl) acrylamide is obtained as a yellow foam. LCMS (M+1)=646.3.

Similar procedures to the ones above can be used to prepare other compounds disclosed herein.

$^1$H NMR and LCMS data for Compounds 1 to 55 is summarized below.

| Compound Id | NMR | MS |
|---|---|---|
| COMPOUND 1 | $^1$H NMR (400 MHz, DMSO-d6) δ 9.60 (s, 1H), 8.48 (s, 1H), 8.355 (m, 1H), 7.93 (d, J = 8.0 Hz, 1H), 6.97 (br s, 2H), 6.76 (dd, J = 16.0, 8.0 Hz, 1H), 6.58 (br s, 1H), 6.23 (d, J = 16.0 Hz, 1H), 5.655 (d, J = 12.0 Hz, 1H), 3.84 (s, 6H), 3.53 (s, 3H). | 350 |
| COMPOUND 2 | | 358 |
| COMPOUND 3 | | 381 |
| COMPOUND 4 | | 382 |
| COMPOUND 5 | | 384 |
| COMPOUND 6 | $^1$H NMR (400 MHz, DMSO-d6) δ 9.60-9.38 (m, 1H), 8.79 (s, 1H), 8.51 (s, 2H), 7.69 (d, J = 8.1 Hz, 1H), 7.19 (t, J = 7.8 Hz, 1H), 7.15-7.06 (m, 1H), 6.67 (d, J = 2.3 Hz, 2H), 6.60-6.45 (m, 2H), 6.22 (dd, J = 17.0, 2.1 Hz, 1H), 5.71 (dd, J = 10.2, 2.1 Hz, 1H), 3.76 (s, 6H), 2.12 (s, 3H). | 415 |
| COMPOUND 7 | $^1$H NMR (400 MHz, DMSO-d6) δ 9.61 (s, 1H), 8.05 (d, J = 4.0 Hz, 1H), 7.96 (d, J = 8.0 Hz, 1H), 7.82 (dd, J = 8.0, 4.0 Hz, 1H), 7.05 (s, | 418 |

-continued

| Compound Id | NMR | MS |
|---|---|---|
| | 1H), 6.79 (dd, J = 16.0. 12.0 Hz, 1H), 6.22 (dd, J = 16.0. 4.0 Hz, 1H), 5.65 (dd, J = 12.0. 4.0 Hz, 1H), 3.98 (s, 6H), 3.53 (s, 3H). | |
| COMPOUND 8 | | 420 |
| COMPOUND 9 | $^1$H NMR (400 MHz, DMSO-d6) δ 9.56 (s, 1H), 9.30 (s, 1H), 8.71 (s, 1H), 8.22-8.04 (m, 3H), 8.03-7.87 (m, 2H), 7.64 (m, 2H), 7.52-7.38 (m, 2H), 7.29-7.08 (m, 2H), 6.48 (dd, J = 17.0, 10.2 Hz, 1H), 6.21 (dd, J = 17.0, 2.1 Hz, 1H), 5.67 (dd, J = 10.2, 2.1 Hz, 1H), 2.18 (s, 3H). | 442 |
| COMPOUND 10 | $^1$H NMR (400 MHz, DMSO-d6) δ 9.57 (s, 1H), 9.30 (br s, 2H), 8.98 (s, 1H), 8.64 (d, J = 2.7 Hz, 1H), 7.76 (s, 1H), 7.24 (t, J = 7.8 Hz, 1H), 7.14 (d, J = 7.5 Hz, 1H), 6.96 (d, J = 2.2 Hz, 2H), 6.56 (t, J = 2.2 Hz, 1H), 6.51 (dd, J = 17.0, 10.2 Hz, 1H), 6.22 (dd, J = 17.0, 2.0 Hz, 1H), 5.68 (dd, J = 10.2, 2.0 Hz, 1H), 3.84 (s, 6H), 2.18 (s, 3H). | 442 |
| COMPOUND 11 | | 445 |
| COMPOUND 12 | | 449 |
| COMPOUND 13 | | 449 |
| COMPOUND 14 | | 452 |
| COMPOUND 15 | | 457 |
| COMPOUND 16 | | 457 |
| COMPOUND 17 | $^1$H NMR (400 MHz, DMSO-d6) δ 9.66 (s, 1H), 9.27 (s, 1H), 8.86 (s, 1H), 8.03-7.96 (m, 1H), 7.91 (d, J = 2.0 Hz, 1H), 7.82 (s, 1H), 7.81-7.76 (m, 1H), 7.53 (dd, J = 19.0, 6.9 Hz, 1H), 7.41 (d, J = 7.8 Hz, 1H), 7.37-7.30 (m, 2H), 6.56 (dd, J = 17.0, 10.2 Hz, 1H), 6.24 (dd, J = 17.0, 1.9 Hz, 1H), 6.20-6.14 (m, 1H), 6.06 (dd, J = 17.2, 2.3 Hz, 1H), 5.71 (dd, J = 10.2, 2.0 Hz, 1H), 5.59 (dd, J = 10.0, 2.3 Hz, 1H), 2.32 (s, 3H). | 457 |
| COMPOUND 17A | $^1$H NMR (400 MHz, DMSO-d6) δ 9.53 (d, J = 9.6 Hz, 1H), 9.25 (s, 1H), 8.71 (s, 1H), 7.89 (d, J = 2.0 Hz, 1H), 7.78-7.61 (m, 2H), 7.53 (s, 1H), 7.42 (dd, J = 9.0, 1.8 Hz, 1H), 7.31-7.18 (m, 2H), 7.13 (d, J = 7.5 Hz, 1H), 6.49 (dd, J = 17.0, 10.2 Hz, 1H), 6.21 (dd, J = 17.0, 2.1 Hz, 1H), 5.67 (dd, J = 10.2, 2.0 Hz, 1H), 3.90 (s, 3H), 2.19 (s, 3H). | 463 |
| COMPOUND 18 | | 471 |
| COMPOUND 19 | | 472 |
| COMPOUND 20 | $^1$H NMR (400 MHz, DMSO-d6) δ 9.34 (s, 1H), 8.92 (s, 1H), 8.47 (d, J = 6.8 Hz, 1H), 7.74 (s, 1H), 7.17 (d, J = 1.9 Hz, 2H), 7.10 (s, 1H), 6.98 (s, 1H), 6.82 (s, 1H), 6.74 (s, 1H), 4.69-4.58 (m, 2H), 3.93 (dd, J = 9.7, 6.4 Hz, 2H), 2.72-2.64 (m, 1H), 1.30-1.19 (m, 6H). | 474 |
| COMPOUND 21 | | 480 |
| COMPOUND 22 | $^1$H NMR (400 MHz, DMSO-d6) δ 9.46 (s, 1H), 9.09 (s, 1H), 8.77 (s, 1H), 7.85 (s, 1H), 7.57 (d, J = 8.1 Hz, 2H), 7.45 (dd, J = 8.8, 7.4 Hz, 1H), 7.27-7.04 (m, 3H), 6.51 (s, 1H), 6.21 (d, J = 17.7 Hz, 1H), 5.68 (d, J = 10.2 Hz, 1H), 3.26 (s, 3H), 2.21 (s, 3H). | 481 |
| COMPOUND 23 | | 483 |
| COMPOUND 24 | $^1$H NMR (400 MHz, DMSO-d6) δ 9.47 (s, 1H), 8.93 (s, 1H), 8.54 (s, 2H), 7.71 (d, J = 8.1 Hz, 1H), 7.19 (t, J = 7.8 Hz, 1H), 7.09 (d, J = 7.4 Hz, 1H), 6.98 (s, 1H), 6.53 (dd, J = 17.0, 10.2 Hz, 1H), 6.22 (dd, J = 17.0, 2.1 Hz, 1H), 5.70 (dd, J = 10.2, 2.1 Hz, 1H), 3.94 (s, 6H), 2.13 (s, 3H). | 483 |
| COMPOUND 25 | $^1$H NMR (400 MHz, DMSO-$d_6$) δ 9.53 (s, 1H), 9.23 (s, 1H), 8.68 (s, 1H), 7.82-7.65 (m, 2H), 7.51 (s, 2H), 7.21 (m, 1H), 7.12 (d, J = 6.8 Hz, 1H), 7.01 (s, 1H), 6.49 (dd, J = 17.0, 10.2 Hz, 1H), 6.28-6.15 (m, 1H), 5.68 (dd, J = 10.2, 2.0 Hz, 1H), 3.97 (s, 6H), 2.19 (s, 3H). | 509 |
| COMPOUND 26 | $^1$H NMR (400 MHz, DMSO-d6) δ 9.53 (s, 1H), 9.35 (s, 1H), 9.06 (s, 1H), 8.70 (s, 1H), 8.27 (d, J = 2.6 Hz, 1H), 7.78 (s, 1H), 7.23 (d, J = 7.9 Hz, 1H), 7.15 (s, 1H), 7.06 (s, 1H), 6.52 (dd, J = 17.0,10.1 Hz, 1H), 6.22 (dd, J = 17.0, 2.0 Hz, 1H), 5.69 (d, J = 10.6 Hz, 1H), 3.98 (s, 6H), 2.20 (s, 3H). | 511 |
| COMPOUND 27 | | 513 |
| COMPOUND 28 | | 523 |
| COMPOUND 29 | $^1$H NMR (400 MHz, DMSO-d6) δ 9.28 (s, 1H), 9.20 (s, 1H), 8.87 (s, 1H), 7.80-7.70 (m, 1H), 7.63 (d, J = 7.9 Hz, 1H), 7.54 (s, 2H), 7.22 (t, J = 7.8 Hz, 1H), 7.14 (d, J = 7.6 Hz, 1H), 7.01 (s, 1H), 5.63 (s, 1H), 5.37 (s, 1H), 3.97 (s, 6H), 2.24 (s, 3H), 1.80 (s, 3H). | 523 |

| Compound Id | NMR | MS |
|---|---|---|
| COMPOUND 30 | ¹H-NMR (400 MHz, DMSO) δ ppm 9.59 (s, 1H), 9.29 (s, 1H), 7.80 (s, 1H), 7.59 (br. s., 4H), 7.28 (t, 1H, J = 28 Hz), 7.01 (s, 1H), 6.94 (d, 1H, J = 8 Hz), 6.53-6.47 (m, 1H), 6.22 (d, 1H, J = 16 Hz), 5.69 (d, 1H, J = 8 Hz), 3.97 (s, 6H), 3.72 (s, 3H). | 525 |
| COMPOUND 31 | ¹H NMR (400 MHz, DMSO-d6) δ 9.75 (s, 1H), 8.72 (s, 1H), 8.51 (s, 1H), 7.76 (s, 1H), 7.73-7.59 (m, 2H), 7.19 (dtd, J = 23.6, 7.5, 1.6 Hz, 2H), 6.98 (s, 1H), 6.53 (s, 1H), 6.48 (dd, J = 17.1, 10.1 Hz, 1H), 6.25 (dd, J = 17.0, 2.0 Hz, 1H), 5.76-5.69 (m, 1H), 3.96 (s, 6H), 3.47 (s, 3H). | 525 |
| COMPOUND 32 | | 527 |
| COMPOUND 33 | ¹H NMR (400 MHz, DMSO-d6) δ 9.52 (s, 1H), 9.20 (s, 1H), 8.79 (s, 1H), 7.75-7.68 (m, 1H), 7.63 (t, J = 7.7 Hz, 1H), 7.48 (s, 2H), 7.10 (t, J = 9.0 Hz, 1H), 6.96 (s, 1H), 6.41 (dd, J = 17.0, 10.2 Hz, 1H), 6.15 (dd, J = 17.0, 2.1 Hz, 1H), 5.63 (dd, J = 10.2, 2.1 Hz, 1H), 3.92 (s, 6H), 2.03 (m, 3H). | 527 |
| COMPOUND 34 | ¹H NMR (400 MHz, DMSO-d6) δ 9.53 (d, J = 27.9 Hz, 1H), 9.28 (s, 1 H), 8.96 (s, 1H), 7.75 (d, J = 29.9 Hz, 1H), 7.59 (d, J = 1.7 Hz, 1H), 7.49 (d, J = 10.8 Hz, 1H), 7.02 (s, 1H), 6.50 (s, 1H), 6.21 (dd, J = 16.9, 2.1 Hz, 1H), 5.75 (s, 1H), 5.68 (dd, J = 10.2, 2.0 Hz, 1H), 3.98 (d, J = 4.6 Hz, 6H), 2.19 (s, 3H). | 527 |
| COMPOUND 35 | ¹H NMR (400 MHz, DMSO-$d_6$) δ 9.63 (s, 1H), 9.25 (s, 1H), 8.90 (s, 1H), 8.01 (dd, J = 7.4, 2.3 Hz, 1H), 7.76 (t, J = 1.3 Hz, 1H), 7.54 (br.s, 2H), 7.41-7.28 (m, 2H), 7.01 (s, 1H), 6.56 (dd, J = 17.0, 10.2 Hz, 1H), 6.24 (dd, J = 17.0, 2.0 Hz, 1H), 5.71 (dd, J = 10.2, 2.0 Hz, 1H), 3.97 (s, 6H). | 529 |
| COMPOUND 36 | ¹H NMR (400 MHz, DMSO-d6) δ 11.11 (s, 1H), 10.27 (s, 1H), 9.79 (s, 1H), 8.91 (s, 1H), 7.93 (d, J = 11.0, 1H), 7.28 (m, 1H), 7.20 (d, J = 8.1 Hz, 1H), 7.11 (m, 2H), 6.97 (s, 1H), 6.70 (dd, J = 17.0, 10.1 Hz, 1H), 6.33 (dd, J = 16.9, 1.8 Hz, 1H), 5.85 (dd, J = 10.3, 1.8 Hz, 1H), 4.54 (s, 2H), 3.94 (s, 6H). | 531 |
| COMPOUND 37 | ¹H NMR (400 MHz, DMSO-d6) δ 9.76 (s, 1H), 9.31 (s, 1H), 9.00 (s, 1H), 7.80 (s, 1H), 7.68-7.57 (m, 1H), 7.53-7.42 (m, 1H), 7.02 (s, 1H), 6.93 (s, 2H), 6.51 (dd, J- = 17.0, 10.2 Hz, 1H), 6.31-6.21 (m, 1H), 5.74 (d, J = 10.2 Hz, 1H), 3.97 (s, 6H). | 531 |
| COMPOUND 38 | | 538 |
| COMPOUND 39 | ¹H NMR (400 MHz, DMSO-d6) δ 9.47 (s, 1H), 8.43 (d, J = 10.0 Hz, 2H), 7.70 (d, J = 12.6 Hz, 2H), 7.22 (t, J = 7.8 Hz, 1H), 7.14 (d, J = 7.6 Hz, 1H), 6.97 (s, 1H), 6.46 (dd, J = 17.0, 10.2 Hz, 1H), 6.18 (dd, J = 17.0, 2.1 Hz, 1H), 6.09 (s, 1H), 5.65 (dd, J = 10.2, 2.1 Hz, 1H), 3.95 (s, 6H), 3.39 (s, 3H), 2.20 (s, 3H). | 539 |
| COMPOUND 41 | ¹H NMR (400 MHz, DMSO-d6) δ 9.57 (s, 1H), 9.15 (s, 1H), 8.74 (s, 1H), 7.74 (s, 1H), 7.28 (d, J = 1.7 Hz, 1H), 7.20 (t, J = 7.8 Hz, 1H), 7.11 (d, J = 7.5 Hz, 1H), 7.01 (s, 2H), 6.48 (dd, J = 17.0, 10.2 Hz, 1H), 6.21 (dd, J = 16.9, 2.0 Hz, 1H), 5.75-5.61 (m, 1H), 3.97 (s, 6H), 3.83 (s, 3H), 2.18 (s, 3H). | 539 |
| COMPOUND 43 | ¹H NMR (400 MHz, DMSO-$d_6$) δ 9.44 (s, 1H), 9.05 (s, 1H), 8.74 (s, 1H), 7.74 (br.s, 2H), 7.20 (m, 1H), 7.11 (s, 1H), 6.97 (s, 1H), 6.50 (m, 2H), 6.26-6.12 (m, 1H), 5.67 (d, J = 10.2 Hz, 1H), 3.94 (s, 6H), 2.19 (s, 3H), N-Methyl group is buried by water peak. | 540 |
| COMPOUND 45 | | 541 |
| COMPOUND 46 | | 543 |
| COMPOUND 47 | ¹H NMR (400 MHz, DMSO-d6) δ 9.78 (s, 1H), 9.20 (s, 1H), 8.88 (s, 1H), 7.80 (d, J = 8.3 Hz, 1H), 7.36-7.23 (m, 2H), 7.15-6.95 (m, 3H), 6.54 (dd, J = 17.0, 10.2 Hz, 1H), 6.26 (dd, J = 17.0, 2.0 Hz, 1H), 5.75 (dd, J = 10.1, 2.1 Hz, 1H), 3.97 (s, 6H), 3.85 (s, 3H). | 543 |
| COMPOUND 48 | ¹H NMR (400 MHz, DMSO-$d_6$) δ 9.48 (s, 1H), 8.35 (s, 1H), 7.99 (s, 1H), 7.66(s, 1H), 7.16 (t, J = 7.8 Hz, 1H), 7.10-7.06 (m, 1H), 6.99 (s, 1H), 6.53 (dd, J = 17.0, 10.2 Hz, 1H), 6.22 (dd, J = 16.9, 2.1 Hz, 1H), 5.71 (dd, J = 10.2, 2.0 Hz, 1H), 4.48 (s, 2H), 3.96 (s, 6H), 3.44 (s, 3H), 2.17 (s, 3H). | 544 |
| COMPOUND 49 | ¹H NMR (400 MHz, DMSO-d6) δ 9.53 (s, 1H), 9.25 (s, 1H), 8.77 (s, 1H), 7.99 (s, 1H), 7.75 (s, 1H), 7.52 (br.s, 2H), 7.20 (d, J = 2.5 Hz, 1H), 7.01 (s, 1H), 6.53 (dd, J = 17.0, 10.2 Hz, 1H), 6.22 (dd, J = 17.0, 2.0 Hz, 1H), 5.69 (dd, J = 10.2, 2.0 Hz, 1H), 3.97 (s, 6H). | 543 |
| COMPOUND 50 | | 546 |
| COMPOUND 51 | ¹H NMR (400 MHz, DMSO-$d_6$) δ 9.50 (s, 1H), 9.22 (s, 1H), 8.76 (s, 1H), 8.31 (d, J = 7.6 Hz, 1H), 7.75 (d, J = 1.4 Hz, 1H), 7.65-7.47 (m, 3H), 7.01 (s, 1H), 6.52 (dd, J = 17.0, 10.2 Hz, 1H), 6.19 (dd, J = 16.9, 2.0 Hz, 1H), 5.66 (dd, J = 10.2, 2.0 Hz, 1H), 3.97 (s, 6H). | 563 |
| COMPOUND 52 | ¹H NMR (400 MHz, DMSO-d6) δ 9.33 (s, 1H), 8.30 (s, 1H), 8.22 (s, 1H), 6.81 (dd, J = 16.0. 12.0 Hz, 1H), 6.68 (m, 3H), 6.19 (dd, J = | 578 |

-continued

| Compound Id | NMR | MS |
|---|---|---|
| | 16.0. 4.0 Hz, 1H), 5.62 (dd, J = 12.0. 4.0 Hz, 1H), 4.12 (t, J = 8.0 Hz, 2H), 3.80 (s, 6H), 2.44 (m, 6H), 1.63 (m, 2H), 1.37-1.327 (m, 11H), 0.92 (t, J = 8.0 Hz, 6H). | |
| COMPOUND 54 | $^1$H NMR (400 MHz, DMSO-d6) δ 9.98 (s, 1H), 9.08 (s, 1H), 8.30 (s, 1H), 8.21-8.07 (m, 3H), 7.93 (d, J = 10.7 Hz, 2H), 7.67 (m, 4H), 6.50 (dd, J = 16.9, 10.2 Hz, 1H), 6.33-6.25 (m, 1H), 5.83-5.76 (m, 1H), 3.78 (m, 2H), 3.59 (m, 4H), 3.43 (m, 4H), 2.92 (d, J = 11.4 Hz, 2H), 2.30 (s, 3H), 2.23 (s, 2H), 2.14 (s, 3H), 1.79 (m, 2H), 1.69-1.54 (m, 2H). | 623 |
| COMPOUND 55 | $^1$H NMR (400 MHz, DMSO-d6) δ 9.32 (s, 1H), 8.24 (m, 3H), 7.07 (s, 1H), 6.86 (dd, J = 16.0. 12.0 Hz, 1H), 6.18 (dd, J = 16.0. 4.0 Hz, 1H), 5.62 (dd, J = 12.0. 4.0 Hz, 1H), 4.14 (t, J = 8.0 Hz, 2H), 3.98 (s, 6H), 2.43 (m, 6H), 1.63 (m, 2H), 1.40-1.30 (m, 11H), 0.90 (t, J = 8.0 Hz, 6H). | 646 |

Compound Selectivity

The selectivity score is an unbiased measure that enables quantitative comparisons between compounds and the detailed differentiation and analysis of interaction patterns. One measure of selectivity is calculated using the percent of control values from a panel of kinase assays. The scores from primary screens (performed at a single concentration) are reported as Percent of DMSO Control (POC) and are calculated in the following manner:

$$\frac{\text{Test compound signal} - \text{positive control signal}}{\text{Negative control signal} - \text{positive control signal}} \times 100$$

where the negative control is a solvent such as DMSO (100% control), and the positive control is a control compound known to bind with high affinity (0% control).

The selectivity score (S) for each compound screened can be calculated by dividing the number of kinases with a POC less than a chosen value, e.g., 10, 20, or 35, when screened at a certain concentration, e.g., 1 µM, 3 µM, 5 µM, or 10 µM, by the total number of distinct kinases tested (excluding mutant variants). For example, a selectivity score (S) can be calculated by dividing the number of kinases with a POC less than 10 when screened at 3 µM by the total number of distinct kinases tested (excluding mutant variants); such a score would be shown as [S(10) at 3 µM]. The selectivity of Compounds COMPOUND 9; COMPOUND 9; COMPOUND 11; COMPOUND 15; COMPOUND 16; COMPOUND 20; COMPOUND 21; COMPOUND 23; COMPOUND 24; COMPOUND 25; COMPOUND 26; COMPOUND 27; COMPOUND 30; COMPOUND 32; COMPOUND 35; COMPOUND 60; COMPOUND 38; COMPOUND 39; COMPOUND 41; COMPOUND 45; COMPOUND 48; COMPOUND 50; COMPOUND 52; COMPOUND 54; COMPOUND 55 was determined; all had selectivity scores [S(10) @3 µM] of 0.030 or lower.

COMPOUND 9; COMPOUND 11; COMPOUND 15; COMPOUND 16; COMPOUND 20; COMPOUND 21; COMPOUND 23; COMPOUND 24; COMPOUND 25; COMPOUND 26; COMPOUND 32; COMPOUND 35; COMPOUND 60; COMPOUND 38; COMPOUND 39; COMPOUND 45; COMPOUND 48; COMPOUND 50; COMPOUND 52 all had selectivity scores [S(10) @3 µM] of 0.010 or lower.

Biochemical Activity Assessment

In order to assess the activity of chemical compounds against the relevant kinase of interest, the Caliper Life-Sciences electrophoretic mobility shift technology platform is utilized. Fluorescently labeled substrate peptide is incubated in the presence dosed levels of compounds, a set concentration of kinase and of ATP, so that a reflective proportion of the peptide is phosphorylated. At the end of the reaction, the mix of phosphorylated (product) and non-phosphorylated (substrate) peptides are passed through the microfluidic system of the Caliper LabChip® EZ Reader II, under an applied potential difference. The presence of the phosphate group on the product peptide provides a difference in mass and charge between the product peptide and the substrate peptide, resulting in a separation of the substrate and product pools in the sample. As the pools pass the LEDS within the instrument, these pools are detected and resolved as separate peaks. The ratio between these peaks therefore reflects the activity of the chemical matter at that concentration in that well, under those conditions.

FGFR-1 wild type assay at Km: In each well of a 384-well plate, 0.1 ng/ul of wild type FGFR-1 (Carna Biosciences, Inc.) was incubated in a total of 12.5 ul of buffer (100 mM HEPES pH 7.5, 0.015% Brij 35, 10 mM MgCl$_2$, 1 mM DTT) with 1 uM CSKtide (5-FAM-KKKKEEIYFFFG-NH$_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35 s).

FGFR-4 wild type assay at Km: In each well of a 384-well plate, 0.5 ng/ul of wild type FGFR-4 (Carna Biosciences, Inc.) was incubated in a total of 12.5 ul of buffer (100 mM HEPES pH 7.5, 0.015% Brij 35, 10 mM MgCl$_2$, 1 mM DTT) with 1 uM CSKtide (5-FAM-KKKKEEIYFFFG-NH$_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper LabChip® EZ Reader II (protocol settings: −1.9 psi, upstream voltage −700, downstream voltage −3000, post sample sip 35 s).

| Compound Id | Structure | FGFR4 IC50 | FGFR1 IC50 | Ratio FGFR1/FGFR4 |
|---|---|---|---|---|
| COMPOUND 1 | (3,5-dimethoxyphenyl)-quinazoline with N-methyl-N-acryloyl substituent | C | D | C |
| COMPOUND 2 | (2,6-dichlorophenyl)-quinazoline with N-methyl-N-acryloyl substituent | C | D | D |
| COMPOUND 3 | | B | D | A |
| COMPOUND 4 | | C | D | B |
| COMPOUND 5 | pyrimido-pyrimidinone with 3,5-dimethoxyphenyl and N-methyl-N-acryloyl substituents | B | D | A |
| COMPOUND 6 | 5-((3,5-dimethoxyphenyl)ethynyl)pyrimidine with 2-methyl-6-acrylamidophenyl amine | C | D | A |

-continued

| Compound Id | Structure | FGFR4 IC50 | FGFR1 IC50 | Ratio FGFR1/FGFR4 |
|---|---|---|---|---|
| COMPOUND 7 | 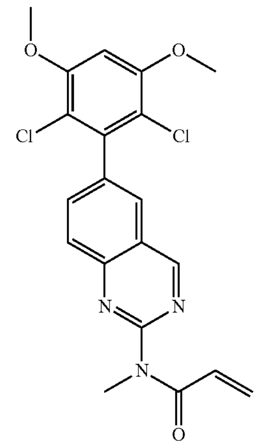 [SMILES: C=CC(=O)N(C)c1ncc2cc(-c3c(Cl)c(OC)cc(OC)c3Cl)ccc2n1] | A | D | A |
| COMPOUND 8 | 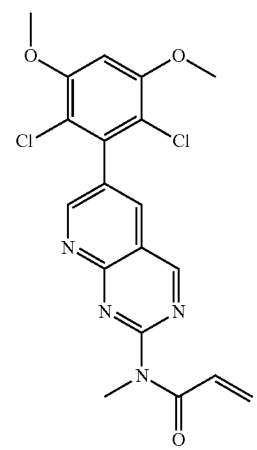 [SMILES: C=CC(=O)N(C)c1ncc2cc(-c3c(Cl)c(OC)cc(OC)c3Cl)cnc2n1] | A | C | E |
| COMPOUND 9 | 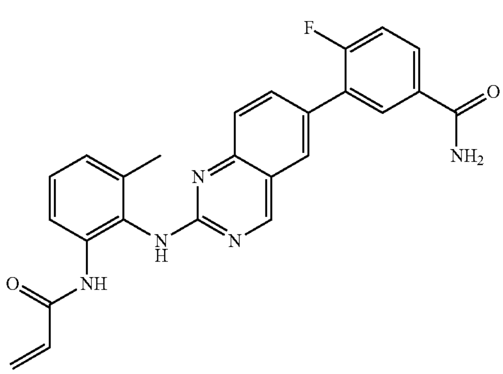 [SMILES: C=CC(=O)Nc1cccc(C)c1Nc1ncc2cc(-c3cc(C(N)=O)ccc3F)ccc2n1] | C | D | D |

-continued

| Compound Id | Structure | FGFR4 IC50 | FGFR1 IC50 | Ratio FGFR1/FGFR4 |
|---|---|---|---|---|
| COMPOUND 10 | 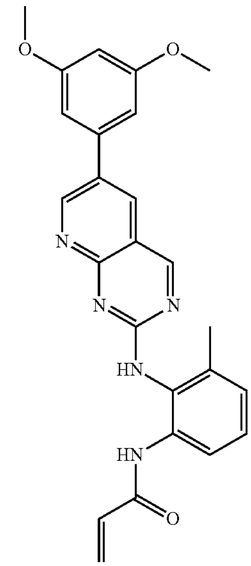 [SMILES: C=CC(=O)Nc1cccc(C)c1Nc1ncc2cc(-c3cc(OC)cc(OC)c3)cnc2n1] | D | D | E |
| COMPOUND 11 | 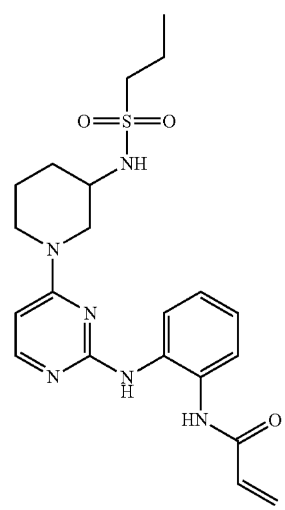 [SMILES: C=CC(=O)Nc1ccccc1Nc1nccc(N2CCCC(NS(=O)(=O)CCC)C2)n1] | C | D | B |
| COMPOUND 12 | 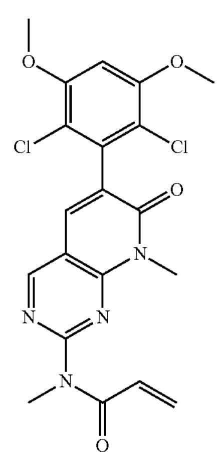 [SMILES: C=CC(=O)N(C)c1ncc2cc(-c3c(Cl)c(OC)cc(OC)c3Cl)c(=O)n(C)c2n1] | A | B | D |

-continued

| Compound Id | Structure | FGFR4 IC50 | FGFR1 IC50 | Ratio FGFR1/FGFR4 |
| --- | --- | --- | --- | --- |
| COMPOUND 13 | 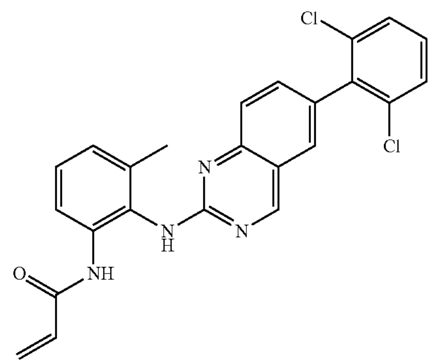 [SMILES: C=CC(=O)Nc1cccc(C)c1Nc1ncc2cc(-c3c(Cl)cccc3Cl)ccc2n1] | B | D | D |
| COMPOUND 14 | 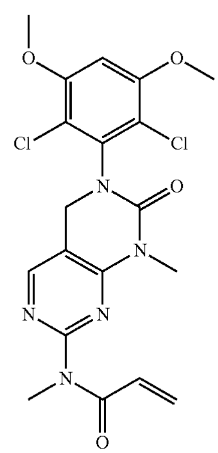 [SMILES: C=CC(=O)N(C)c1ncc2c(n1)N(C)C(=O)N(c1c(Cl)c(OC)cc(OC)c1Cl)C2] | B | C | F |
| COMPOUND 15 | 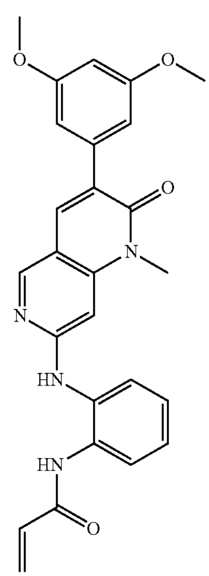 [SMILES: C=CC(=O)Nc1ccccc1Nc1cc2c(cn1)cc(-c1cc(OC)cc(OC)c1)c(=O)n2C] | B | D | B |

-continued

| Compound Id | Structure | FGFR4 IC50 | FGFR1 IC50 | Ratio FGFR1/FGFR4 |
|---|---|---|---|---|
| COMPOUND 16 | 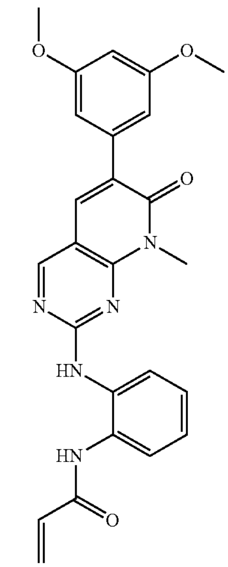 [SMILES: C=CC(=O)Nc1ccccc1Nc1ncc2cc(-c3cc(OC)cc(OC)c3)c(=O)n(C)c2n1] | C | D | D |
| COMPOUND 17 | 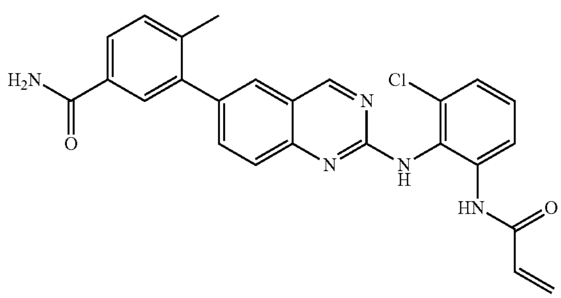 [SMILES: C=CC(=O)Nc1cccc(Cl)c1Nc1ncc2cc(-c3cc(C(N)=O)ccc3C)ccc2n1] | B | D | B |
| COMPOUND 17A | 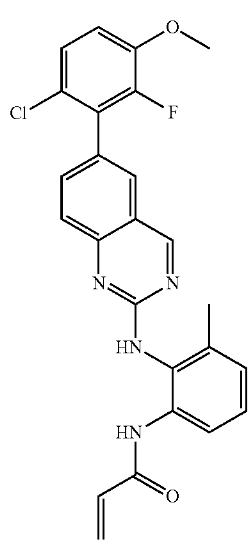 [SMILES: C=CC(=O)Nc1cccc(C)c1Nc1ncc2cc(-c3c(Cl)ccc(OC)c3F)ccc2n1] | B | D | E |

-continued

| Compound Id | Structure | FGFR4 IC50 | FGFR1 IC50 | Ratio FGFR1/FGFR4 |
|---|---|---|---|---|
| COMPOUND 18 | 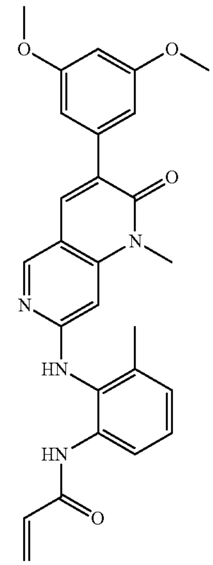 [SMILES: C=CC(=O)Nc1cccc(C)c1Nc1cc2c(cn1)cc(-c1cc(OC)cc(OC)c1)c(=O)n2C] | B | D | B |
| COMPOUND 19 | 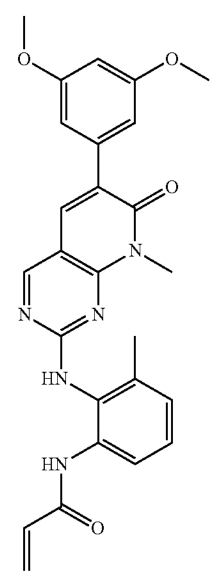 [SMILES: C=CC(=O)Nc1cccc(C)c1Nc1ncc2cc(-c3cc(OC)cc(OC)c3)c(=O)n(C)c2n1] | B | D | B |

-continued
| Compound Id | Structure | FGFR4 IC50 | FGFR1 IC50 | Ratio FGFR1/FGFR4 |
|---|---|---|---|---|
| COMPOUND 20 | 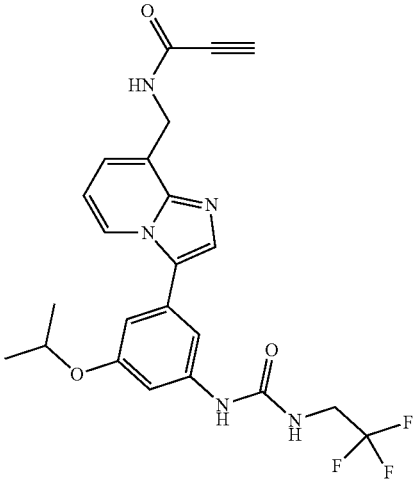 [SMILES: C#CC(=O)NCc1cccn2c(-c3cc(NC(=O)NCC(F)(F)F)cc(OC(C)C)c3)cnc12] | B | D | E |
| COMPOUND 21 | 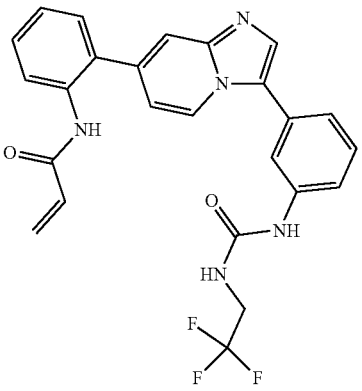 [SMILES: C=CC(=O)Nc1ccccc1-c1ccn2c(-c3cccc(NC(=O)NCC(F)(F)F)c3)cnc2c1] | C | D | B |
| COMPOUND 22 | 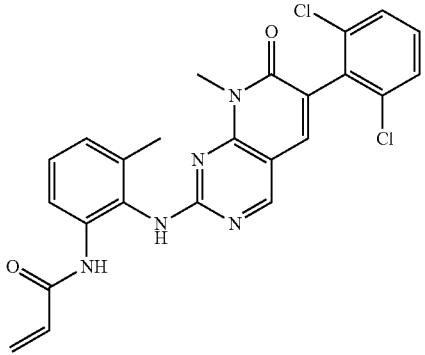 | B | D | B |
| COMPOUND 23 | 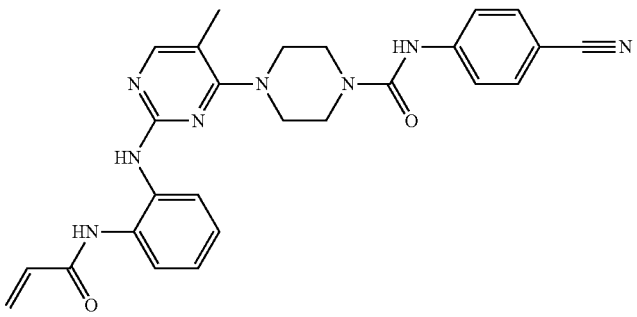 [SMILES: C=CC(=O)Nc1ccccc1Nc1ncc(C)c(N2CCN(C(=O)Nc3ccc(C#N)cc3)CC2)n1] | C | D | A |

| Compound Id | Structure | FGFR4 IC50 | FGFR1 IC50 | Ratio FGFR1/FGFR4 |
|---|---|---|---|---|
| COMPOUND 24 | 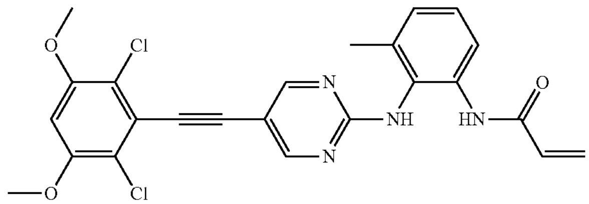 [SMILES: C=CC(=O)Nc1cccc(C)c1Nc1ncc(C#Cc2c(Cl)c(OC)cc(OC)c2Cl)cn1] | B | D | B |
| COMPOUND 25 | 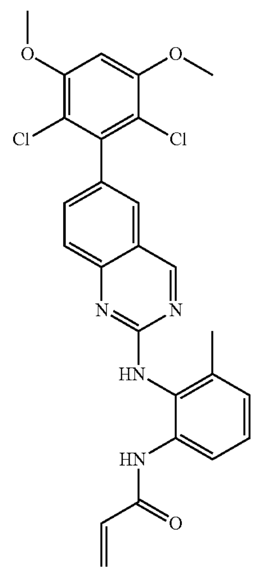 [SMILES: C=CC(=O)Nc1cccc(C)c1Nc1ncc2cc(-c3c(Cl)c(OC)cc(OC)c3Cl)ccc2n1] | A | C | E |
| COMPOUND 25A | 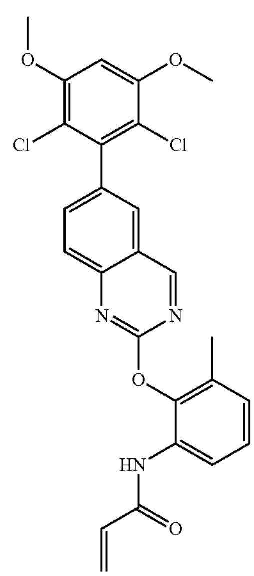 [SMILES: C=CC(=O)Nc1cccc(C)c1Oc1ncc2cc(-c3c(Cl)c(OC)cc(OC)c3Cl)ccc2n1] | C | D | D |

-continued
| Compound Id | Structure | FGFR4 IC50 | FGFR1 IC50 | Ratio FGFR1/FGFR4 |
|---|---|---|---|---|
| COMPOUND 26 | 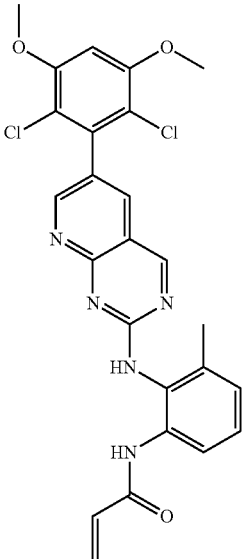 | A | C | A |
| COMPOUND 27 | 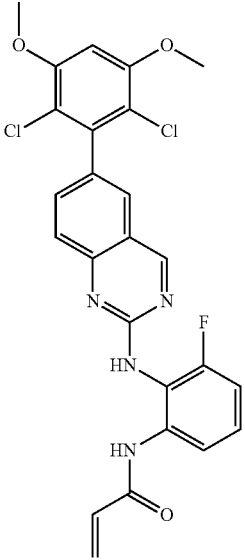 | A | B | C |

| Compound Id | Structure | FGFR4 IC50 | FGFR1 IC50 | Ratio FGFR1/FGFR4 |
|---|---|---|---|---|
| COMPOUND 28 | 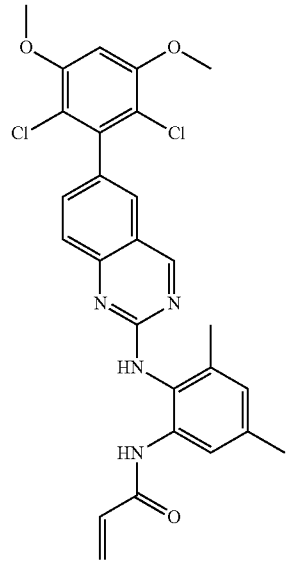 [SMILES: C=CC(=O)Nc1cc(C)cc(C)c1Nc1ncc2cc(-c3c(Cl)c(OC)cc(OC)c3Cl)ccc2n1] | B | D | B |
| COMPOUND 29 | 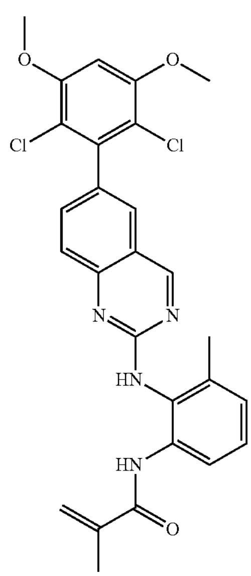 [SMILES: C=C(C)C(=O)Nc1cccc(C)c1Nc1ncc2cc(-c3c(Cl)c(OC)cc(OC)c3Cl)ccc2n1] | C | C | D |

-continued

| Compound Id | Structure | FGFR4 IC50 | FGFR1 IC50 | Ratio FGFR1/FGFR4 |
|---|---|---|---|---|
| COMPOUND 30 | 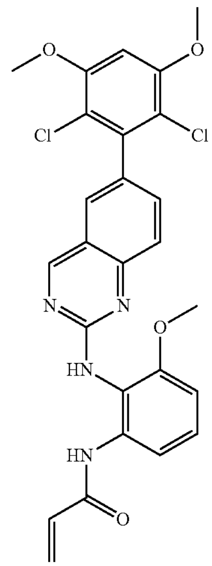 | A | C | E |
| COMPOUND 31 | 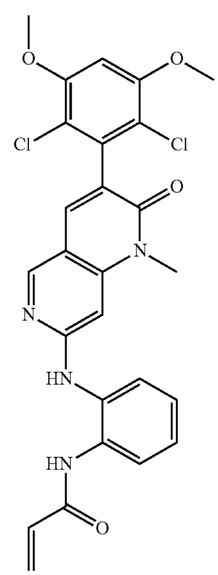 [SMILES: C=CC(=O)Nc1ccccc1Nc1cc2c(cn1)cc(-c1c(Cl)c(OC)cc(OC)c1Cl)c(=O)n2C] | A | B | B |

-continued
| Compound Id | Structure | FGFR4 IC50 | FGFR1 IC50 | Ratio FGFR1/FGFR4 |
|---|---|---|---|---|
| COMPOUND 32 | 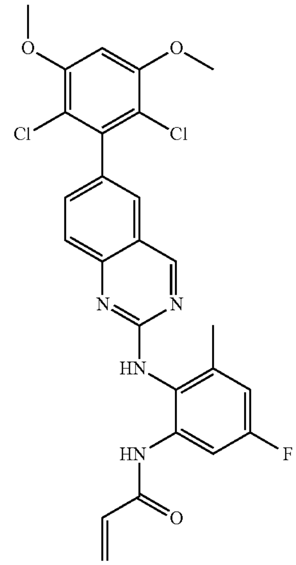 [SMILES: C=CC(=O)Nc1cc(F)cc(C)c1Nc1ncc2cc(-c3c(Cl)c(OC)cc(OC)c3Cl)ccc2n1] | A | D | C |
| COMPOUND 33 | 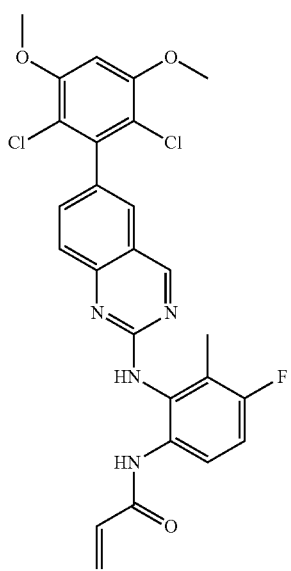 | B | D | F |

| Compound Id | Structure | FGFR4 IC50 | FGFR1 IC50 | Ratio FGFR1/FGFR4 |
|---|---|---|---|---|
| COMPOUND 34 | 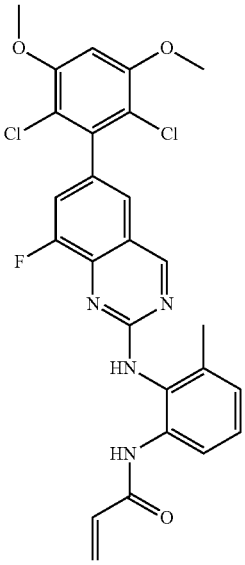 [SMILES: C=CC(=O)Nc1cccc(C)c1Nc1ncc2cc(-c3c(Cl)c(OC)cc(OC)c3Cl)cc(F)c2n1] | A | C | D |
| COMPOUND 35 | 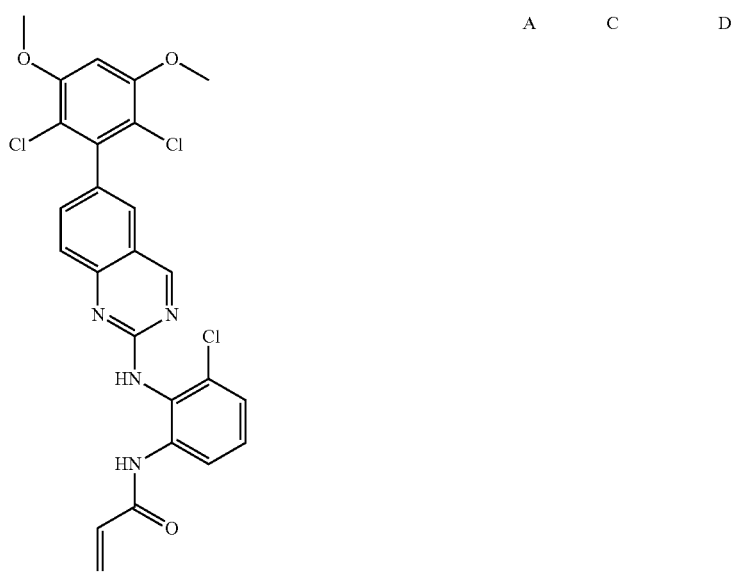 | A | C | D |

-continued

| Compound Id | Structure | FGFR4 IC50 | FGFR1 IC50 | Ratio FGFR1/FGFR4 |
|---|---|---|---|---|
| COMPOUND 36 | 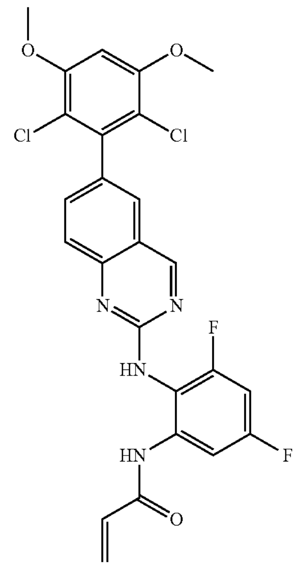 [SMILES: C=CC(=O)Nc1cc(F)cc(F)c1Nc1ncc2cc(-c3c(Cl)c(OC)cc(OC)c3Cl)ccc2n1] | C | D | B |
| COMPOUND 37 | 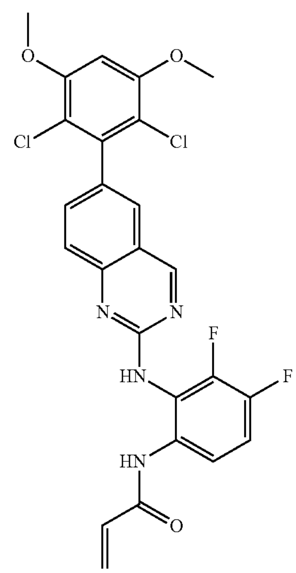 | A | C | C |
| COMPOUND 38 | 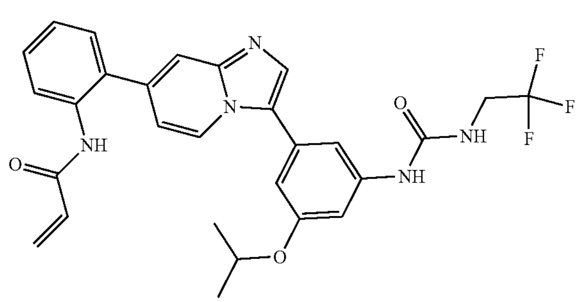 [SMILES: C=CC(=O)Nc1ccccc1-c1ccn2c(-c3cc(NC(=O)NCC(F)(F)F)cc(OC(C)C)c3)cnc2c1] | C | D | E |

| Compound Id | Structure | FGFR4 IC50 | FGFR1 IC50 | Ratio FGFR1/FGFR4 |
| --- | --- | --- | --- | --- |
| COMPOUND 39 | 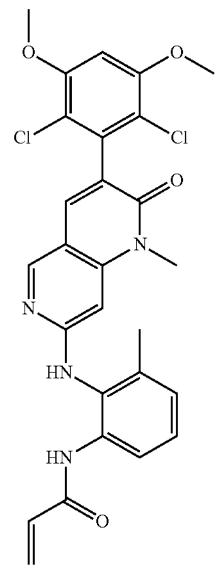 | A | D | E |
| COMPOUND 40 | 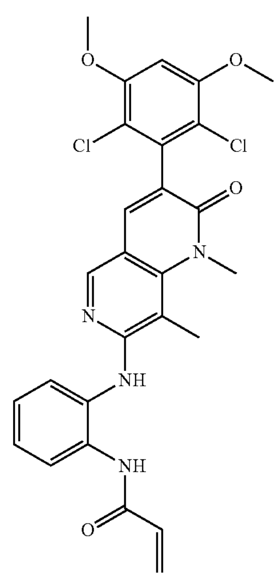 [SMILES: C=CC(=O)Nc1ccccc1Nc1ncc2cc(-c3c(Cl)c(OC)cc(OC)c3Cl)c(=O)n(C)c2c1C] | C | D | A |

| Compound Id | Structure | FGFR4 IC50 | FGFR1 IC50 | Ratio FGFR1/FGFR4 |
| --- | --- | --- | --- | --- |
| COMPOUND 41 | 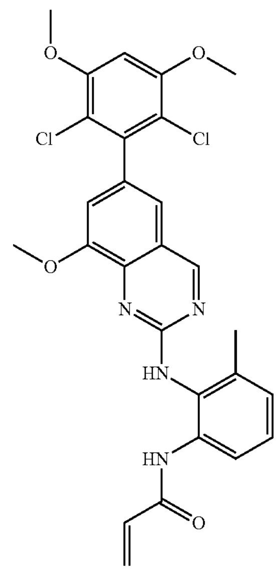 | A | C | A |
| COMPOUND 42 | 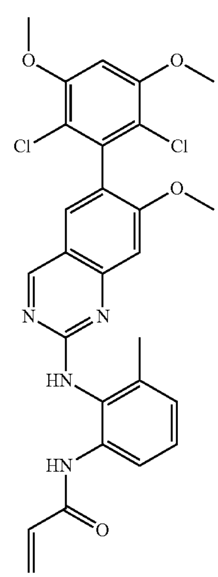 [SMILES: C=CC(=O)Nc1cccc(C)c1Nc1ncc2cc(-c3c(Cl)c(OC)cc(OC)c3Cl)c(OC)cc2n1] | A | B | F |

-continued

| Compound Id | Structure | FGFR4 IC50 | FGFR1 IC50 | Ratio FGFR1/FGFR4 |
|---|---|---|---|---|
| COMPOUND 43 | 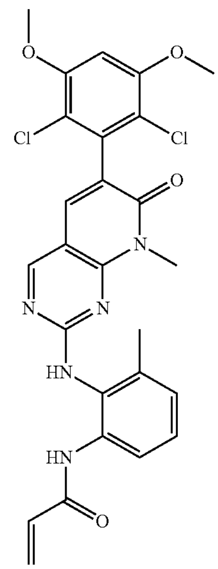 [SMILES: C=CC(=O)Nc1cccc(C)c1Nc1ncc2cc(-c3c(Cl)c(OC)cc(OC)c3Cl)c(=O)n(C)c2n1] | A | C | A |
| COMPOUND 44 | 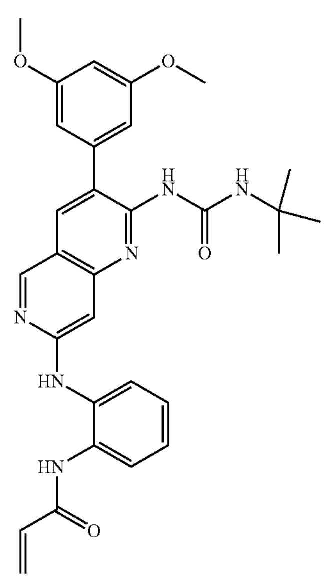 [SMILES: C=CC(=O)Nc1ccccc1Nc1cc2nc(NC(=O)NC(C)(C)C)c(-c3cc(OC)cc(OC)c3)cc2cn1] | C | D | E |

| Compound Id | Structure | FGFR4 IC50 | FGFR1 IC50 | Ratio FGFR1/FGFR4 |
|---|---|---|---|---|
| COMPOUND 45 | 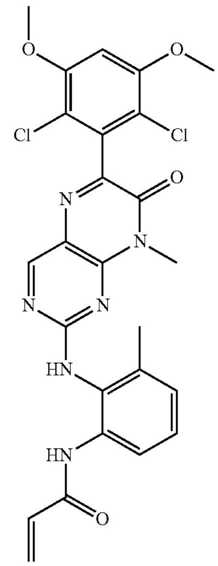 [SMILES: C=CC(=O)Nc1cccc(C)c1Nc1ncc2nc(-c3c(Cl)c(OC)cc(OC)c3Cl)c(=O)n(C)c2n1] | A | D | E |
| COMPOUND 46 | 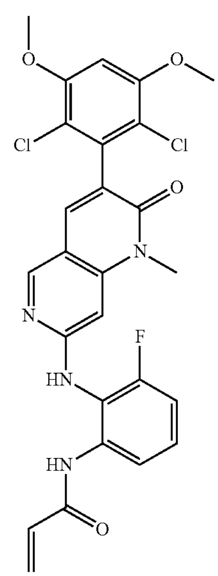 [SMILES: C=CC(=O)Nc1cccc(F)c1Nc1cc2c(cn1)cc(-c1c(Cl)c(OC)cc(OC)c1Cl)c(=O)n2C] | A | C | E |

| Compound Id | Structure | FGFR4 IC50 | FGFR1 IC50 | Ratio FGFR1/FGFR4 |
|---|---|---|---|---|
| COMPOUND 47 | 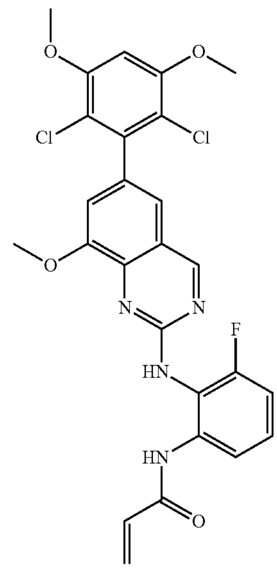 [SMILES: C=CC(=O)Nc1cccc(F)c1Nc1ncc2cc(-c3c(Cl)c(OC)cc(OC)c3Cl)cc(OC)c2n1] | A | B | B |
| COMPOUND 48 | 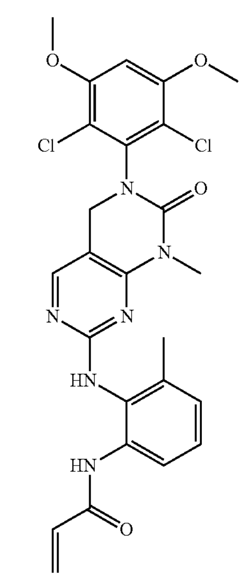 [SMILES: C=CC(=O)Nc1cccc(C)c1Nc1ncc2c(n1)N(C)C(=O)N(c1c(Cl)c(OC)cc(OC)c1Cl)C2] | A | C | E |

-continued

| Compound Id | Structure | FGFR4 IC50 | FGFR1 IC50 | Ratio FGFR1/FGFR4 |
|---|---|---|---|---|
| COMPOUND 49 | 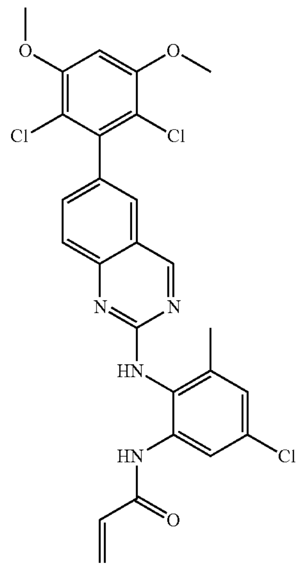 [SMILES: C=CC(=O)Nc1cc(Cl)cc(C)c1Nc1ncc2cc(-c3c(Cl)c(OC)cc(OC)c3Cl)ccc2n1] | B | D | A |
| COMPOUND 49A | 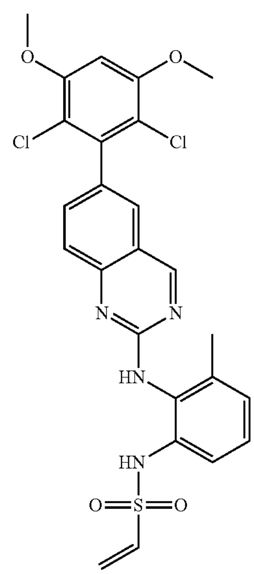 [SMILES: C=CS(=O)(=O)Nc1cccc(C)c1Nc1ncc2cc(-c3c(Cl)c(OC)cc(OC)c3Cl)ccc2n1] | B | C | E |
| COMPOUND 50 | 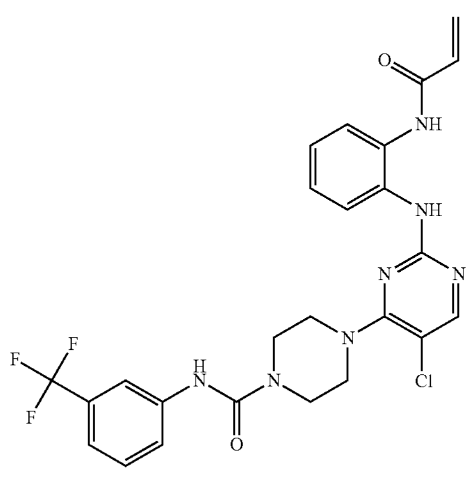 [SMILES: C=CC(=O)Nc1ccccc1Nc1ncc(Cl)c(N2CCN(C(=O)Nc3cccc(C(F)(F)F)c3)CC2)n1] | C | D | B |

| Compound Id | Structure | FGFR4 IC50 | FGFR1 IC50 | Ratio FGFR1/FGFR4 |
|---|---|---|---|---|
| COMPOUND 51 | 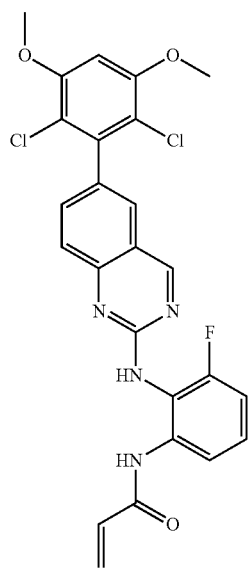 | B | D | F |
| COMPOUND 52 | 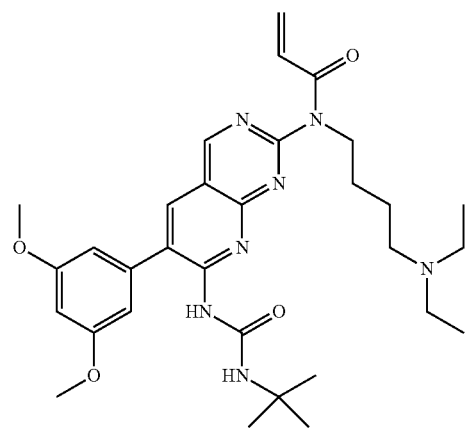 [SMILES: C=CC(=O)N(CCCCN(CC)CC)c1ncc2cc(-c3cc(OC)cc(OC)c3)c(NC(=O)NC(C)(C)C)nc2n1] | A | B | C |

| Compound Id | Structure | FGFR4 IC50 | FGFR1 IC50 | Ratio FGFR1/FGFR4 |
|---|---|---|---|---|
| COMPOUND 53 | 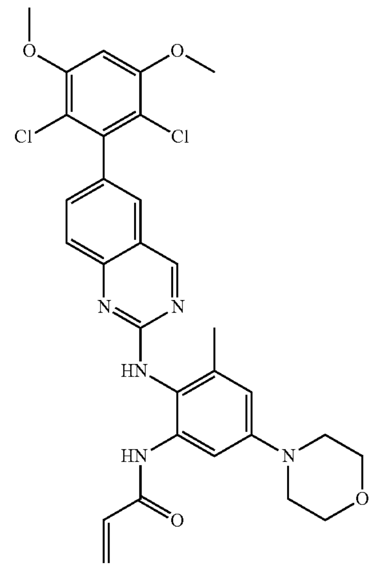 [SMILES: C=CC(=O)Nc1cc(N2CCOCC2)cc(C)c1Nc1ncc2cc(-c3c(Cl)c(OC)cc(OC)c3Cl)ccc2n1] | A | C | C |
| COMPOUND 54 | 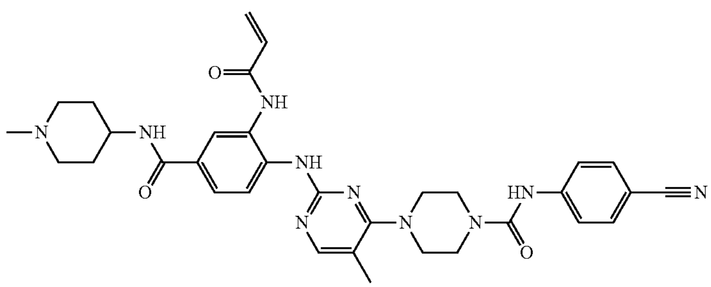 [SMILES: C=CC(=O)Nc1cc(C(=O)NC2CCN(C)CC2)ccc1Nc1ncc(C)c(N2CCN(C(=O)Nc3ccc(C#N)cc3)CC2)n1] | B | D | B |
| COMPOUND 55 | 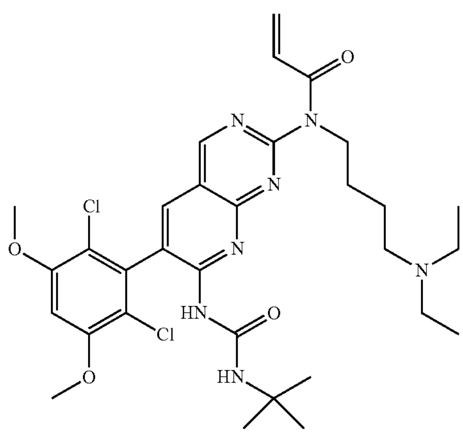 [SMILES: C=CC(=O)N(CCCCN(CC)CC)c1ncc2cc(-c3c(Cl)c(OC)cc(OC)c3Cl)c(NC(=O)NC(C)(C)C)nc2n1] | A | B | A |

In the table above, for FGFR1 and FGFR4: "A" means that the $IC_{50}$ is less than 10 nM; "B" means the $IC_{50}$ is greater than or equal to 10 and less than 100 nM; "C" means that the $IC_{50}$ is greater than or equal to 100 and less than 1000 nM; "D" means that the $IC_{50}$ is greater than 1000 nM.

For the ratio: "F" means that the ratio of [$IC_{50}$ for FGFR1]/[$IC_{50}$ for FGFR4] is less than 10; "E" means that the ratio is >10 and <50; "D 'means the ratio is ≥50 and <100; "C" means the ratio is ≥100 and <200; "B" means the ratio is ≥200 and <500; "A" means the ratio is >500. The higher the ratio, the more selective the compound is for FGFR4 vs. FGFR1.

Cellular Potency

Dose response in MDA-MB-453 cells, which harbor an activating FGFR4 mutation, was measured as follows. Briefly, MDA-MB-453 cells were seeded at $2.5 \times 10^6$ cells/6 well, and starved overnight. Compounds were added at varying concentrations (3000, 1000, 300, 100, and 30 nM) for 1 hour. Samples were collected and lysed for immunoblot analysis. The phosphorylation of Erk was measured and the average pErk value of three replicates was plotted with three parameter dose-response (inhibition) curve fit using Prism GraphPad software, which was used to determine the $IC_{50}$ values. The data are shown in the table below.

| Compound Id | Potency |
| --- | --- |
| COMPOUND 18 | C |
| COMPOUND 20 | D |
| COMPOUND 25 | B |
| COMPOUND 26 | B |
| COMPOUND 27 | B |
| COMPOUND 31 | A |
| COMPOUND 33 | B |
| COMPOUND 34 | B |
| COMPOUND 60 | B |
| COMPOUND 61 | B |
| COMPOUND 38 | C |
| 'COMPOUND 39 | A |
| COMPOUND 41 | B |
| COMPOUND 43 | A |
| COMPOUND 45 | A |
| COMPOUND 46 | A |
| COMPOUND 53 | B |

In the Table, "A" means the IC50 is <1 nM; "B" means the IC50 is ≥1 and <10 nM; "C" means the IC50 is ≥10 and <100 nM; "D" means the IC50 is ≥100 nM.

These data indicate that FGFR-4 inhibition by these compounds results in blockade of downstream oncogenic signaling.

Induction of Apoptosis with an Inhibitor of FGFR4

Figure 3:
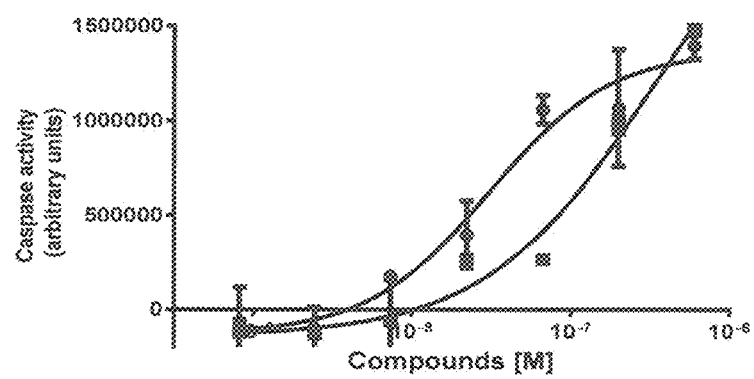
FIG. 3 is a graph showing caspase activity of a Compound 25.

Hep3B cells were seeded at 20 k/well in 96-well white plates in 200 ul of DMEM/5% FBS overnight. The next day compound was added at a final DMSO concentration of 0.1% and incubated for 6 hours. Caspase activity was measured according to manufacture instruction (Caspase-Glo3/7 Assay (Promega)). Briefly, 100 ul of Caspase-Glo3/7 reagent was added to each well and incubated for 1 hour in the dark. Luminescence was measured using EnVision. The average Caspase activity of 2 replicates was plotted with three parameter dose-response (inhibition) curve fit using Prism GraphPad software, which was used to determine the IC50 values. As shown in FIG. 3, in Hep3B cells treatment with COMPOUND 25 for 6 hours leads to potent induction of apoptosis. BGJ398, a pan-FGFR inhibitor, also results in induction of apoptosis, although at a higher concentration.

Covalency

Figure 1B:
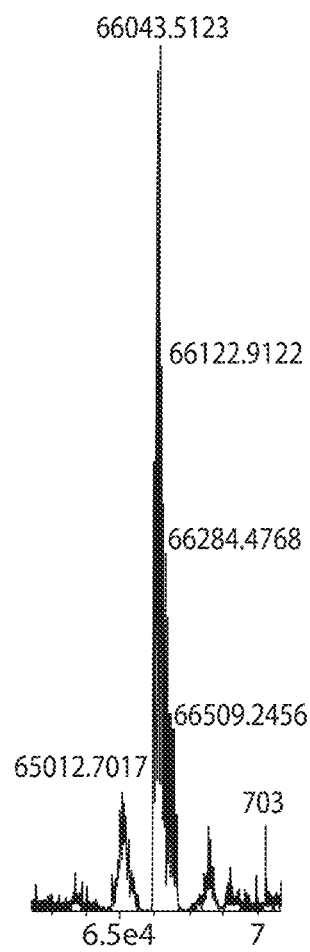
FIG. 1B shows the mass of the protein-inhibitor complex.

Evidence that COMPOUND 52 covalently binds to FGFR-4 is shown by the mass spectrometric data shown in FIG. 1A and FIG. 1B. In 60 ul of buffer, 300 uM Compound 1 was incubated with 50 ug (75 uM) of GST-tagged recombinant wild type FGFR-4 (Carna Biosciences) for 3 hours at room temperature and subsequently at 4° C. for 13 hours. The protein-inhibitor complex was then desalted using Pierce detergent removal columns (Thermo Pierce). The unmodified protein and protein-inhibitor complex were analyzed by electron spray mass spectrometry to determine their respective molecular weights. FIG. 1A shows the mass of the unmodified protein. As shown, the major relevant peak has a mass of 65468.371 daltons. FIG. 1B shows the mass of the protein-inhibitor complex. As shown there, the major relevant peak had a mass of 66043.5123 daltons. The difference between these masses is 575.1252, which is within the instrumental accuracy of the mass of Compound 1, 577.34 daltons.

Figure 2:
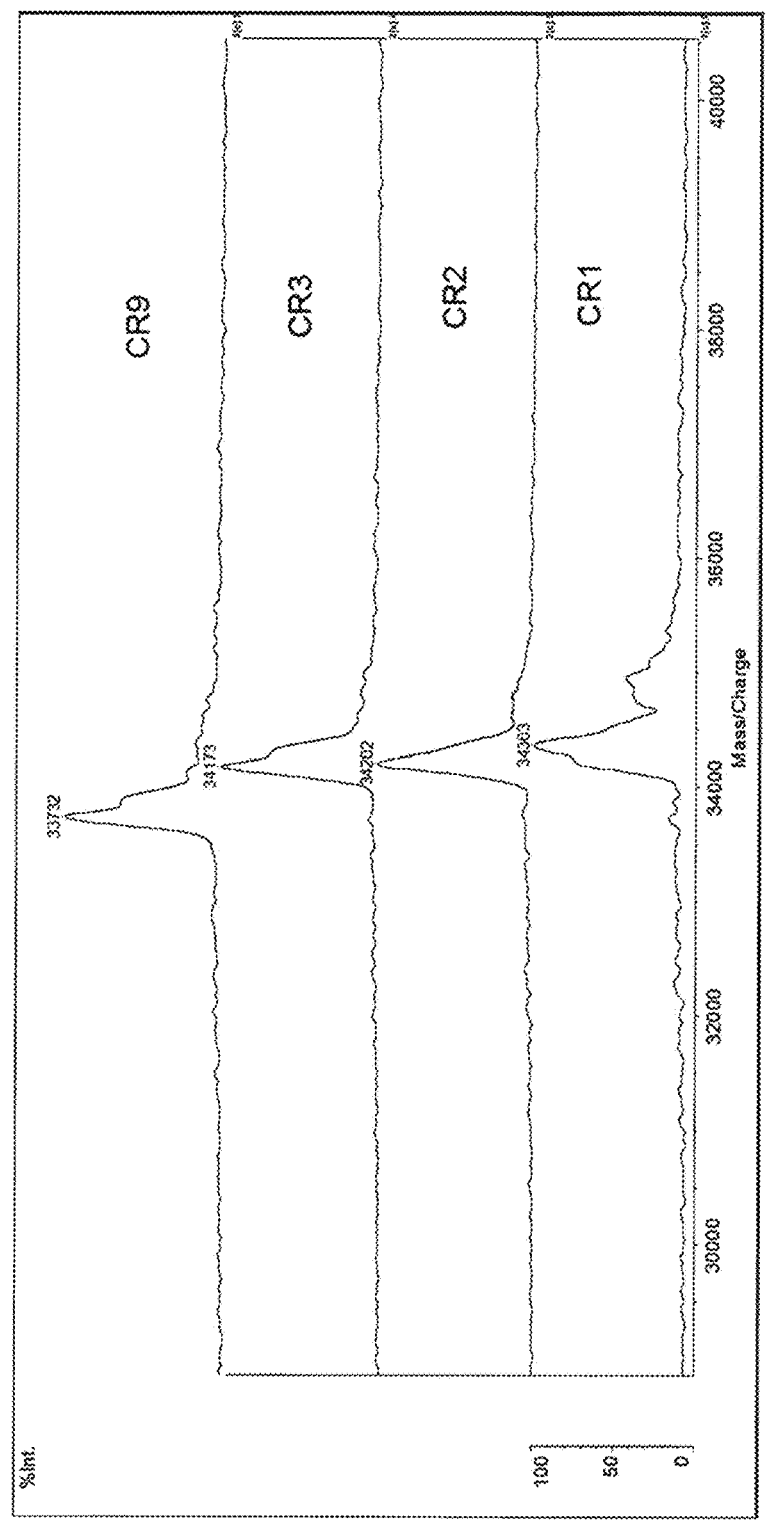
FIG. 2 is a spectrum showing masses for FGFR4 protein without, and with bound inhibitors.

The masses of protein-inhibitor complexes of FGFR-4 and Compounds COMPOUND 11, COMPOUND 20, and COMPOUND 54 are shown in FIG. 2. CR9 is the peak for FGFR4 protein. As shown by peak CR3, the complex showed a +441 da shift when the MW of the compound (COMPOUND 11) was 444.6 (within instrumental accuracy). In another example, the complex showed a +470 da shift (peak CR2), when the MW of the compound (COMPOUND 20) was 473.4. In yet another example, the complex showed a +631 da shift (peak CR1) when the MW of the compound (COMPOUND 54) was 622.7.

This demonstrates that compounds from a wide variety of scaffolds are all capable of forming covalent complexes with FGFR4.

Binding to Cys552

Figure 4:
FIG. 4 is a drawing of the crystal structure of Compound 52 bound to FGFR4 protein.

The crystal structure of COMPOUND 52 bound to FGFR-4 is shown in FIG. 4. As shown there, COMPOUND 52 binds to the cysteine at residue 552 of FGFR-4.

Figure 5:
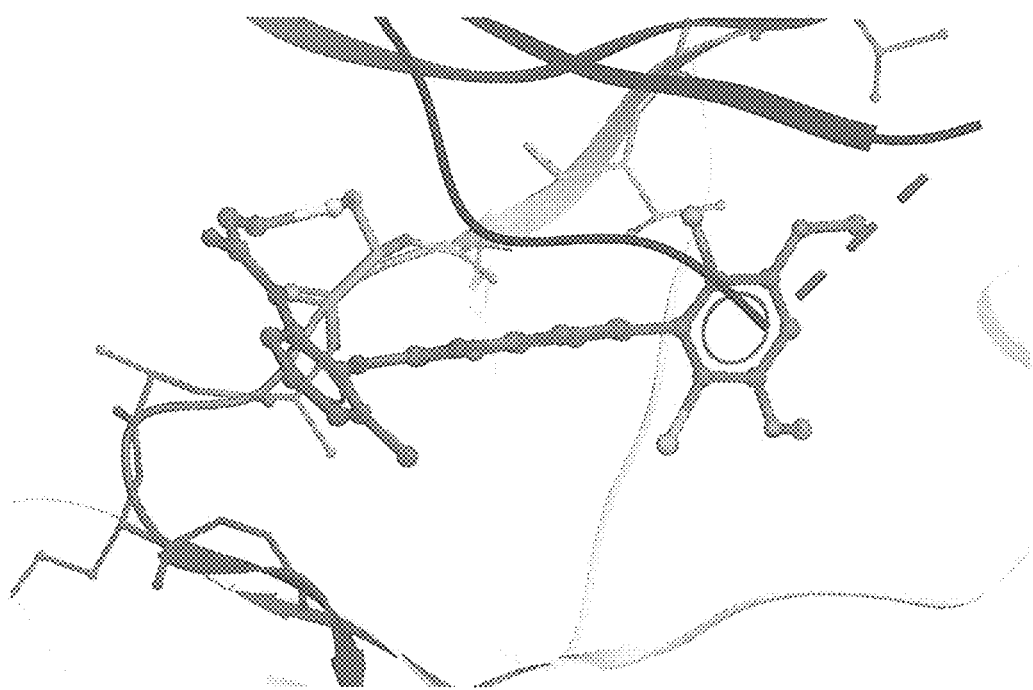
FIG. 5 is a drawing of the crystal structure of Compound 25 bound to FGFR4 protein.

The crystal structure of COMPOUND 25 bound to FGFR-4 is shown in FIG. 5. As shown there, COMPOUND 25 also binds to the cysteine at residue 552 of FGFR-4.

In Vivo Efficacy Data

The effects of COMPOUND 25, BGJ398 (a pan-FGFR inhibitor) and Sorafenib on tumor growth inhibition in Hep3B liver cancer cell subcutaneous xenograft model with different dosages were studied.

Six female nude mice (*Mus Musculus*) age 6 to 8 weeks were used. Tumor cell culture and inoculation: Hep3B cells were cultured with EMEM medium (Invitrogen, USA) supplemented with 10% FBS (Gibco, Australia). The cells were harvested in 90% confluence, and the viability was no less than 90%. Mice were implanted subcutaneously (s.c.) with 200 µL of $10 \times 10^6$ Hep3B cells in 50% Matrigel in the right flank at the beginning of the study.

Animal grouping and dosing schedule: Ten days after cell implantation, when tumors reached an average volume of 199 $mm^3$, 45 mice were selected based on tumor volume and randomly assigned to 5 treatment groups (n=9). The day of randomization was denoted as Do and the treatment was started from then on.

Tumor volume and body weight measurements: Tumor size was measured twice per week in two dimensions using a caliper, and the volume was expressed in $mm^3$ using the formula: $V=0.5$ a×$b^2$ where a and b were the long and short diameters of the tumor, respectively. Body weight was measured at least twice weekly.

End of in vivo portion: Blood, tumors and livers were collected from 3 mice in each treated group at 4, 12 and 24 hours after the last dose. The left lobe of the liver was collected for pharmacodynamic (PD) studies, and the rest of the liver was stored in formalin for histology.

The small tumors were prioritized for use in pharmacokinetic studies. Any remaining tumor was fixed for histological analysis first, and then was snap-frozen for the PD study.

Figure 6:
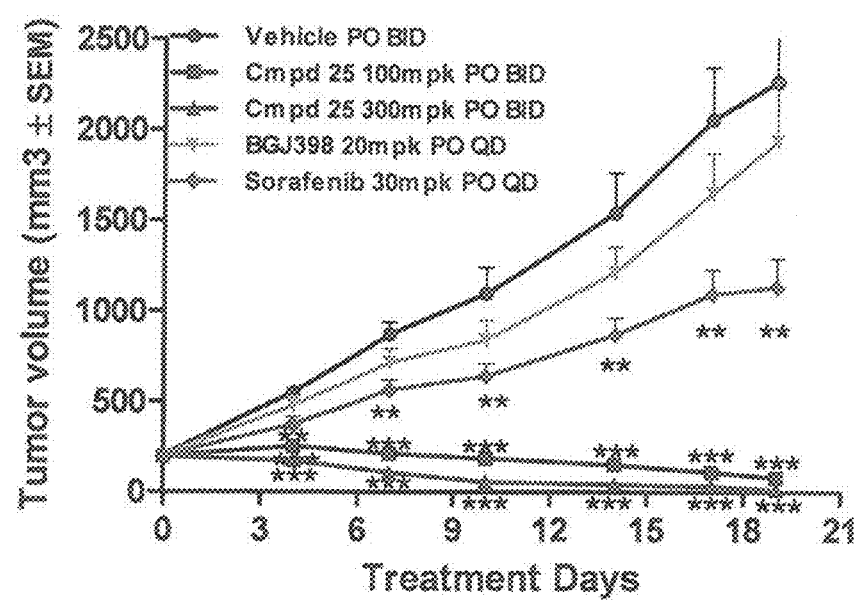
FIG. 6 is a line graph depicting the antitumor effect of Compound 25 at 100 mg/kg PO BID (■), Compound 25 at 300 mg/kg PO BID (▲), BGJ398 at 20 mg/kg PO QD (▼), and Sorafenib at 30 mg/kg PO QD (♦) against Hep3b xenograft tumors in nude mice.
Figure 7:
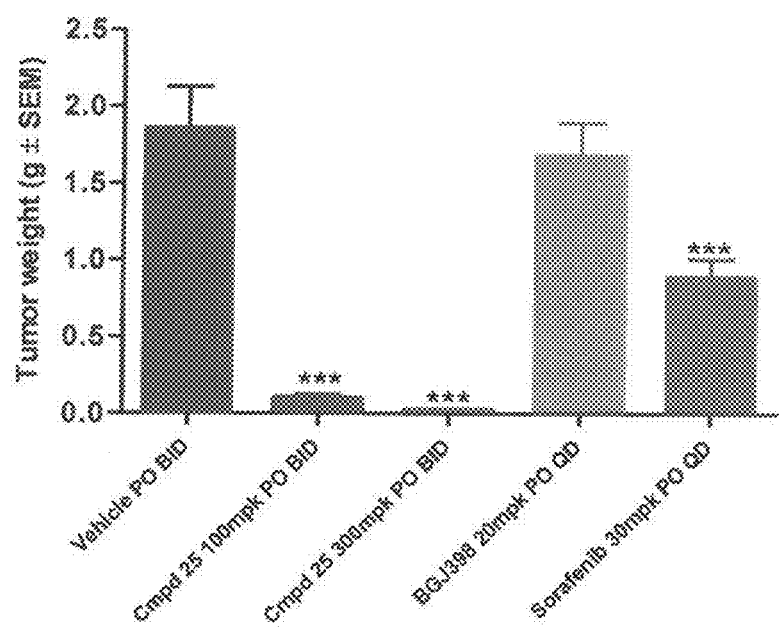
FIG. 7 is a bar graph depicting the tumor weights of Hep3B-bearing nude mice following administration of vehicle and Compound 25 at 100 mg/kg PO BID, Compound 25 at 300 mg/kg PO BID, BGJ398 at 20 mg/kg PO QD, and Sorafenib at 30 mg/kg PO QD.

Tumor volumes of Hep3B-bearing nude mice: FIG. 6 is a line graph depicting the growth inhibition of COMPOUND 25-treated (100 mg/kg PO BID), COMPOUND 25-treated (300 mg/kg PO BID), BGJ398-treated (20 mg/kg PO QD), and Sorafenib-treated (30 mg/kg PO QD) groups against Hep3B xenograft tumors in nude mice. Statistically significant reduction of tumor volumes was observed in COMPOUND 25 (100 mg/kg PO BID), COMPOUND 25 (300 mg/kg PO BID) and Sorafenib (30 mg/kg PO QD) efficacy groups when compared with vehicle group, all starting from Day 4 after the first administration of the compounds and persisted to the end (Day 19) (FIG. 7). However, a significant difference in tumor volume between BGJ398 (20 mg/kg PO QD) and vehicle groups was not observed during the entire study (FIG. 7). Increasing dosage of COMPOUND 25 from 100 mg/kg to 300 mg/kg enhanced the tumor inhibition efficiency. Tumors in both COMPOUND 25-treated (100 mg/kg PO BID) and COMPOUND 25-treated (300 mg/kg PO BID) groups regressed, and tumors in the COMPOUND 25-treated (300 mg/kg PO BID) group almost disappeared. In this study, the COMPOUND 25-treated (100 mg/kg PO BID) and the COMPOUND 25-treated (300 mg/kg PO BID) groups displayed superiority in tumor growth inhibition.

Figure 8:
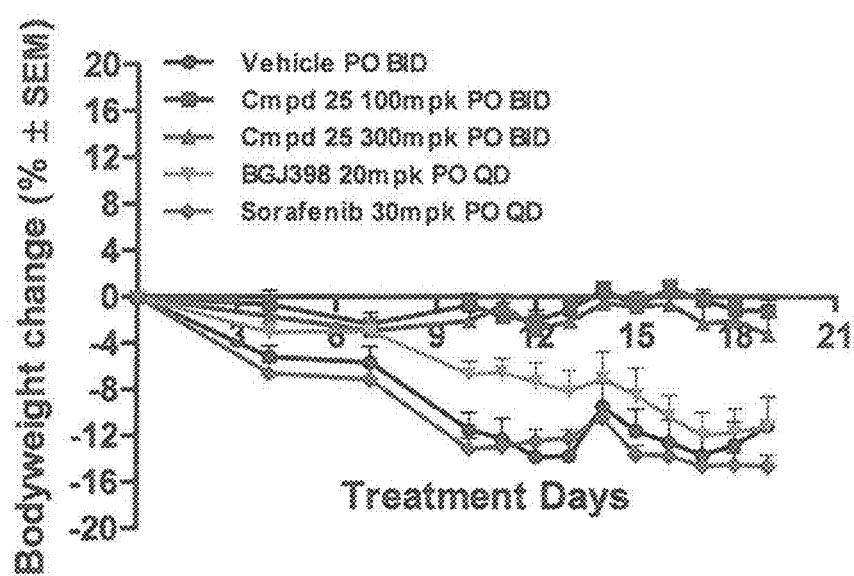
FIG. 8 is a line graph depicting body weight change (%) of Hep3B-bearing nude mice following administration of vehicle and Compound 25 at 100 mg/kg PO BID (■), Compound 25 at 300 mg/kg PO BID (▲), BGJ398 at 20 mg/kg PO QD (▼), and Sorafenib at 30 mg/kg PO QD (♦).

Body weight change (%) of Hep3B-bearing nude mice: FIG. 8 is a line graph depicting the body weight change (%) during the entire study period. All the mice except for the mice in the COMPOUND 25-treated groups showed significant loss in bodyweight. The body weight of mice in the vehicle group decreased by approximately 10% by Day 10 for the burden of tumor. This result indicated that COMPOUND 25 was well tolerated at the current dosages and dosing schedule in nude mice, and that COMPOUND 25 could alleviate body weight loss by inhibiting tumor growth.

Mice treated with COMPOUND 25 (100 mg/kg PO BID), COMPOUND 25 (300 mg/kg PO BID) and Sorafenib (30 mg/kg PO QD) exhibited a significant reduction of tumor volume as compared with the vehicle group during the entire study. Increasing the dosage of COMPOUND 25 from 100 mg/kg to 300 mg/kg enhanced the tumor inhibition efficiency. Tumors of mice in both the COMPOUND 25-treated (100 mg/kg PO BID) and the COMPOUND 25-treated (300 mg/kg PO BID) groups regressed, and tumors in the COMPOUND 25-treated (300 mg/kg PO BID) group almost disappeared. All mice except for those in the COMPOUND 25-treated groups lost a significant amount of bodyweight. The bodyweight of the mice in the vehicle group decreased by approximately 10% by Day 10 for the burden of tumor. These results indicated that COMPOUND 25 was well tolerated at the current dosages and at the dosing schedule in nude mice, and that COMPOUND 25 could alleviate body weight loss by inhibiting tumor growth.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound which is:

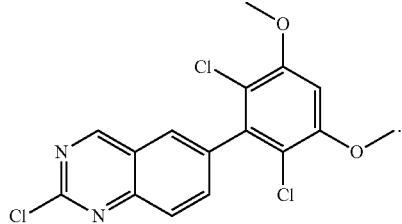 [SMILES: COc1cc(OC)c(Cl)c(-c2ccc3nc(Cl)ncc3c2)c1Cl]

* * * * *